United States Patent
McGrath et al.

(10) Patent No.: US 12,303,324 B2
(45) Date of Patent: May 20, 2025

(54) METHOD OF MEDICAL IMAGING USING MULTIPLE ARRAYS

(71) Applicant: Faction Imaging Inc., New York, NY (US)

(72) Inventors: Matthew McGrath, New York, NY (US); Evan Alexander Dewhirst, San Francisco, CA (US)

(73) Assignee: Faction Imaging Inc., Dover, DE (US)

( * ) Notice: Subject to any disclaimer, the term of this patent is extended or adjusted under 35 U.S.C. 154(b) by 0 days.

(21) Appl. No.: 17/058,976

(22) PCT Filed: May 31, 2019

(86) PCT No.: PCT/US2019/035019
§ 371 (c)(1),
(2) Date: Nov. 25, 2020

(87) PCT Pub. No.: WO2019/232451
PCT Pub. Date: Dec. 5, 2019

(65) Prior Publication Data
US 2021/0228186 A1     Jul. 29, 2021

Related U.S. Application Data

(60) Provisional application No. 62/678,868, filed on May 31, 2018, provisional application No. 62/678,854, (Continued)

(51) Int. Cl.
*A61B 8/00*     (2006.01)
*A61B 8/06*     (2006.01)
(Continued)

(52) U.S. Cl.
CPC ............... *A61B 8/085* (2013.01); *A61B 8/06* (2013.01); *A61B 8/4245* (2013.01);
(Continued)

(58) Field of Classification Search
CPC ......... A61B 8/085; A61B 8/06; A61B 8/4245; A61B 8/4281; A61B 8/4477;
(Continued)

(56) References Cited

U.S. PATENT DOCUMENTS

| | | | |
|---|---|---|---|
| 3,306,290 A | 2/1967 | Weltman |
| 4,002,221 A | 1/1977 | Buchalter |

(Continued)

FOREIGN PATENT DOCUMENTS

| | | | |
|---|---|---|---|
| CA | 2029172 A1 | 5/1991 |
| CN | 103974664 A | 8/2014 |

(Continued)

OTHER PUBLICATIONS

Partial International Search Report including the Provisional Opinion from Application No. PCT/US2019/035022 mailed Aug. 22, 2019, pp. 1-13.

(Continued)

*Primary Examiner* — Christopher Koharski
*Assistant Examiner* — Zainab Mohammed Aldarraji
(74) *Attorney, Agent, or Firm* — Lerner David LLP

(57) ABSTRACT

Disclosed herein are systems and methods for visualizing a target anatomical site of a patient using one or more imagers. The method can include placing multiple imagers on multiple locations at an anatomical site. The method can further include generating separate image data sets from the multiple images and combining the image data sets to generate a volumetric imaging data of the anatomical site. The volumetric imaging data can include all anatomical features within the target anatomical site. A visualization system for medical imaging can include transducers on the imagers to visualize the target anatomical site. The system can further include a processor to combine the image data sets to generate the volumetric imaging data set. The system can (Continued)

further include a display device to display the volumetric imaging data set.

19 Claims, 160 Drawing Sheets

Related U.S. Application Data filed on May 31, 2018, provisional application No. 62/678,885, filed on May 31, 2018.

(51) Int. Cl.

| | | |
|---|---|---|
| *A61B 8/08* | (2006.01) | |
| *A61B 34/00* | (2016.01) | |
| *A61B 34/10* | (2016.01) | |
| *A61B 34/20* | (2016.01) | |
| *A61B 90/50* | (2016.01) | |
| *A61B 5/15* | (2006.01) | |
| *A61B 17/132* | (2006.01) | |
| *A61M 5/42* | (2006.01) | |

(52) U.S. Cl.
CPC .......... *A61B 8/4281* (2013.01); *A61B 8/4477* (2013.01); *A61B 8/4494* (2013.01); *A61B 8/461* (2013.01); *A61B 8/466* (2013.01); *A61B 8/483* (2013.01); *A61B 8/488* (2013.01); *A61B 34/10* (2016.02); *A61B 34/20* (2016.02); *A61B 34/25* (2016.02); *A61B 90/50* (2016.02); *A61B 5/150083* (2013.01); *A61B 5/150748* (2013.01); *A61B 17/1322* (2013.01); *A61B 2034/107* (2016.02); *A61B 2034/2048* (2016.02); *A61B 2034/2063* (2016.02); *A61B 2034/2065* (2016.02); *A61B 2090/502* (2016.02); *A61M 5/427* (2013.01)

(58) Field of Classification Search
CPC ....... A61B 8/4494; A61B 8/461; A61B 8/466; A61B 8/483; A61B 8/488; A61B 34/10; A61B 34/20; A61B 34/25; A61B 90/50; A61B 5/150083; A61B 5/150748; A61B 17/1322; A61B 2034/107; A61B 2034/2048; A61B 2034/2063; A61B 2034/2065; A61B 2090/502; A61B 8/4227; A61B 90/11; A61B 2017/00106; A61B 2017/00216; A61B 2017/00274; A61B 2017/00924; A61B 2017/22072; A61B 2017/2253; A61B 2017/3405; A61B 2017/3409; A61B 2017/3413; A61B 2034/105; A61B 2090/365; A61B 2090/367; A61B 2090/371; A61B 2090/372; A61B 2090/378; A61B 2090/3937; A61B 8/0841; A61B 8/145; A61B 8/5246; A61B 17/3403; A61B 8/0808; A61B 8/0891; A61B 5/15003; A61B 5/1535; A61B 5/489; A61M 5/427; G01S 7/52079; G01S 15/8915; G01S 15/8929; G01S 15/8993; G01S 15/8979; A61F 2007/0285
See application file for complete search history.

(56) References Cited

U.S. PATENT DOCUMENTS

| | | |
|---|---|---|
| 4,211,289 A | 7/1980 | Klein |
| 4,243,039 A | 1/1981 | Aginsky |
| 4,250,881 A | 2/1981 | Smith |
| 4,306,563 A | 12/1981 | Iwatschenko |
| 4,324,595 A | 4/1982 | Kasprzak |
| 4,441,504 A | 4/1984 | Peterson et al. |
| 4,459,854 A | 7/1984 | Richardson et al. |
| 4,466,437 A | 8/1984 | Dyck et al. |
| 4,469,099 A | 9/1984 | McEwen |
| 4,479,494 A | 10/1984 | McEwen |
| 4,556,066 A | 12/1985 | Semrow |
| 4,596,563 A | 6/1986 | Pande |
| 4,605,010 A | 8/1986 | McEwen |
| 4,727,885 A | 3/1988 | Ruff |
| 4,770,175 A | 9/1988 | McEwen |
| 4,838,863 A | 6/1989 | Allard et al. |
| 4,846,812 A | 7/1989 | Walker et al. |
| 4,867,981 A | 9/1989 | Grof |
| 4,869,265 A | 9/1989 | McEwen |
| 4,935,016 A | 6/1990 | Deleo |
| 4,936,835 A | 6/1990 | Haaga |
| 4,976,704 A | 12/1990 | McLees |
| 4,988,341 A | 1/1991 | Columbus et al. |
| 5,032,637 A | 7/1991 | Therriault et al. |
| 5,048,536 A | 9/1991 | McEwen |
| 5,092,323 A | 3/1992 | Riedel et al. |
| 5,156,911 A | 10/1992 | Stewart |
| 5,181,522 A | 1/1993 | McEwen |
| 5,261,409 A | 11/1993 | Dardel |
| 5,265,614 A | 11/1993 | Hayakawa et al. |
| 5,312,431 A | 5/1994 | McEwen |
| 5,314,437 A | 5/1994 | Holtsch |
| 5,336,207 A | 8/1994 | Norcia |
| 5,387,450 A | 2/1995 | Stewart |
| 5,412,035 A | 5/1995 | Schmitt et al. |
| 5,453,099 A | 9/1995 | Lee et al. |
| 5,454,831 A | 10/1995 | McEwen |
| 5,522,878 A | 6/1996 | Montecalvo et al. |
| 5,569,207 A | 10/1996 | Gisselberg et al. |
| 5,578,055 A | 11/1996 | McEwen |
| 5,584,853 A | 12/1996 | McEwen |
| 5,619,476 A | 4/1997 | Haller et al. |
| 5,628,723 A | 5/1997 | Grau |
| 5,647,373 A | 7/1997 | Paltieli |
| 5,649,954 A | 7/1997 | McEwen |
| 5,727,550 A | 3/1998 | Montecalvo |
| 5,728,071 A | 3/1998 | Watson et al. |
| 5,741,295 A | 4/1998 | McEwen |
| 5,762,630 A | 6/1998 | Bley et al. |
| 5,770,801 A | 6/1998 | Wang et al. |
| 5,855,589 A | 1/1999 | McEwen et al. |
| 5,891,039 A | 4/1999 | Bonnefous et al. |
| 5,911,735 A | 6/1999 | McEwen et al. |
| 5,931,853 A | 8/1999 | McEwen et al. |
| 5,935,146 A | 8/1999 | McEwen et al. |
| 6,007,562 A | 12/1999 | Harren et al. |
| 6,014,473 A | 1/2000 | Hossack et al. |
| 6,039,694 A | 3/2000 | Arson et al. |
| 6,056,718 A | 5/2000 | Funderburk et al. |
| 6,063,231 A | 5/2000 | Adler et al. |
| 6,107,988 A | 8/2000 | Phillipps |
| 6,139,496 A | 10/2000 | Chen et al. |
| 6,149,666 A | 11/2000 | Marsden |
| 6,213,939 B1 | 4/2001 | McEwen |
| 6,251,073 B1 | 6/2001 | Imran et al. |
| 6,264,610 B1 | 7/2001 | Zhu |
| 6,283,942 B1 | 9/2001 | Staehlin et al. |
| 6,333,093 B1 | 12/2001 | Burrell et al. |
| 6,359,367 B1 | 3/2002 | Sumanaweera et al. |
| 6,423,002 B1 | 7/2002 | Hossack |
| 6,443,901 B1 | 9/2002 | Fraser |
| 6,443,928 B1 | 9/2002 | Francis |
| 6,524,284 B1 | 2/2003 | Marshall |
| 6,524,297 B1 | 2/2003 | Newman |
| 6,556,858 B1 | 4/2003 | Zeman |
| 6,577,496 B1 | 6/2003 | Gioscia et al. |
| 6,610,013 B1 | 8/2003 | Fenster et al. |
| 6,610,762 B1 | 8/2003 | Webster |
| 6,690,958 B1 | 2/2004 | Walker et al. |
| 6,695,786 B2 | 2/2004 | Wang et al. |
| 6,733,458 B1 | 5/2004 | Steins et al. |
| 6,746,470 B2 | 6/2004 | McEwen et al. |
| 6,755,789 B2 | 6/2004 | Stringer et al. |

(56) References Cited

U.S. PATENT DOCUMENTS

| | | |
|---|---|---|
| 6,815,694 B2 | 11/2004 | Sfez et al. |
| 6,854,338 B2 | 2/2005 | Khuri-Yakub et al. |
| 6,875,179 B2 | 4/2005 | Ferguson et al. |
| 6,921,366 B2 | 7/2005 | Jeon et al. |
| 7,078,582 B2 | 7/2006 | Stebbings et al. |
| 7,129,389 B1 | 10/2006 | Watson |
| 7,239,909 B2 | 7/2007 | Zeman |
| 7,285,092 B2 | 10/2007 | Duric et al. |
| 7,326,177 B2 | 2/2008 | Williamson, IV et al. |
| 7,399,800 B2 | 7/2008 | Burch |
| 7,494,494 B2 | 2/2009 | Stoianovici et al. |
| 7,699,776 B2 | 4/2010 | Walker et al. |
| 7,766,839 B2 | 8/2010 | Rogers et al. |
| 7,815,575 B2 | 10/2010 | Lo et al. |
| 7,863,496 B2 | 1/2011 | Harren et al. |
| 7,874,698 B2 | 1/2011 | Mullani |
| 7,922,688 B2 | 4/2011 | Bodduluri et al. |
| 7,962,192 B2 | 6/2011 | Bodduluri et al. |
| 7,972,298 B2 | 7/2011 | Wallace et al. |
| 8,032,205 B2 | 10/2011 | Mullani |
| 8,036,448 B2 | 10/2011 | Gildenberg |
| 8,043,604 B2 | 10/2011 | Wiley et al. |
| 8,070,682 B2 | 12/2011 | Zhu |
| 8,078,263 B2 | 12/2011 | Zeman et al. |
| 8,105,288 B2 | 1/2012 | Keyser et al. |
| 8,108,022 B2 | 1/2012 | Balberg et al. |
| 8,128,568 B2 * | 3/2012 | Wang ................ A61B 10/0233 600/459 |
| 8,177,808 B2 | 5/2012 | Mullani |
| 8,199,189 B2 | 6/2012 | Kagenow et al. |
| 8,221,322 B2 | 7/2012 | Wang et al. |
| 8,231,533 B2 | 7/2012 | Buchalter |
| 8,308,740 B2 | 11/2012 | Tolley et al. |
| 8,308,741 B2 | 11/2012 | Hyde et al. |
| 8,333,703 B2 | 12/2012 | Kanda et al. |
| 8,335,557 B2 | 12/2012 | Maschke |
| 8,463,364 B2 | 6/2013 | Wood et al. |
| 8,478,386 B2 | 7/2013 | Goldman et al. |
| 8,489,178 B2 | 7/2013 | Wood et al. |
| 8,494,616 B2 | 7/2013 | Zeman |
| 8,498,178 B2 | 7/2013 | Antoine et al. |
| 8,509,503 B2 | 8/2013 | Nahum et al. |
| 8,529,454 B2 | 9/2013 | Chen |
| 8,594,770 B2 | 11/2013 | Wood et al. |
| 8,622,909 B1 | 1/2014 | O'Ruanaidh et al. |
| 8,665,507 B2 | 3/2014 | Luciano et al. |
| 8,702,653 B2 | 4/2014 | Samandi et al. |
| 8,706,200 B2 | 4/2014 | Goldman et al. |
| 8,712,498 B2 | 4/2014 | Goldman et al. |
| 8,723,824 B2 | 5/2014 | Myers et al. |
| 8,730,321 B2 | 5/2014 | Luciano et al. |
| 8,761,862 B2 | 6/2014 | Ridley et al. |
| 8,764,663 B2 | 7/2014 | Smok et al. |
| 8,766,459 B2 | 7/2014 | Degertekin et al. |
| 8,818,493 B2 | 8/2014 | Goldman et al. |
| 8,834,423 B2 | 9/2014 | Falo, Jr. et al. |
| 8,852,104 B2 | 10/2014 | Oralkan et al. |
| 8,852,111 B2 | 10/2014 | Park et al. |
| 8,867,314 B2 | 10/2014 | Murakami |
| 8,936,581 B2 | 1/2015 | Bihlmaier |
| 8,975,096 B2 | 3/2015 | Kim et al. |
| 9,022,940 B2 | 5/2015 | Meier |
| 9,035,532 B2 | 5/2015 | Chowdhury |
| 9,042,966 B2 | 5/2015 | Goldman et al. |
| 9,044,207 B2 | 6/2015 | Goldman et al. |
| 9,061,109 B2 | 6/2015 | Wood et al. |
| 9,074,985 B2 | 7/2015 | Lebental et al. |
| 9,079,219 B2 | 7/2015 | Chen |
| 9,125,629 B2 | 9/2015 | Goldman et al. |
| 9,161,817 B2 | 10/2015 | Olson et al. |
| 9,180,056 B2 | 11/2015 | Rea |
| 9,192,306 B2 | 11/2015 | Chen |
| 9,221,077 B2 | 12/2015 | Chen et al. |
| 9,226,664 B2 | 1/2016 | Wood et al. |
| 9,241,651 B2 | 1/2016 | Fedder et al. |
| 9,278,375 B2 | 3/2016 | Angle et al. |
| 9,327,967 B2 | 5/2016 | Huang |
| 9,345,427 B2 | 5/2016 | Wood et al. |
| 9,364,171 B2 | 6/2016 | Harris et al. |
| 9,364,634 B2 | 6/2016 | Adams et al. |
| 9,430,819 B2 | 8/2016 | Luciano et al. |
| 9,456,766 B2 | 10/2016 | Cox et al. |
| 9,492,097 B2 | 11/2016 | Wilkes et al. |
| 9,492,117 B2 | 11/2016 | Goldman et al. |
| 9,499,852 B2 | 11/2016 | Jenkins et al. |
| 9,504,170 B2 | 11/2016 | Rothkopf et al. |
| 9,521,991 B2 | 12/2016 | Rothberg et al. |
| 9,662,679 B2 | 5/2017 | Chen et al. |
| 9,667,889 B2 | 5/2017 | Rothberg |
| 9,675,319 B1 | 6/2017 | Razzaque et al. |
| 9,789,282 B2 | 10/2017 | McKinnon et al. |
| 9,844,328 B2 | 12/2017 | Simpson et al. |
| 10,791,984 B2 * | 10/2020 | Kantrowitz .......... A61B 5/0004 |
| 2002/0083771 A1 | 7/2002 | Khuri-Yakub et al. |
| 2003/0139671 A1 | 7/2003 | Walston et al. |
| 2003/0149366 A1 | 8/2003 | Stringer et al. |
| 2004/0122304 A1 | 6/2004 | Duric et al. |
| 2004/0158230 A1 | 8/2004 | Hunn et al. |
| 2006/0184035 A1 | 8/2006 | Kimura et al. |
| 2006/0224053 A1 | 10/2006 | Black et al. |
| 2007/0097014 A1 | 5/2007 | Solomon et al. |
| 2007/0238981 A1 | 10/2007 | Zhu et al. |
| 2007/0255137 A1 | 11/2007 | Sui et al. |
| 2008/0015441 A1 | 1/2008 | Kanda et al. |
| 2008/0015442 A1 | 1/2008 | Watson et al. |
| 2008/0123083 A1 | 5/2008 | Wang et al. |
| 2008/0154135 A1 | 6/2008 | Kimura et al. |
| 2008/0200810 A1 | 8/2008 | Buchalter |
| 2008/0221448 A1 | 9/2008 | Khuri-Yakub et al. |
| 2008/0242979 A1 | 10/2008 | Fisher et al. |
| 2008/0249419 A1 * | 10/2008 | Sekins ...................... A61B 8/08 600/463 |
| 2008/0300491 A1 | 12/2008 | Bonde et al. |
| 2009/0024039 A1 | 1/2009 | Wang et al. |
| 2009/0054781 A1 | 2/2009 | Stonefield et al. |
| 2010/0179429 A1 * | 7/2010 | Ho ........................ A61B 8/4461 600/446 |
| 2010/0228091 A1 | 9/2010 | Widenhouse et al. |
| 2010/0268058 A1 | 10/2010 | Chen |
| 2010/0268111 A1 | 10/2010 | Drinan et al. |
| 2010/0268152 A1 | 10/2010 | Oralkan et al. |
| 2011/0301451 A1 * | 12/2011 | Rohling ............... A61B 8/4477 600/443 |
| 2011/0306025 A1 | 12/2011 | Sheehan et al. |
| 2012/0095343 A1 | 4/2012 | Smith et al. |
| 2012/0116218 A1 | 5/2012 | Martin et al. |
| 2012/0133752 A1 | 5/2012 | Bry |
| 2012/0136256 A1 | 5/2012 | Nozaki et al. |
| 2012/0163129 A1 | 6/2012 | Antoine et al. |
| 2012/0289820 A1 | 11/2012 | Rohling |
| 2013/0150719 A1 | 6/2013 | Orderud |
| 2013/0163383 A1 | 6/2013 | Murakami |
| 2013/0247350 A1 * | 9/2013 | Specht .................... A61B 8/42 29/407.09 |
| 2013/0301394 A1 | 11/2013 | Chen et al. |
| 2013/0307935 A1 | 11/2013 | Rappel et al. |
| 2013/0341303 A1 | 12/2013 | Kim et al. |
| 2013/0345566 A1 | 12/2013 | Weitzel et al. |
| 2014/0012125 A1 | 1/2014 | Chen |
| 2014/0046186 A1 | 2/2014 | Mauldin, Jr. et al. |
| 2014/0121518 A1 | 5/2014 | Baba et al. |
| 2014/0125193 A1 | 5/2014 | Chowdhury |
| 2014/0187945 A1 | 7/2014 | Sandy et al. |
| 2014/0207001 A1 | 7/2014 | Seo et al. |
| 2014/0265943 A1 | 9/2014 | Angle et al. |
| 2014/0288428 A1 | 9/2014 | Rothberg et al. |
| 2014/0343426 A1 | 11/2014 | Kolen et al. |
| 2014/0371584 A1 | 12/2014 | Cleary et al. |
| 2015/0011884 A1 | 1/2015 | Walker et al. |
| 2015/0038844 A1 | 2/2015 | Blalock et al. |
| 2015/0141820 A1 | 5/2015 | Yamada et al. |
| 2015/0181348 A1 | 6/2015 | Huang |
| 2015/0196276 A1 | 7/2015 | Seo et al. |
| 2015/0257732 A1 | 9/2015 | Ryan |

(56) References Cited

U.S. PATENT DOCUMENTS

| | | |
|---|---|---|
| 2015/0257735 A1 | 9/2015 | Ball et al. |
| 2015/0289750 A1 | 10/2015 | Stigall et al. |
| 2015/0289853 A1 | 10/2015 | Cho et al. |
| 2015/0305709 A1 | 10/2015 | Tomassi et al. |
| 2016/0015363 A1 | 1/2016 | Tahmasebi Maraghoosh et al. |
| 2016/0022308 A1 | 1/2016 | Rohling |
| 2016/0037625 A1 | 2/2016 | Huitema et al. |
| 2016/0038119 A1 | 2/2016 | Desjardins |
| 2016/0066883 A1 | 3/2016 | Mickelsen |
| 2016/0101437 A1 | 4/2016 | Chen et al. |
| 2016/0199027 A1 | 7/2016 | Scully |
| 2016/0213321 A1 | 7/2016 | Bernstein et al. |
| 2016/0270760 A1 | 9/2016 | Janicki et al. |
| 2016/0328998 A1 | 11/2016 | Pedersen et al. |
| 2016/0331353 A1 | 11/2016 | Ralston et al. |
| 2016/0331358 A1 | 11/2016 | Gordon |
| 2016/0374644 A1 | 12/2016 | Mauldin, Jr. et al. |
| 2017/0034918 A1 | 2/2017 | Huitema et al. |
| 2017/0084022 A1 | 3/2017 | Naidu et al. |
| 2017/0095296 A1 | 4/2017 | Olivan Bescos et al. |
| 2017/0119348 A1 | 5/2017 | Degertekin et al. |
| 2017/0128042 A1 | 5/2017 | Desai et al. |
| 2017/0157646 A1 | 6/2017 | Alie et al. |
| 2017/0181726 A1 | 6/2017 | Schneider et al. |
| 2017/0209121 A1* | 7/2017 | Davis, Sr. ............ A61B 8/4494 |
| 2017/0265947 A1 | 9/2017 | Dyer et al. |
| 2017/0296144 A1 | 10/2017 | Rothberg et al. |
| 2017/0312032 A1 | 11/2017 | Amanatullah et al. |
| 2017/0360414 A1 | 12/2017 | Rothberg et al. |
| 2017/0360415 A1 | 12/2017 | Rothberg et al. |
| 2018/0014811 A1 | 1/2018 | Sonnenschein |
| 2018/0046875 A1 | 2/2018 | Caluser |
| 2018/0049721 A1 | 2/2018 | Ben-Lavi et al. |
| 2018/0070917 A1 | 3/2018 | Rothberg et al. |
| 2018/0092698 A1 | 4/2018 | Chopra et al. |
| 2018/0101711 A1 | 4/2018 | D'Souza et al. |
| 2018/0125605 A1 | 5/2018 | Kim-Whitty |
| 2018/0130457 A1 | 5/2018 | Hakkens et al. |
| 2018/0132827 A1* | 5/2018 | Nakanishi ............... A61B 8/54 |
| 2018/0161502 A1 | 6/2018 | Nanan et al. |
| 2018/0214125 A1 | 8/2018 | Tola et al. |
| 2018/0263597 A1 | 9/2018 | Tchang et al. |
| 2019/0328354 A1 | 10/2019 | Xu et al. |
| 2019/0328359 A1 | 10/2019 | Hakkens et al. |
| 2019/0380679 A1* | 12/2019 | Bharat ................ A61B 8/5253 |
| 2021/0077061 A1 | 3/2021 | Pinkovich et al. |

FOREIGN PATENT DOCUMENTS

| | | | |
|---|---|---|---|
| CN | 105120760 A | 12/2015 | |
| CN | 107550519 A | 1/2018 | |
| CN | 107580474 A | 1/2018 | |
| CN | 105073015 B | 1/2019 | |
| EP | 0420758 A1 | 4/1991 | |
| EP | 0516582 A1 | 12/1992 | |
| EP | 0763344 A2 | 3/1997 | |
| EP | 0800788 A1 | 10/1997 | |
| EP | 0815793 A2 | 1/1998 | |
| EP | 1479412 A1 | 11/2004 | |
| EP | 2361502 A1 | 8/2011 | |
| EP | 2913005 A1 | 9/2015 | |
| EP | 2533740 B1 | 11/2015 | |
| GB | 2400176 A * | 10/2004 | ......... A61B 17/3403 |
| JP | S55148548 A | 11/1980 | |
| JP | 2010029281 A | 2/2010 | |
| JP | 2013-173039 A | 9/2013 | |
| JP | 2016-523573 A | 8/2016 | |
| JP | 2017-042646 A | 3/2017 | |
| JP | 2018015035 A | 2/2018 | |
| WO | 9855072 A2 | 12/1998 | |
| WO | 2000043046 A2 | 7/2000 | |
| WO | 2003077744 A1 | 9/2003 | |
| WO | 2003101530 A2 | 12/2003 | |
| WO | 2013066401 A1 | 5/2013 | |
| WO | 2013163591 A1 | 10/2013 | |
| WO | 2014208977 A1 | 12/2014 | |
| WO | 2016006769 A1 | 1/2016 | |
| WO | 2016209398 A1 | 12/2016 | |
| WO | 2017062431 A1 | 4/2017 | |
| WO | 2017211626 A1 | 12/2017 | |
| WO | 2018050885 A1 | 3/2018 | |

OTHER PUBLICATIONS

International Search Report including Written Opinion for Application No. PCT/US2019/034985 dated Sep. 9, 2019, pp. 1-11.
Partial International Search including the Provisional Opinion from Application No. PCT/US2019/035012 dated Sep. 10, 2019, pp. 1-14.
International Search Report including the Written Opinion from Application No. PCT/US2019/035019 mailed Sep. 18, 2019, 13 pages.
International Search Report including the Written Opinion from Application No. PCT/US2019/034967 dated Oct. 9, 2019, 14 pages.
International Search Report including Written Opinion for Application No. PCT/US2019/035022 dated Oct. 18, 2019, pp. 1-22.
International Search Report for Application No. PCT/US2019/035012, mailed Nov. 12, 2019, pp. 1-2.
Office Action for European Application No. 19734189.4 mailed Aug. 9, 24. 4 pgs.
Chinese Search Report from 23209138.9, dated Sep. 3, 2024, 3 pages.
Chinese Search Report from CN Appl. No. 201980050066.2 , dated Dec. 4, 2024, 2 pages.

* cited by examiner

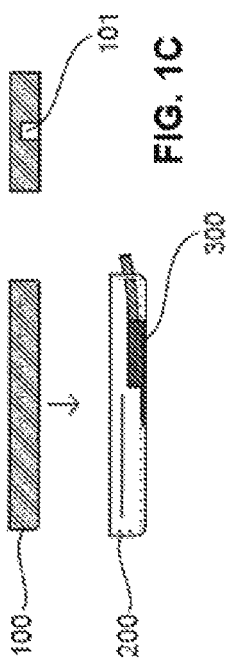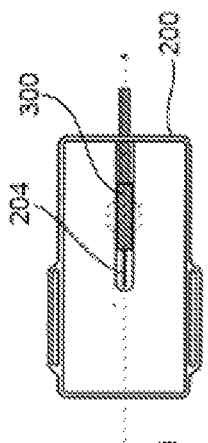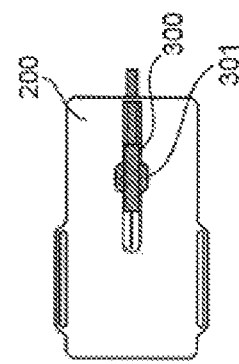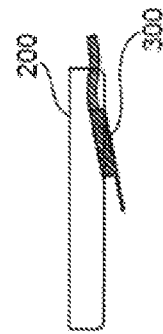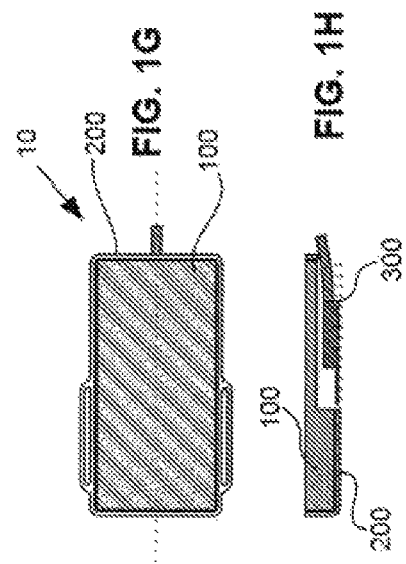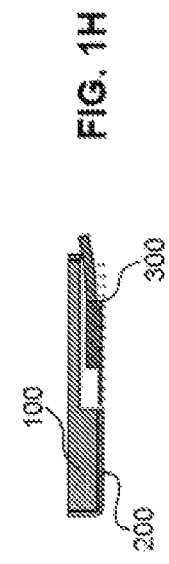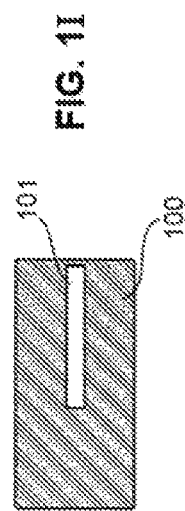

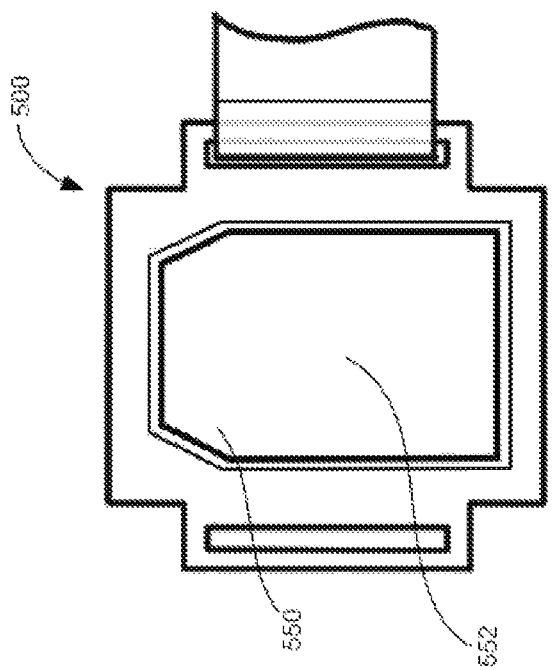
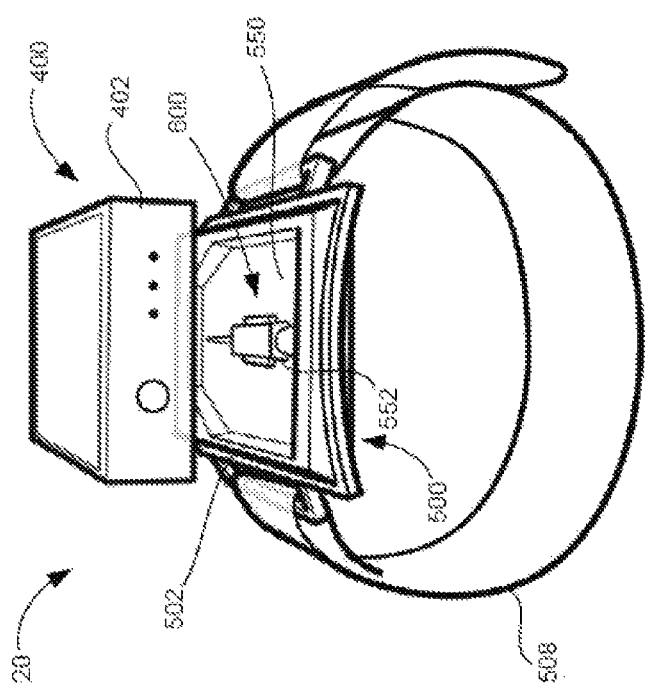

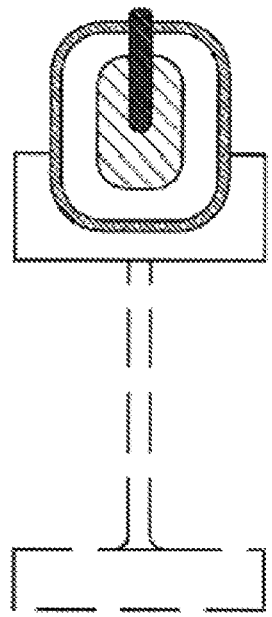
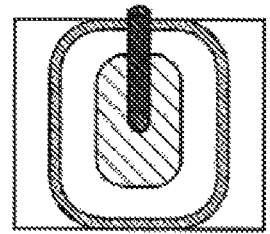
FIG. 4B
FIG. 4D
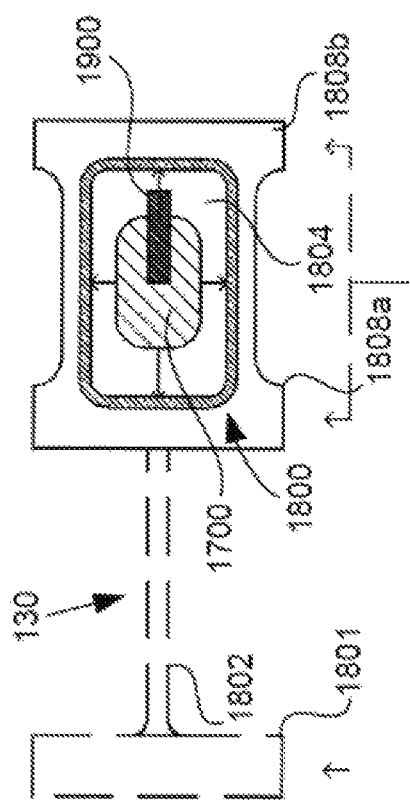
FIG. 4A
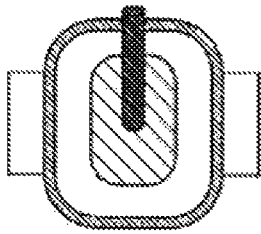
FIG. 4C

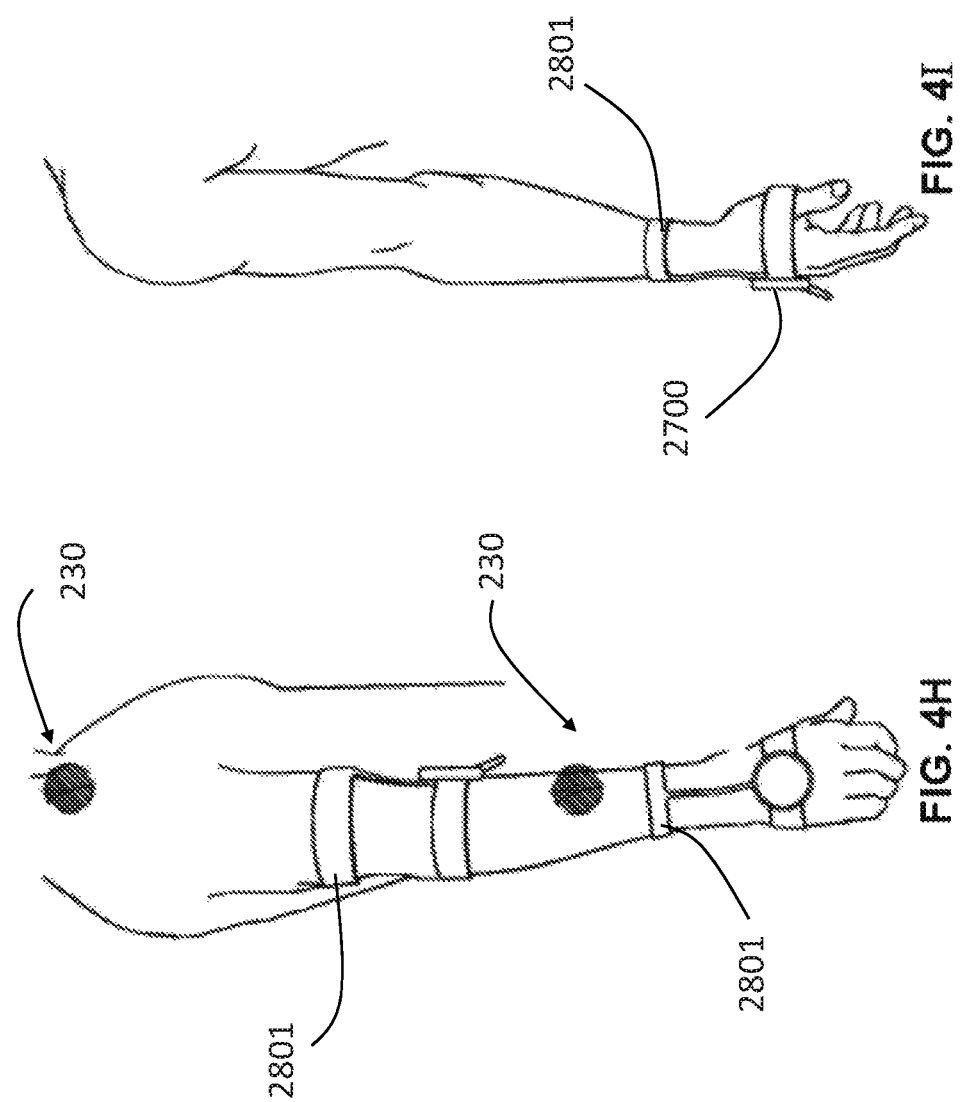

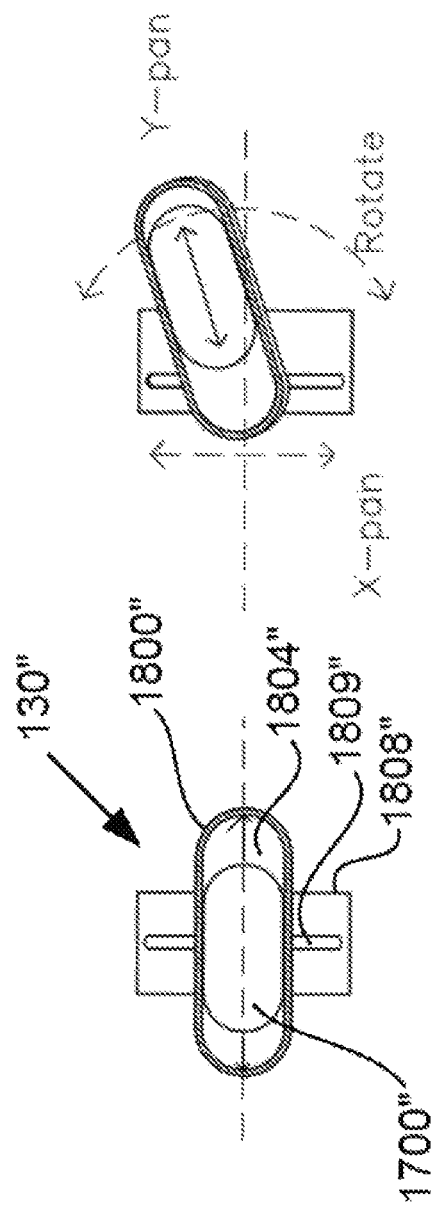

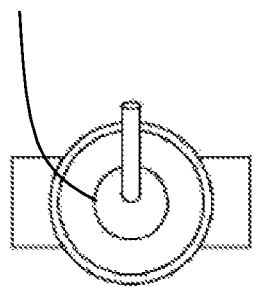
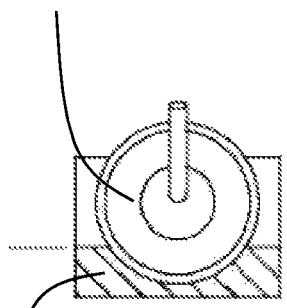
FIG. 8B
FIG. 8C

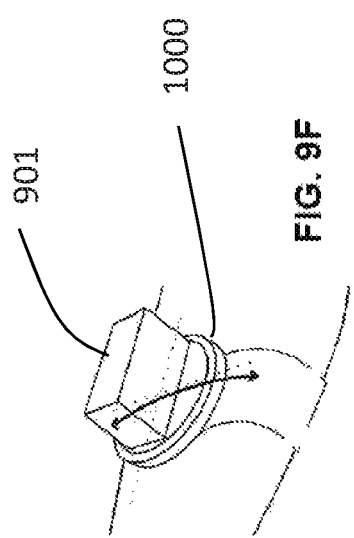
FIG. 9G
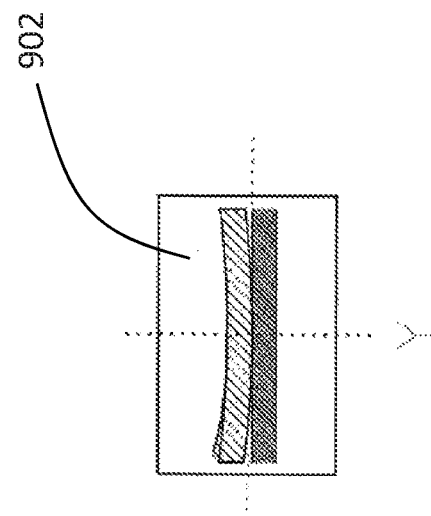
FIG. 9F
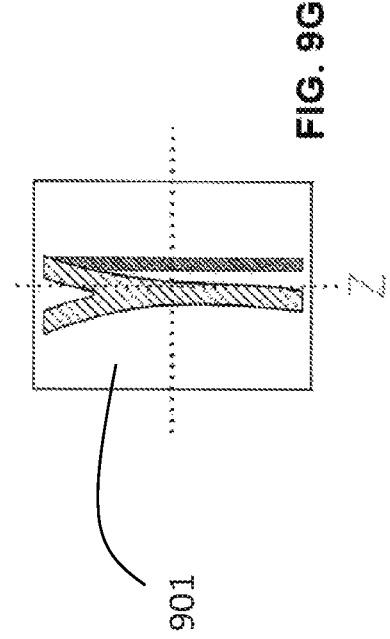
FIG. 9H
FIG. 9I

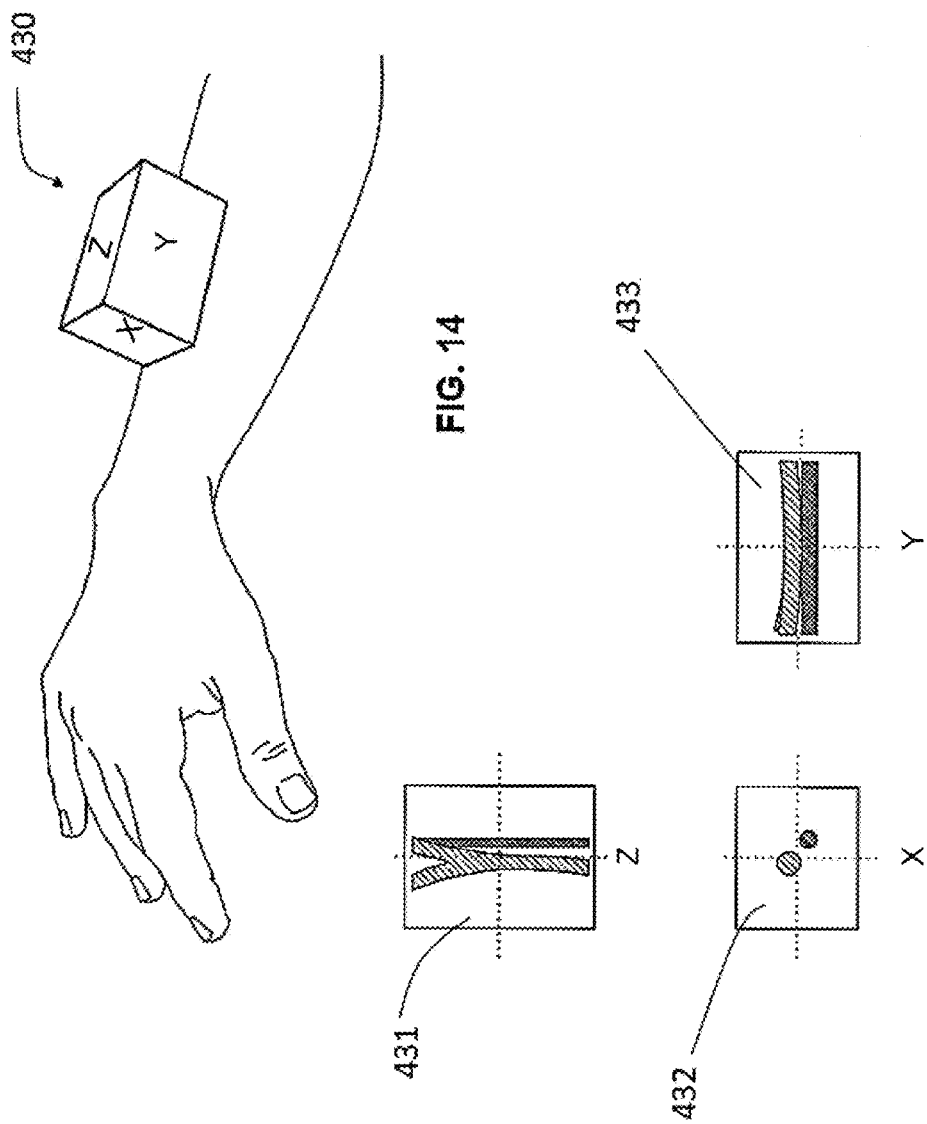

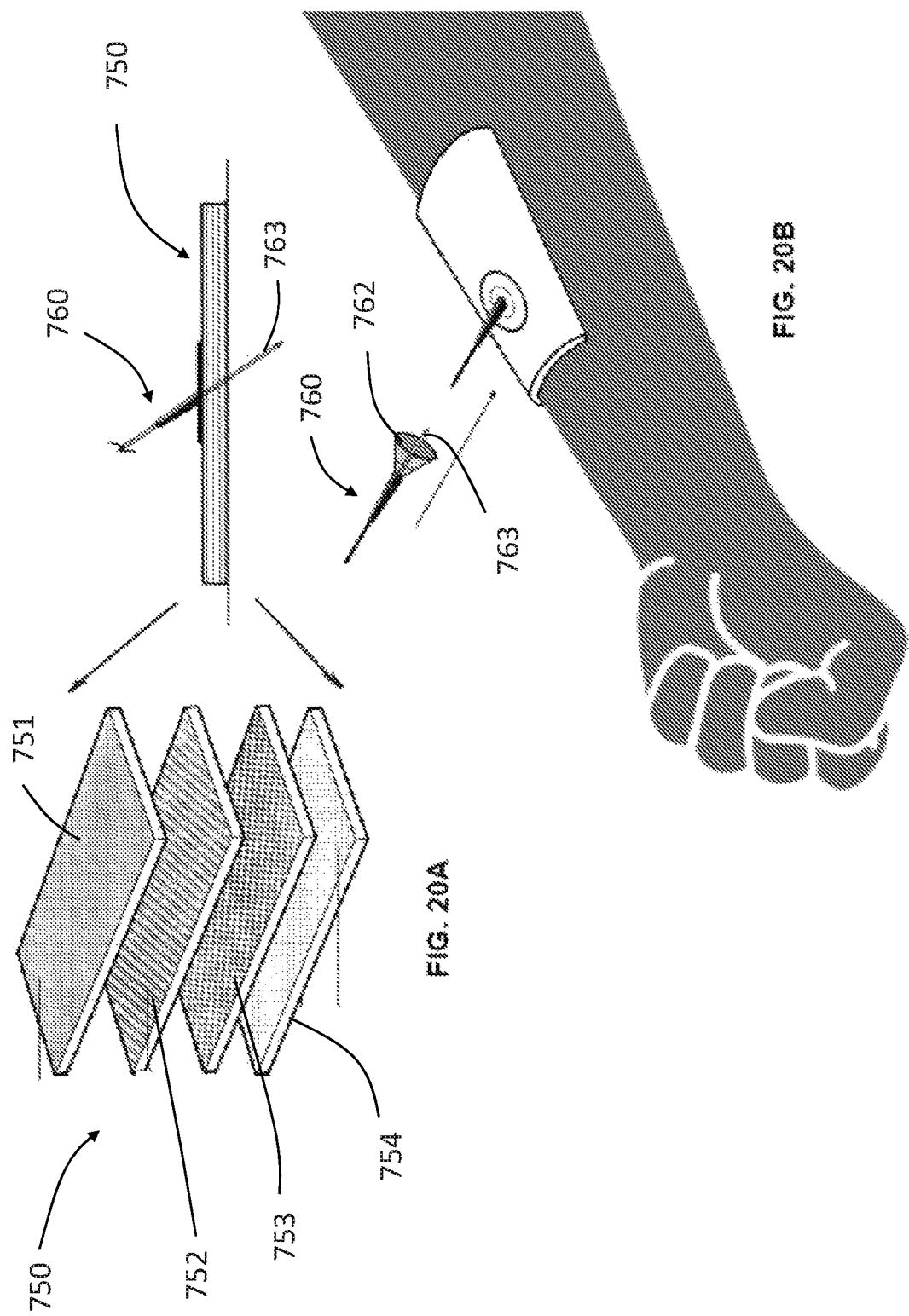

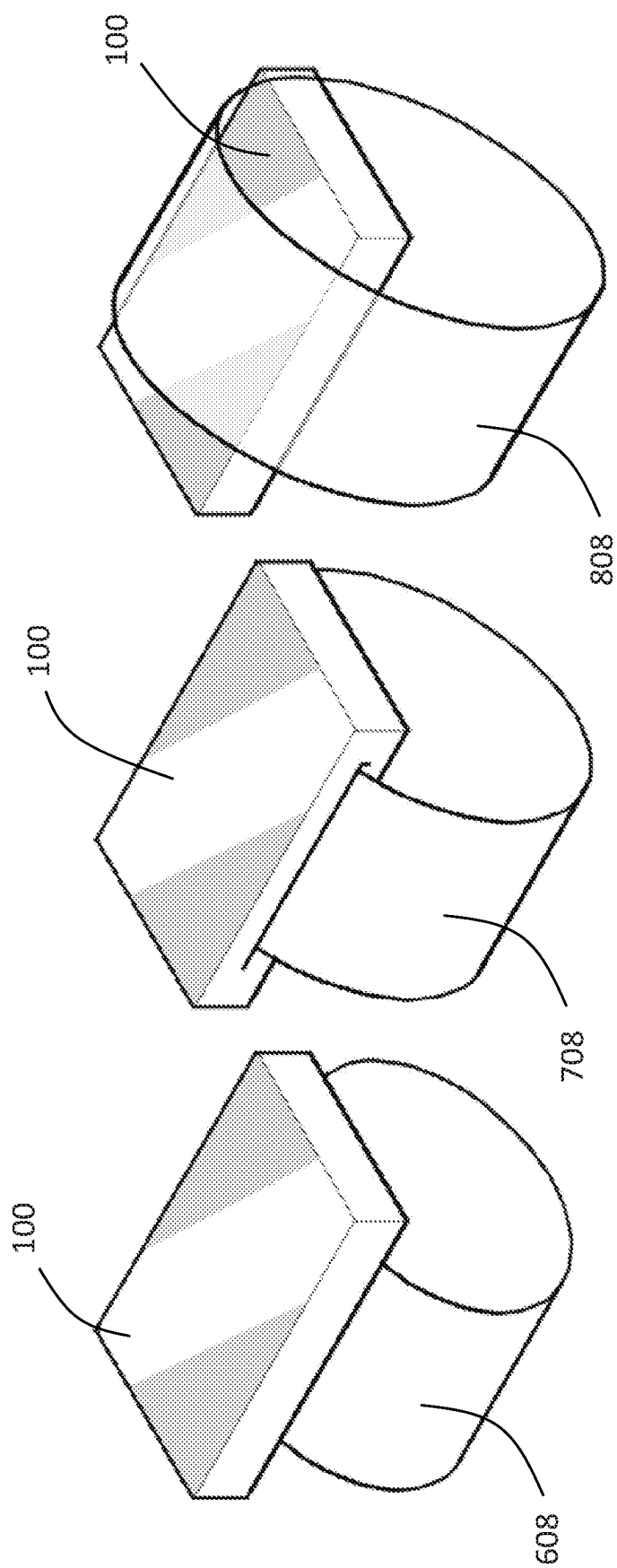

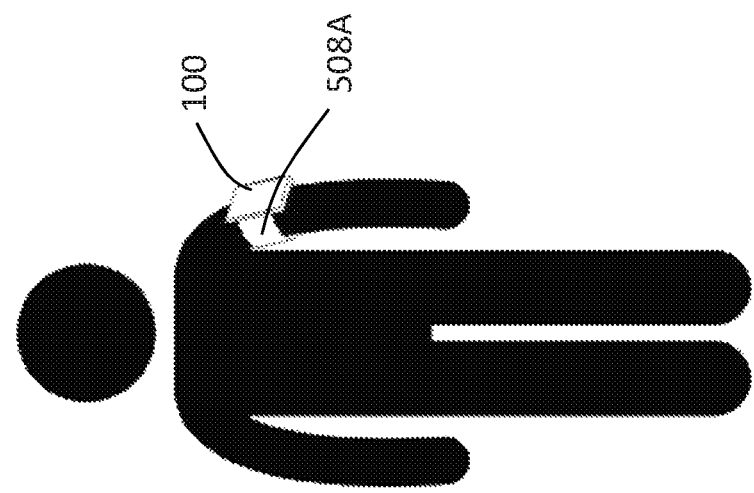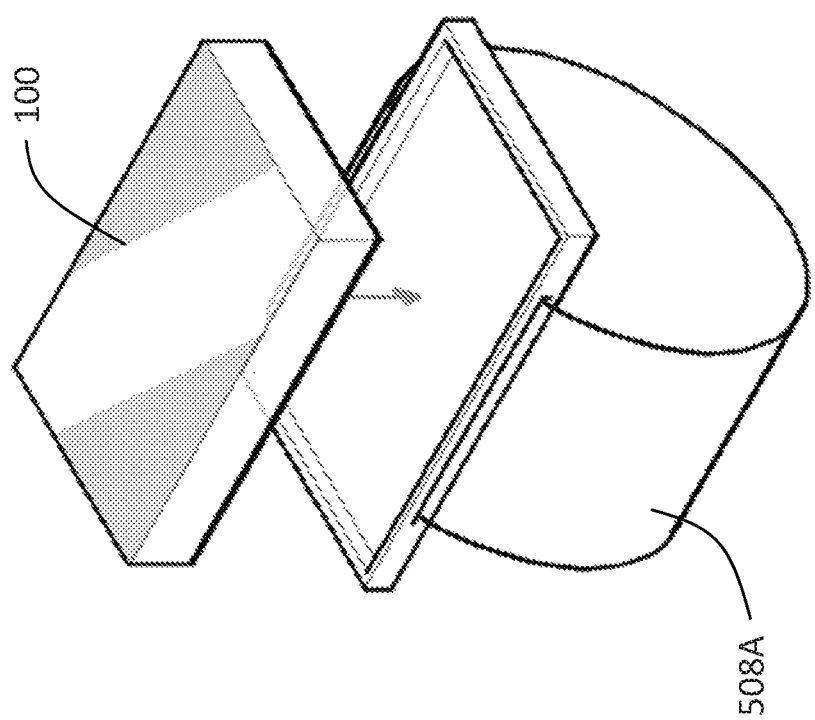
FIG. 25A

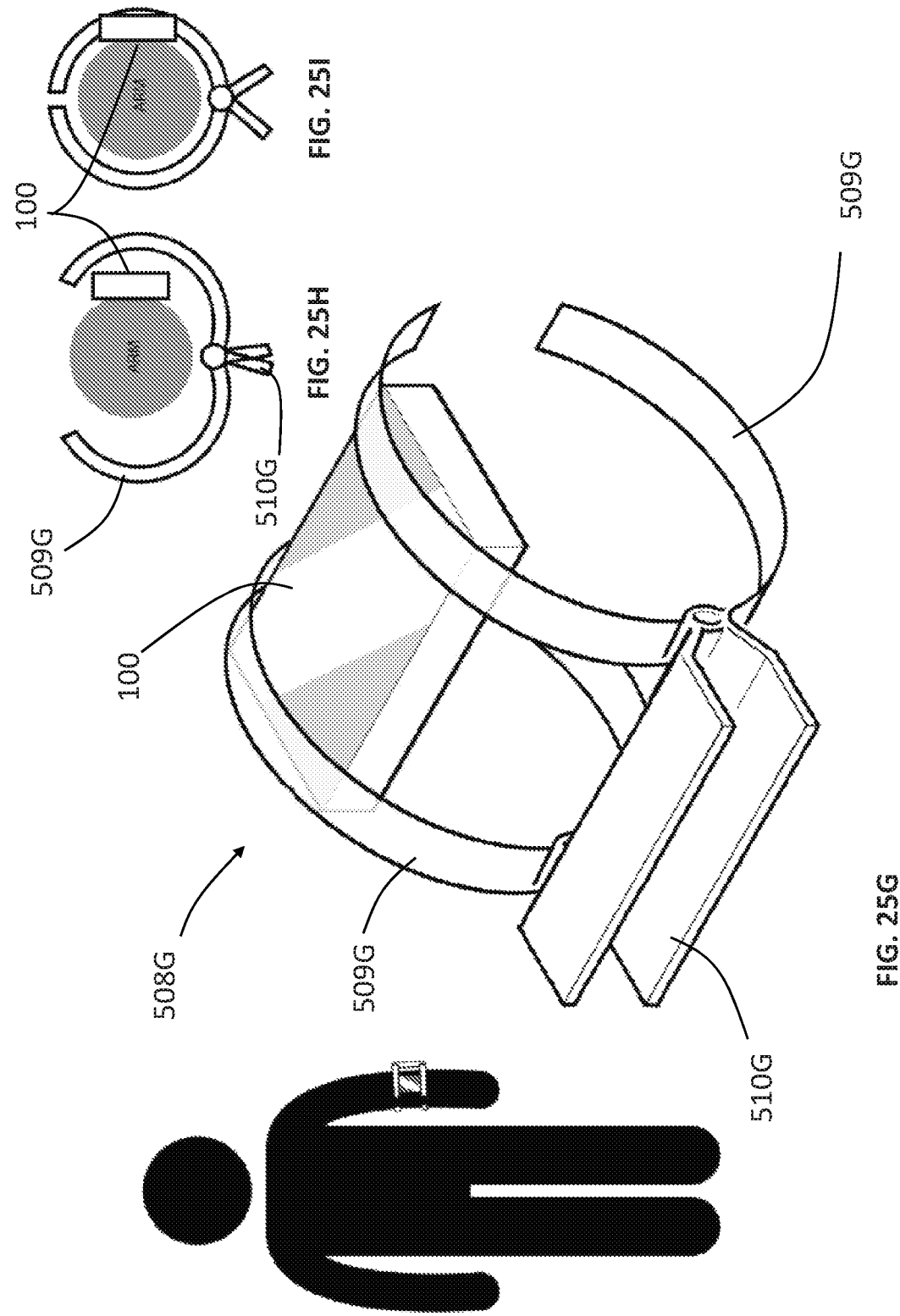

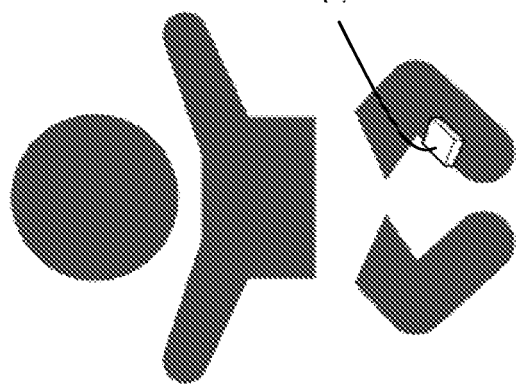
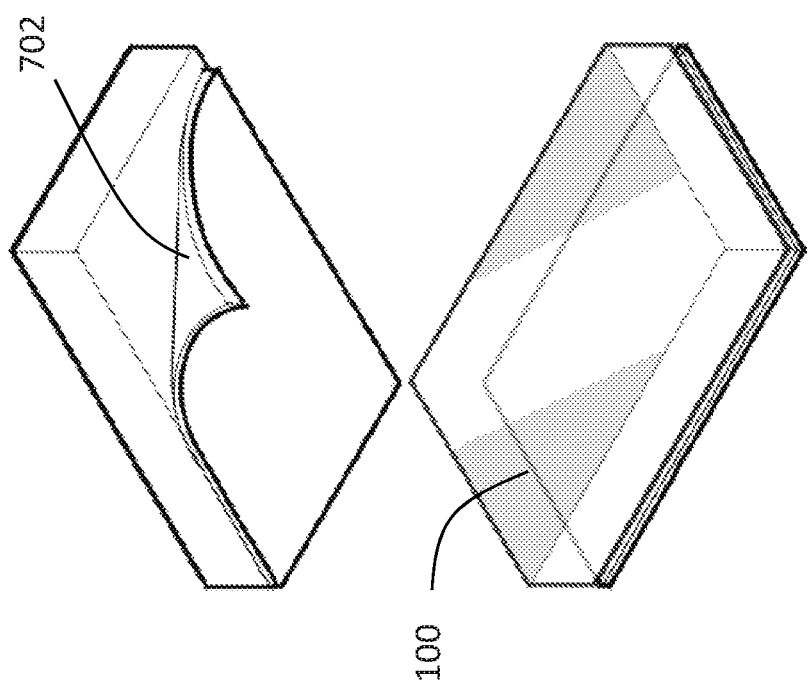
FIG. 26A

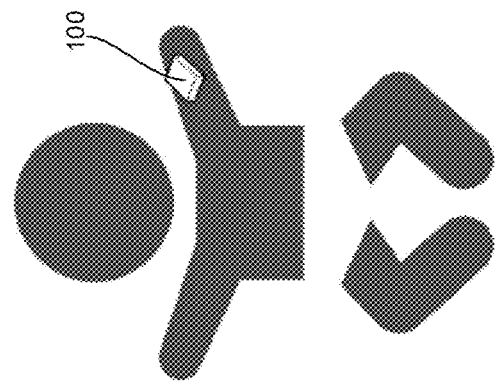
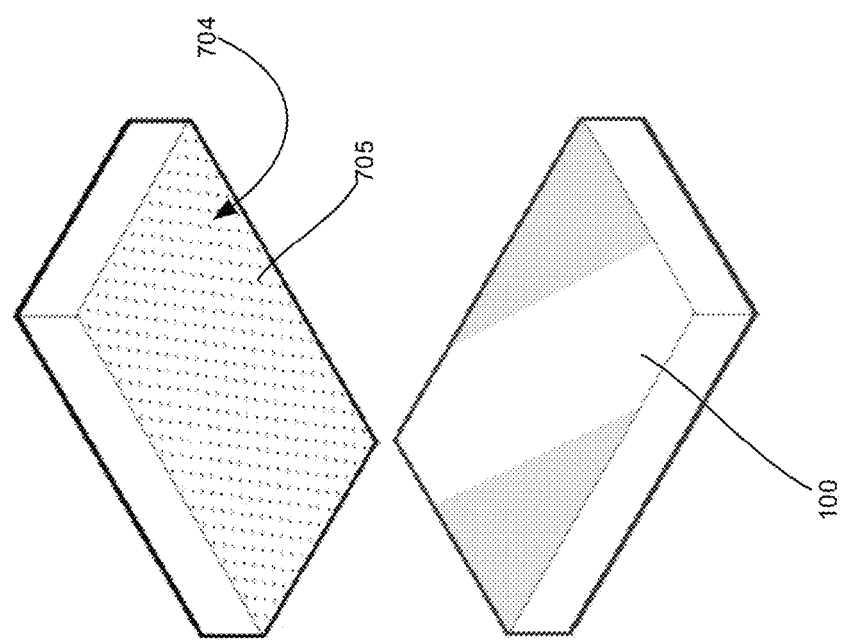
FIG. 26B

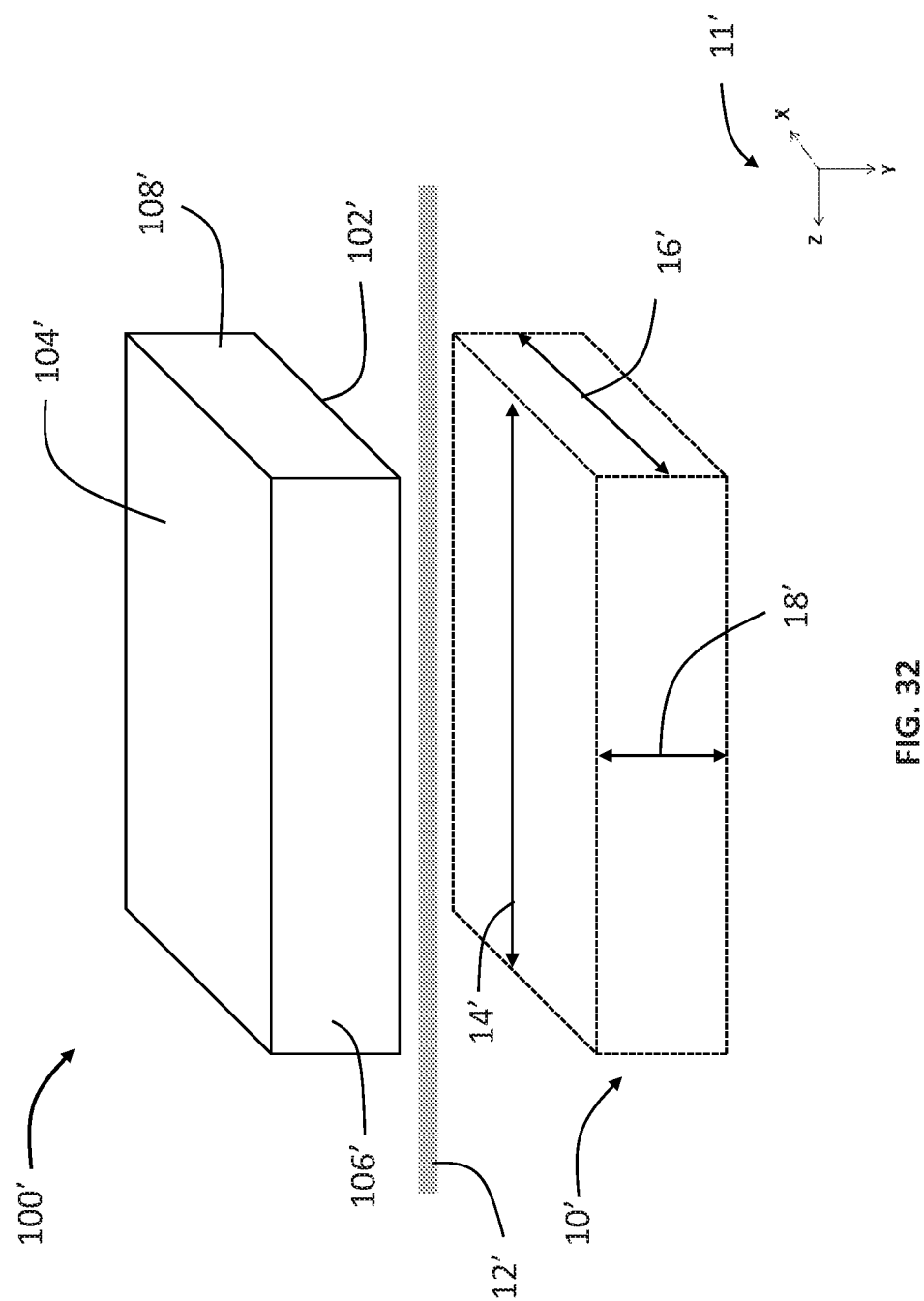

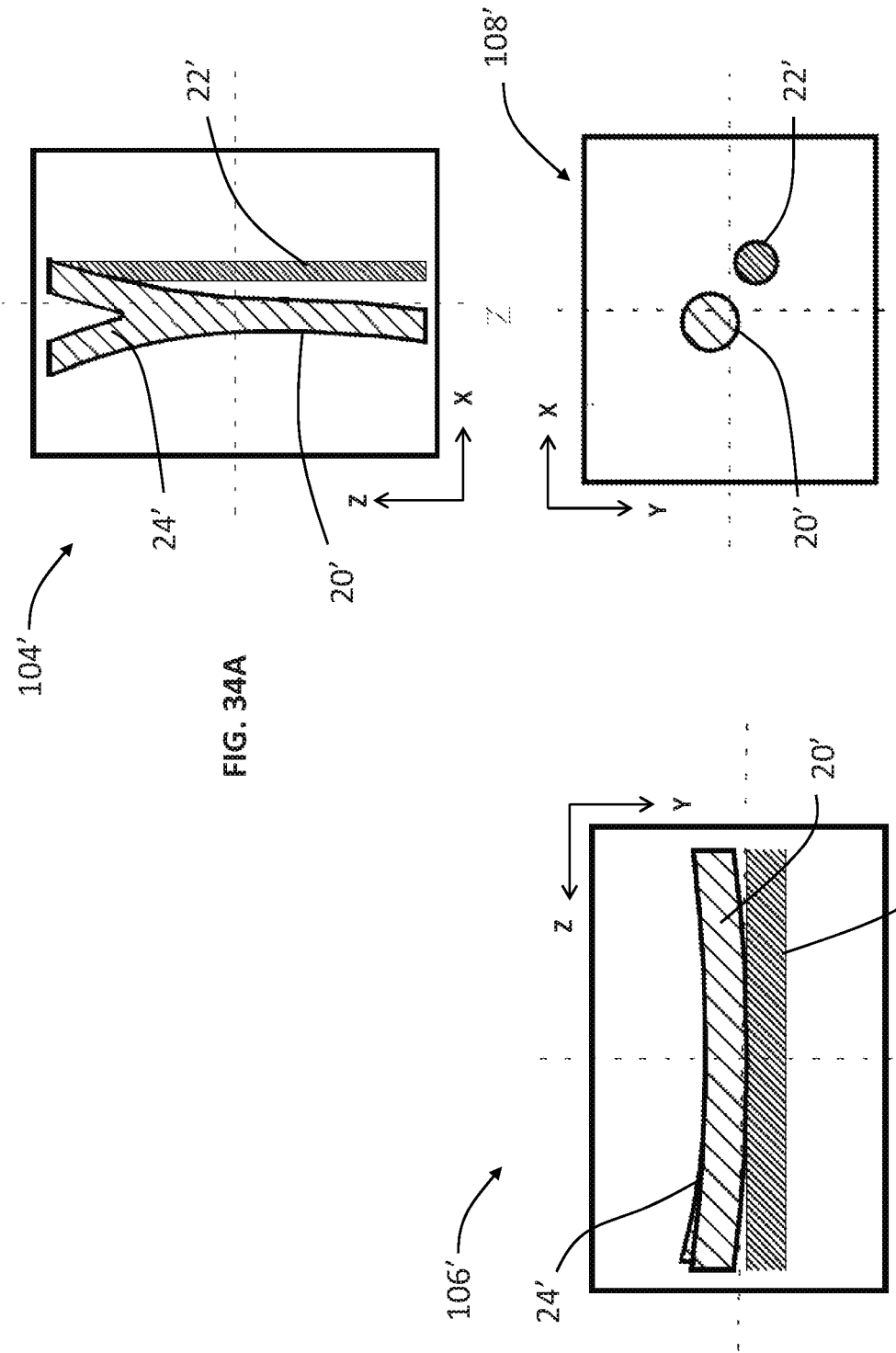

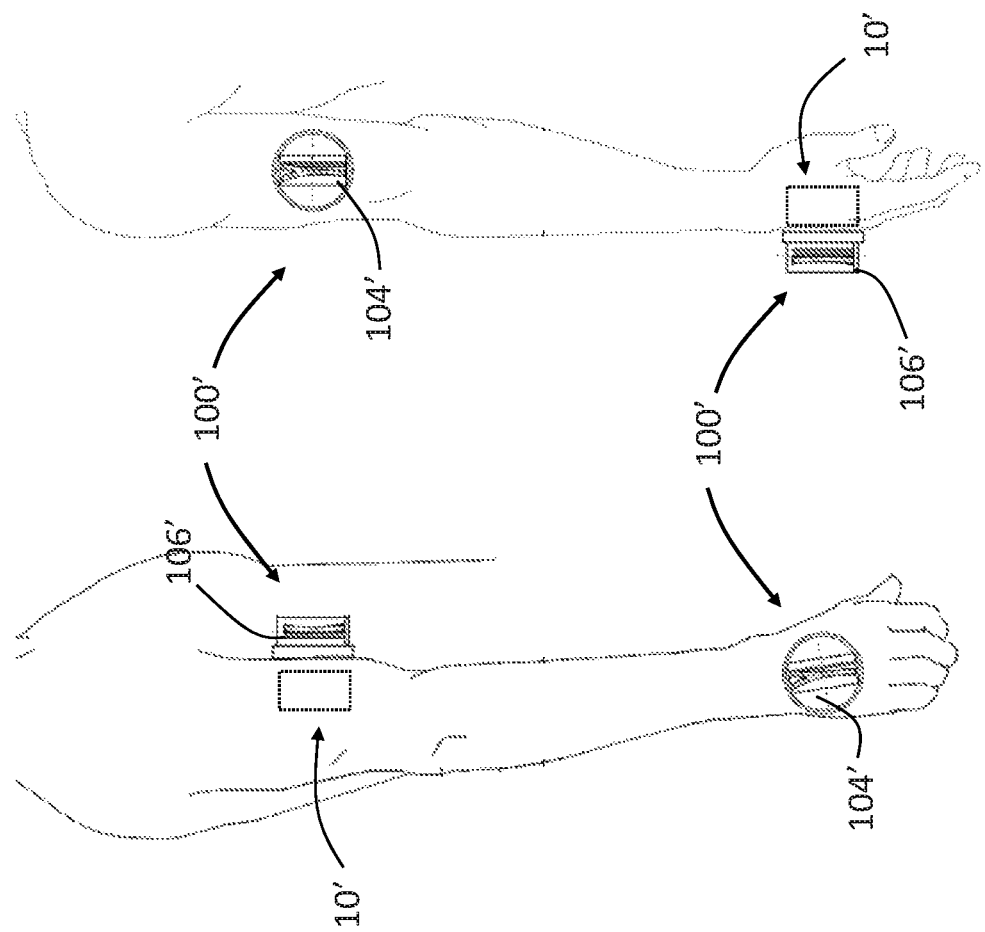

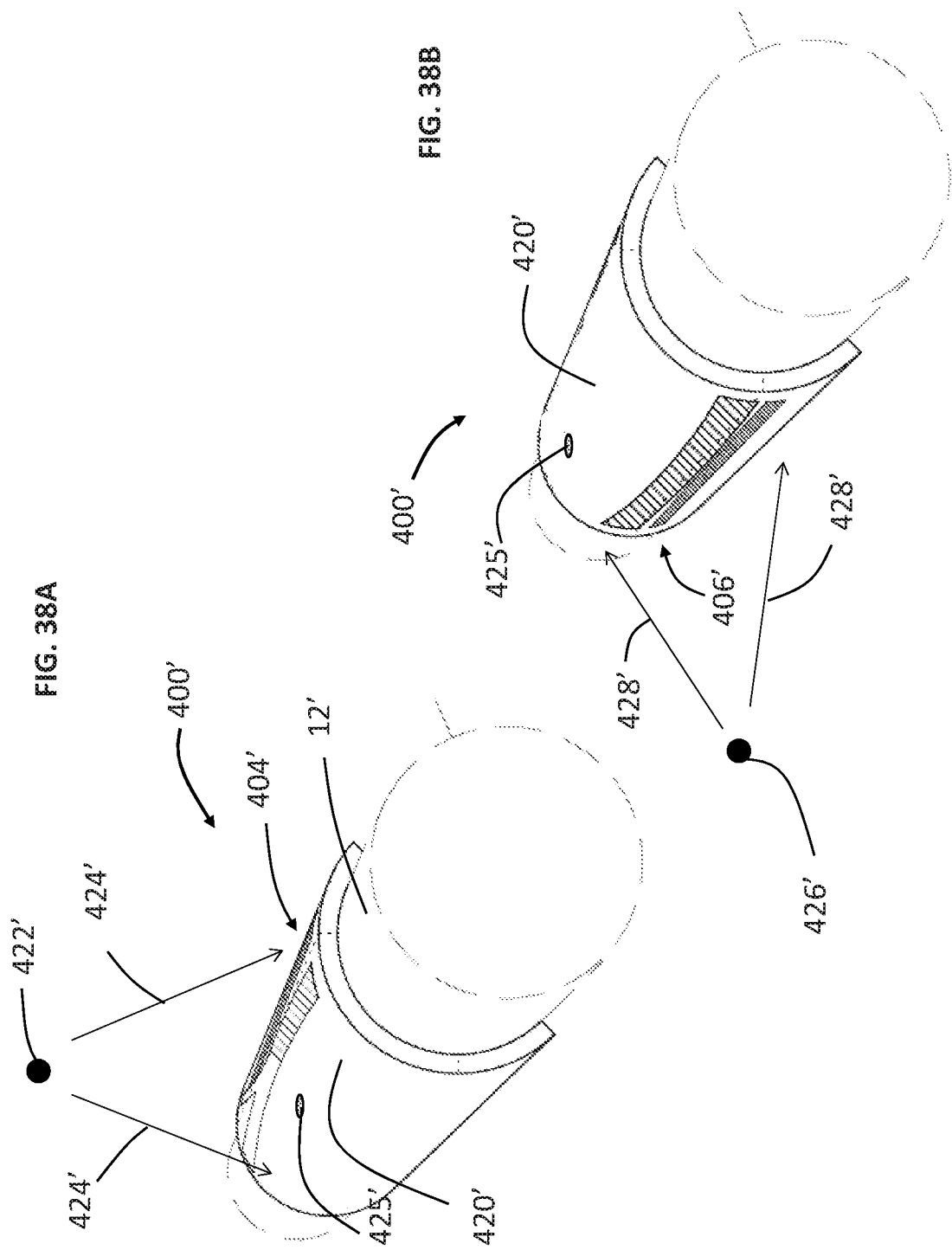

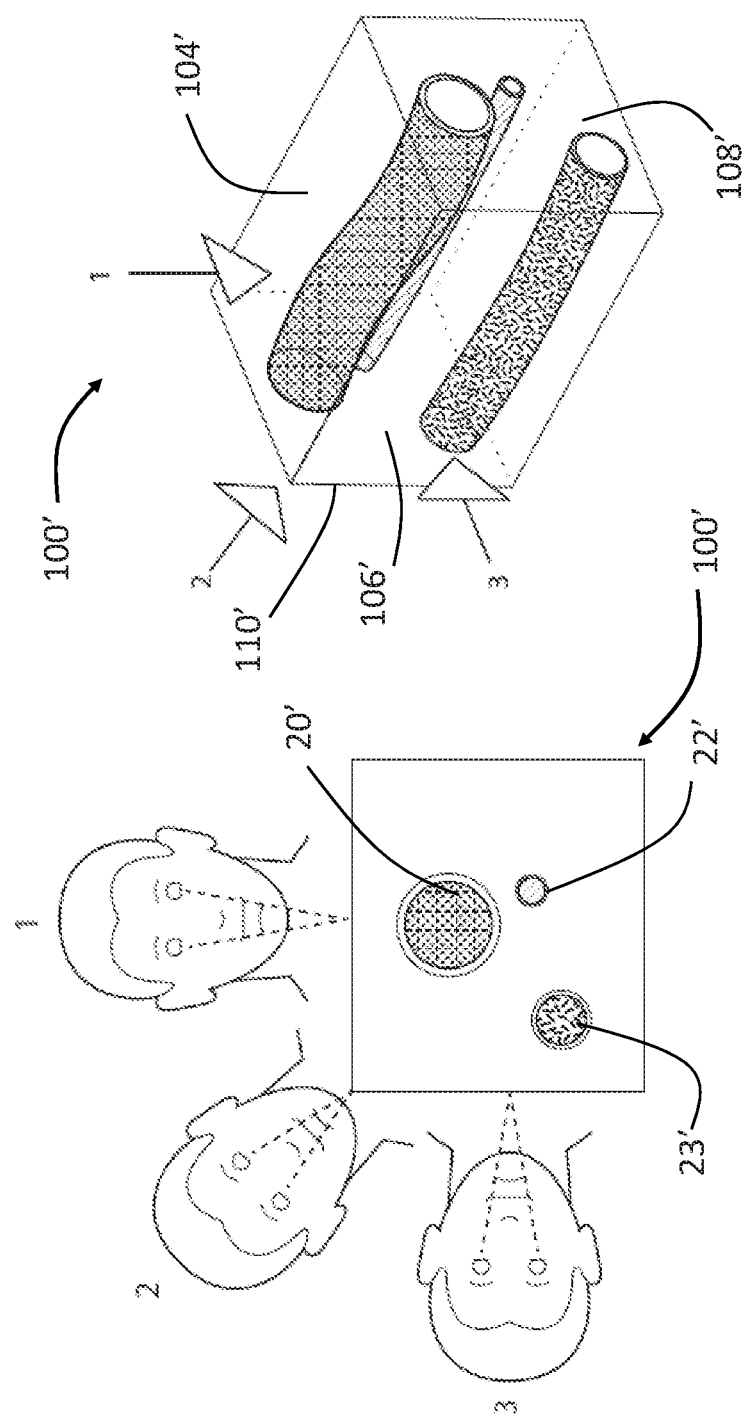

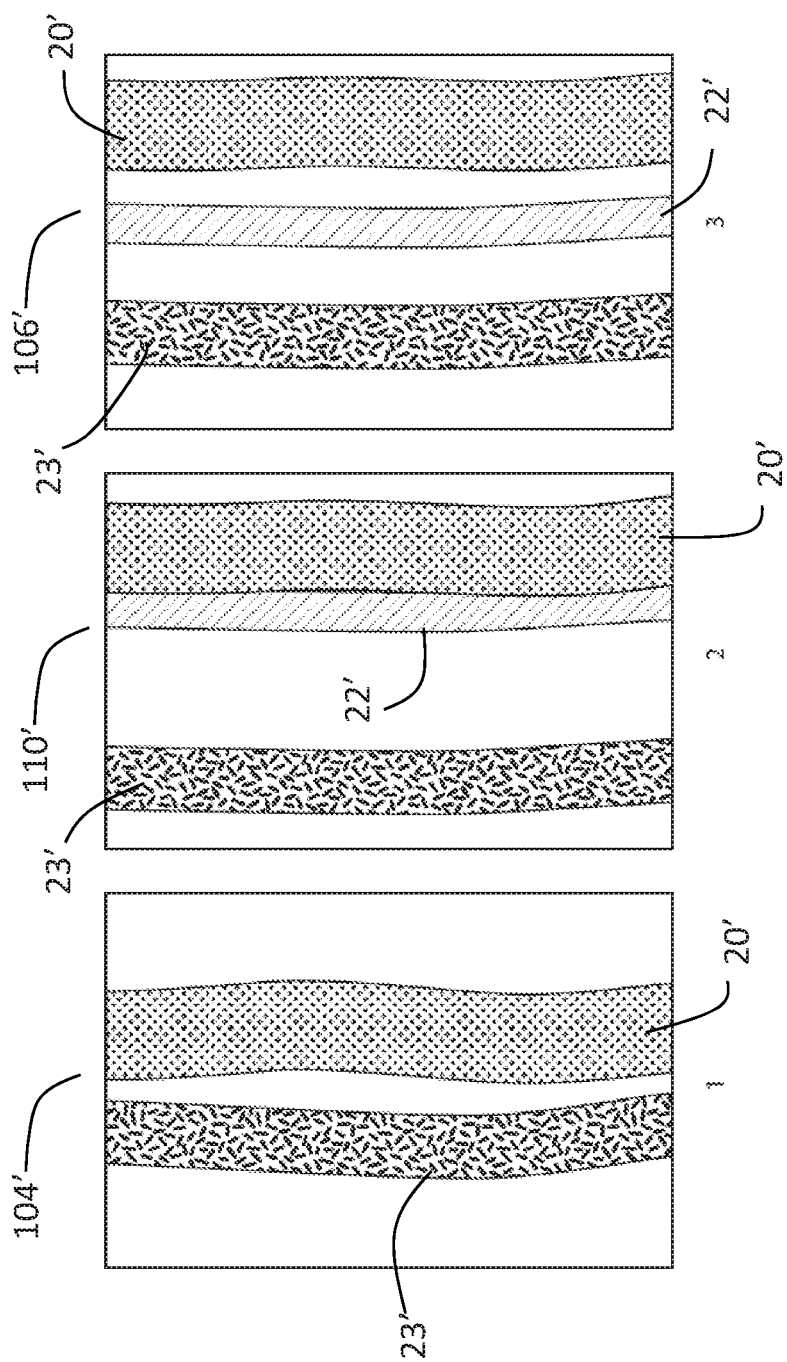

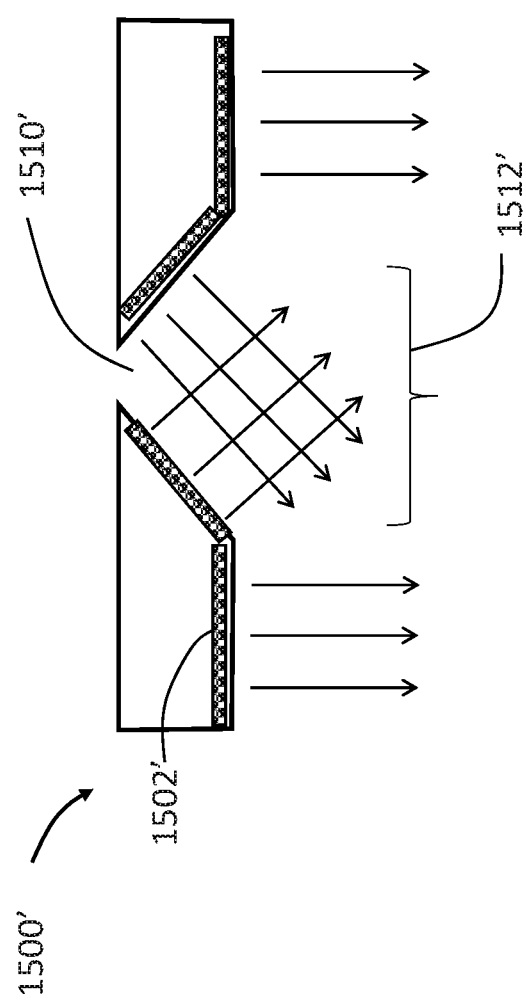

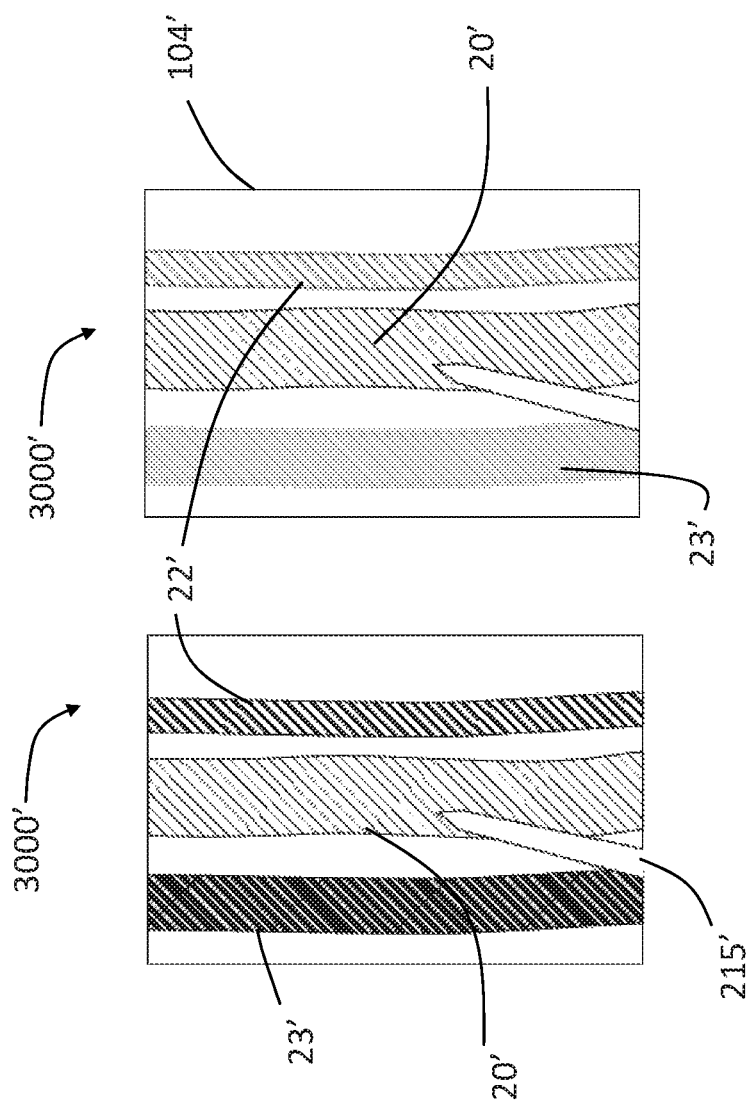

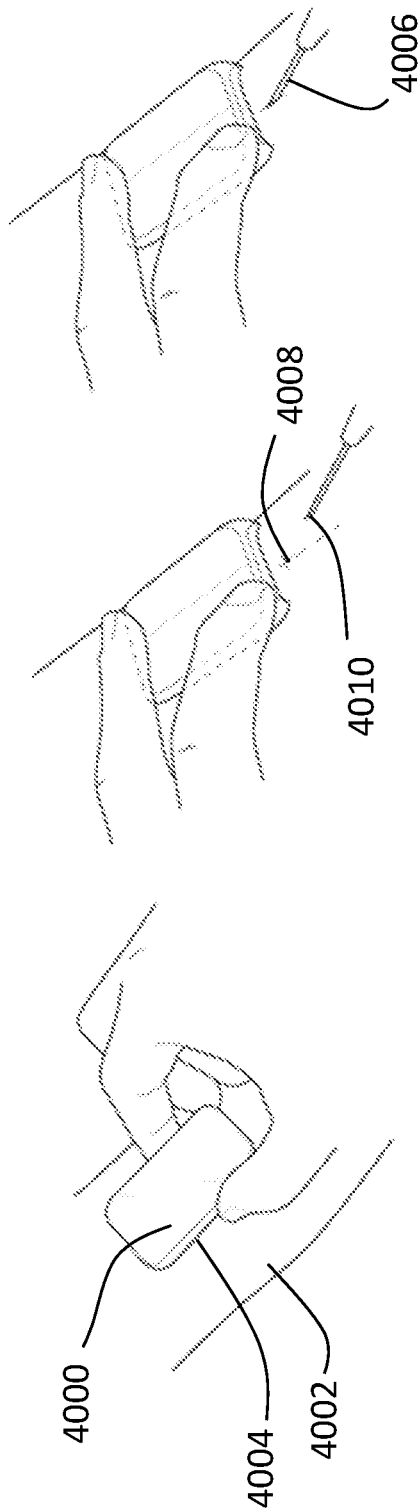
FIG. 65A
FIG. 65B
FIG. 65C
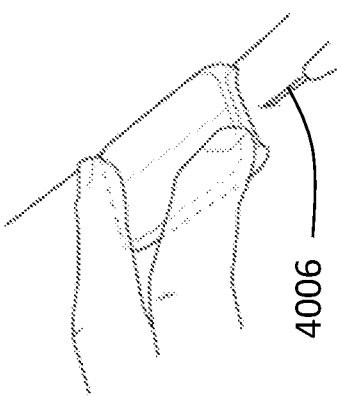
FIG. 65D
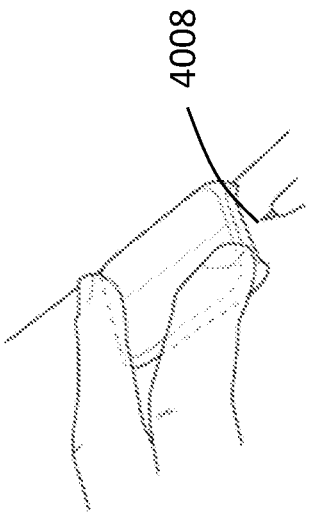
FIG. 65E

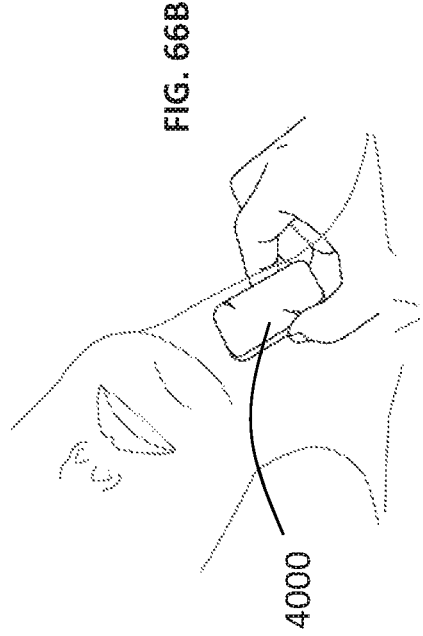
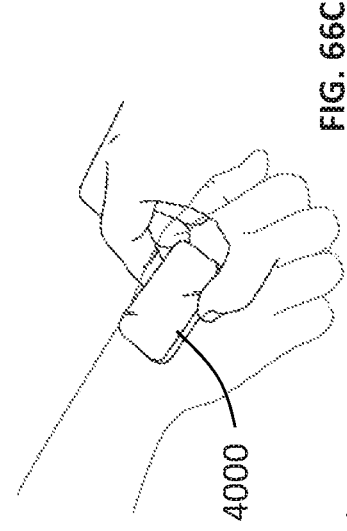
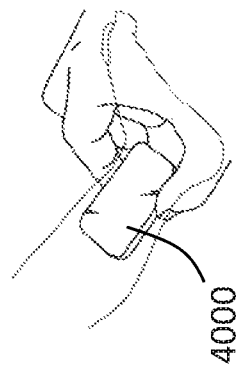
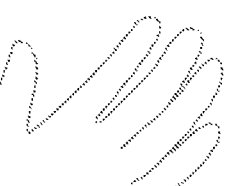
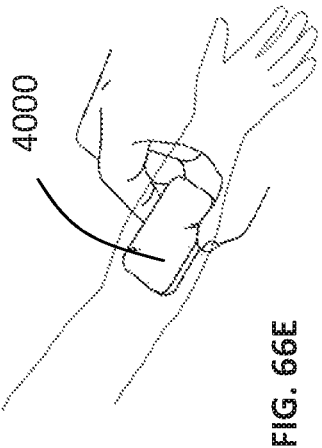

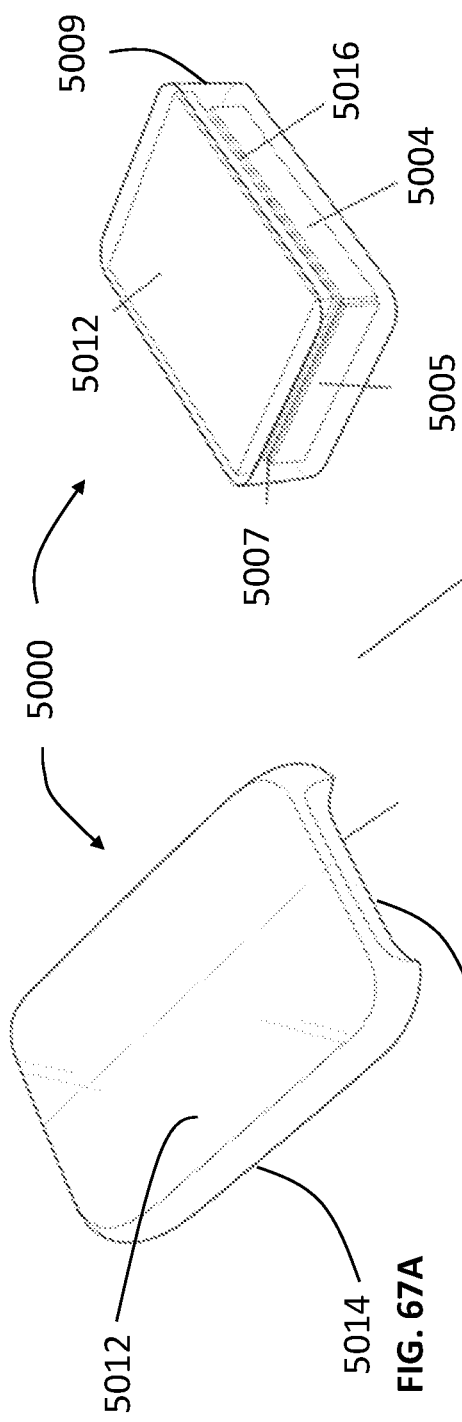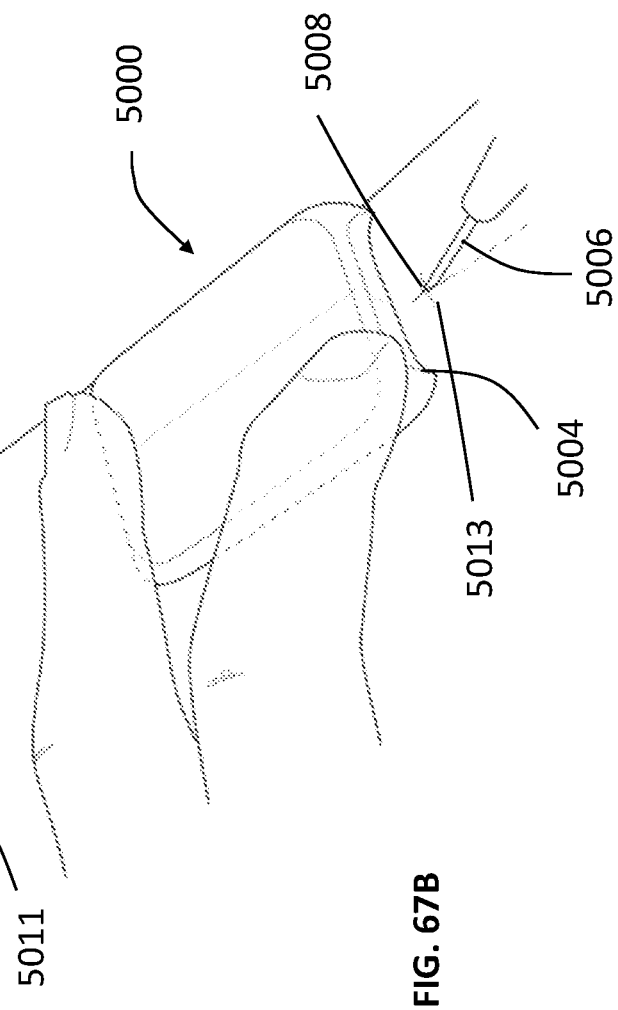
FIG. 67A
FIG. 67B
FIG. 67C

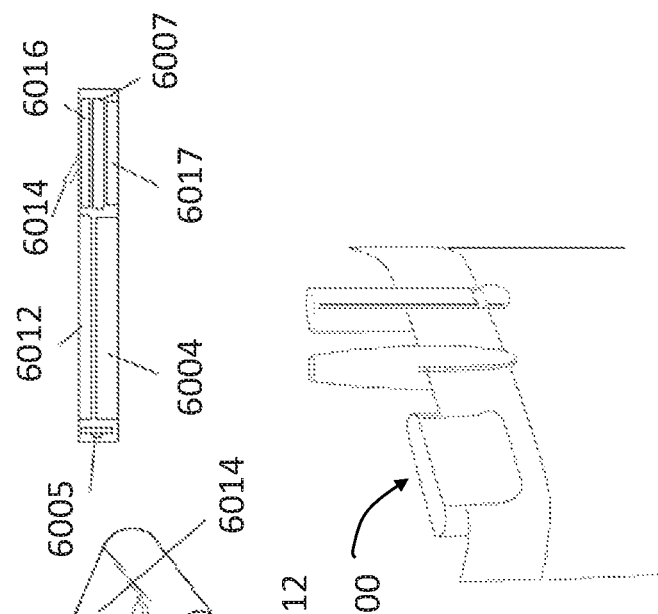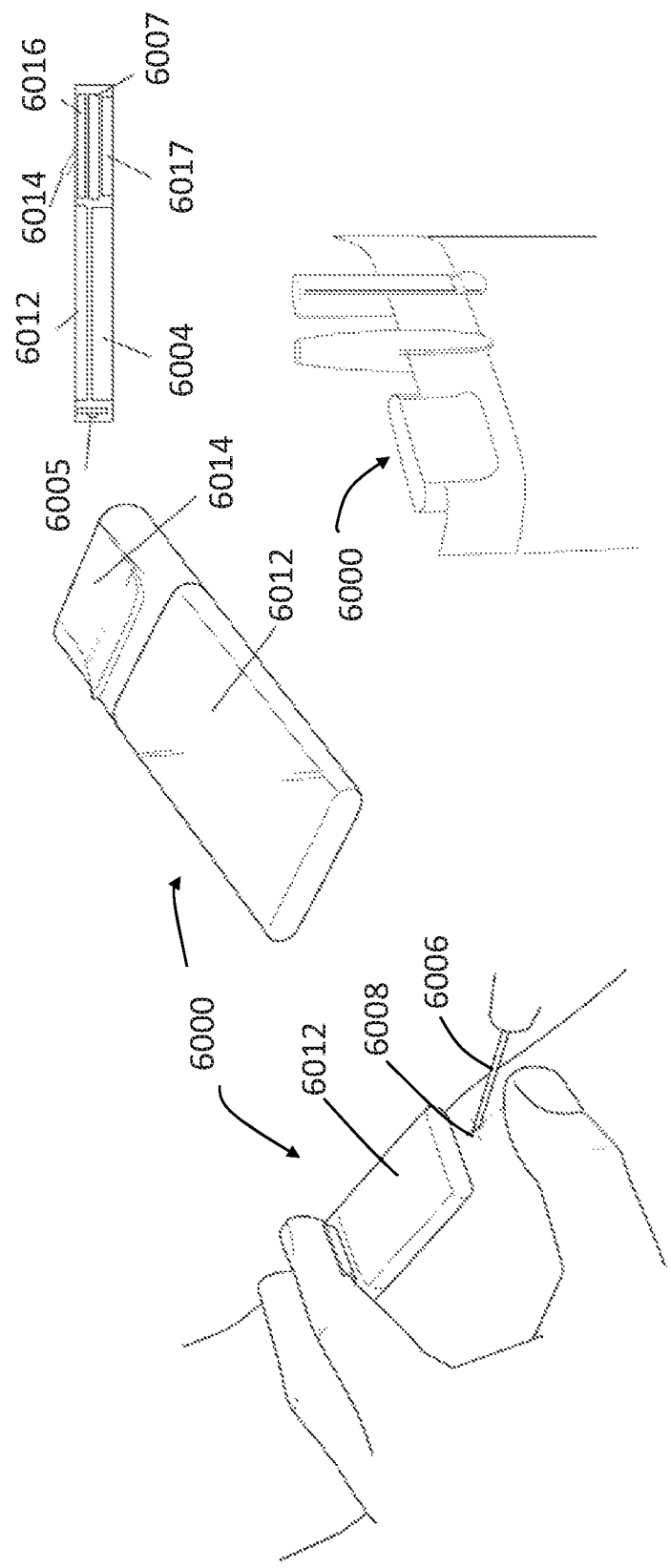

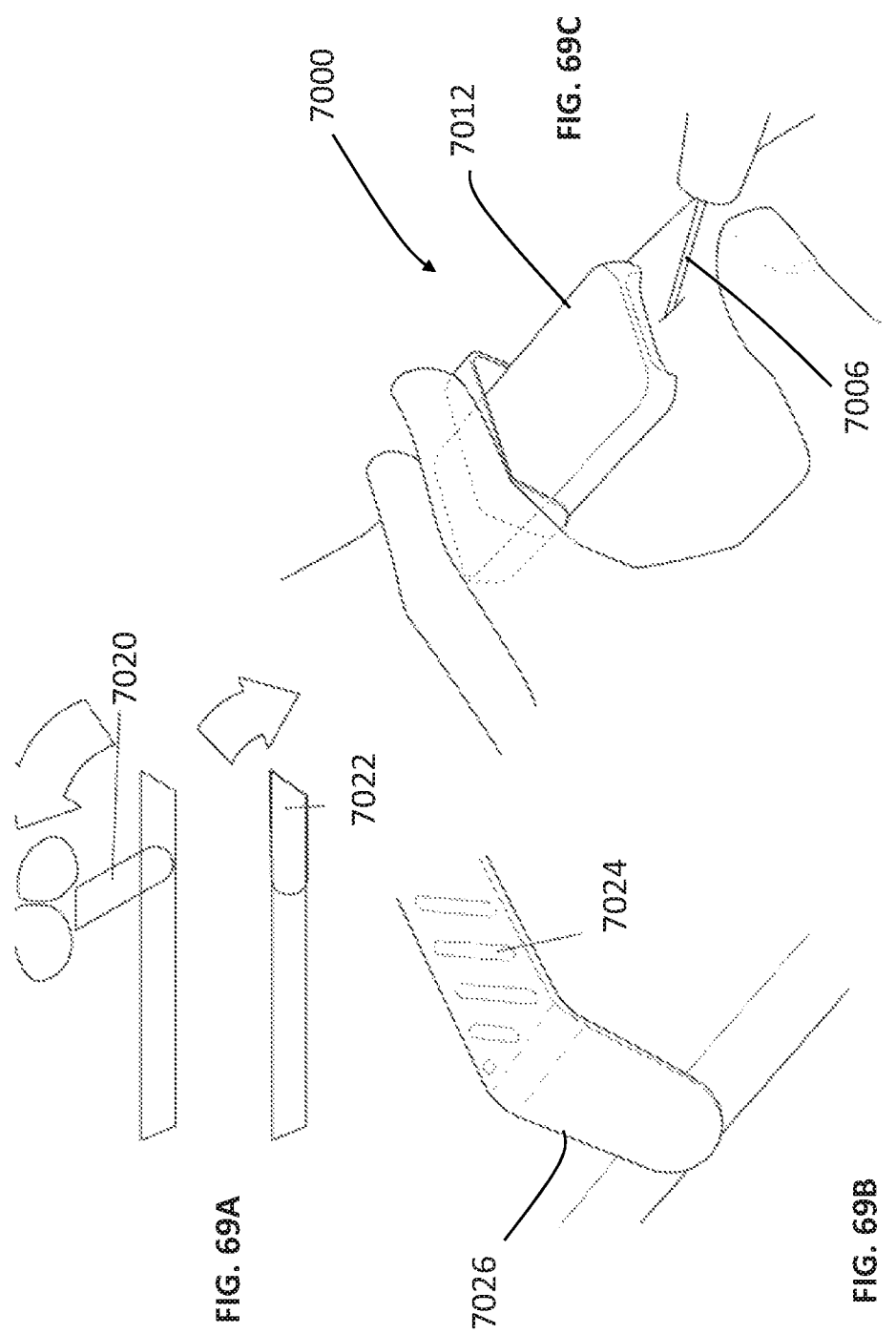

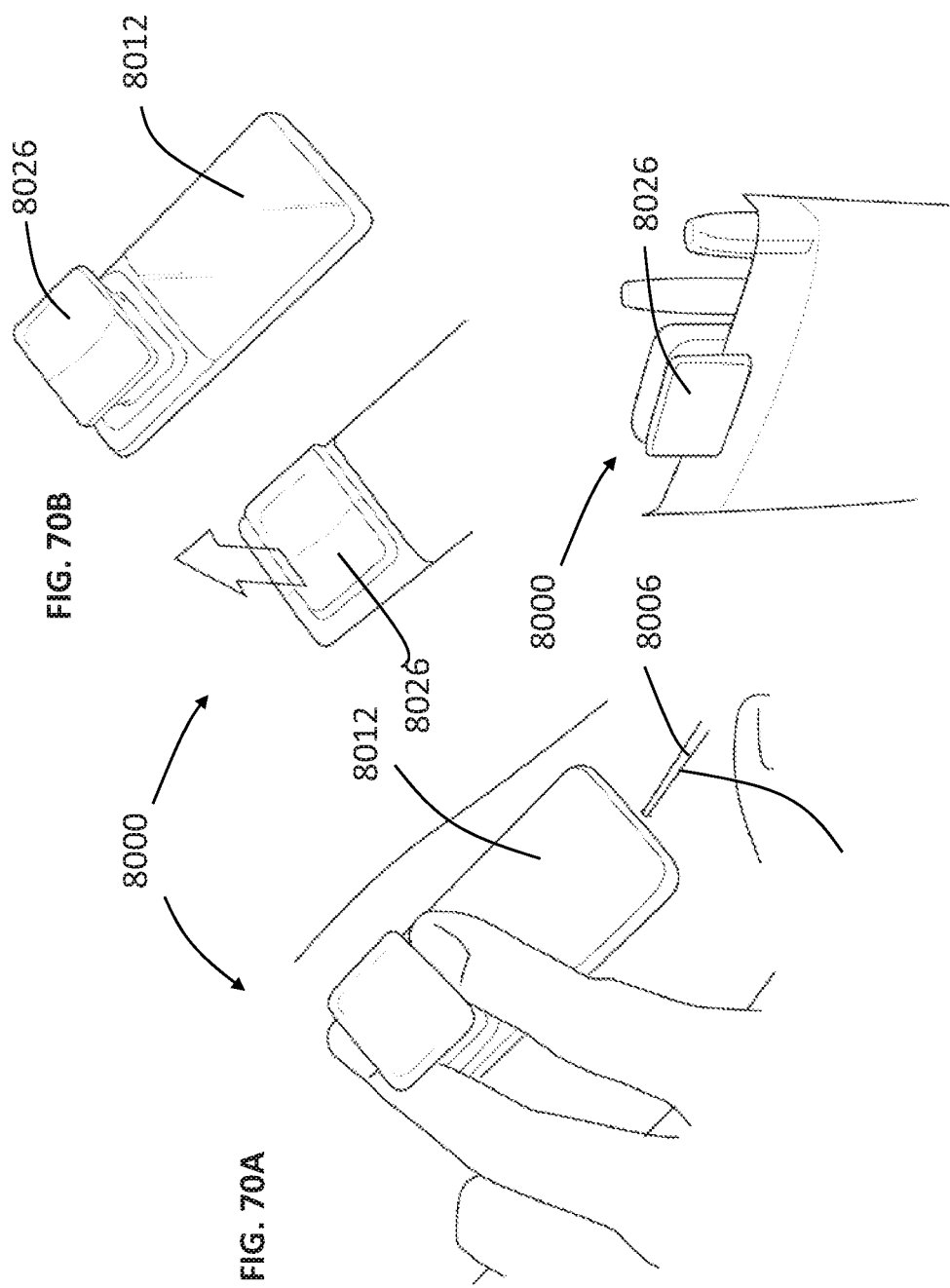

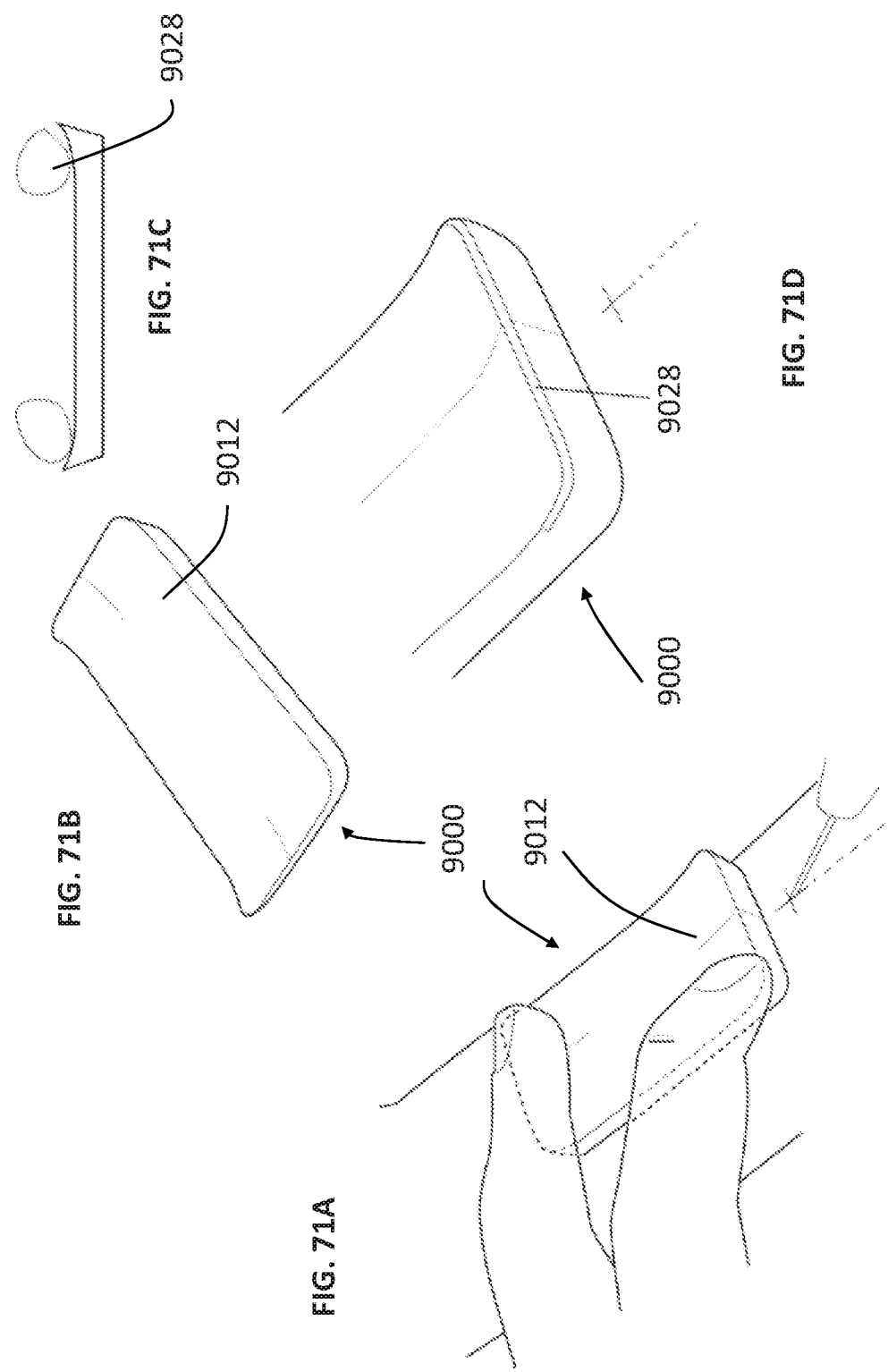

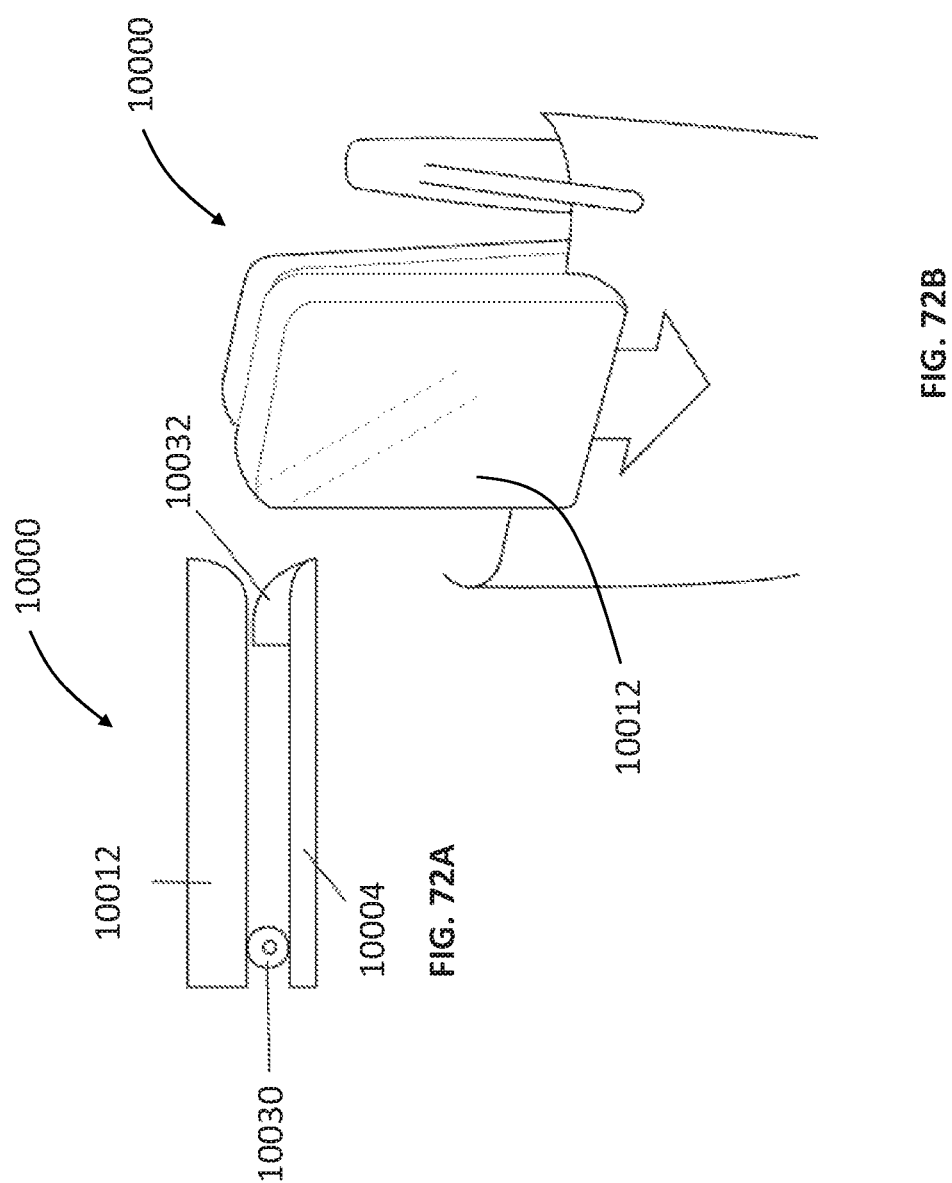

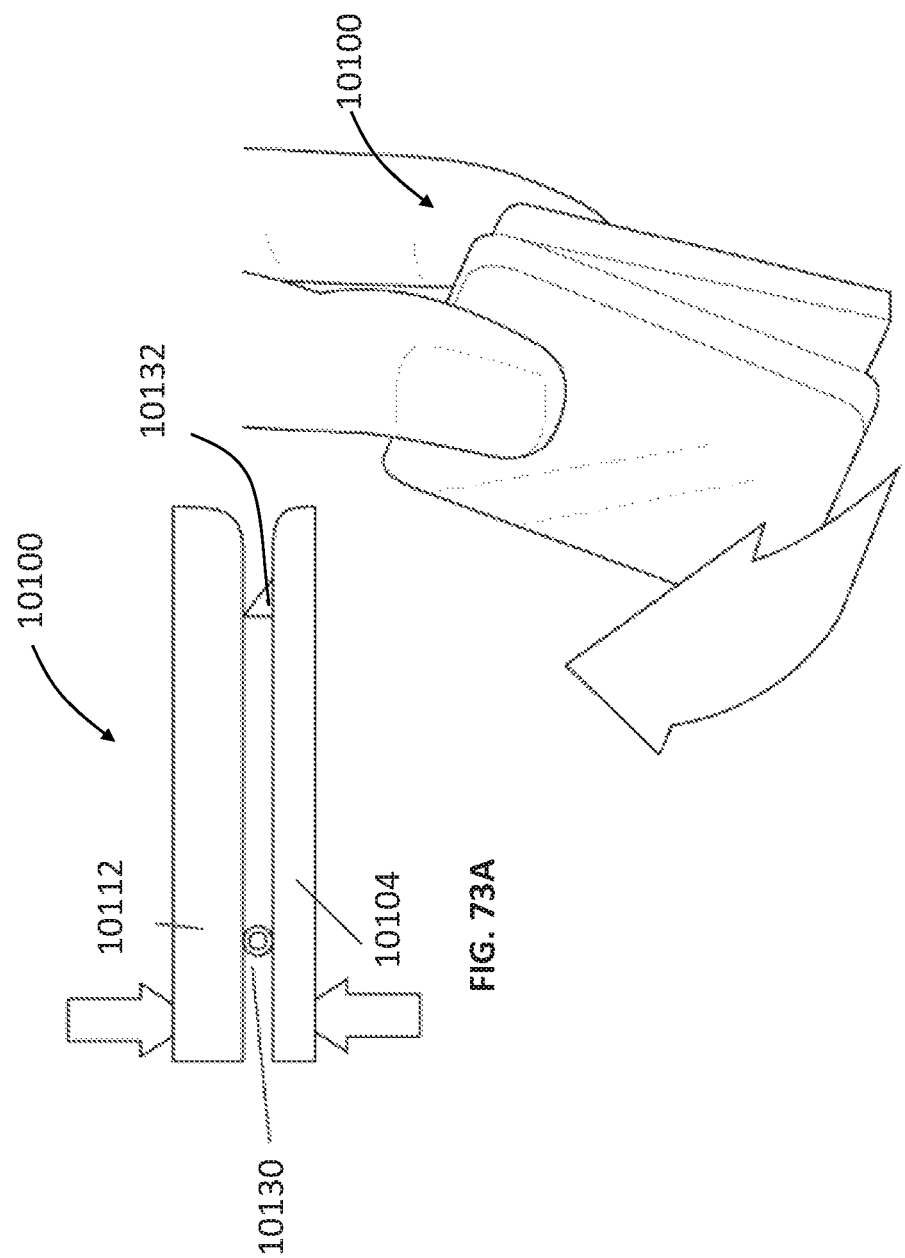

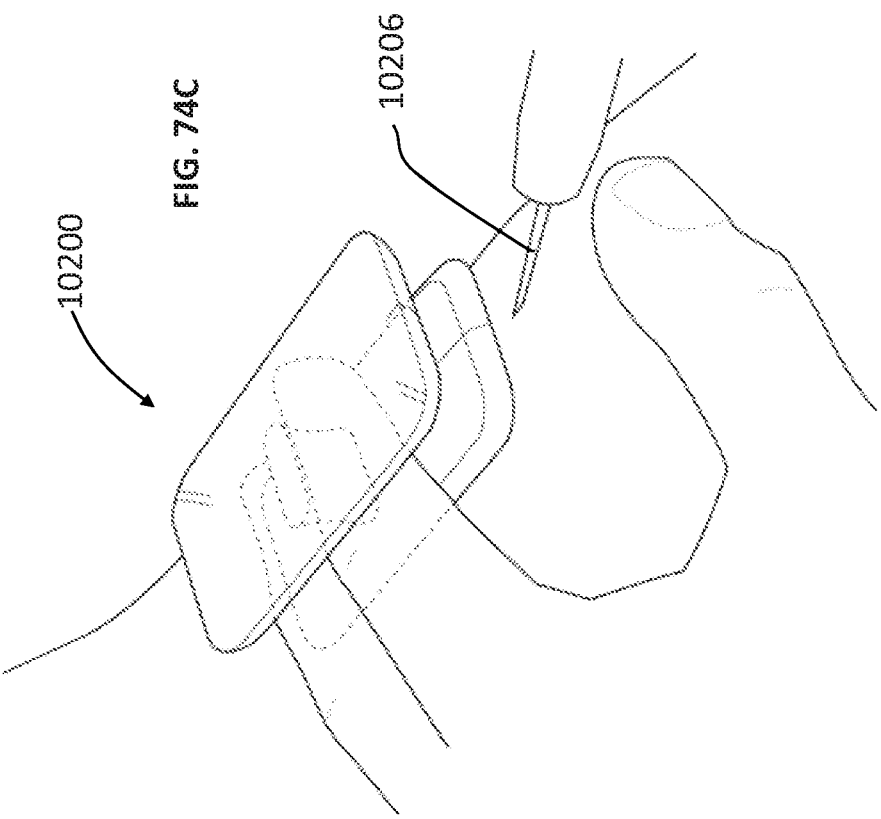
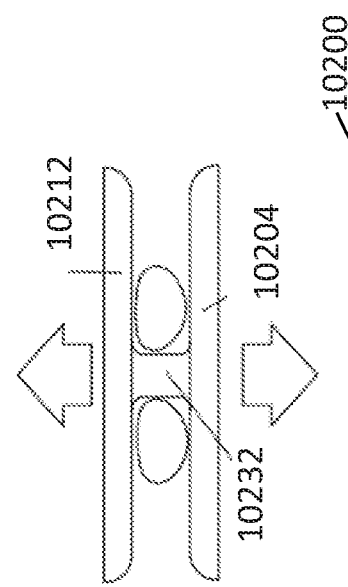
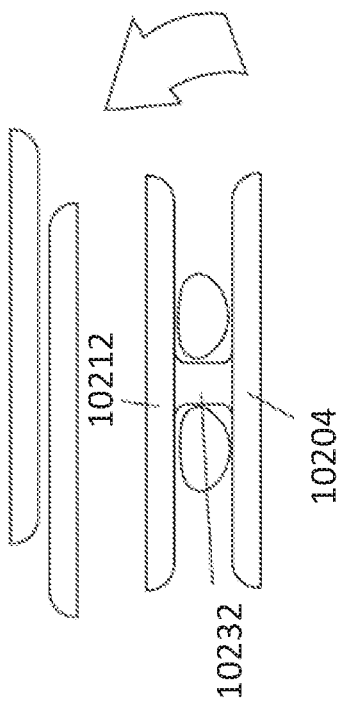

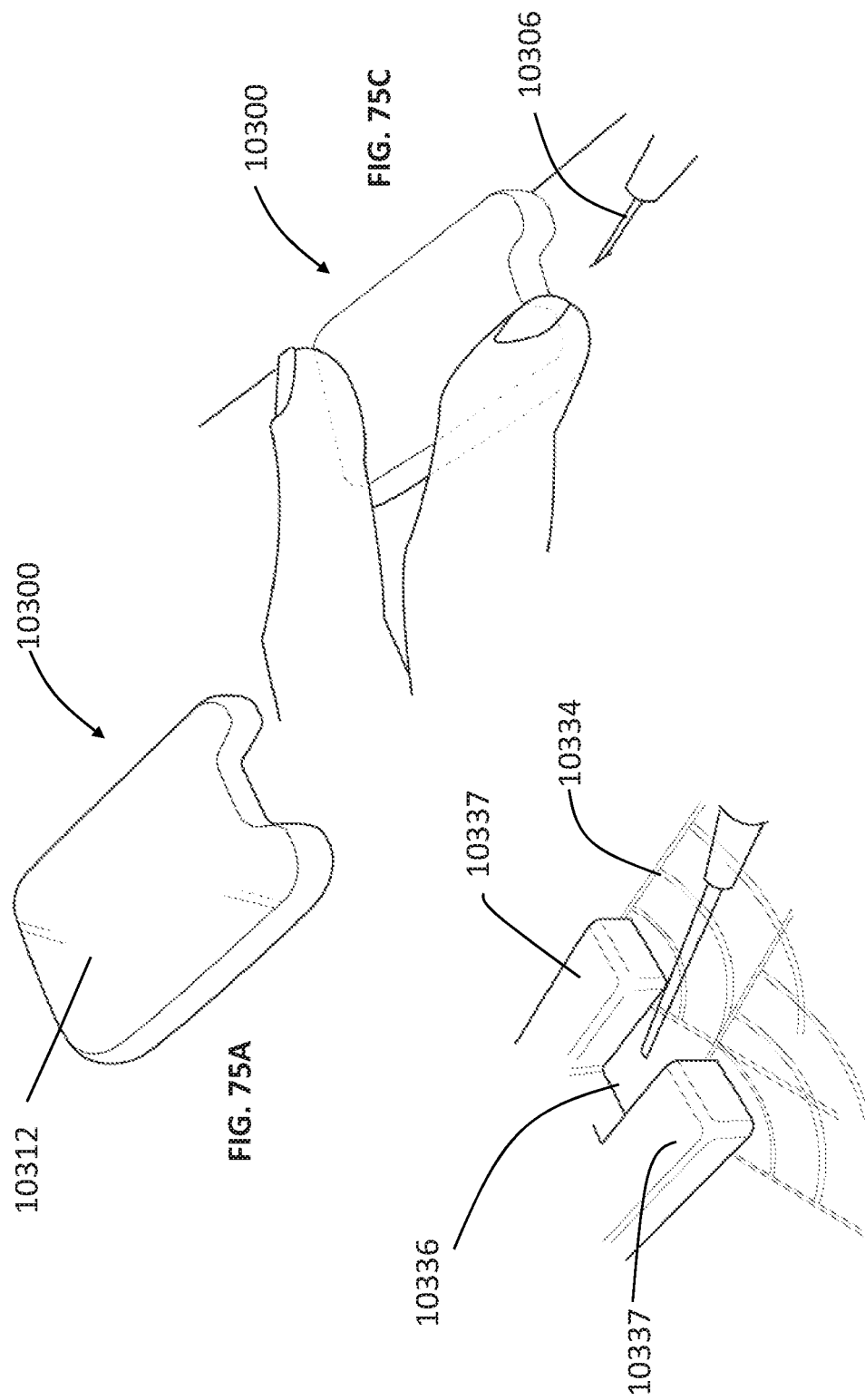

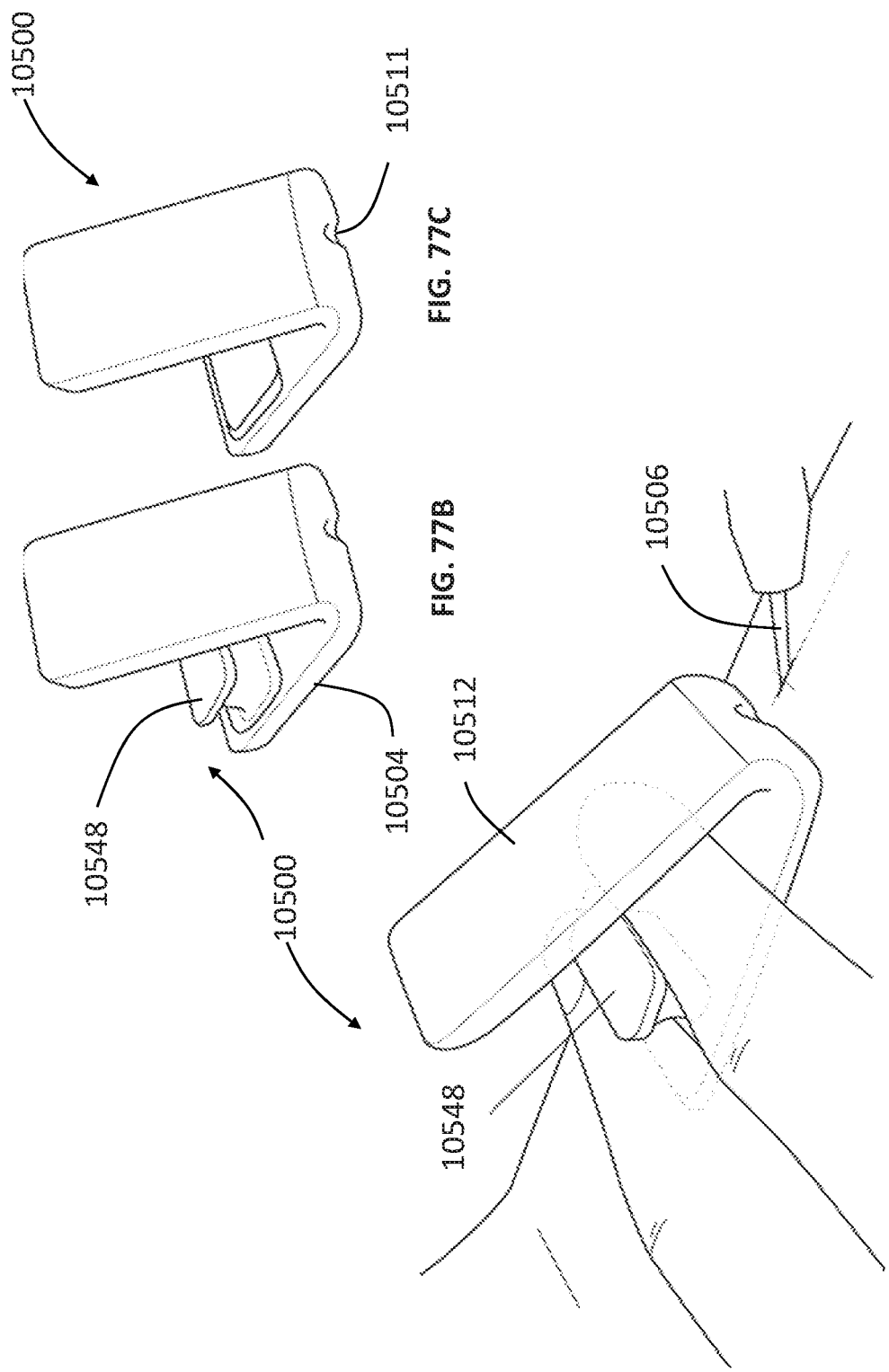

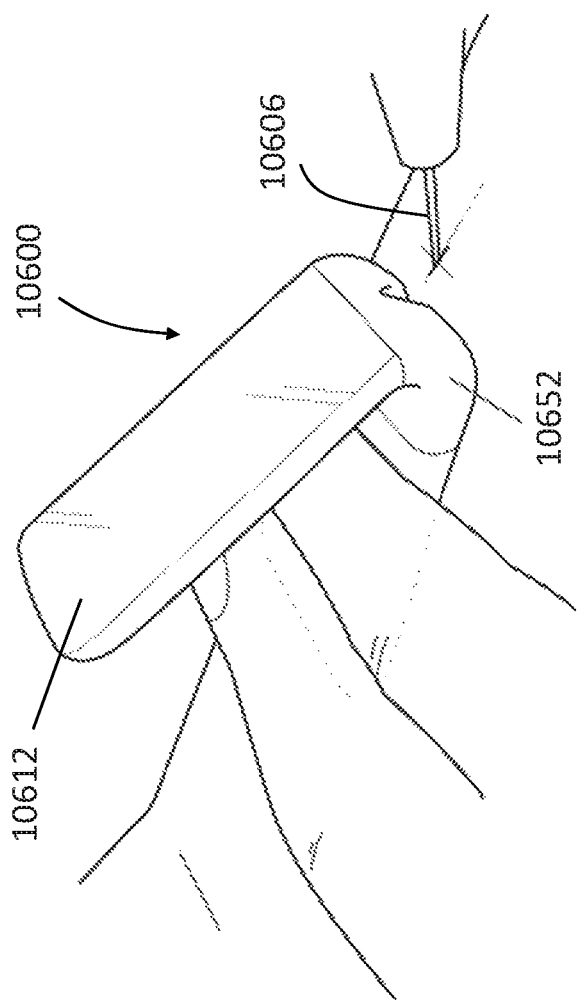
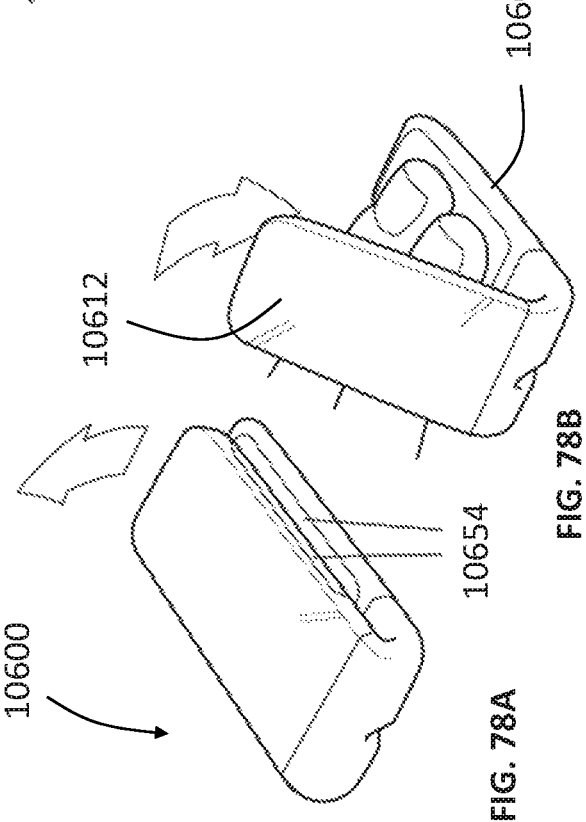
FIG. 78C
FIG. 78B
FIG. 78A

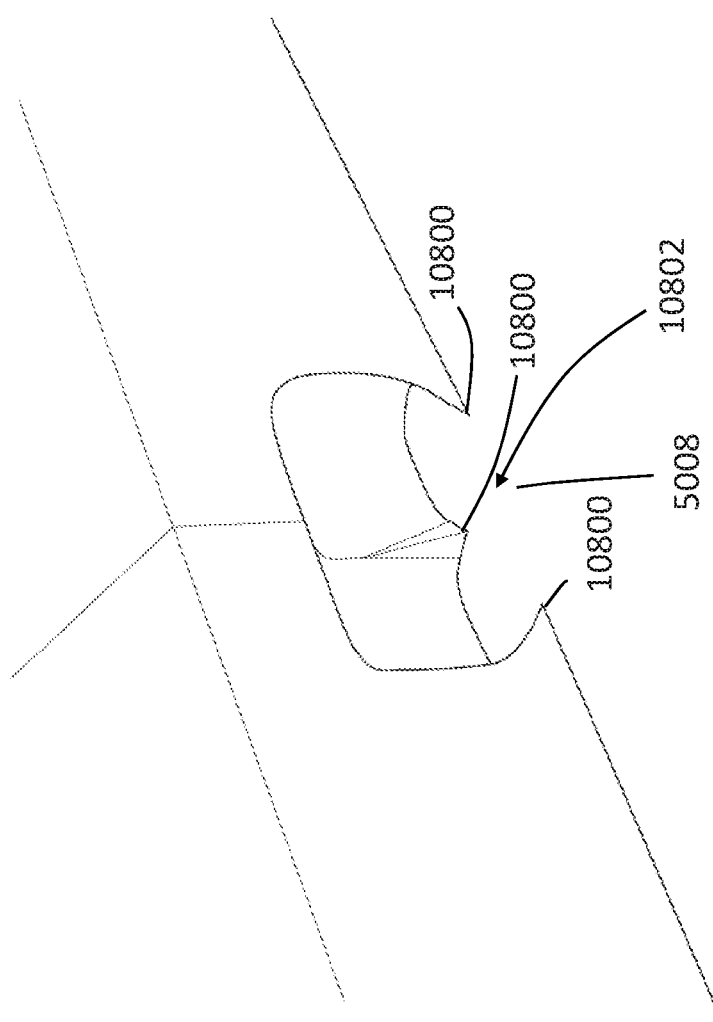

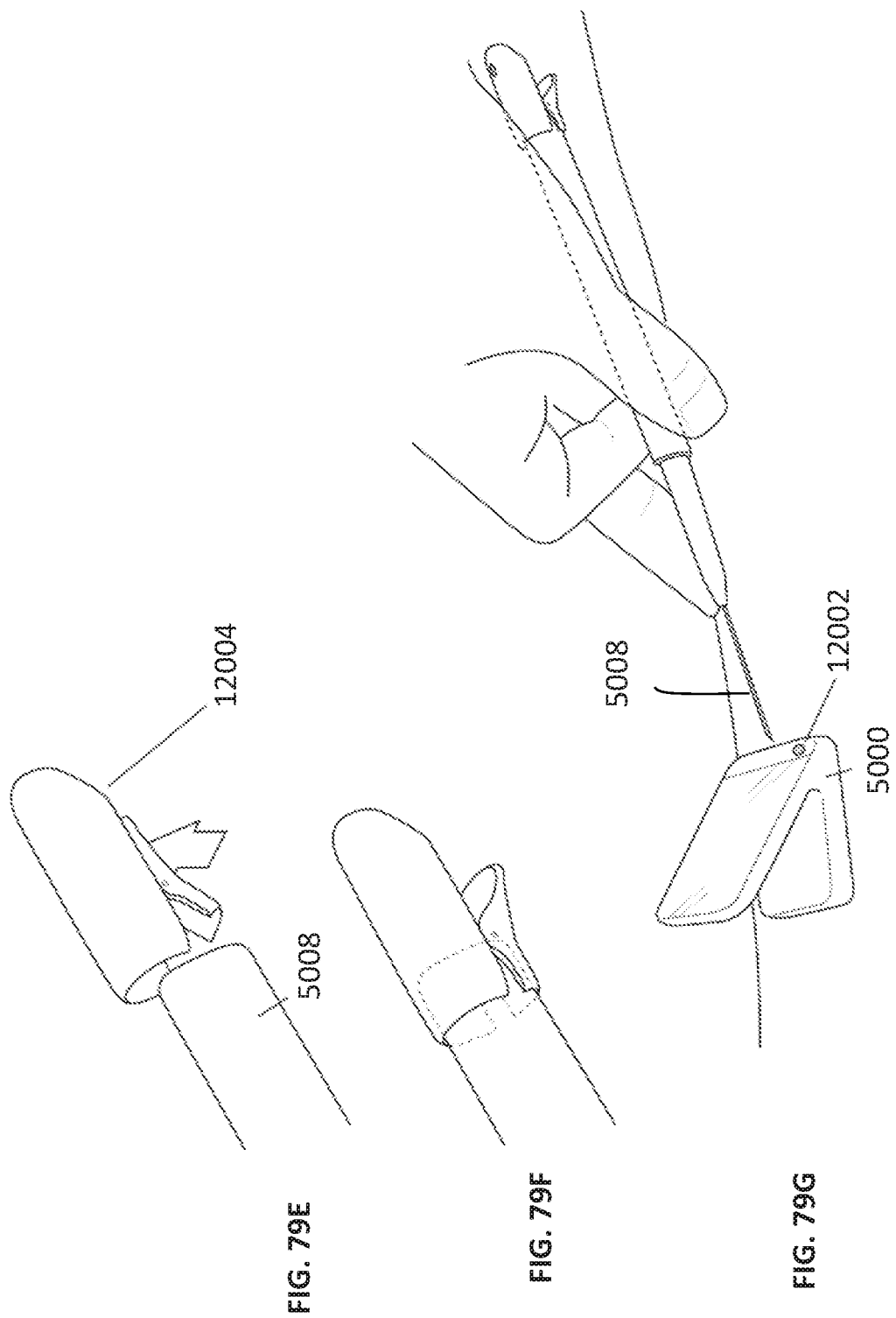

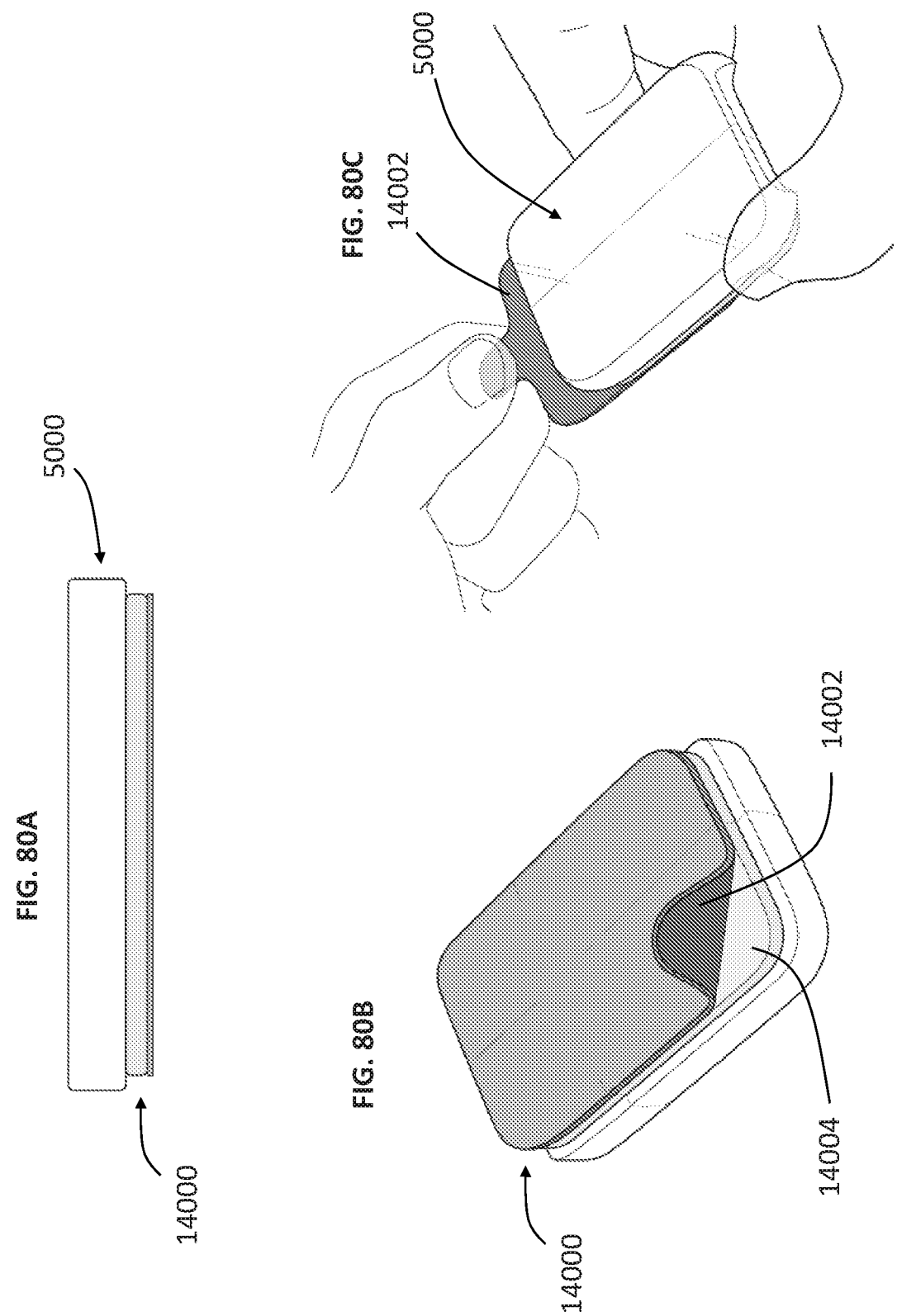

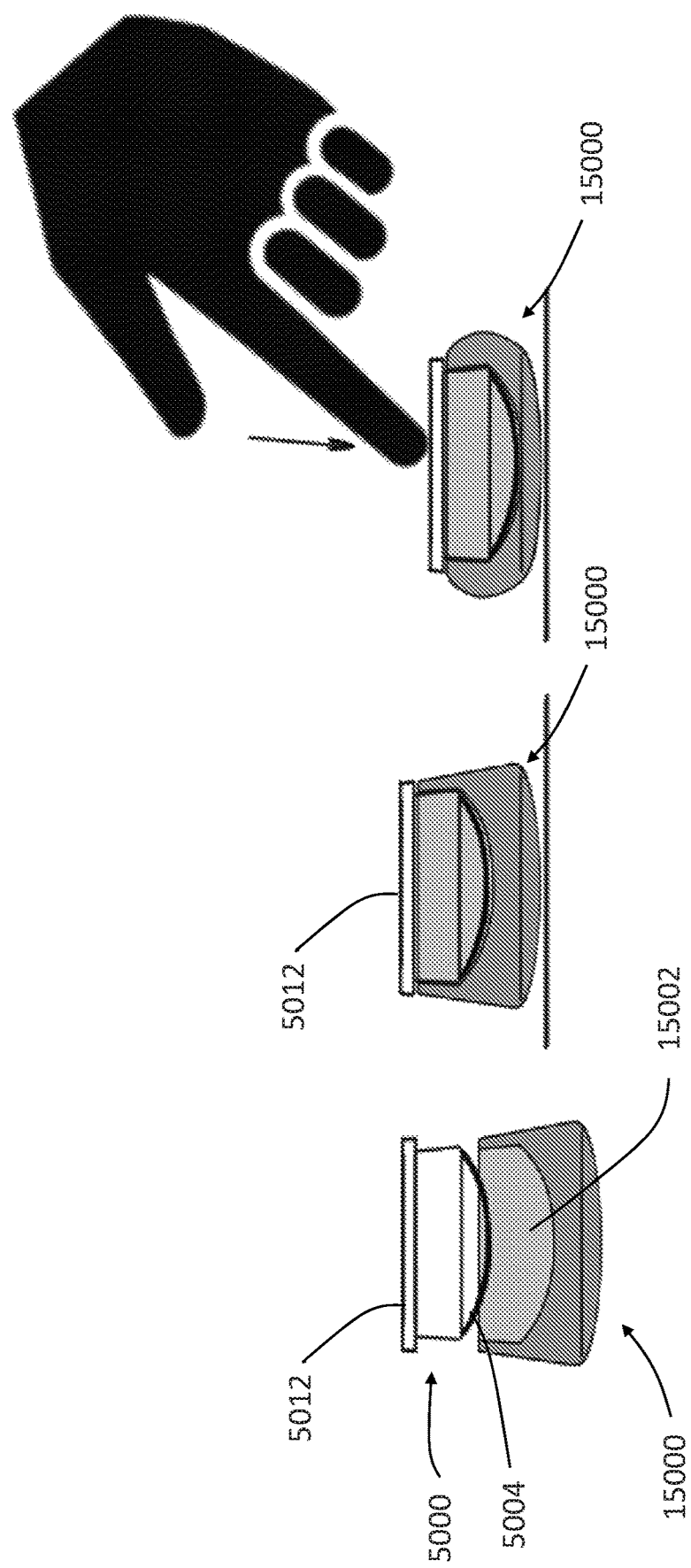

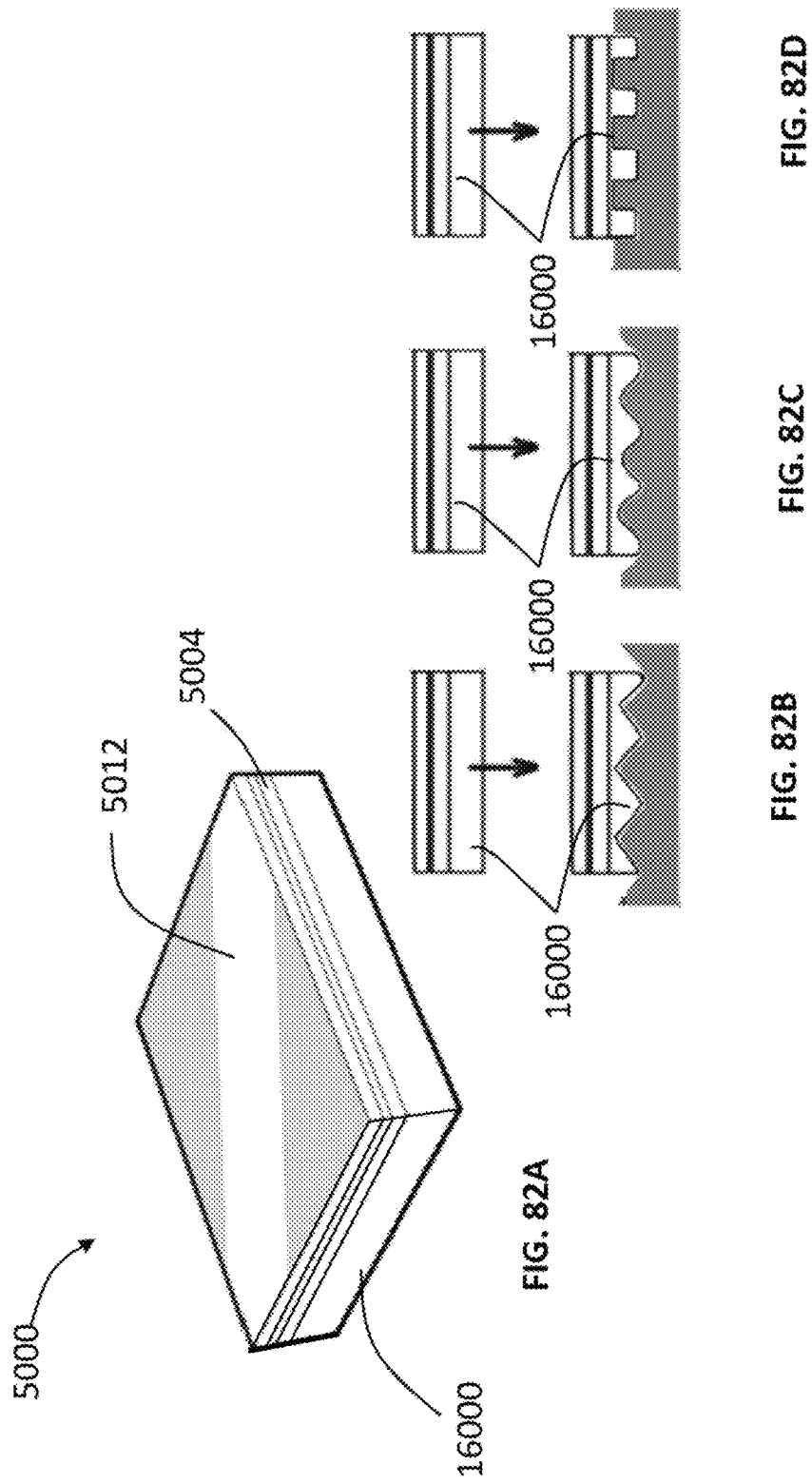

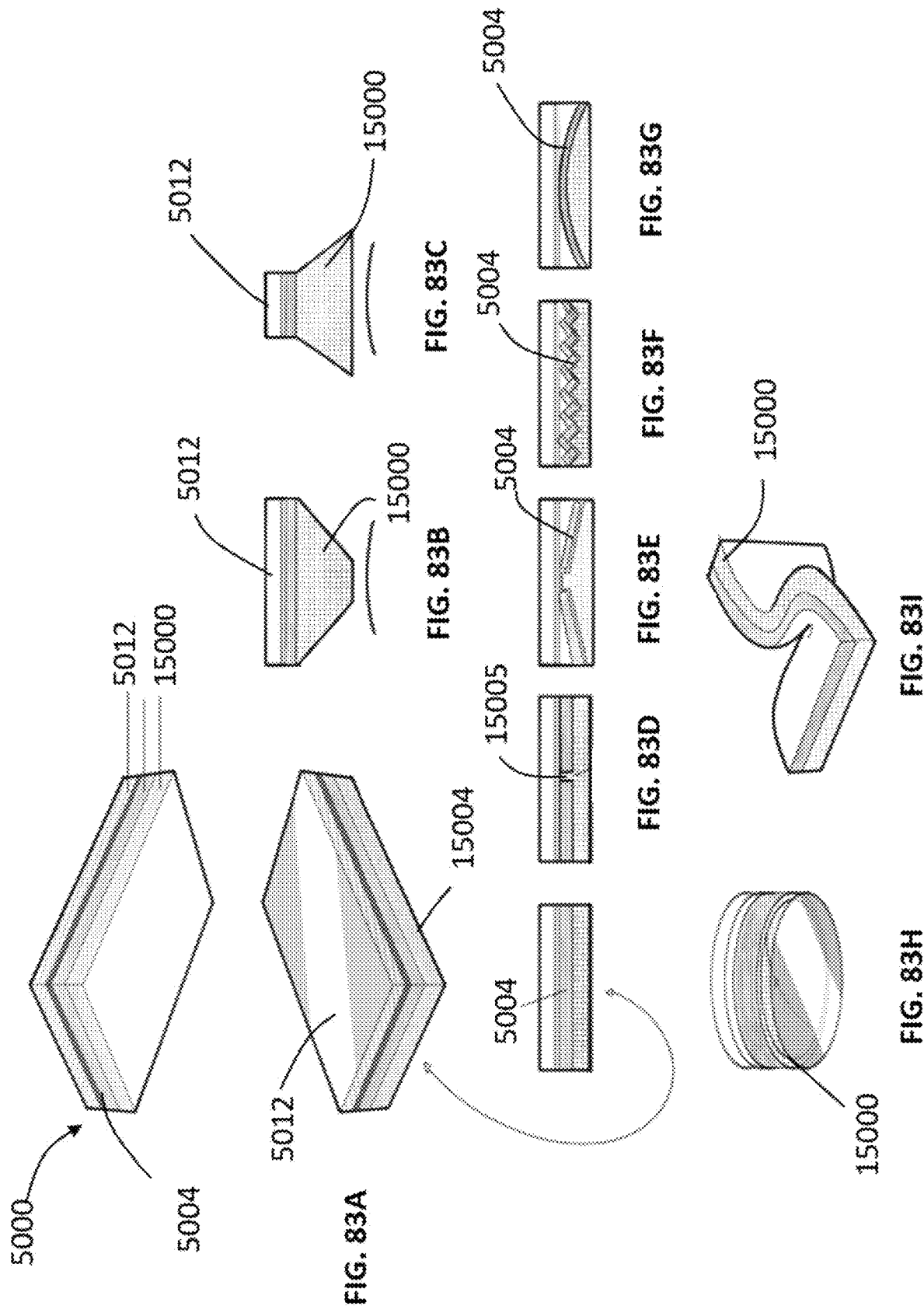

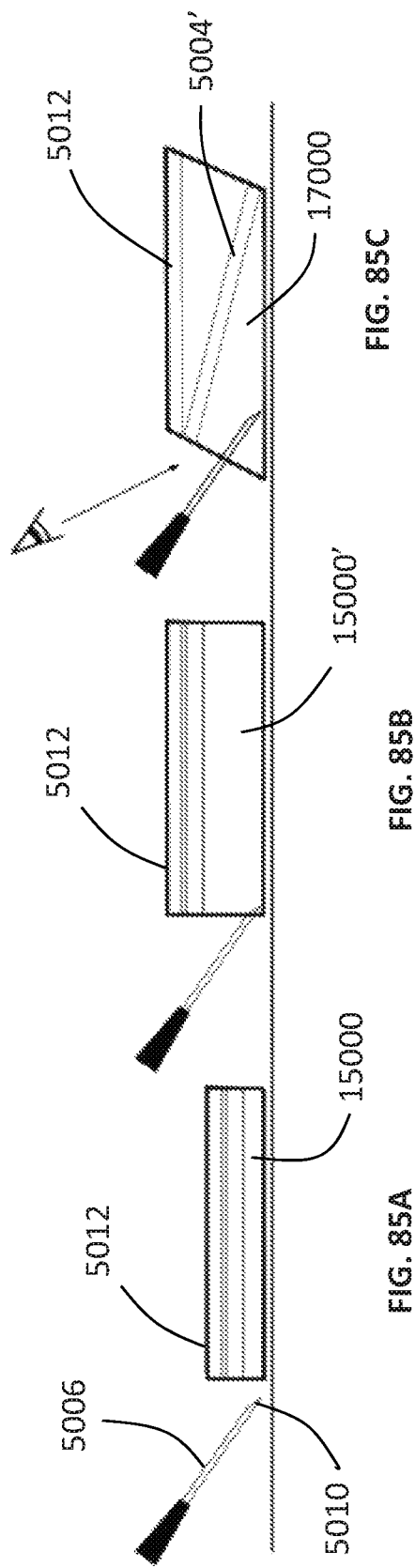

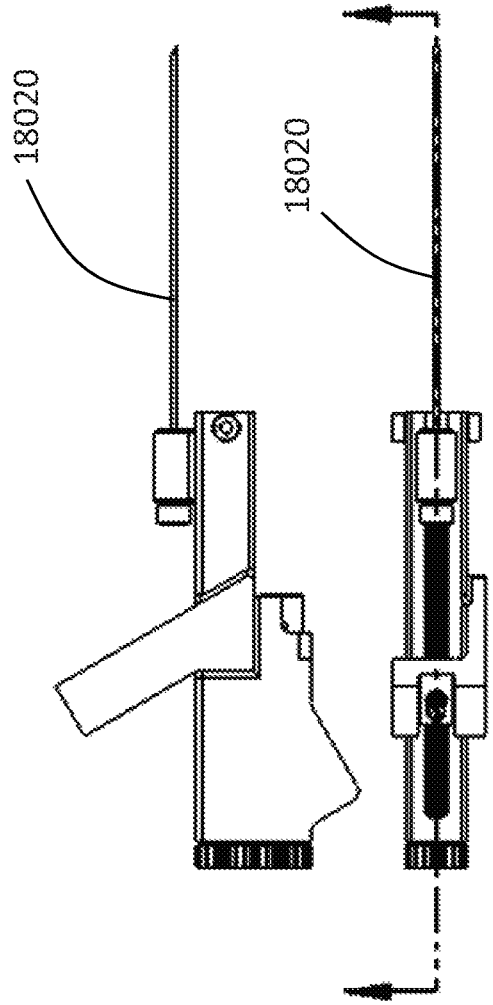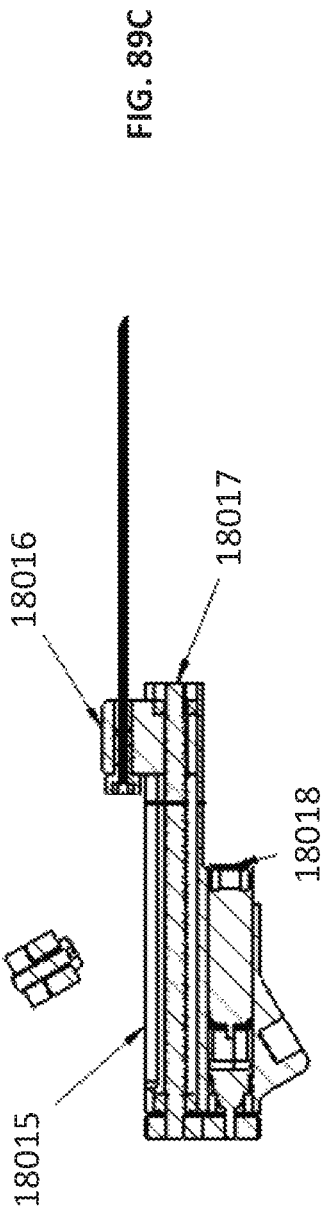

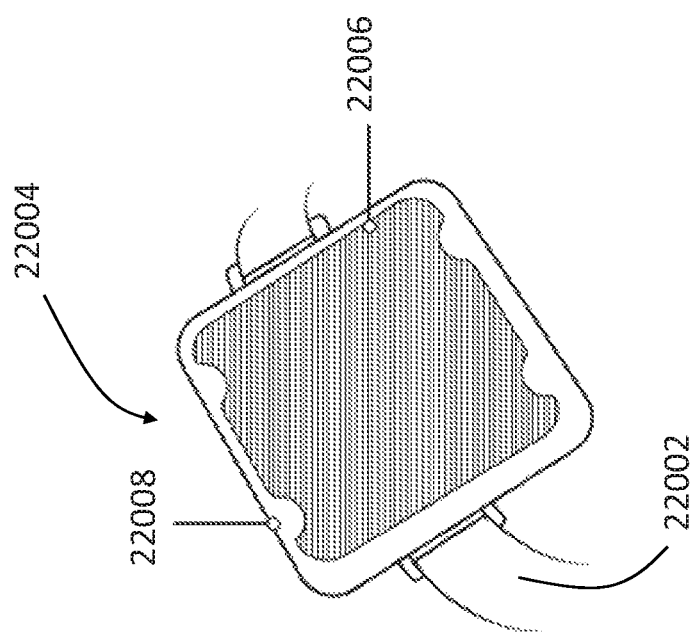
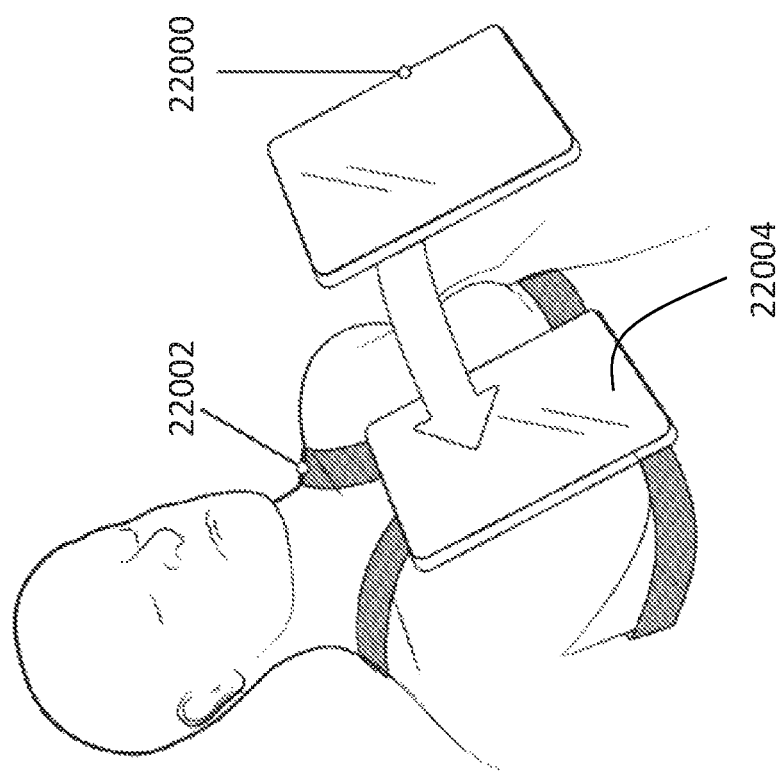
FIG. 101B
FIG. 101A

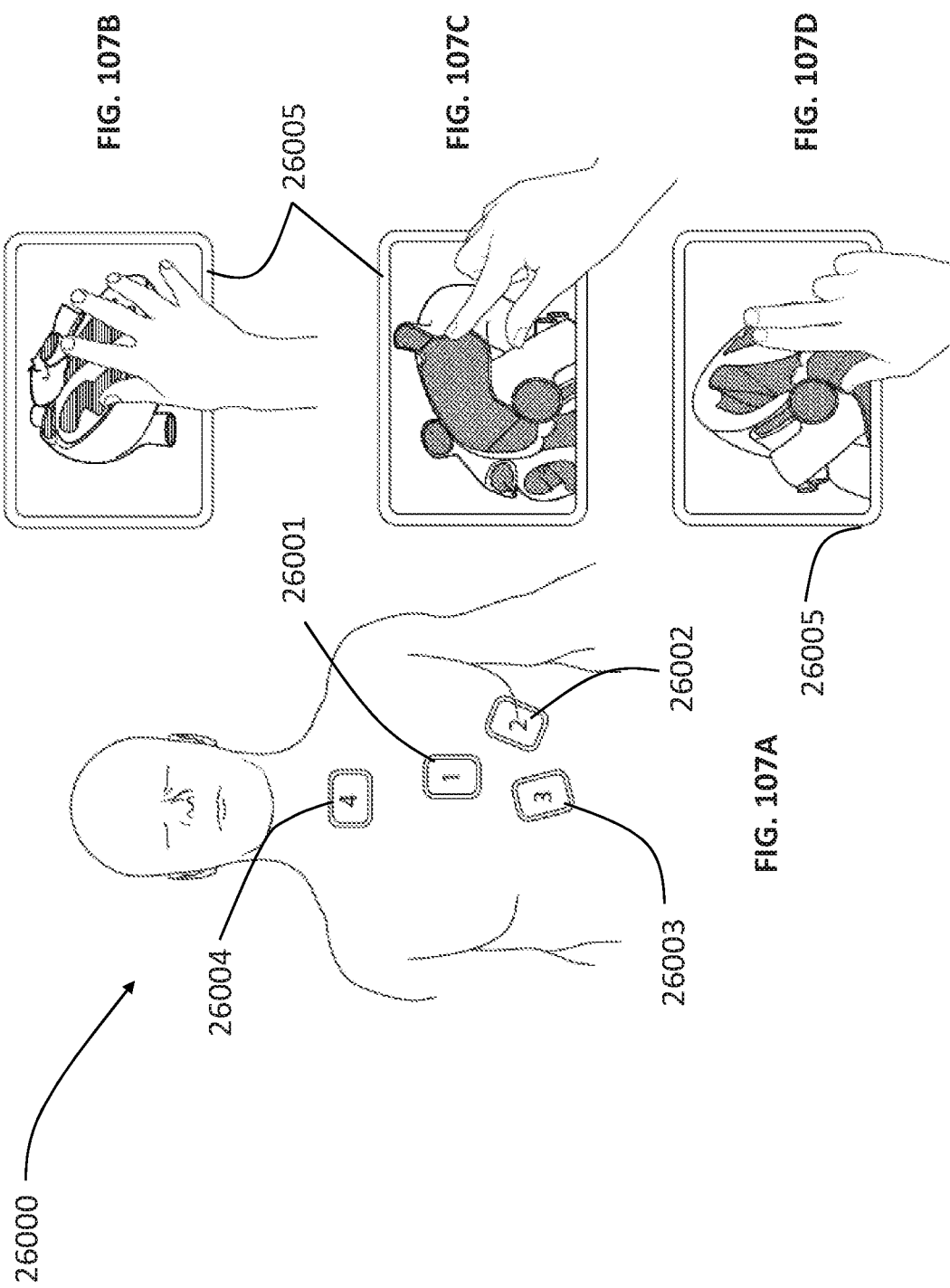

| Device Size | Footprint (") | Voltage (V) | Frequency (MHz) | Bandwidth (MHz) | Depth (cm) | Battery Capacity (Ah) | Elements (#) | Pitch (µm) | Resolution (µm) | Refresh Rate (vols/s) |
|---|---|---|---|---|---|---|---|---|---|---|
| Small | 2.7 x 1.5 | 5 | 10 | 8 | 3-4 | 0.57 | 116129 | 150 | 200 x 200 x 150 | 10 |
| Medium | 5.4 x 2.6 | 5 | 3 | 2.5 | 20 | 2.0 | 226451 | 400 | 600 x 600 x 450 | 10 |
| Large | 9.4 x 6.6 | 5 | 3 | 2.5 | 25 | 8.8 | 250161 | 400 | 600 x 600 x 450 | 30 |

FIG. 108H

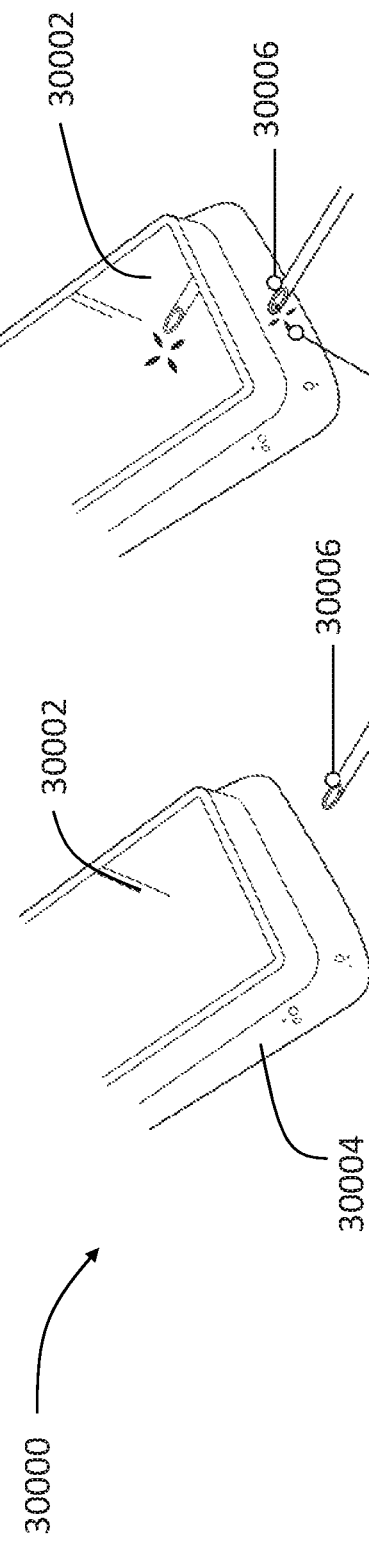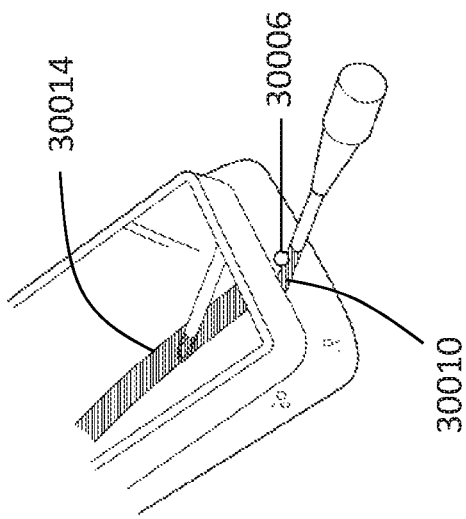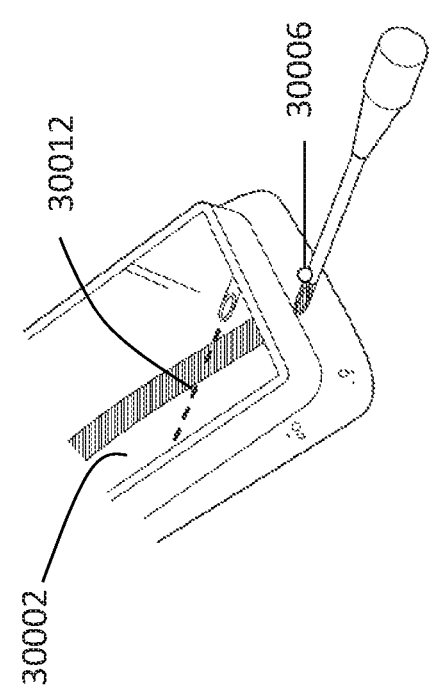
FIG. 110A
FIG. 110B
FIG. 110C
FIG. 110D

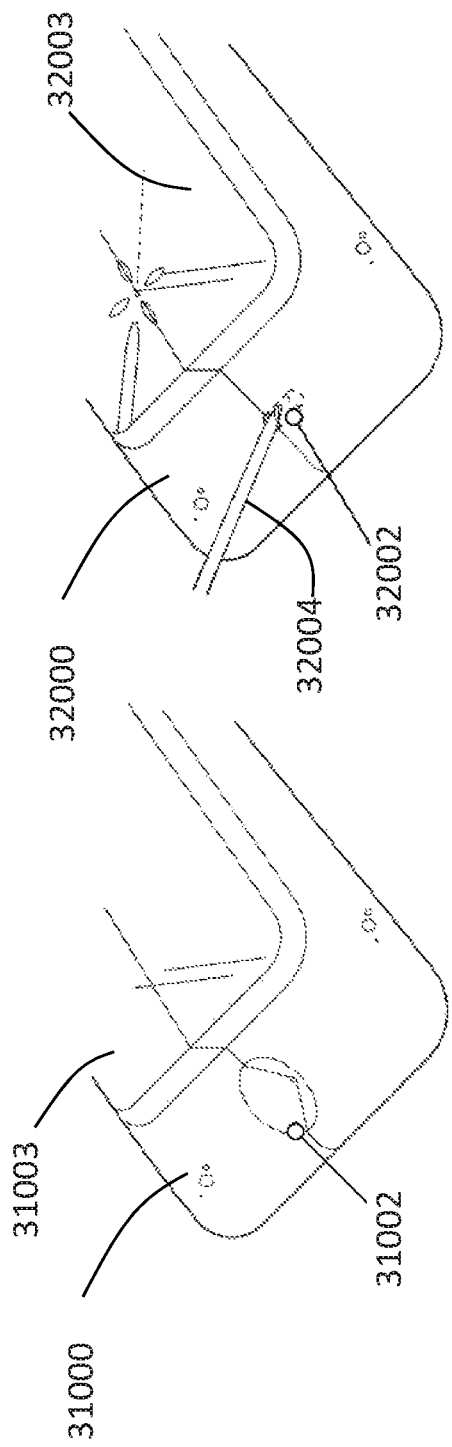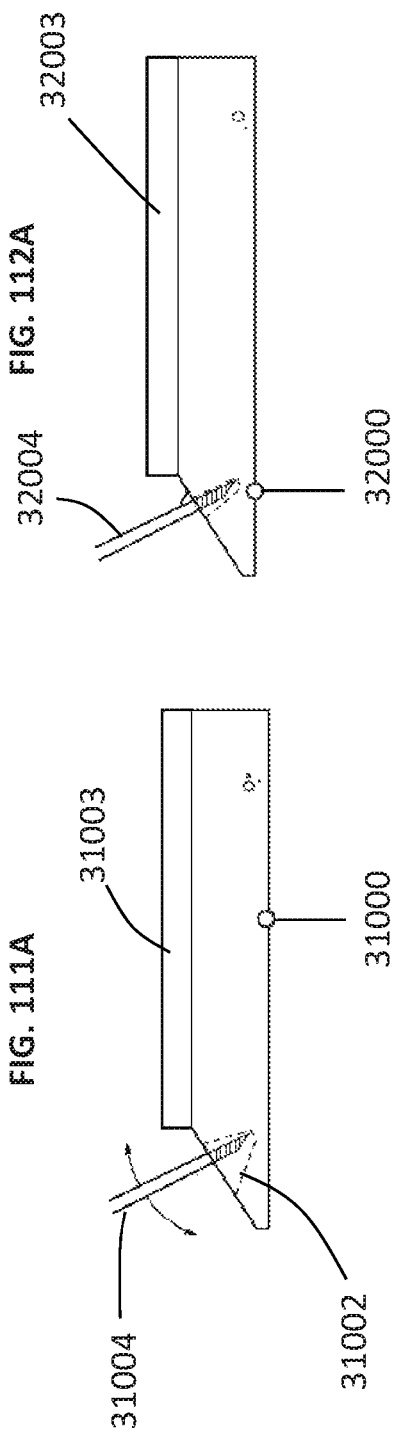

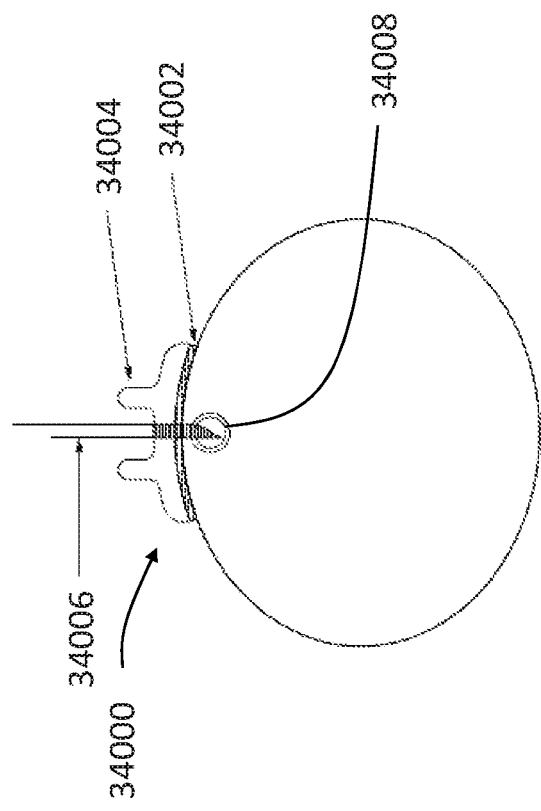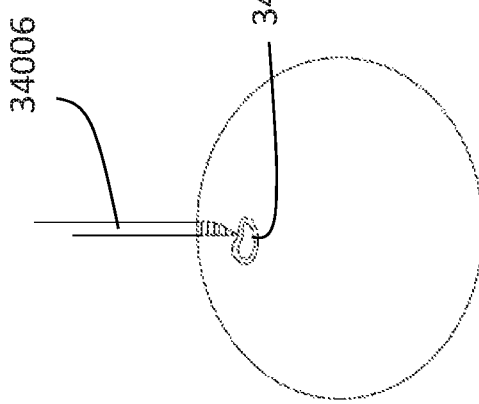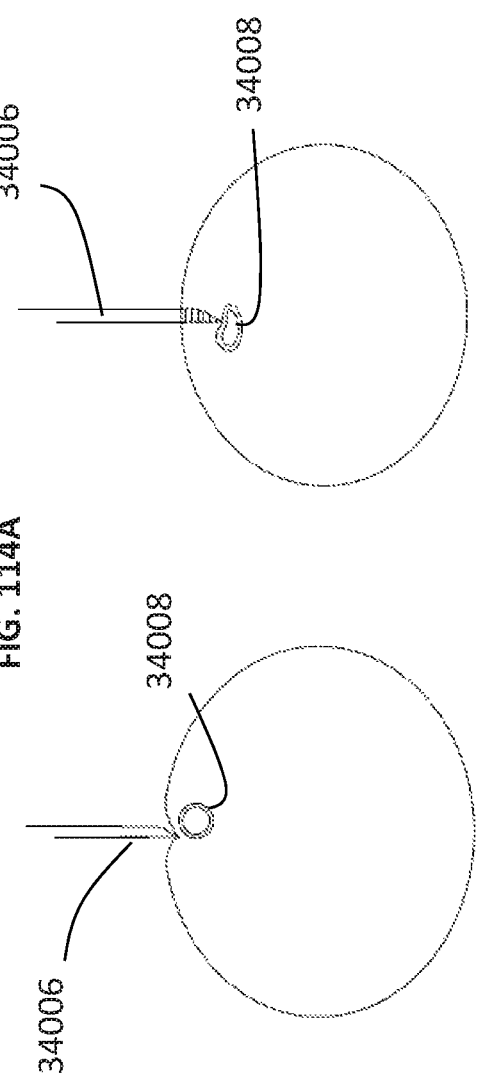

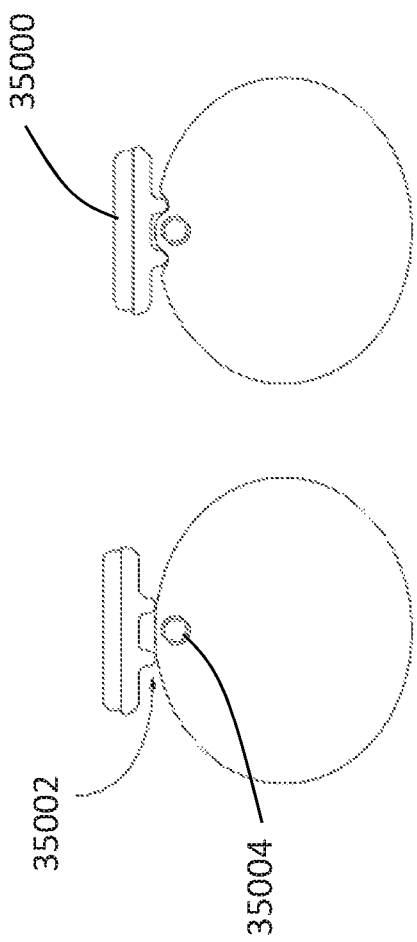
FIG. 115A
FIG. 115B
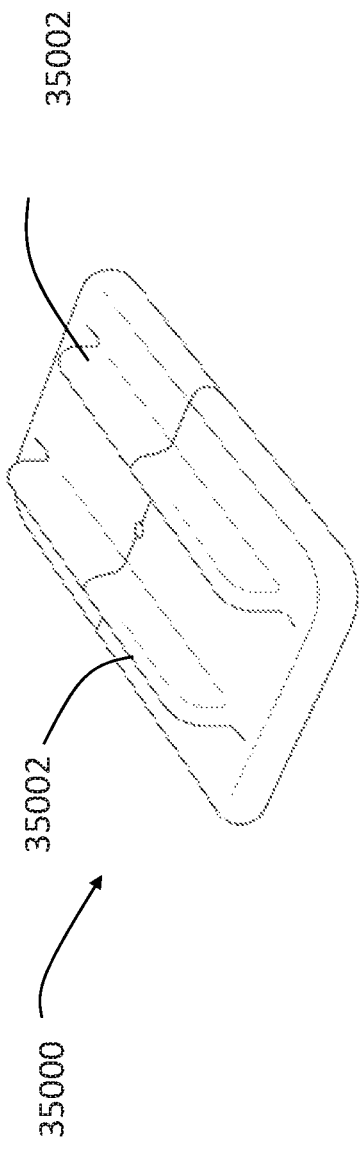
FIG. 115C

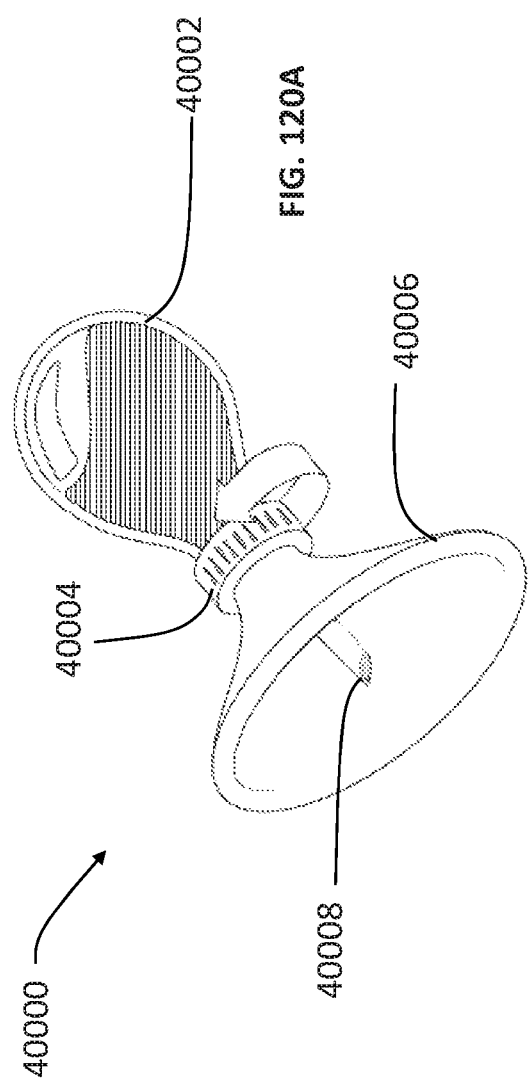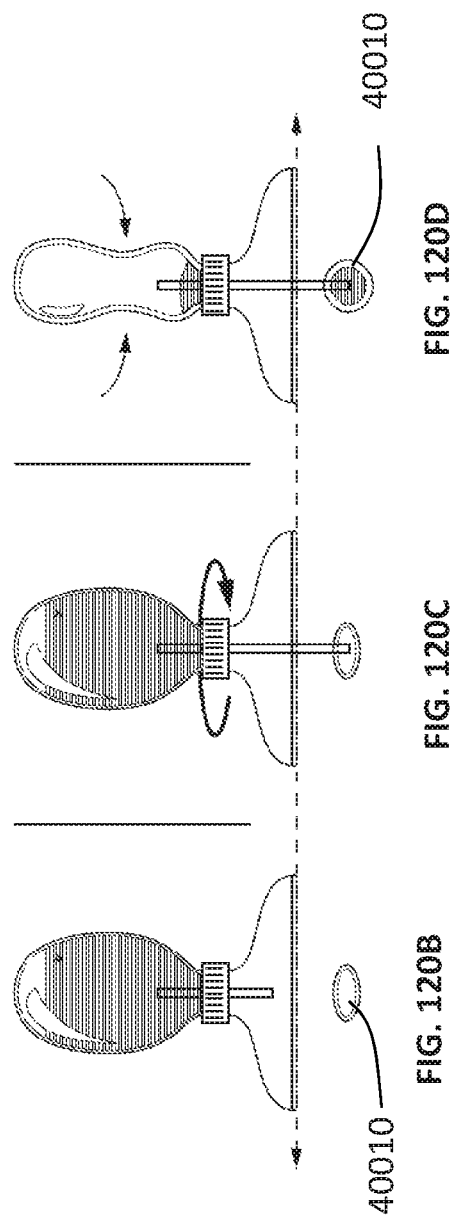

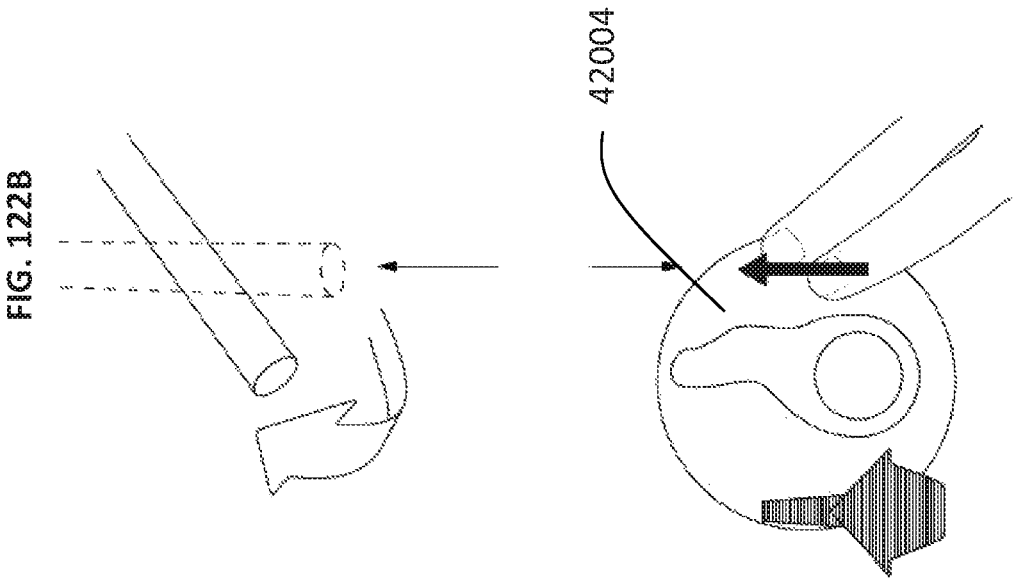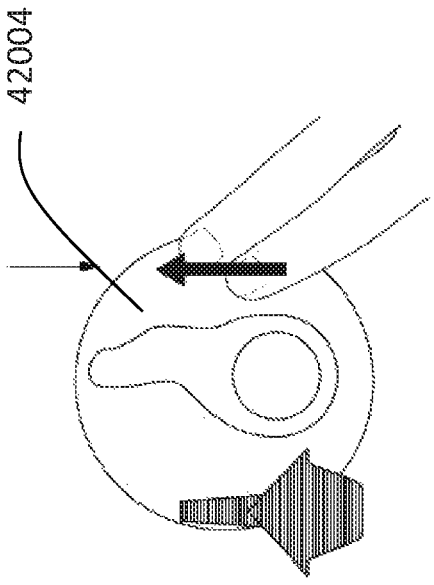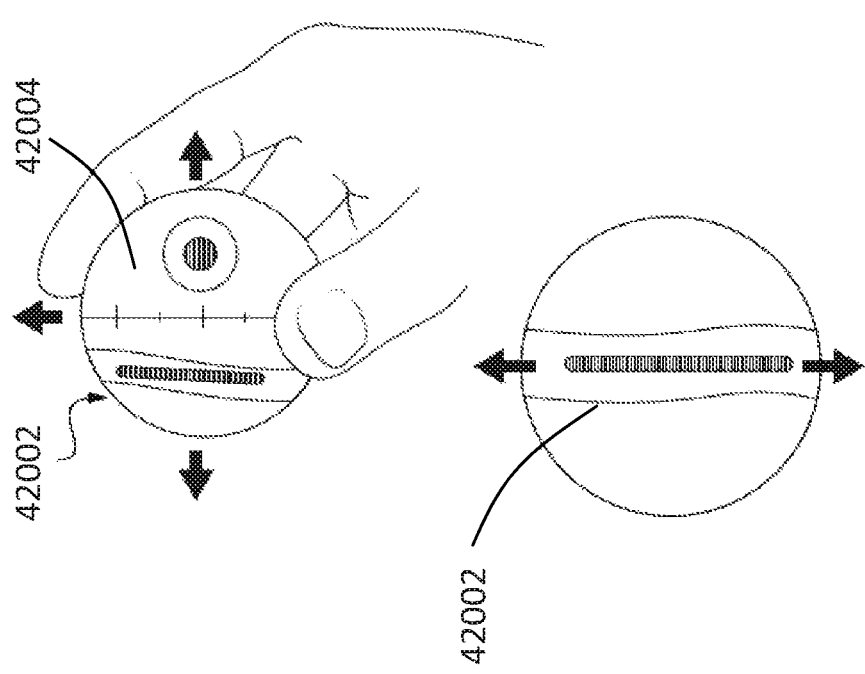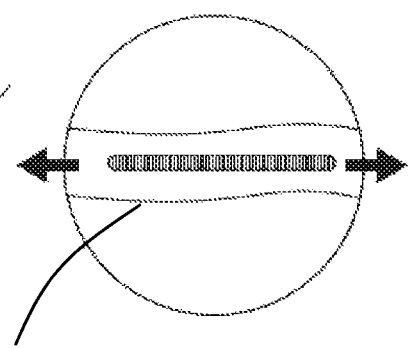

METHOD OF MEDICAL IMAGING USING MULTIPLE ARRAYS

CROSS-REFERENCE TO RELATED APPLICATIONS

The present application is a national phase entry under 35 U.S.C. § 371 of International Application No. PCT/US2019/035019 filed May 31, 2019, published in English, which claims priority from U.S. Provisional Application No. 62/678,885 filed May 31, 2018, U.S. Provisional Application No. 62/678,868 filed May 31, 2018, and U.S. Provisional Application No. 62/678,854 filed May 31, 2018, all of which are incorporated herein by reference.

BACKGROUND OF THE INVENTION

The insertion of intravenous needles and cannulae is one of the most widely performed medical procedures in modern medicine, whether for drawing blood, administration of a drug or other composition, or the like.

Despite its widespread use in numerous applications, the insertion of needles and cannulae into the circulatory system of a patient (e.g., blood vessel, vein, artery, microvasculature, or the like) is an inaccurate science, often relying on the experience of the user or operator (e.g., doctor, nurse, phlebotomist, technician, or the like) to locate a hidden and unstable target, which in some cases, could require multiple attempts. The inexactness of this procedure leads to patient apprehension, discomfort and potentially mental and/or physical trauma.

In recent years, there have been many attempts to modernize this process with the introduction of automation and imaging and computerization assistance, as well as distraction from the pain. However, particularly in terms of imaging and automation, the resulting concepts and designs are proving to be non-intuitive for operators, rather cumbersome and, in many instances, just as inaccurate and unpredictable as traditional methods. Thus, there is a need for an improved device that provides for greater accuracy in needle placement while also having a manageable design and size for simplified use by an operator, including less experienced and skilled operators.

Visualization of a body region is a critical requirement for successfully diagnosing various medical conditions and/or performing various surgical procedures. Complex and expensive visualization devices, such as current ultrasonic imaging systems, limit or prevent application of three dimensional visualization for many surgical procedures. For example, despite its widespread use in numerous applications, the insertion of needles and cannulae into the circulatory system of a patient (e.g., blood vessel, vein, artery, microvasculature, or the like) is an inaccurate science, often relying on the experience of the user or operator (e.g., doctor, nurse, phlebotomist, technician, or the like) to locate a hidden and unstable target, which in some cases, could require multiple attempts. The inexactness of this procedure leads to patient apprehension, discomfort and potentially mental and/or physical trauma.

The inexactness of this procedure can be intensified by certain characteristics of the circulatory system of a patient. For example, blood vessels are often superficial, small, and mobile. Additionally, blood vessels may be blocked by bone or tissue during computerized imaging, resulting in incomplete volumetric cardiac images. Such characteristics can make image data sets less robust and less reliable, increasing the risk of inaccuracy.

In recent years, there have been many attempts to improve visualization devices and system to readily aid in medical diagnosis and treatment. However, particularly in terms of complexity and cost, the resulting concepts and designs are proving to be rather cumbersome and, in many instances, just as inaccurate and unpredictable as traditional methods. Further, current visualization devices suffer from an inability to adequately image anatomy that may be hidden by dense structures, such as bone, which may hamper the ability of the operator to obtain a clear image of the target anatomy, resulting in an inadequate procedure.

Thus, there is a need for an improved visualization device that provides real time three dimensional visualization of body regions for medical diagnosis and/or to conduct medical procedures.

BRIEF SUMMARY OF THE INVENTION

The present disclosure generally relates generally to visualization techniques associated with devices used in medical procedures. In particular, the present disclosure relates to such devices that can perform a variety of functions including, for example, locating potential intravenous puncture sites on the patient, navigating and manipulating a needle or cannula to the located puncture site (which may include fine-tuning or auto-correction of the position and/or trajectory of a manually or semi-manually inserted needle or cannula through target and/or needle stabilization), and moving the needle or cannula into and through the puncture site to a desired location within a circulatory system of the patient. Navigation of the needle is improved by the ability to image a patient's anatomy from different locations using triangulation. In particular, if anatomical features (e.g., bone, tissue) are obstructing the view of a blood vessel in one plane, multi-panel imaging can be used to obtain a complete volumetric image of the patient's anatomy for needle insertion.

In a first aspect of the present disclosure, a method of medical imaging using a plurality of imagers is provided. The method may include the steps of: placing a first imager on a first location with respect to an anatomical site, placing a second imager on a second location with respect to the anatomical site, generating a first volumetric image data set using the first imager, generating a second volumetric image data set using the second imager, and combining the first volumetric image data set and the second volumetric image data set to generate a third volumetric imaging data set of the anatomical site. The third volumetric imaging data set of the anatomical site may include all anatomical features within a volume defined by the volumetric imaging data In accordance with the first aspect, the anatomical features may include hard and soft tissues.

In accordance with the first aspect, the method may include the step of displaying the third volumetric imaging data set on a display screen.

In accordance with the first aspect, the first imager may be on a first plane in the first location. The second imager may be on a second plane in the second location. The first and second planes may be on opposite sides of the anatomical site.

In accordance with the first aspect, the step of combining the first volumetric image data set and the second volumetric image data to generate a third volumetric imaging data set of the anatomical site may further include the step of combining volumetric image data from a third image data set and a fourth image data set.

In a second aspect of the present disclosure, a medical imaging system is provided. The medical imaging system may include a first imager, a second imager, a processor, and a display device. The first imager may be configured to generate a first image data set of an anatomical site from a first position. The second imager may be configured to generate a second image data set of an anatomical site from a second position. The processor may combine the first image data set with the second image data set to generate a volumetric image data set. The display device may display the volumetric image data set. The volumetric imaging data set of the anatomical site may include all anatomical features within a volume defined by the volumetric imaging data set.

In accordance with the second aspect, the display device may include a plurality of screens. Each screen may be perpendicular to at least one other screen.

In accordance with the second aspect, the first imager may have a length and a width defining a first foot print. The second imager may have a second foot print defined by a depth and the length such that the volume of the volumetric image data set is defined by the length, width and depth.

In accordance with the second aspect, the volumetric imaging data may display all anatomic features within the volume.

In accordance with the second aspect, the anatomical features obstructed by bones in the first image data may be captured by the second image data.

In a third aspect of the present disclosure, a medical imaging system is provided. The medical imaging system may include an imager and an array of transducers. The imager may be configured to generate a volumetric image data set of an anatomical site. The array of transducers may be located on a distal face of the imager. The array may have a length and a width defining a first footprint. The array may generate the volumetric image data set. The volumetric image data set may be defined by a volume defined by the length, width and a depth. The volumetric imaging data set of the anatomical site may include all anatomical features within the volume.

In a fourth aspect of the present disclosure, a medical imaging system is provided. The medical imaging system may include an imager and an array of transducers. The imager may be configured to generate a volumetric image data set of an anatomical site. The array of transducers may be located on a distal face of the imager. The array may have a length and a width defining a first footprint. The array may generate the volumetric image data set. The volumetric image data set may be defined by a volume defined by the length, width and a depth such that all anatomic features within the volume are contained in the volumetric image data set.

In a fifth aspect of the present disclosure, a medical imaging system is provided. The medical imaging system may include an imager, a first array of transducers, and a second array of transducers. The imager may be configured to generate a volumetric image data set of an anatomical site. The first array of transducers may be located on a first planar surface of the imager. The first array may have a first length and a first width defining a first footprint. The second array of transducers may be located on a second planar surface of the imager. The second array may have a second length and a second width defining a second footprint. The first planar surface may be inclined and away from the second planar surface to define a gap between the first and second planar surfaces. A projected area of the first foot print and a projected area of the second foot print may intersect such that a volume below the gap is included in the volumetric image data set generated by the imager.

In a sixth aspect of the present disclosure, a medical imaging system is provided. The medical imaging system may include an imager, a first array of transducers, and a second array of transducers. The imager may be configured to generate a volumetric image data set of an anatomical site. The first array of transducers may be located on a first surface of the imager. The first array may define a first footprint. The second array of transducers may be located on a second surface of the imager. The second array may define a second footprint. The first surface may be separated from the second surface to define a gap between the first and second surfaces. A projected area of the first foot print and a projected area of the second foot print may intersect such that a volume below the gap is included in the volumetric image data set generated by the imager.

In a seventh aspect of the present disclosure, a method of medical imaging using an imager is provided. The method may comprise steps of: placing an imager adjacent an anatomical site, the imager including a plurality of transducers, the plurality of transducers defining an area bounded by a length and a width, the anatomical site including hard and soft tissue, the hard tissue located between the imager and the soft tissue, the hard tissue including one or more gaps; generating image data sets from signals transmitted and received by each of the plurality of transducers, and generating a volumetric image data set by combining the image data sets, the volumetric image data set being defined by a volume bounded by the area and a depth such that the hard tissue and the soft tissue are contained in the volumetric image data set. The signals transmitted by each of the transducers located directly above the hard tissue may propagate through the gaps and diverge to contact the soft tissue.

In accordance with the seventh aspect, the hard tissue may be bone and the soft tissue may be an organ.

In accordance with the seventh aspect, the propagated signals may collect data of all or substantially all of the soft tissue.

In accordance with the seventh aspect, the imager may include a display screen to display the volumetric image data set. The display may be coupled to the imager. The display may include parallax display to move the volumetric image data set relative to a line of sight of an operator. The parallax may allow the operator to view portions of a target anatomy which may be underneath other portions of the anatomy. The parallax display may allow the operator to view the soft tissue located underneath the hard tissue.

In an eight aspect of the present disclosure, a method of medical imaging using an imager is provided. The method according to this aspect may comprise the steps of: placing an imager adjacent an anatomical site, generating image data sets from signals transmitted and received by individual transducer arrays, and generating a volumetric image data set by combining the image data sets. The imager may include a plurality of transducer arrays. The plurality of transducer arrays may define an area bounded by a length and a width. The anatomical site may include hard and soft tissue. The hard tissue may be located between the imager and the soft tissue. The hard tissue may include one or more gaps. A processor may select the individual transducer arrays to generate and receive signals. The volumetric image data set may be defined by a volume bounded by the area and a depth such that the hard tissue and the soft tissue may be contained in the volumetric image data set. The processor may combine the individual image data sets with position information of the corresponding individual transducer array to generate the volumetric image data set. The signals transmitted by each of the transducers located directly above the hard tissue may propagate through the gaps and diverge to contact the soft tissue.

BRIEF DESCRIPTION OF THE DRAWINGS

A more complete appreciation of the subject matter of the present invention and the various advantages thereof can be realized by reference to the following detailed description, in which reference is made to the following accompanying drawings:

FIGS. 1A-1I illustrate various views of one embodiment of a device of the present disclosure.

FIGS. 2A-2E illustrate various views of another embodiment of a device of the present disclosure.

FIGS. 4A-4G illustrate various embodiments of a device of the present disclosure.

FIGS. 4H-4I illustrate representative and exemplary placements of the devices of the present disclosure on a patient.

FIGS. 6A-6B illustrate various embodiments of a device of the present disclosure.

FIGS. 8A-8E illustrate various embodiments of a tourniquet of the present disclosure.

FIGS. 9E-9I illustrate another embodiment, and representative display images, of a device of the present disclosure.

FIGS. 14-15 illustrate various embodiments of a display of the present disclosure.

FIGS. 20A and 20B illustrates one embodiment of a skirt of the present disclosure.

FIGS. 23A-C illustrate various embodiments of a strap of the present disclosure.

FIGS. 25A-25I illustrate various embodiments of a strap of the present disclosure.

FIGS. 26A and 26B illustrate embodiments of attachment means of the present disclosure.

FIG. 32 is schematic perspective view of a visualization device according to one embodiment of the present disclosure.

FIG. 34A is a plan view display of the visualization device of FIG. 32.

FIG. 34B is a first depth view display of the visualization device of FIG. 32.

FIG. 34C is a second depth view display of the visualization device of FIG. 32.

FIG. 35A is a side view of the visualization device of FIG. 32 placed on target body zones.

FIG. 35B is a front view of the visualization device of FIG. 35A placed on target body zones.

FIG. 38A is a schematic perspective view of a visualization device according to yet another embodiment of the present disclosure viewed from a first perspective.

FIG. 38B is a schematic perspective view of the visualization device of FIG. 38B viewed from a second perspective.

FIG. 38C is a schematic front view of the visualization device 100 displaying a parallax view according to another embodiment of the present disclosure.

FIG. 38D is a schematic perspective view of the visualization device of FIG. 38C.

FIGS. 38E-38G are schematic top views of the visualization device of FIG. 38C.

FIG. 50 is a side view of a transducer array according to another embodiment of the present disclosure.

FIGS. 64A and 64B are schematic top views of the visualization device of FIG. 32 showing a graphical user interface display according to one embodiment of the present disclosure.

FIGS. 65A-65E illustrate an embodiment of a method of use of the device of the present disclosure.

FIGS. 66A-66E illustrate various positions that a device of the present disclosure can be used.

FIGS. 67A-67C illustrate an embodiment of a device of the present disclosure.

FIGS. 68A-68D illustrate another embodiment of a device of the present disclosure.

FIGS. 69A-69C illustrate another embodiment of a device of the present disclosure.

FIGS. 70A-70C illustrate another embodiment of a device of the present disclosure.

FIGS. 71A-71D illustrate another embodiment of a device of the present disclosure.

FIGS. 72A and 72B illustrate another embodiment of a device of the present disclosure.

FIGS. 73A and 73B illustrate another embodiment of a device of the present disclosure.

FIGS. 74A-74C illustrate another embodiment of a device of the present disclosure.

FIGS. 75A-74C illustrate another embodiment of a device of the present disclosure.

FIGS. 77A-77C illustrate another embodiment of a device of the present disclosure.

FIGS. 78A-78C illustrate another embodiment of a device of the present disclosure.

FIGS. 79A-79H illustrate various embodiments of a targeting feature of the present disclosure.

FIGS. 80A-80C illustrate an embodiment of a pad of the present disclosure.

FIGS. 81A-81C illustrate another embodiment of a pad of the present disclosure.

FIGS. 82A-82D illustrate another embodiment of a pad of the present disclosure.

FIGS. 83A-83I illustrate various embodiment of the pad shown in FIGS. 81A-81C.

FIGS. 85A-85C illustrate needle insertion procedures according to various embodiments of the present disclosure.

FIGS. 89A-89C illustrate a needle drive of the inserter assembly of FIG. 86B.

FIGS. 101A-102B illustrate a visualization device according to another embodiment of the present disclosure.

FIGS. 107A-107E illustrate a visualization system according to another embodiment of the present disclosure.

FIG. 108H shows a table of visualization device specifications according to another embodiment of the present disclosure.

FIGS. 110A-110D illustrate a visualization system according to another embodiment of the present disclosure.

FIGS. 111A and 111B illustrate a pad according to an embodiment of the present disclosure.

FIGS. 112A and 112B illustrate a pad according to another embodiment of the present disclosure.

FIG. 114A illustrates a pad according to another embodiment of the present disclosure.

FIGS. 114B and 114C illustrate a vein insertion without the pad of FIG. 114A.

FIGS. 115A-115C illustrate a pad according to another embodiment of the present disclosure.

FIG. 116 illustrates a visualization system according to another embodiment of the present disclosure.

FIG. 117 illustrates a visualization system according to another embodiment of the present disclosure.

FIGS. 118A and 118B illustrate an inserter assembly according to another embodiment of the present disclosure.

FIGS. 119A and 119B illustrate a visualization system according to another embodiment of the present disclosure.

FIGS. 120A-120D illustrate a vein distender according to an embodiment of the present disclosure.

FIG. 121 illustrates an inserter assembly according to another embodiment of the present disclosure.

FIGS. 122A-122D illustrate a visualization device according to another embodiment of the present disclosure.

FIG. 123 illustrates a visualization device according to another embodiment of the present disclosure.

FIG. 124 illustrates a sterile adhesive according to another embodiment of the present disclosure.

Figure 125B:
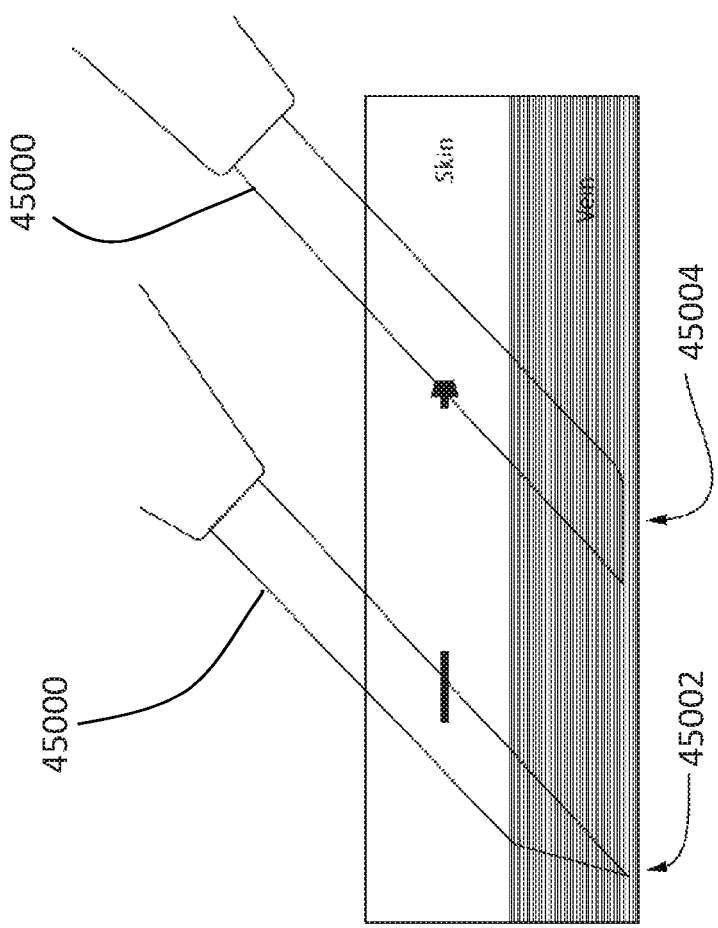
Figure 125A:
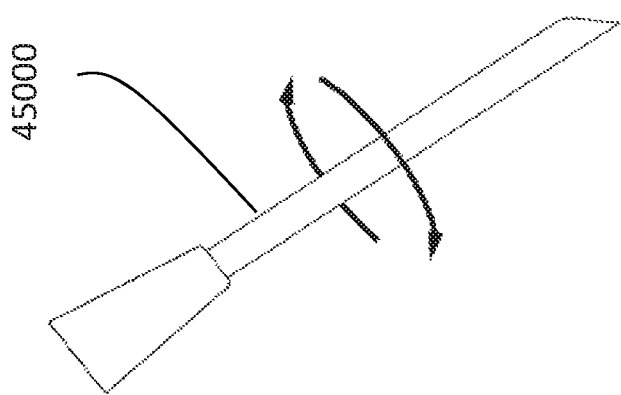

FIGS. 125A and B illustrate a needle according to an embodiment of the present disclosure.

Figure 126:
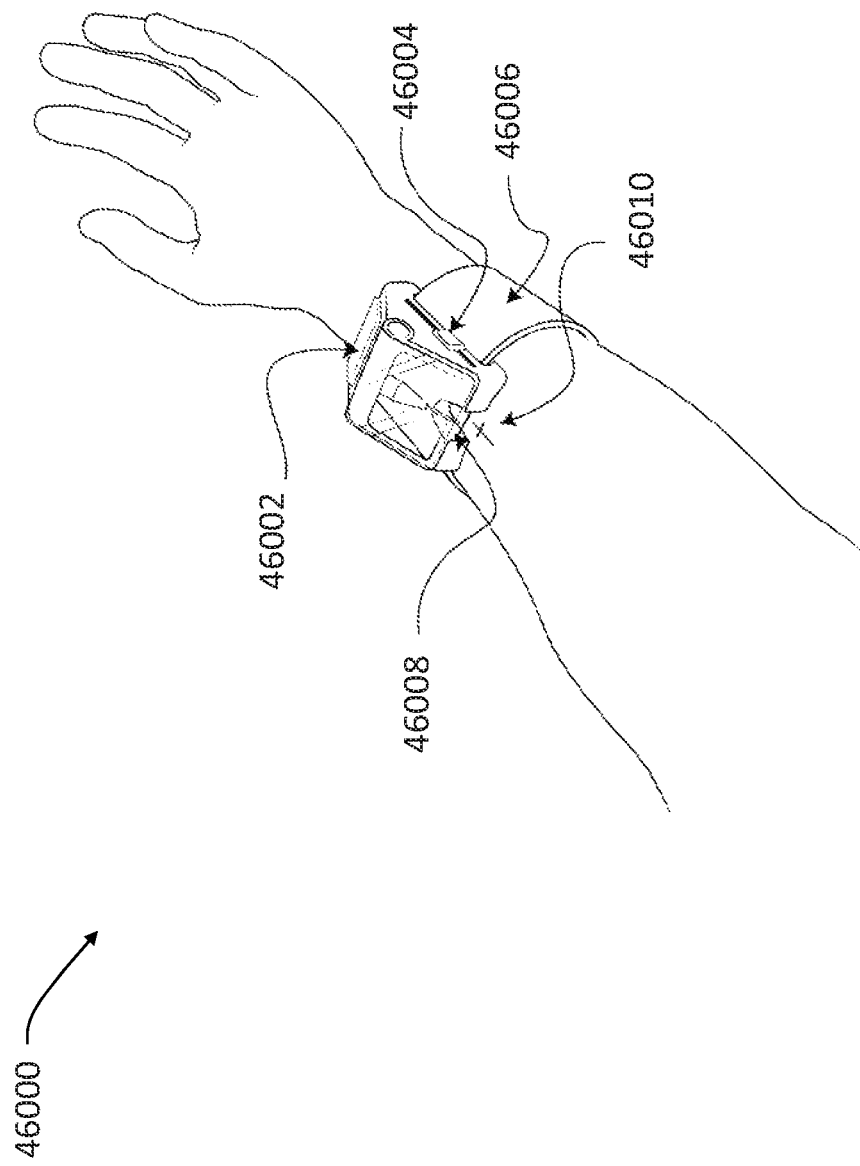

FIG. 126 illustrates an inserter assembly according to another embodiment of the present disclosure.

FIGS. 127A-127D illustrate a visualization assembly according to another embodiment of the present disclosure.

Figure 128B:
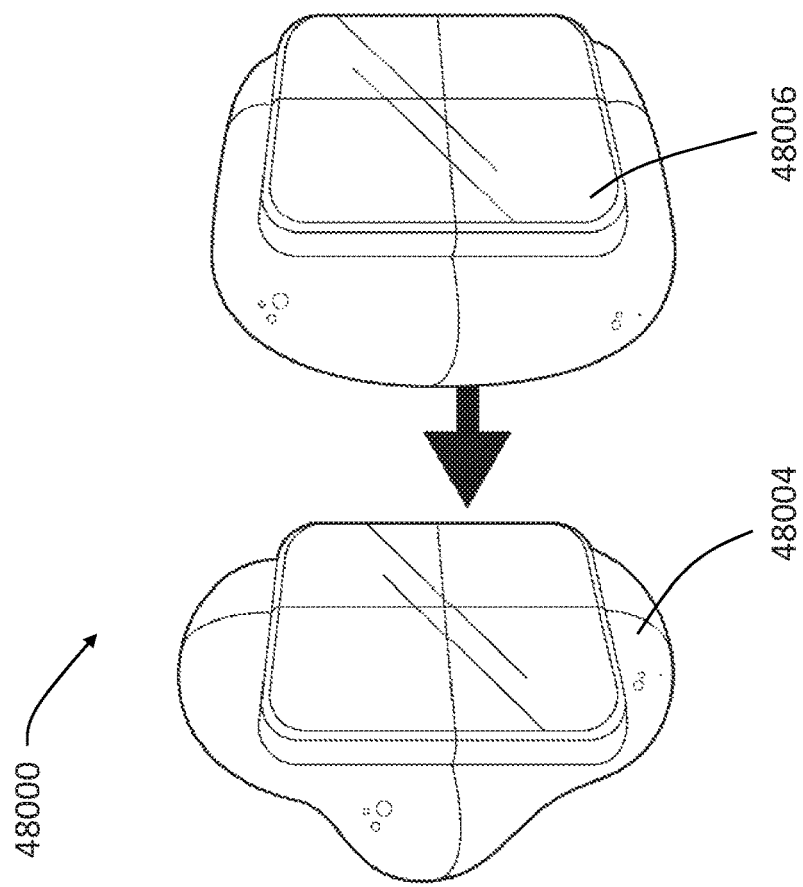
Figure 128A:
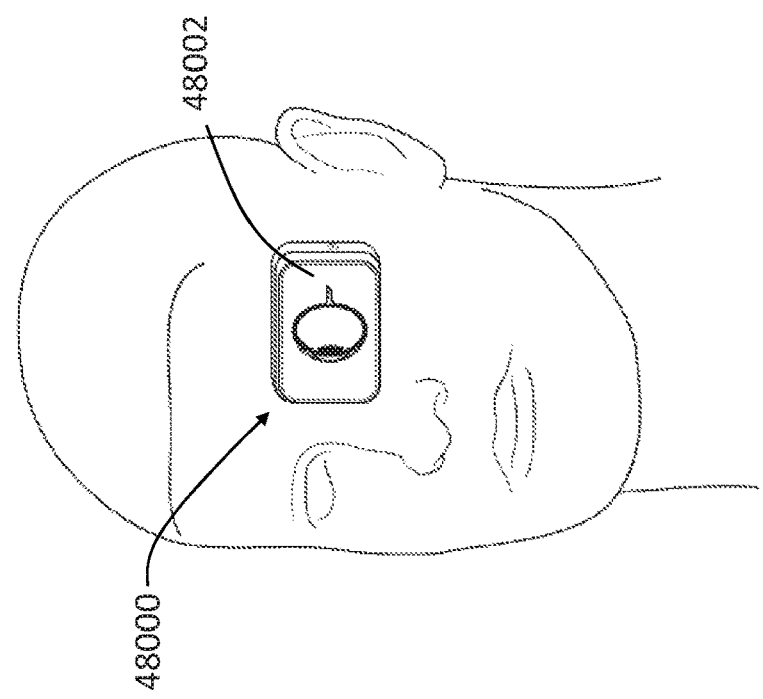

FIGS. 128A and 128B illustrate a visualization assembly according to another embodiment of the present disclosure.

DETAILED DESCRIPTION

As used herein, the terms "needle" and "cannula" will be used interchangeably and as such, unless otherwise stated, the explicit use of either term is inclusive of the other term. And typically, a cannula will be positioned into a patient by the use of a needle, whereby the needle is inserted first and the cannula is slid into the patient over the needle, at which time the needle is removed, leaving the cannula behind. The interchangeable terms needle and cannula also include similar devices such as micro-cannulae, sharp and blunt variations thereof, stiff or flexible variations thereof, and other tubular structures. Similarly, the term "circulatory system" means any blood vessel, vein, artery, microvasculature or the like. The term "puncture site" means a location on a patient through which an operator passes the needle or cannula, typically percutaneously, to position at least a portion of the needle or cannula into the patient. While the devices, techniques, systems, kits, and methods of the present disclosure typically refer to, or provide examples of, insertion of the needle or cannula into the circulatory system, the present disclosure also envisions positioning a needle or cannula into other anatomical locations, such as a "transosseous" technique where at least a portion of the needle is positioned within a bone (e.g., within the intramedullary canal) of the patient.

As used herein, "semi-autonomous" means that a device can perform a function with some degree of operator (e.g., nurse, technician, doctor, etc.) interaction. For example, a "semi-autonomous" feature may require that the operator assist in navigating the device to a general area of an intended puncture site by viewing a user-interface and manipulating device, while the device itself, once in the general area, can further navigate to the exact puncture site location. Semi-autonomous may additionally include, for example, an operator holding or controlling the cannula or a connected structure to perform some or all of the positioning degrees of motion, under image guidance, and supplemented with partial robotic positioning assist—such as a robotic auto-correct capability. On the other hand, an "autonomous" or a "fully autonomous" feature would be able to perform a particular function entirely without or with minimal need for operator interaction, or with minimal need for operator interaction. For example, once a puncture site has been located, the operator can confirm the location is correct by pressing a button, actuator, display screen gesture, or the like, and that act initiates the device to manipulate the needle to the puncture site and insert the needle at the puncture site and to the circulatory system, all without any interaction from the operator. The terms "semi-autonomous" and "autonomous" can be used to describe the device generally, describe a particular function, or any group of functions.

The "operator" or "user," defined above and used throughout, may be a single individual or more than one individuals, as the case may be. For example, while it is possible that a single user performs all of the steps of a particular use of one of the devices herein, it may also be possible that more than one user is involved, such that each user performs some but not all of the steps. Furthering this example, a first user (e.g., a lay person, assistant, first responder, member of the public, or the like) may perform the less skilled steps of attaching the device to the patient, while a skilled individual (e.g., a technician, doctor, nurse, or the like) performs the subsequent steps of positioning and inserting the needle, and so on.

As used herein, the terms "gel pad," "patch," and "pad" will be used interchangeably and as such, unless otherwise stated, the explicit use of any of these terms is inclusive of the other terms. As used herein, the terms "needle actuation system," "inserter assembly," and "cannulation module" will be used interchangeably and as such, unless otherwise stated, the explicit use of any of these terms is inclusive of the other terms. As used herein, the terms "sensor array," "sensor(s)," and "transducers" will be used interchangeably and as such, unless otherwise stated, the explicit use of any of these terms is inclusive of the other terms.

The present invention may be used to visualize any anatomy and/or medical device or instrument desired, and further may be used on its own as a visualization tool (e.g., for diagnosis, to view healing following trauma or surgery, or the like) or in conjunction with any medical devices or instruments desired. Similarly, the present invention is envisioned as being used on any anatomy desired. However, for the ease of review and explanation, most examples discussed herein will focus on use with a needle being used to puncture the skin and/or access the vasculature of a patient. While such embodiments are merely exemplary, they do provide an illustration of the benefits associated with the present invention. Further, the present invention may be used as a stand-alone imaging system for any imaging procedures such as abdominal, venous, pelvic, transabdominal, transvaginal, transrectal, obstetric, carotid and abdominal aorta imaging.

A sensor for visualization disclosed herein can include capacitive micromachined ultrasonic transducers (CMUT), piezoelectric micromachined ultrasonic transducers (PMUT), or any other suitable transducers. However, for the ease of review and explanation, most examples discussed herein will focus on use of CMUT sensors.

The Device, Generally

Devices of the present disclosure are generally applicable to semi- or fully autonomous positioning of needles or cannulae into a patient. Such devices can include various features to provide semi- or fully autonomous functionality, such as gross and/or fine positioning, mapping and tracking elements, needle control and positioning elements, sanitization and puncture site preparation elements, pain management elements, patient distraction elements, and/or the like.

A device of the present disclosure can be laid on the skin of patient to produce an image on the other side from the side in contact with the skin. Therefore, in certain embodiments, these devices are configured to be light, thin, and/or have the capability of generating images with sufficient resolution and/or to maintain real-time scan control for various procedures. CMUT, PMUT or other suitable transducers can be used to capture real-time images. A combination of CMUT and PMUT can be used in some embodiments to optimize the device for specific applications. For example, the device can include CMUT transducers in some regions to obtain detailed imaging data, and PMUT transducers can be utilized in other regions to reduce power consumption of the device. In addition to the transducers, these devices can include mixed signal electronics on an integrated circuit, which can be bonded to the transducers. The device can receive data from the sensing integrated circuit and interface with a display subsystem. For each beam in a scan, a digital component such as a Field Programmable Gate Array ("FPGA") can transmit parameters required by the integrated circuit to determine beam angle, frequency and a host of other parameters.

As illustrated in FIGS. 1A-H, in one embodiment of such a device, a device 10 of the present disclosure includes generally three components—a housing 100, a base 200, and an inserter assembly 300. The housing 100 includes the various elements that provide functionality to the device, such as positioning, mapping and tracking elements, needle control and positioning elements, pain management capabilities, patient distraction capabilities, and the like. Thus, housing 100 must be of a size sufficient to house all such elements. For example, a device used in a hospital for performing multiple daily needle insertions and requiring the ability to be coupled with multiple needles and other accessories may require a relatively large housing, whereas a device configured to be a portable and designed for specific applications without requiring to be coupled with various needles and other accessories may have a more compact housing.

The base 200 provides for positioning and securing the device adjacent to the skin surface of a patient. As illustrated, the base may include an outer frame 202 defining an internal volume and having an aperture 204 therethrough on at least one surface of frame 202. Base 200 can be mounted on the skin surface of a patient and secured thereto by at least one strap attached to the base. The aperture 204 provides a window 206 through which the inserter assembly 300, which includes a needle and/or cannula, can be positioned. Further, the aperture 204 allows for navigational aids (as discussed below), and/or other elements of housing 100 to interact with the patient.

Housing 100 may also include attachment features to allow for the housing to be readily attached and detached from the base 200. For example, at least a portion of the housing 100 may be positioned within the internal volume of the base 200 and held in place by friction fit, magnetic attraction, snap fit, or the like. Such positioning may allow the housing 100 to be in close proximity to window 206 which may provide for improved functionality of the various elements in the housing, as discussed in greater detail below. In an alternative arrangement, instead of being separate, connectable structures, the housing 100 and base 200 may be an integrated structure, or further may be a monolithic structure.

The insertion assembly 300 can be packaged or housed in a manner that allows for simplified engagement with the housing 100. As illustrated, housing 100 can include a recess 101 (FIGS. 1C and 1H-1I) to provide clearance for insertion assembly 300 once the device 10 is assembled, though other ways to configure the various elements to fit together are also envisioned. Insertion assembly 300 may include features contributing to its improved fit within device 10, improved stability, improved functionality, such as fins 301 (FIG. 1E) which may both lay flat against base 200 on either side of aperture 204, prior to use to maintain relative positioning of base 200, assembly 300 and optional protective visor 700, and provide a stable contact base for the assembly 300 against the patient's skin during use.

In addition to the needle and/or cannula, the inserter assembly 300 can also include clamps and valves, a length of tubing, filters, the catheter body back to a luer lock, any combination of these, or the like. As such, the insertion assembly 300 can include the entire intravenous system (as commonly known in the art) or any portion of the intravenous system, though the inserter assembly would typically include at least the needle and/or cannula to initiate the intravenous installation process. Alternatively, the inserter assembly 300 could include just the needle, or the needle and a vial, for less complex procedures, such as for taking a blood sample from the patient. Additional examples of inserter assemblies are discussed below. In the above alternative arrangement of an integrated or monolithic structure, the insertion assembly 300 may similarly be part of an integrated or monolithic structure.

Figure 1B:
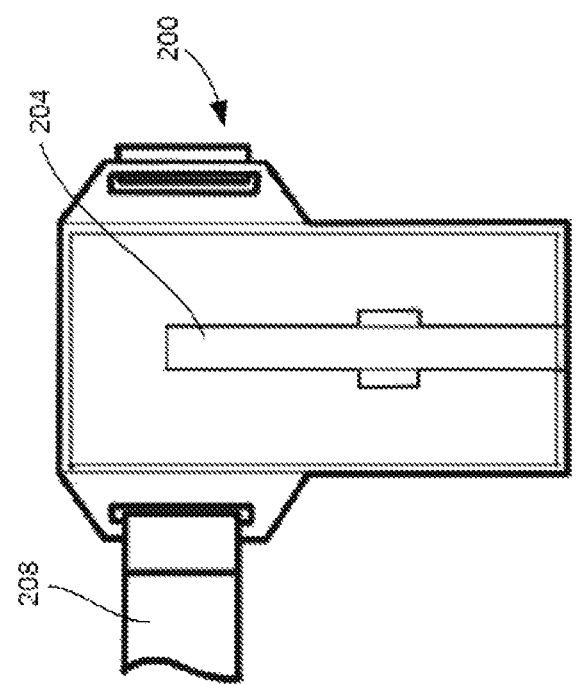
Figure 1A:
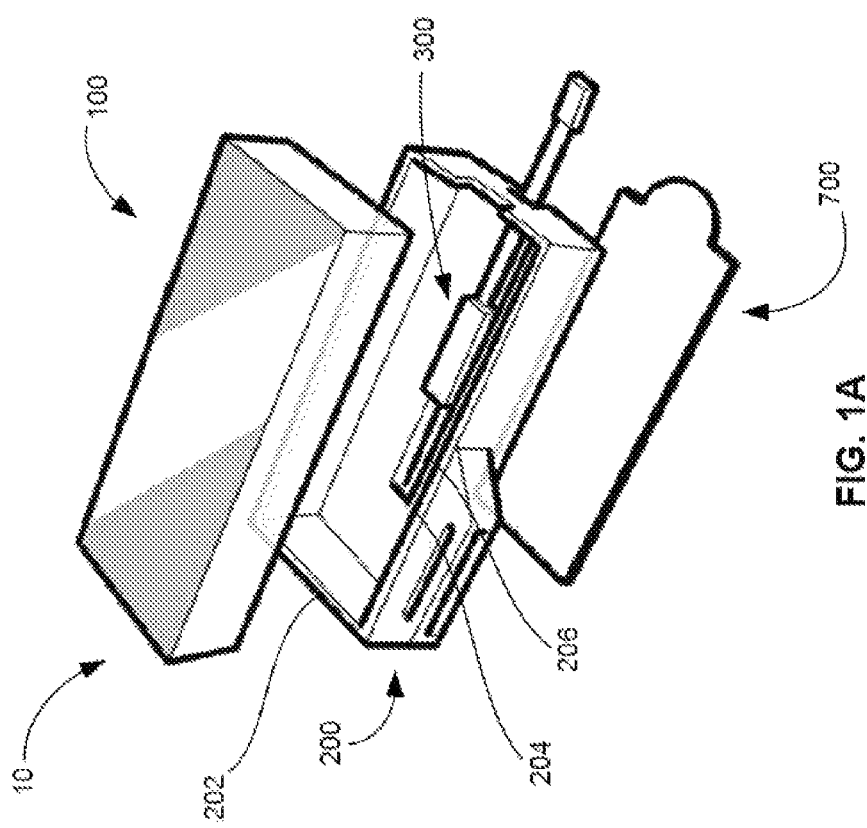

The device 10 may further include a protective visor 700 which may be positioned on the underside of base 200, as illustrated in FIG. 1A, such that it is positioned between base 200 and the skin surface of the patient. Prior to use, and/or prior to connection of housing 100 to base 200, visor 700 may serve to maintain inserter assembly 300 within aperture 204. Further, visor 700 can have other features such that it can perform other functions. For example, visor 700 could provide a nonsterile surface for use while locating a puncture site, such that, once the puncture site is determined, it can be removed to expose a sterile base 200 surface for positioning at the puncture site. Alternatively, for example, visor 700 could include a sterilizing composition on it to sterilize the skin surface during the positioning process of locating the puncture site. Still further, for example, visor could include optical properties such that it may aid the scanning and visualization of the puncture site and/or could include a layer of saline hydrogel for use with ultrasound, if included on the device.

FIGS. 2A-E illustrate a device 20 according to another embodiment of the present disclosure. Device 20 is similar to device 10 in some aspects and includes a housing 400 that may be docked on a base 500. Base 500 may include a patient engagement feature, such as at least one strap 508, as illustrated, to mount and secure the device on the skin surface of a patient. Further, base 500 is constructed to be thinner than base 200 of FIG. 1, and thus housing 400 may engage base 500 in any way desired, such as by magnetic interaction, snap fit, press fit, or the like. Further, since base 500 is of a thinner construction, housing 400 need not be positioned within the volume of the base since the aperture 504 and inserter assembly 600 are close to the upper edge of base 500. Device 20 may perform a range of functions depending on the elements disposed within or attached to housing 400 and may include other features such as a patch or the like, as discussed above.

Figure 2D:
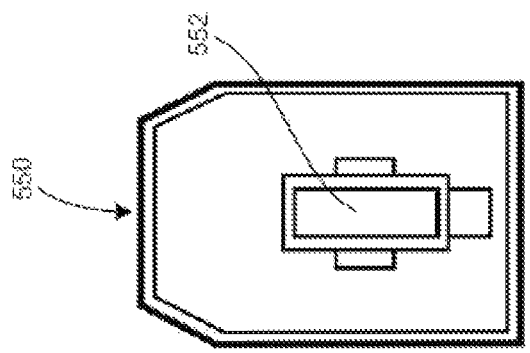
Figure 2C:
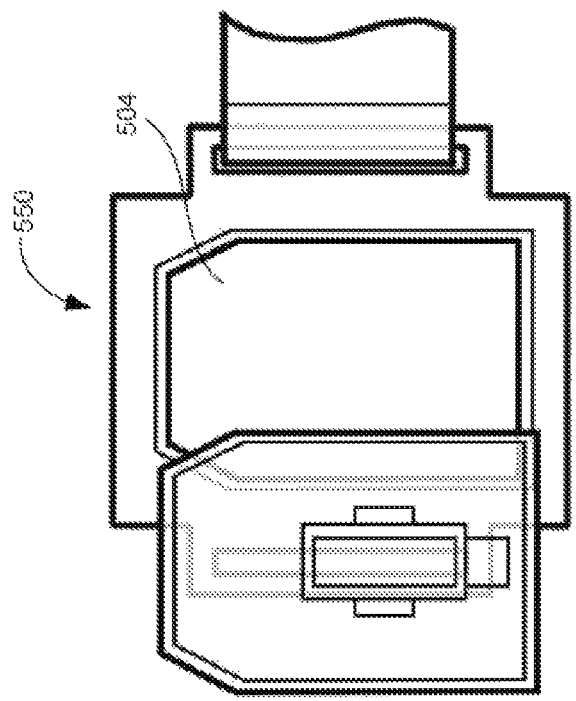
Figure 2E:
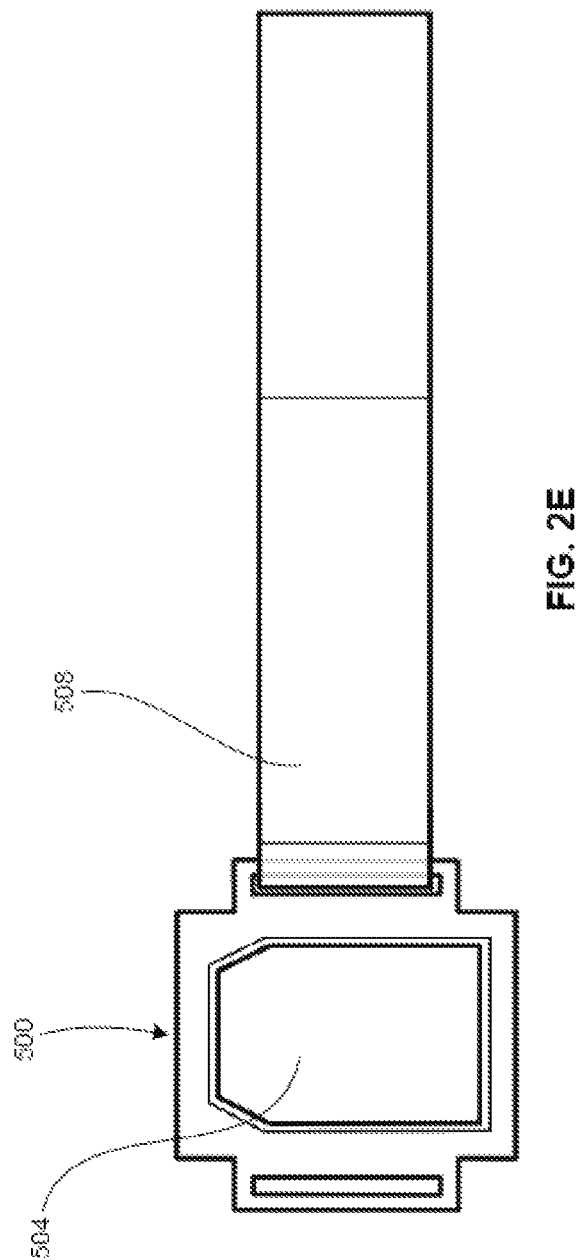

The device 20 includes aperture 504, as illustrated in FIG. 2C, and a plate 550 is positioned therein prior to use. As illustrated, plate 550 includes a holder 552 which may hold inserter assembly 600 in position relative to base 500 until housing 400 is coupled to the base, at which time housing 400 would also engage inserter assembly 600, rendering plate 550 unnecessary. As such, plate 550 is particularly useful to maintain the relative position of inserter assembly 600 to base 500 within its packaging and prior to use. For example, the plate 500 may remain in place once the base is removed from its package, and the base is positioned on the patient at or near a puncture site. Alternatively, for example, once the base is removed from its package, it may be coupled to the housing 400 such that the plate 550 is removed before the base is positioned on the skin surface. The aperture 504 may be of any size desired, and as illustrated, is quite large to allow freedom of access of the base and the various elements therein to the skin surface.

Figure 3A:
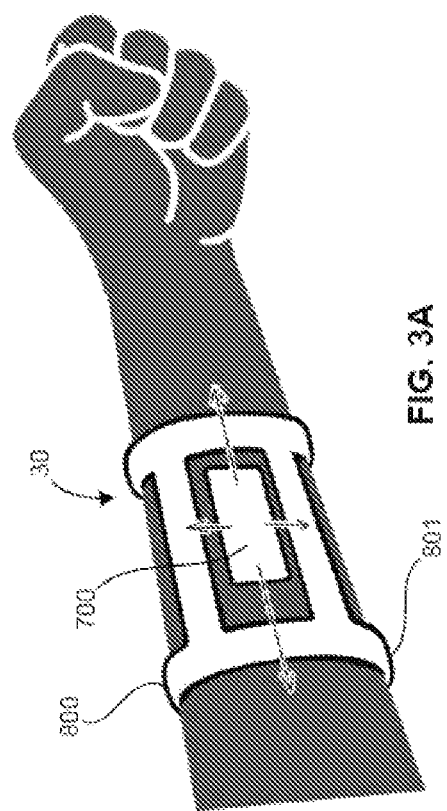
FIGS. 3A-3B illustrate various views of still another embodiment of a device of the present disclosure.
Figure 3B:
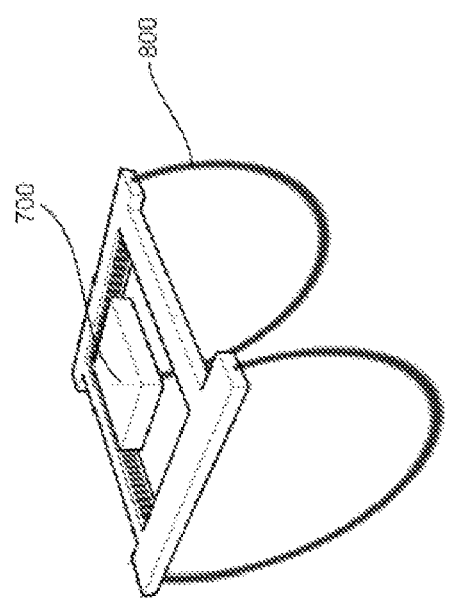

FIGS. 3A-3B illustrate another embodiment of the present disclosure. As illustrated, device 30 includes a housing 700 and a base 800, where the base in this embodiment is in the form of a wrap-around brace. Such a base 800 may be particularly useful for locating a puncture site and positioning the inserter assembly (not shown) therethrough on a hand or foot. Further to this embodiment, the housing 700 may not be stationary relative to base 800, but instead may be movable in at least one degree of motion. As discussed above, the housing may include various electronics to impart functionality to the device. Whereas the devices of FIGS. 1A-2E can be moveable along the length of the arm, base 800 is strapped around the specific anatomy of the hand or foot. Thus, as the base may have limited motion available to it, the housing 700 can move relative to the base to locate a puncture site and navigate the inserter assembly therethrough, as discussed below. Base 800 may also include a tourniquet 801 positioned proximal to the puncture site (i.e., between the puncture site and the heart) which is either physically and/or electronically integrated with the base, as illustrated, or separate and independent from the base (such as tourniquet 1801 of FIG. 4A). As discussed further below, an integrated tourniquet, whether physically, electrically, and/or via software, may provide additional functionality to the housing.

In a further embodiment, FIGS. 4A-4I illustrate various embodiments of a device including a base, housing, and each may include optionally an integrated tourniquet (though for ease of illustration only FIGS. 4A, 4B, 4H and 4I illustrate the tourniquet). Each of these embodiments may include a separate or modular setup including a base that is separate from the housing and which may be connected to one another in use, or alternatively, the base and housing may be integrated structures, or further may be a monolithic structure.

FIG. 4A illustrates one such embodiment in which device 130 includes base 1800 and housing 1700. As illustrated, base 1800 is elongate in shape with a generally rectangular aperture 1804 which accepts housing 1700, which is also generally rectangular in shape. Base 1800 is illustrated with two straps 1808*a*, 1808*b*, though any number of straps, or indeed, any other securement feature to secure the base to the patient, may be included. Housing 1700 may also include an inserter assembly 1900 thereon. Optionally, device 130 may also include tourniquet 1801 which may be connected to base 1800 and/or housing 1700 via connector 1802. As illustrated, connector 1802 can be rigid, such that the distance between the tourniquet and the base remains constant, which can result in a more stable structure once positioned on the patient. Alternatively, as discussed in greater detail below, connector 1802 may be flexible, or even may simply be a wire connection (e.g., for communication, power, or the like) between the tourniquet and the housing.

Device 130 may provide for a simplified setup in that housing 1700 and aperture 1804 allow for relative movement between base 1800 and housing 1700, such that base 1800 (and optionally tourniquet 1801) may be secured to the patient such that aperture 1804 comports with a general location of an intended puncture site (e.g., on the upper forearm of the patient). With base 1800 secured, the user may navigate housing 1700 within aperture 1804 and along and/or above the patient's skin until a desired puncture site is located and inserter assembly 1900 is aligned therewith. As illustrated, housing 1700 can move in any direction within aperture 1804, that is, along any of the x- (i.e., side to side), y- (i.e., along the length, or towards/away from tourniquet), and/or z-direction (i.e., towards/away from patient's skin).

Figure 4E:
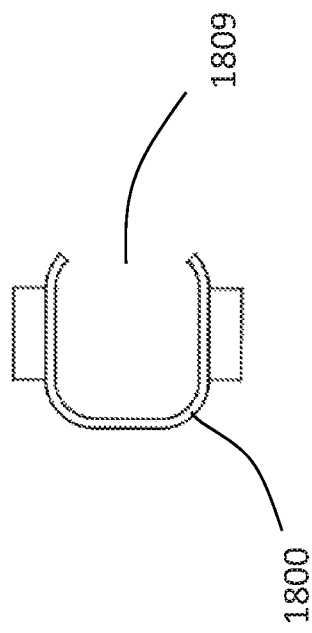

FIGS. 4B-4E illustrate various alternative embodiments to device 130. Specifically, while each of FIGS. 4B-4D include a similar housing and body to device 130, the strap associated with the body differs. For example, the device of FIG. 4B includes a single, offset strap which may be suited for attachment to a patient's hand or foot. That is, the strap is positioned proximal relative to the housing (and inserter assembly), such that the strap may be positioned on a more stable, wider portion of the hand or foot while the inserter assembly would be better positioned for alignment with a desired puncture site. FIG. 4C, on the other hand, includes a strap that is generally centered and aligned with the body and housing. While such a variation may still be suitable for positioning on the hand or foot, this variation may also be better suited for positioning elsewhere, such as on the forearm. Similarly, the device of FIG. 4D includes a strap that is much wider, and thus may be more suitable for positioning on the forearm or even larger anatomy, such as the upper arm or leg. The wider strap may provide added securement and stabilization to the device, similar to the two-strap variation of FIG. 4A. The straps can be formed of any material desired and suitable for use with a medical device which contacts a patient's skin, and may further include a coating if desired. For example, the strap may be formed of or include a conductive material, such as a hydrogel or the like, which can aid the navigational and other functions associated with housing 1700.

FIG. 4E illustrates a variation of base 1800 wherein the base may not completely surround the housing. Instead, the base may be incomplete such that an aperture 1809 within the base is open-ended. The degree to which the base is complete or incomplete can result in any shape desired.

Figure 4G:
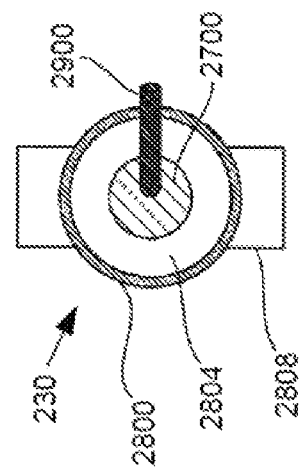
Figure 4F:
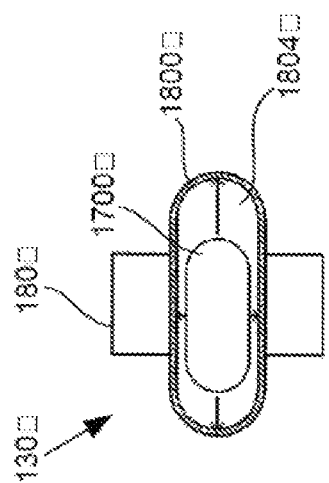

FIG. 4F provides yet another embodiment of a device 130', but instead of a generally rectangular shape, the base 1800' instead includes curved ends, and is thus a rectangle with curves at opposite ends. Housing 1700' is of a similar shape, as is aperture 1804'. A strap 1808' may also be included, and may be of any shape desired. In this embodiment, the width of aperture 1804' and the width of housing 1700' may be similar or close to similar, such that the housing 1700' can move in the y-direction (e.g., along the length of aperture 1804', and towards either of the curved ends) but has limited or zero movement in the x-direction (e.g., side to side). Such an embodiment may, for example, be useful in instances where longitudinal panning of the housing 1700' imaging or navigation feature is desired, along with limiting most if not all side-to-side motion of housing 1700'. Alternatively, the strap may also include a strap aperture which allows for the housing to slide in the side-to-side (X-direction) direction (as discussed below as to FIG. 6A).

FIGS. 4G-4I illustrate yet another alternative embodiment of a device 230 which is similar in certain ways as to device 130, as it includes base 2800 and housing 2700, but in this embodiment base and housing are both generally circular in shape and base 2800 includes an aperture 2804 that is also generally circular in shape and a single strap 2808. As in the other embodiments discussed above, device 230 may also include a tourniquet 2801 which can be an integrated aspect of device 230. FIGS. 4G-4I, however, illustrate another variation of a tourniquet which can be used with any embodiment disclosed herein, whereby in this variation tourniquet 2801 can be electrically connected via wired connection 2802 to the housing 2700, though this connection may be via Bluetooth or other wireless capability (e.g., as illustrated in FIGS. 8D-8E), or other connection. Alternatively, the tourniquet may be completely independent of device 230, both physically and communicatively. Further, FIGS. 4H-4I illustrate various potential anatomical positions of the devices disclosed herein, whereby the device 230 is illustrated as positioned on the hand, on the forearm, on the upper arm, or on the neck. Further, where a tourniquet is used, for example where device 230 is position on the hand, the tourniquet 2801 is positioned proximal to the housing 2700 and injection assembly 2900, to manage blood flow to the puncture site.

Figure 5B:
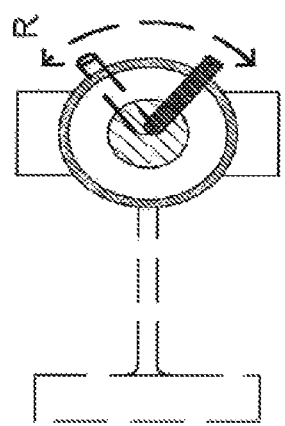
FIGS. 5A-5D illustrate representative movement of a housing of one embodiment of the present disclosure.
Figure 5D:
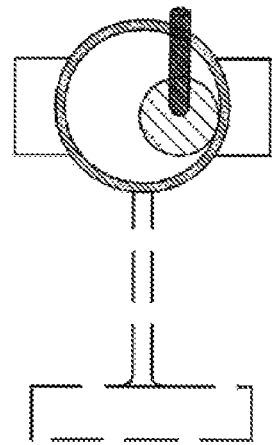
Figure 5A:
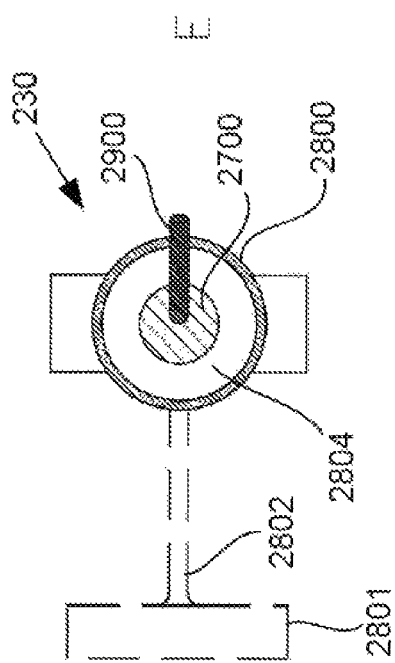
Figure 5C:
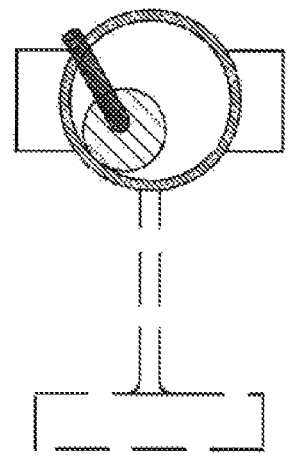

FIGS. 5A-5D illustrate representative directional movements of housing 2700 of the device 230 of FIG. 4G. FIG. 5A illustrates device 230 with integrated tourniquet 2801 in communication via wired connection 2802. FIG. 5B, for example, illustrates how housing 2700, and inserter assembly 2900, can rotate relative to body 2800, such that inserter assembly rotates along arc R. This rotational capability, along with the ability to move the housing 2700 within aperture 2804 in the x-, y-, and z-directions, as discussed above, allows for an infinite number of possible positions of inserter assembly 2900 within aperture 2804, whereby two such positions are illustrated in FIGS. 5C-5D.

In another embodiment, FIGS. 6A-6B illustrate another embodiment of device 130" which is similar to the shape of device 130' of FIG. 4F, though the aforementioned x-direction movement (e.g., side-to-side) is substantially eliminated such that housing 1700" may only pan in the y-direction within aperture 1804". Additionally, device 130" includes within strap 1808" a strap aperture 1809" within which a portion of base 1800" (or housing 1700" or other structure) can travel, thereby providing an additional direction of motion to housing 1700". Thus, as illustrated in FIG. 6B, housing 1700" can travel in each of the x-direction (i.e., X-pan), y-direction (i.e., Y-pan) and rotationally along an arc (i.e., Rotate). The ability for housing 1700" to travel in each of these directions, much like housing 2700 of FIGS. 5A-5D, provides for an infinite number of possible positions of housing 1700" (and an inserter assembly, if present) relative to the patient.

Figures 7A, 7B:
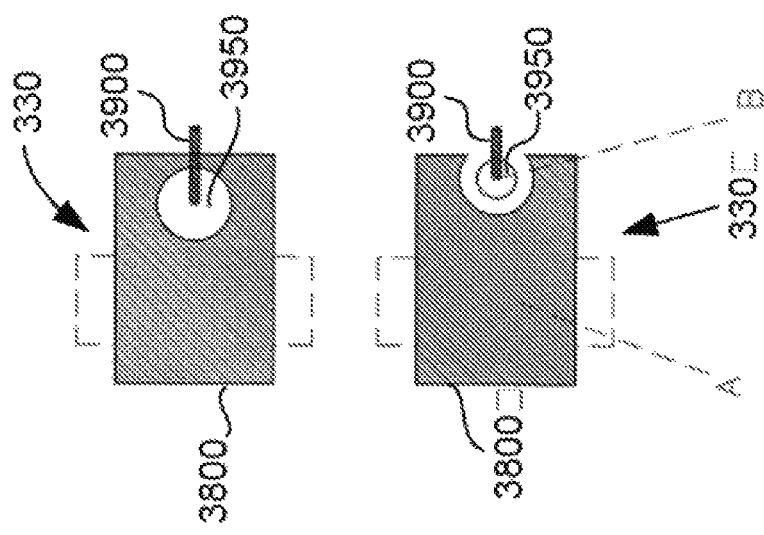
FIGS. 7A-7B illustrate various embodiments of a device of the present disclosure.

FIGS. 7A-7B illustrate yet further embodiments of a device 330, 330' including a monolithic body and housing 3800, 3800' and an inserter assembly 3900, 3900' that can move relative to body/housing 3800, 3800'. For instance, in FIG. 7A, assembly 3900 may be movable relative to body/housing 3800 via one or more micromotion mechanisms 3950 to allow for subtle movements of assembly 3900 relative to the patient's anatomy. Similarly, assembly 3900', illustrated in FIG. 7B, may be connected to body/housing 3800' via a ball joint mechanism 3950' which may similar provide for movement of assembly 3900. Either mechanism 3950, 3950' may allow for movement of assembly 3900, 3900' in any of the "XYZRTD" directions (as defined below) and may provide such motion at small increments.

While the various devices of FIGS. 1A-6B provide for a relatively large amount of movement, device 330, 330' of FIGS. 7A-7B are directed to a relatively small amount of movement. Thus, these devices may be used in different manners. For example, device 330, 330' would be positioned once the puncture site is already determined (whether by use of body/housing 3800, 3800' or by another device), and thus device 330 would not be secured to the patient until the puncture site is exactly determined. Alternatively, the other devices discussed above may be positioned at a general area where a puncture site is desired, such device is then secured to the patient, then the housing and/or inserter assembly can be moved to find a desired puncture site. Of course, any of the devices discussed herein could include a combination of these motion features, such that, for example, a device could be capable of both relatively large motion as well as relatively small motion (i.e., the relatively larger motions could be used to locate the puncture site, and then the relatively small motions could be used to navigate a needle tip to and through the puncture site).

Figure 8A:
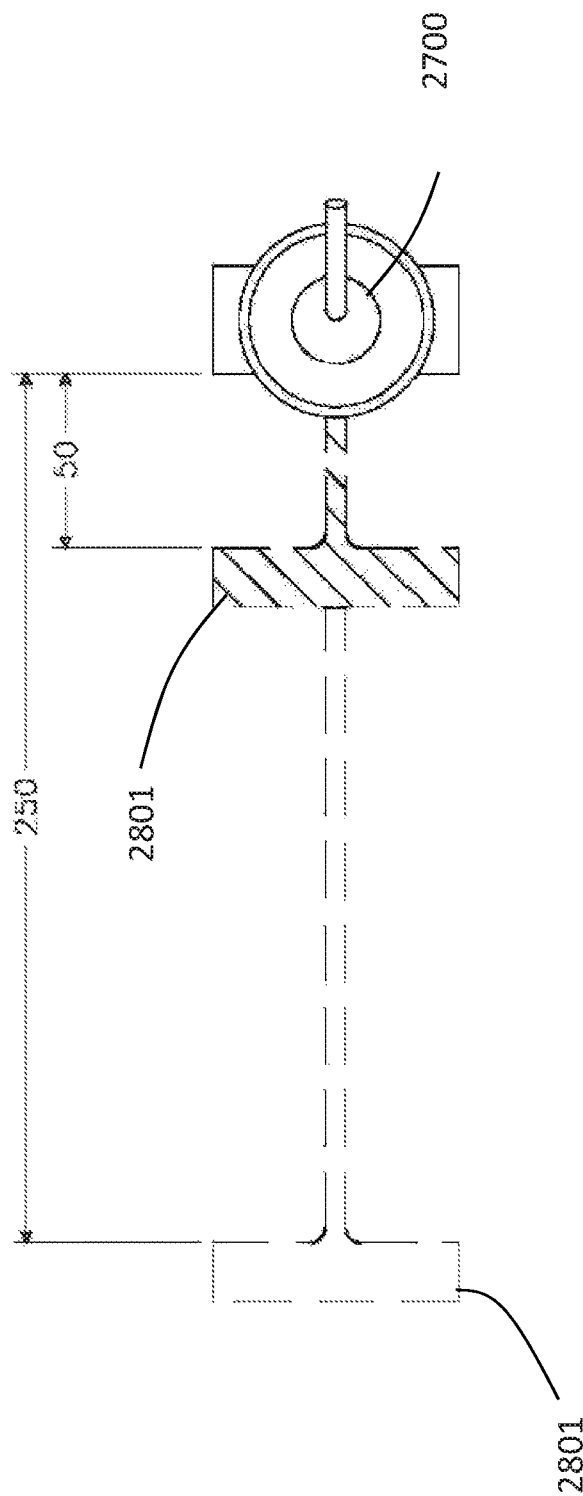
Figure 8E:
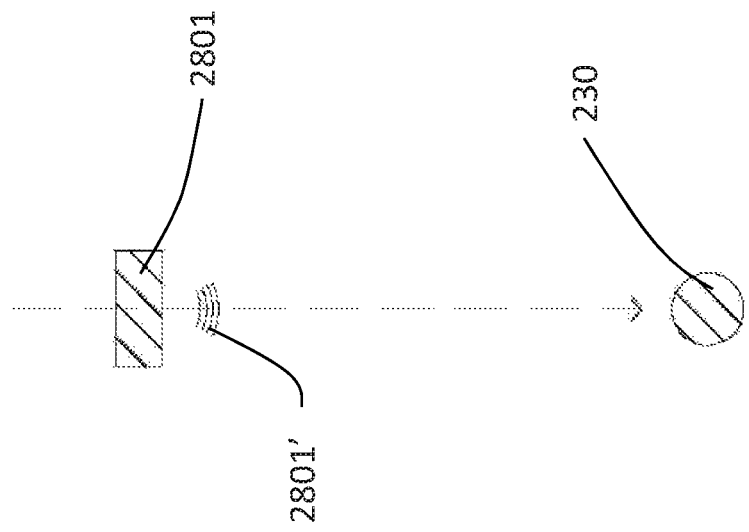
Figure 8D:
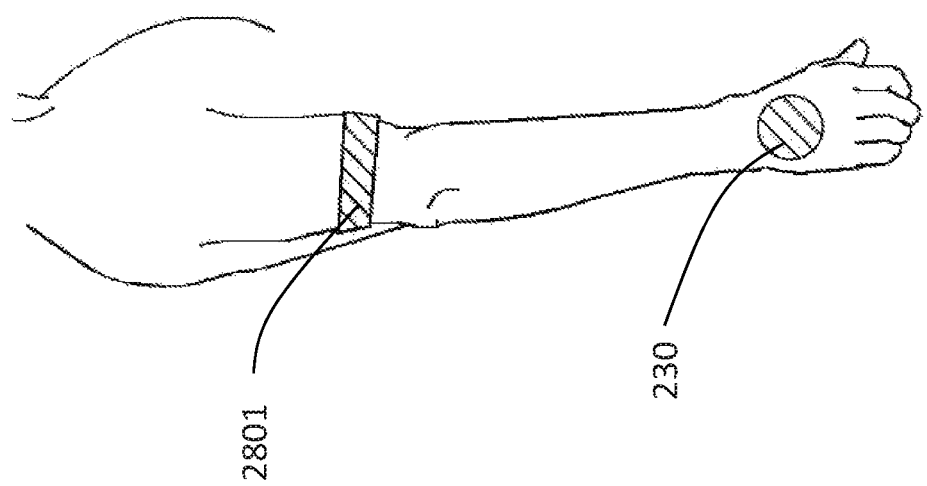

Turning back to the optional tourniquet, FIGS. 8A-8C illustrate various locations of optional tourniquet 2801 relative to the device (i.e., the housing/body). While the variations illustrated are possible locations, any other locations of a tourniquet relative to the housing/body of the device are envisioned. Likewise, a wireless 2801' (or otherwise not physically connected) tourniquet 2801, such as is illustrated in FIGS. 8D-8E, may also be positioned at any distance relative to the housing/body 230 as desired.

Figure 105:
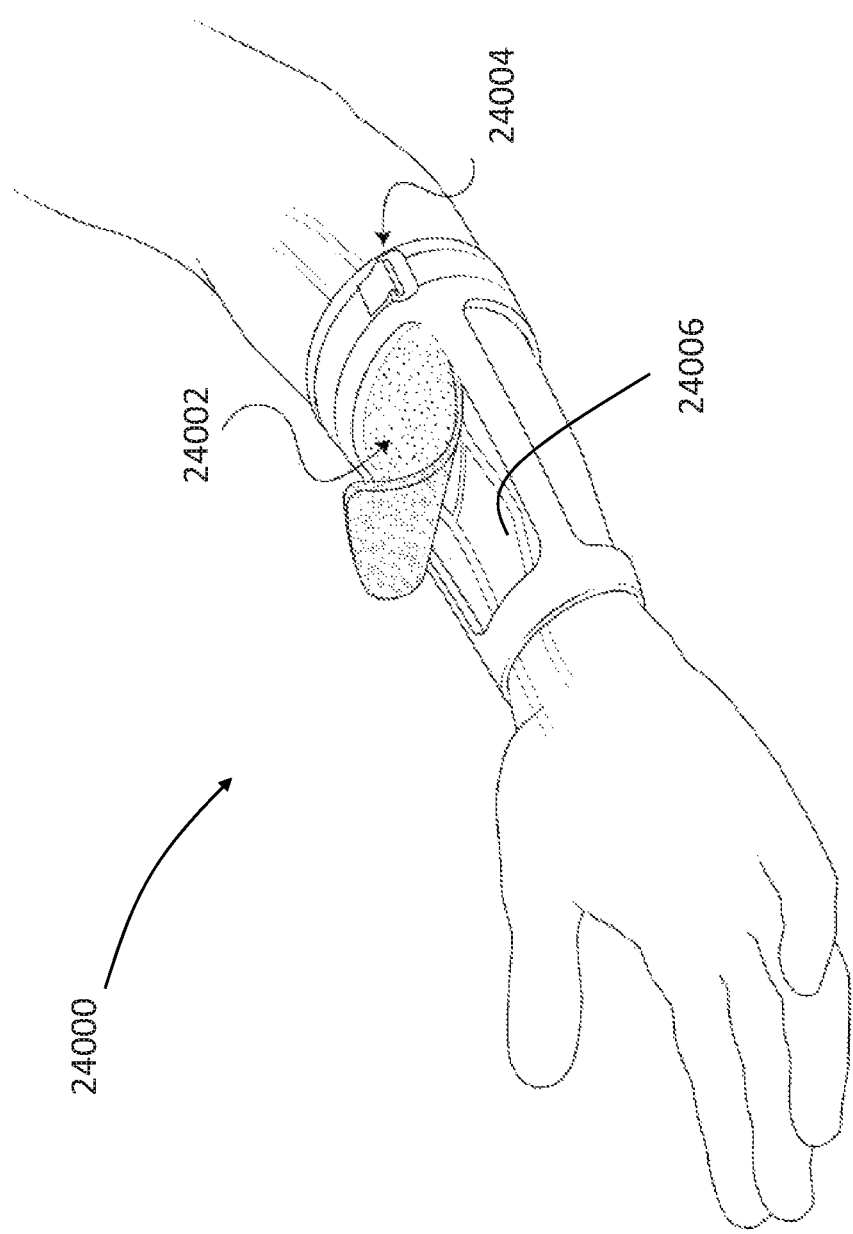
FIG. 105 illustrates a brace according to another embodiment of the present disclosure.
Figure 106:
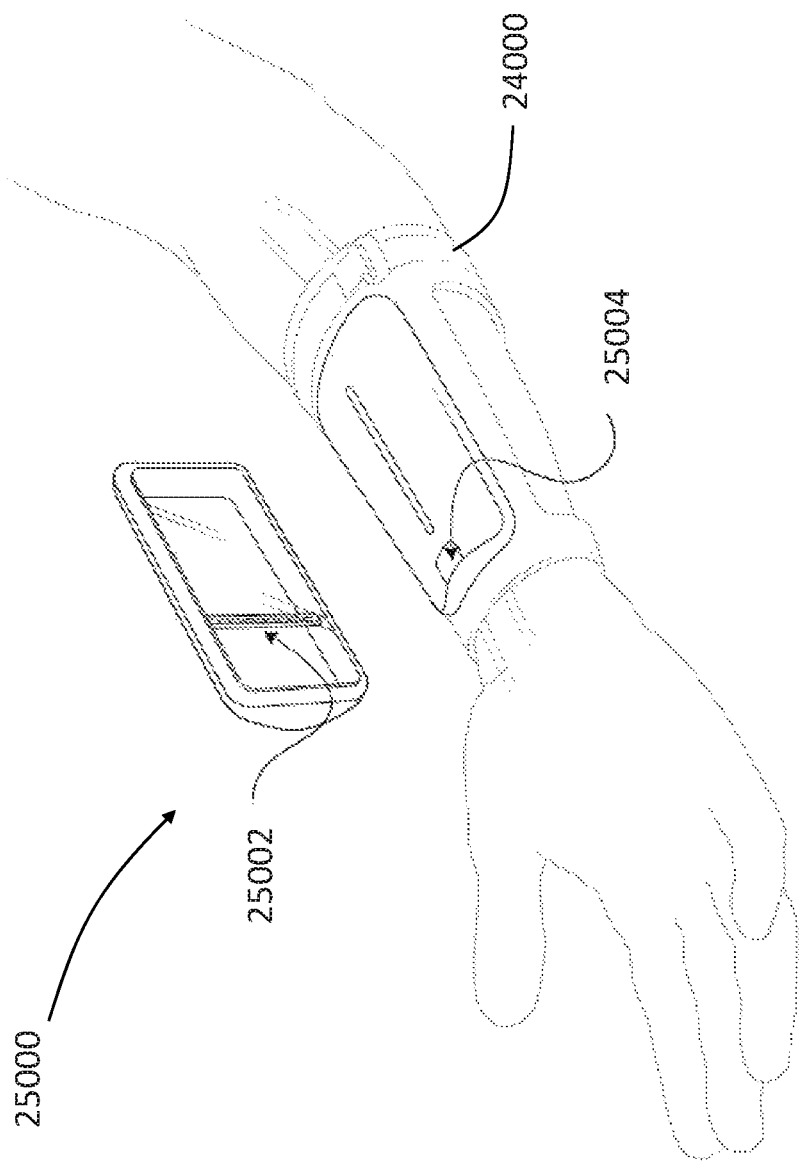
FIG. 106 illustrates a visualization device according to another embodiment of the present disclosure coupled to the brace of FIG. 105.

Referring now to FIG. 105, there is shown a brace 24000 according to another embodiment of the present disclosure. Brace 24000 includes a tourniquet 24004 with an integrated strap to adjust tension of the tourniquet. A window 24006 to receive a pad 24002 is provided. Various devices including visualization devices and inserter assemblies can be docket to window 24006.

Various other types of straps may also be used with any of the devices discussed above, some of which are disclosed and illustrated more fully below. Further, instead of just a single base and a single housing, a device of the present disclosure may include multiple housings, each of which capable of performing a separate function or a portion of the desired functions.

Figure 21B:
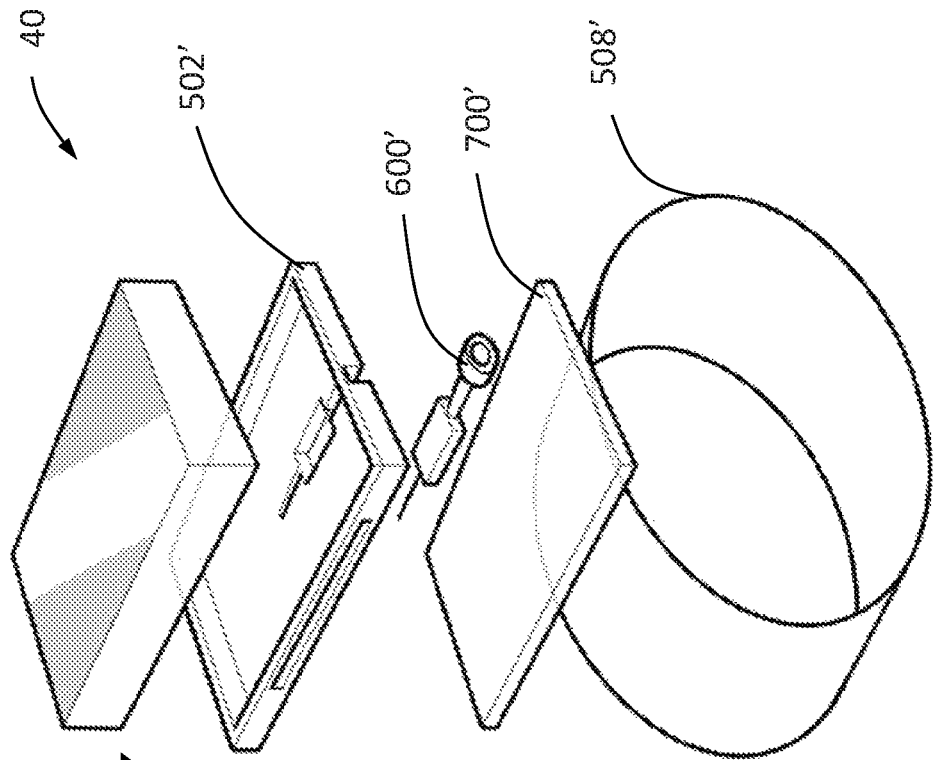
FIGS. 21A and 21B illustrate another embodiment of a device of the present disclosure in a perspective and exploded view, respectively.
Figure 21A:
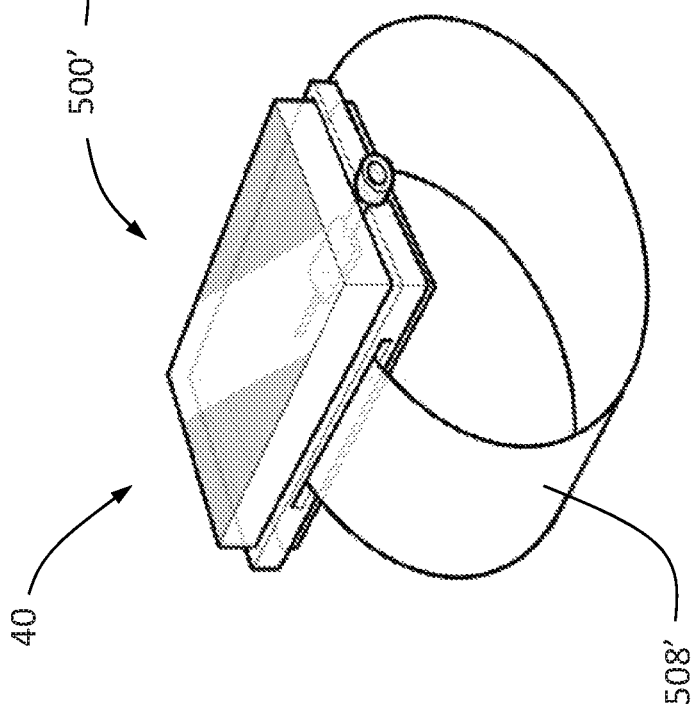

FIGS. 21A and 21B show device 40 according to another embodiment of the present disclosure. Device 40 is generally similar to device 20, but includes strap 508' that extends through outer frame 502' as best shown in FIG. 21A. This arrangement allows pre-injection patch 700' to be placed over strap 508' (FIG. 21B) or under strap 508' (not shown). Strap 508' can be used to secure injection pre-injection patch 700' when strap 508' is placed over the pre-injection patch.

Figure 22:
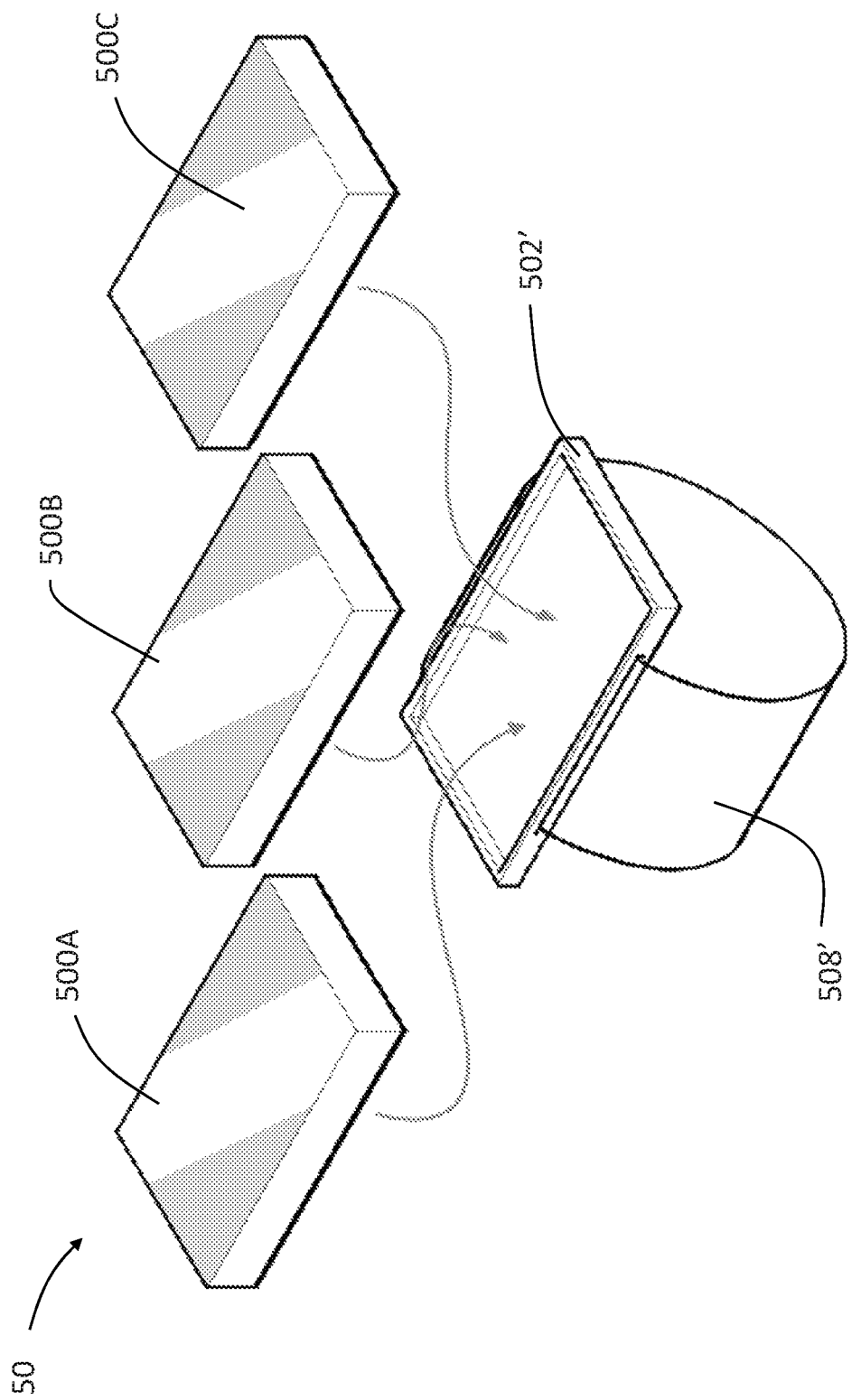
FIG. 22 illustrates another embodiment to a device of the present disclosure.

Referring now to FIG. 22, there is shown a device 50 according to another embodiment of the present disclosure. Device 50 is generally similar to device 50, but includes multiple modules that interface with outer frame 502'. A vein preparation module 500A is attached to outer frame 502' which is attached to a patient by strap 508'. Vein preparation module 500A assists in determining a vein, versus a (typically less compressible) artery. Vein preparation module 500A can additionally vibrate or implement a tapping motion to stimulate vessels so as to be more optimal, more dilated, and/or raise closer to the dermal surface, for more cannulation conditions—i.e., so to increase the size of the lumen, and become an easier target. Vein preparation module 500A can then be replaced with imager module 500B to investigate vasculature and identify ideal injection sites. Finally, cannulation module 500C can be coupled to outer frame 502' to place the needle into the prepared and predetermined vein location. While a device with three modules for a needle insertion procedure is described here, other embodiments may have two, four or more modules configured specifically for other procedures.

Various strapping configuration according to another embodiment of the present disclosure are shown in FIGS. 23A-23C. FIG. 23A shows a strap 608 that can be applied below base 100. Strap 708 extents through base 100 as shown in FIG. 23B. Strap 808 can be placed on top of base 100 as shown in FIG. 23C. The required strapping configuration can be selected depending on the securement required to attach a device to a patient.

Figure 24B:
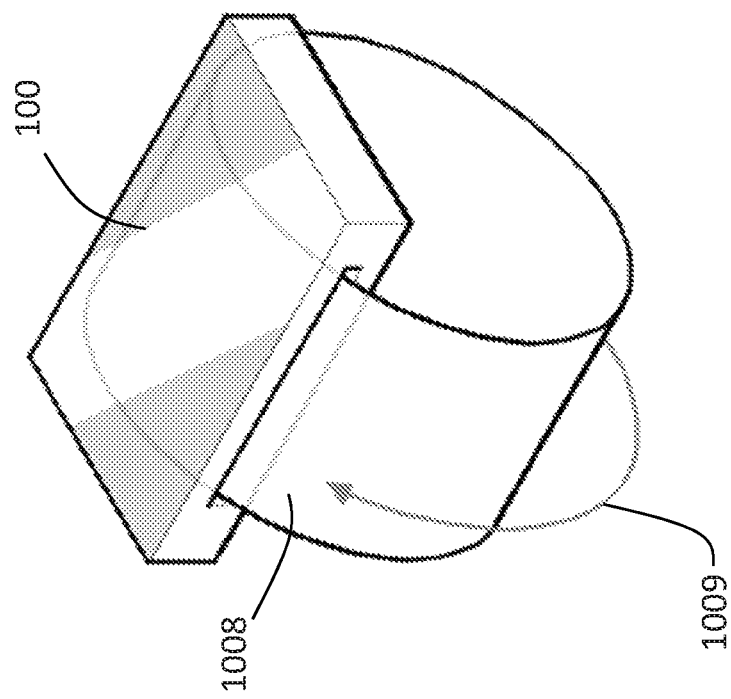
FIGS. 24A-24C illustrate another embodiment of a strap of the present disclosure.
Figure 24A:
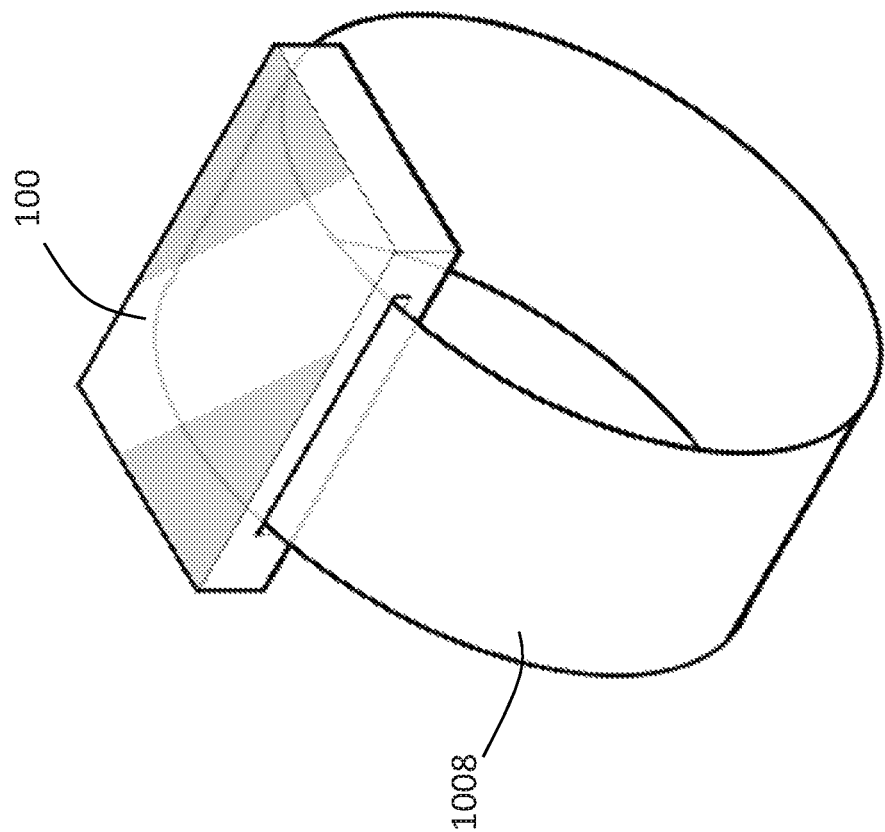
Figure 24C:
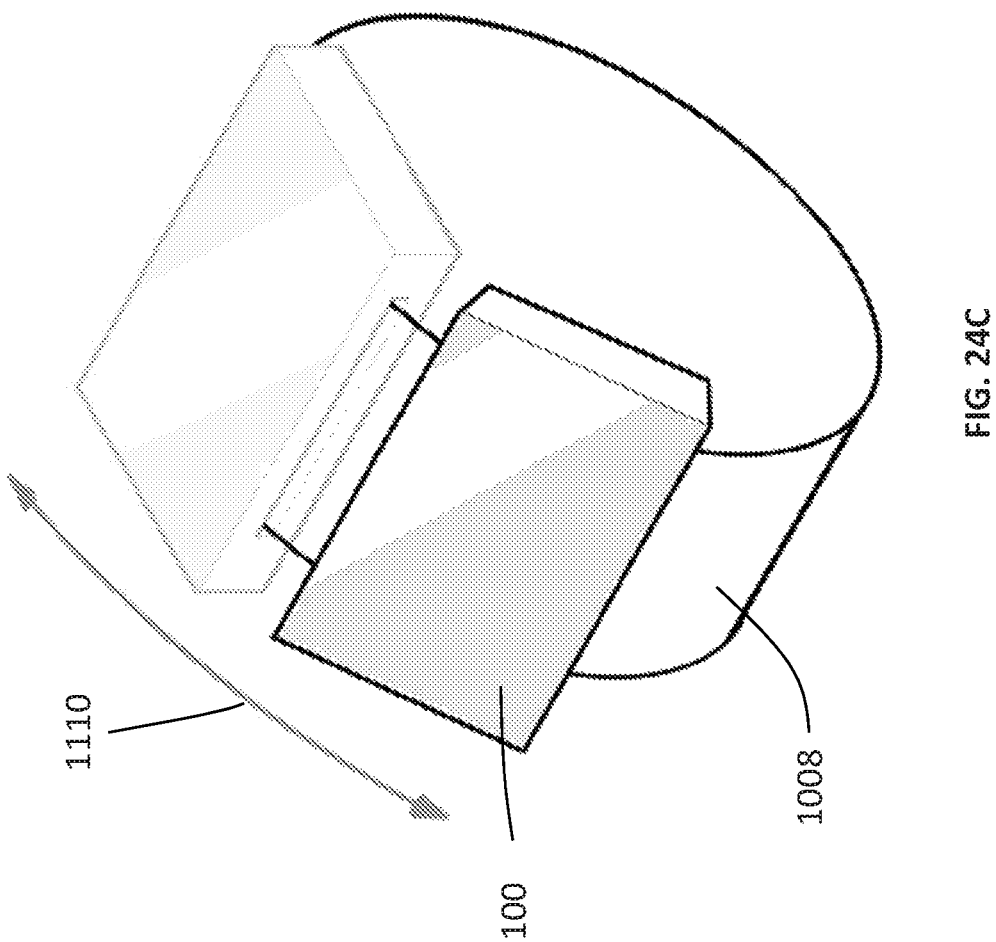

In another embodiment, an auto-tightening strap 1008 as shown in FIGS. 24A-24C is provided. Auto-tightening strap 1008 is configured to automatically tighten around an appendage as indicated by direction arrow 1009 to secure the device. Auto-tightening strap 1008 can be calibrated to tighten to a desired tension to provide precise tension during the procedure. As the auto-tightening strap is a self-tightening strap, no manipulation from an operator is required to secure the device to an appendage. As best seen in FIG. 24C, auto-tightening strap 1008 allows device to be automatically adjusted along an axis of securement 1110 to find the ideal location for the device.

Referring now to FIGS. 25A-25 I, there are shown various embodiments of a strap of the present disclosure. Strap 508A shown in FIG. 25A can be worn by a patient, allowing an operator to attach housing 100 prior to the needle insertion. Upon completion of the needle insertion or other procedure, housing 100 can be readily detached from strap 508A leaving strap 508A at the surgical site. Attached strap 508A can be reused to access the same surgical site if necessary.

Figure 25B:
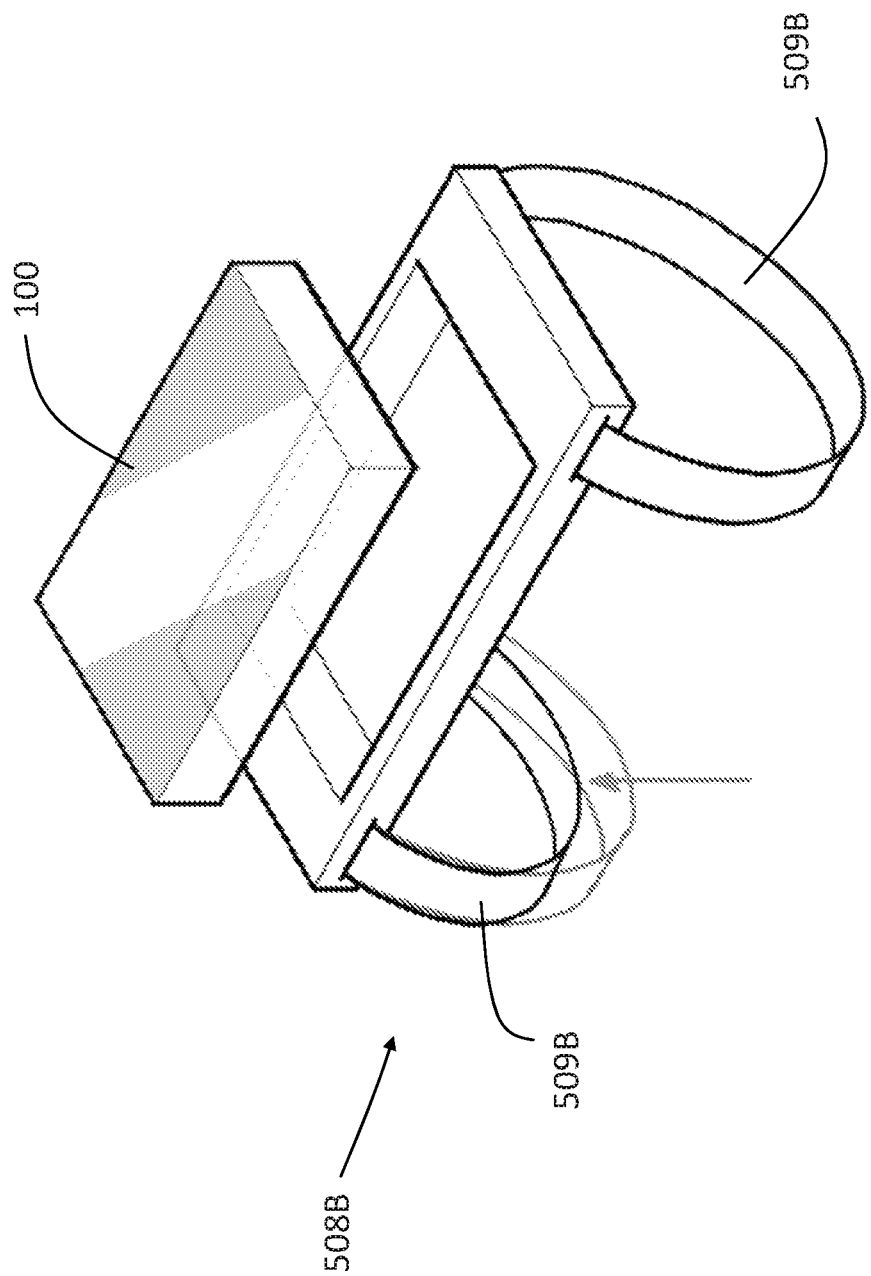

Strap 508B shown in FIG. 25B includes one or more self-tightening tourniquets 509B. Self-tightening tourniquet 509B can automatically tighten around veins to block venous blood flow during needle insertion.

Figure 25C:
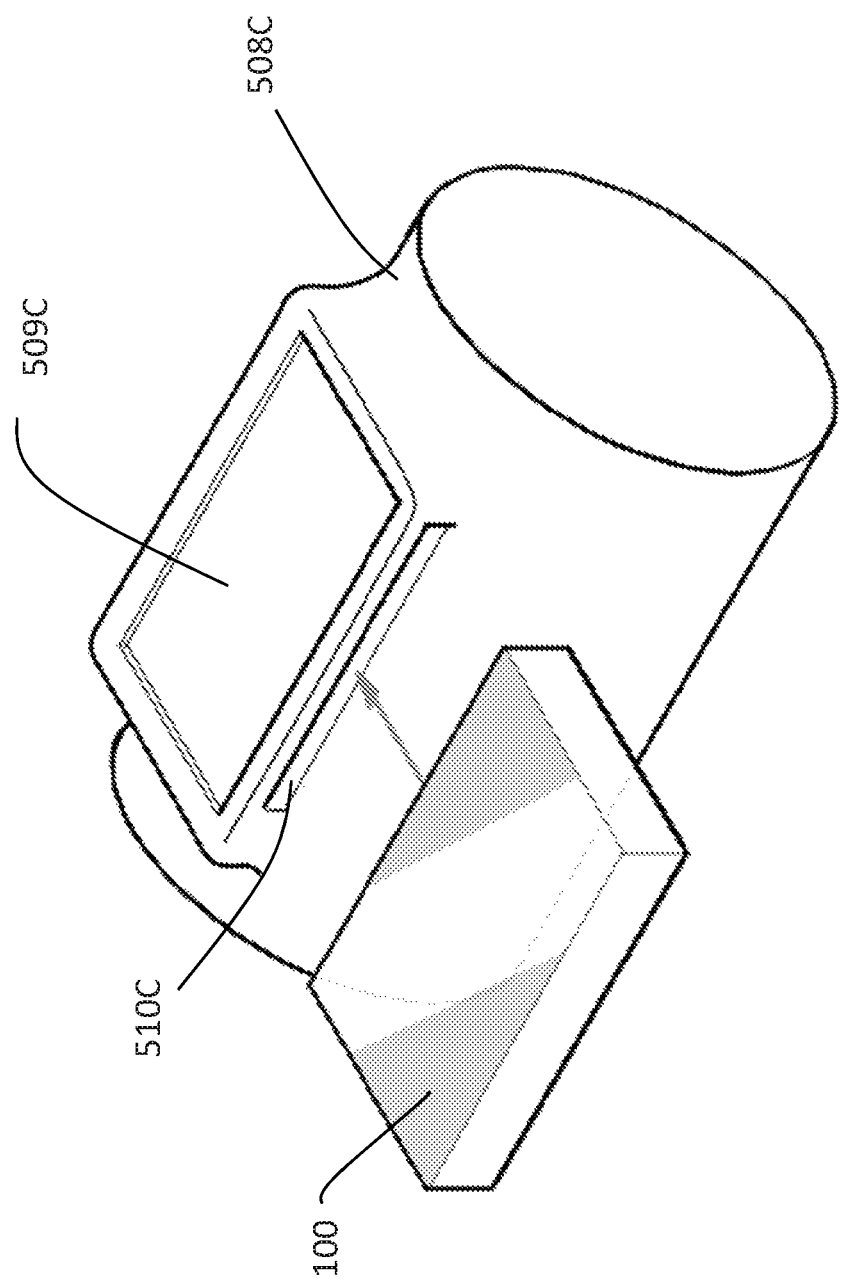

FIG. 25C shows a strap 508C according to another embodiment of the present disclosure. Strap 508C is configured as a sleeve that can be attached to patient's appendage such as an arm or a leg. Housing 100 can be attached to strap 508C via an opening 509C or a side slot 510C on the sleeve. Strap 508C can be made of polyester, spandex, etc. to form a low profile sleeve that can be integrated with a patient's body.

Figure 25D:
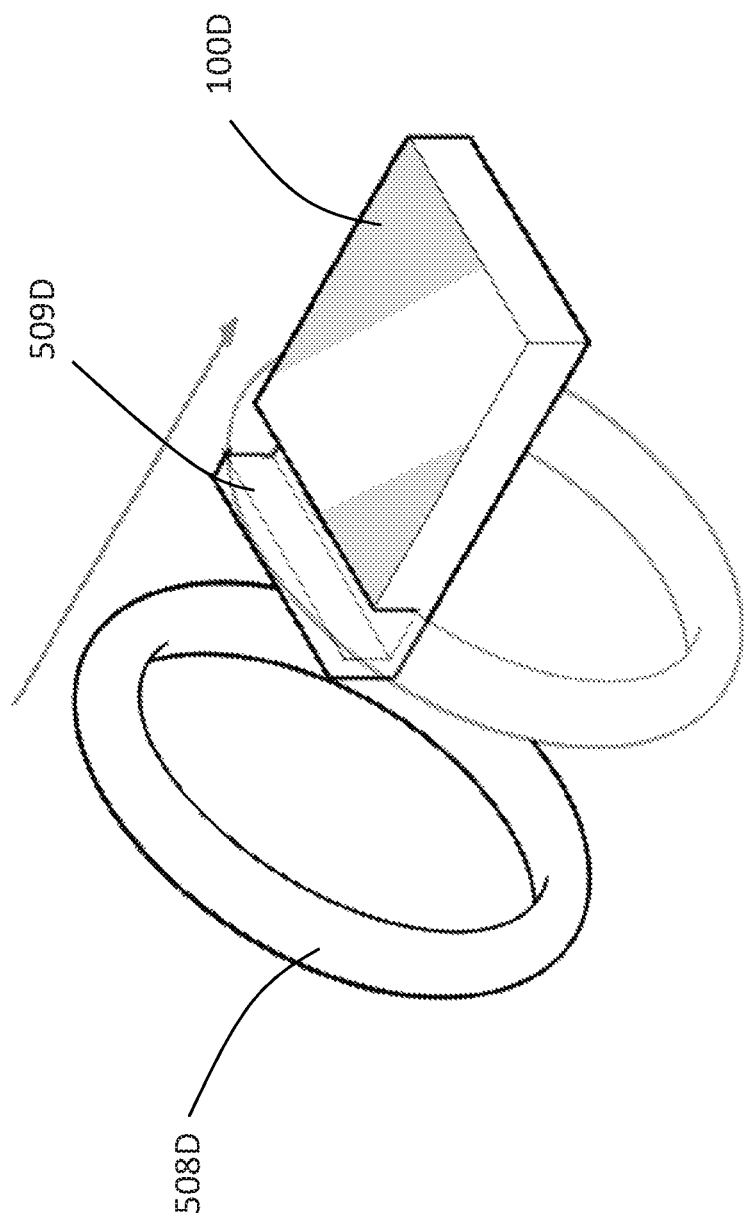

FIG. 25D shows a strap 508D according to another embodiment of the present disclosure. Strap 508D is configured to secure a housing 100D having a slot 509D to receive the strap. Strap 508D can be slid over housing 100D onto to slot 509D as shown in FIG. 25D to secure housing 100D to the strap.

Figure 25E:
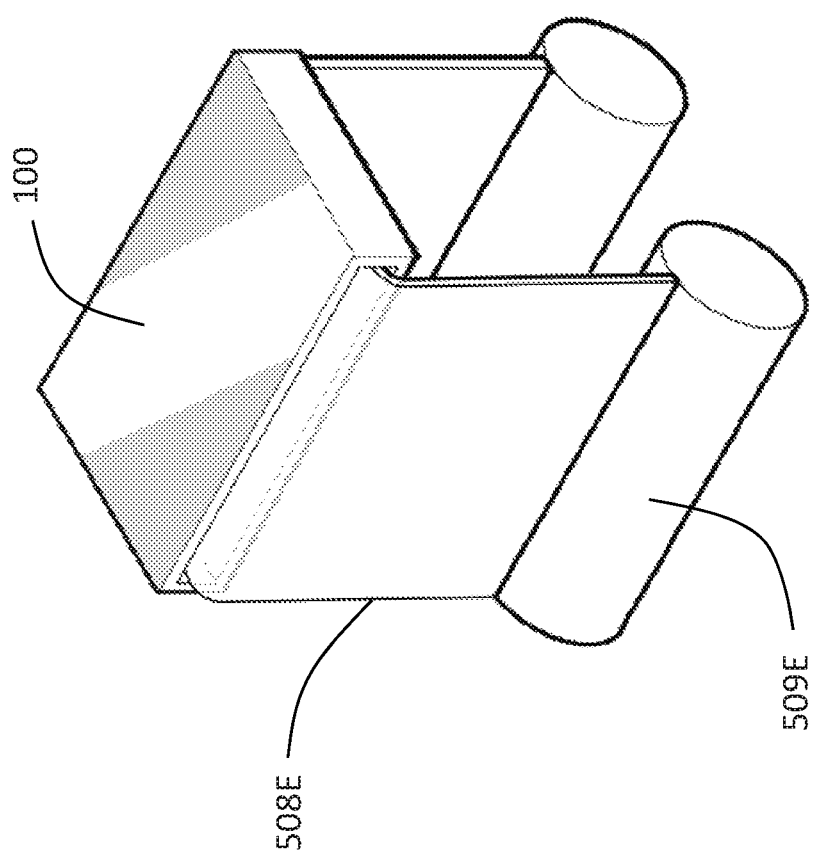

FIG. 25E shows a strap 508E according to another embodiment of the present disclosure. Strap 508E includes weights 509E that secure housing 100 to the target surgical site. An operator can place housing 100 at the surgical site and allowing weights 509E to hang freely on either side of the appendage. Thus, house 100 can be securely attached to the surgical site by utilizing only the weight action of weights 509E.

Figure 25F:
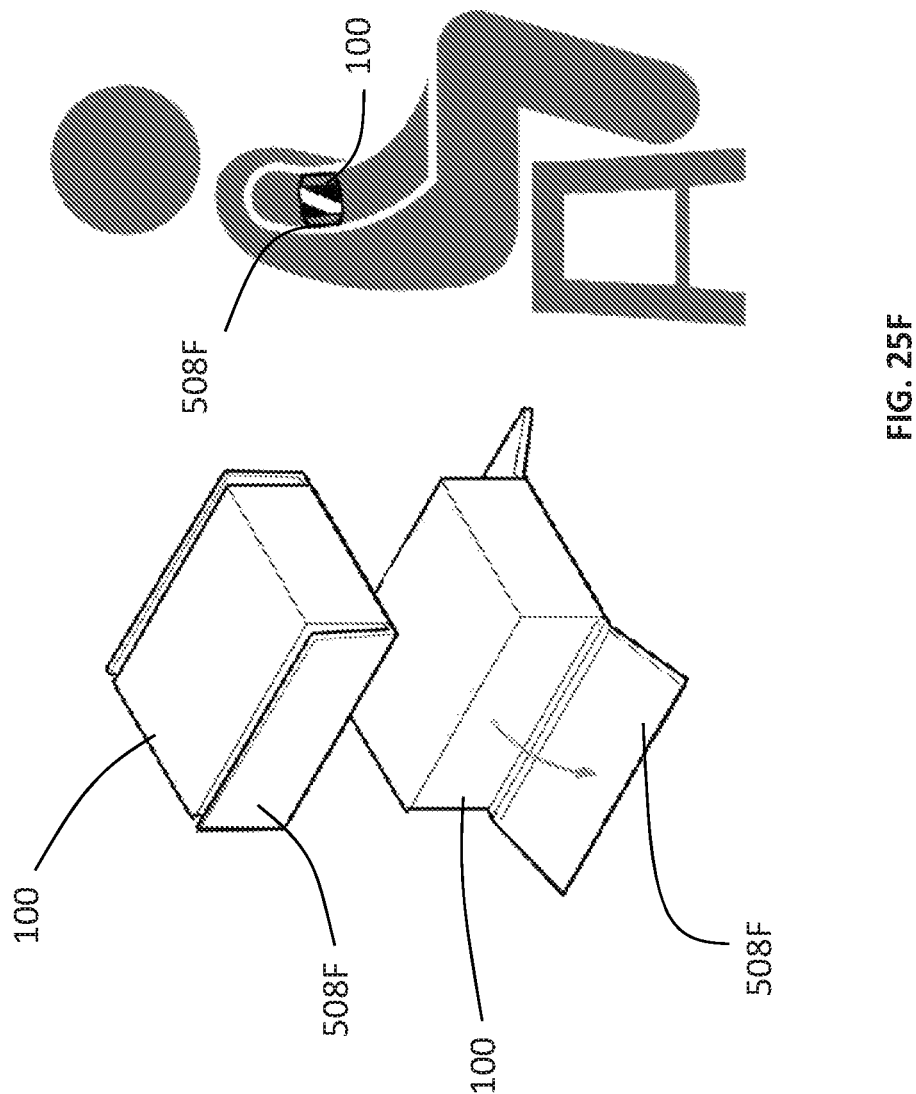

Referring now to FIG. 25F, there is shown a strap 508F according to another embodiment of the present disclosure. Strap 508F is configured as a foldable body with wings that wrap around housing 100 when the device is not in use. Thus, strap 508F can conveniently be opened to extend laterally from housing 100 to attach the device to a patient as shown in FIG. 25F. Adhesives or other securements means can be added to strap 508F to enhance the attachment of the strap to the patient.

FIGS. 25F-25I show a strap 508G according to another embodiment of the present disclosure. Strap 508G includes one or more tourniquets 509G that can be opened (FIG. 25H) and closed (FIG. 25I) by a clamp 510G. Once an ideal surgical location is identified by housing 100, clamp 510G can be locked to secure the device to the target location as shown in FIG. 25I. While a clamp is shown in this embodiment, other securement means such as clasps, brackets, grips, etc. can be used.

FIGS. 26A and 26B show embodiment of attachment means of the present disclosure. FIG. 26A shows housing 100 with an adhesive layer 702 attached to the distal end. An operator can peel away adhesive layer 702 and securely attach housing 100 to the desired surgical site as shown in FIG. 26A. FIG. 26B depicts a housing 100 with suction layer 704 at a distal surface having multiple holes 705. A suction creation means (not shown) creates a vacuum to allow housing 100 to be securely attached to an appendage. Housing 100 can be easily detached and removed from the surgical site by turning off the suction. Attachment means 702 and 704 allow for secure placement of the device without strapping to an appendage, and therefore these attachment means can be particularly useful when performing procedures with the device on children.

Figure 27:
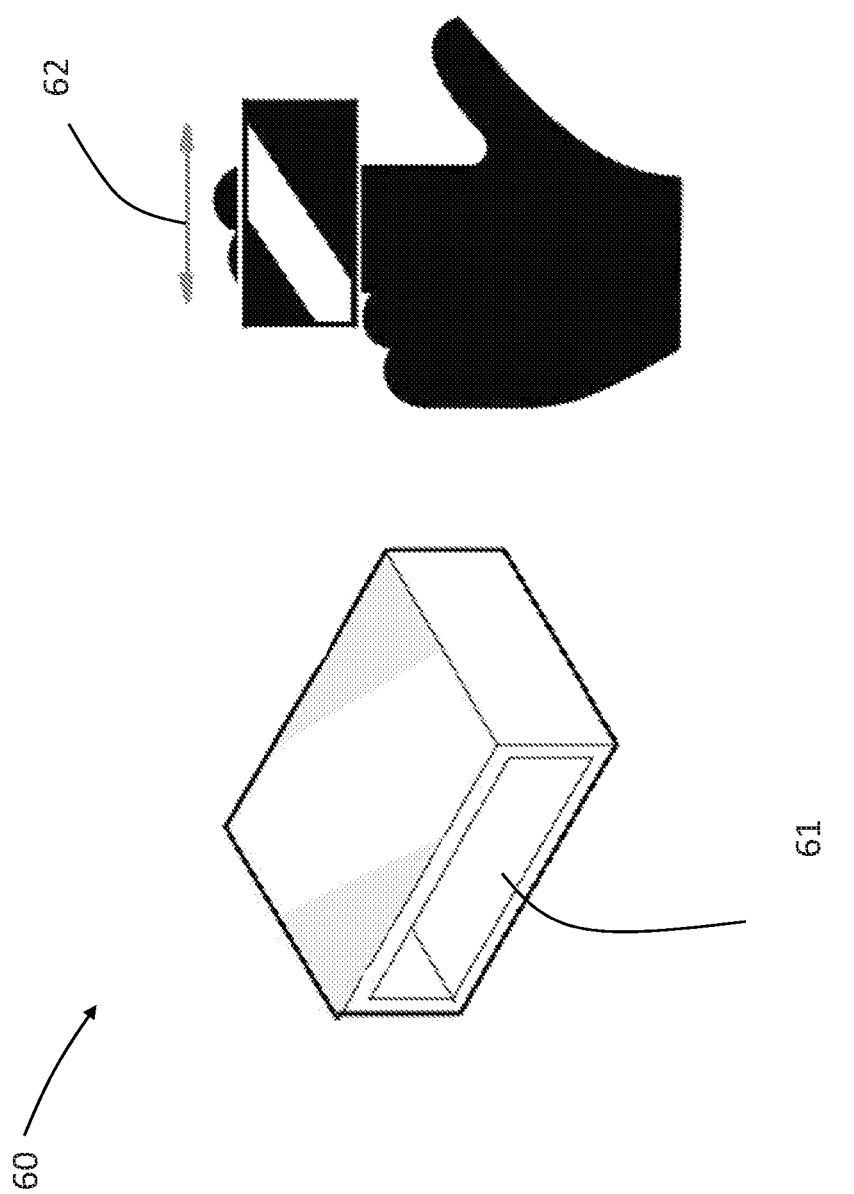
FIG. 27 illustrates another embodiment of a device of the present disclosure.

FIG. 27 shows a device 60 according to another embodiment of the present disclosure. Device 60 includes a slot 61 to allow an operator to place their fingers in the slot to securely hold the device on a target surgical site. Therefore, device 60 requires no attachment or securement means as the operator can simply use his/her fingers to hold and secure device 60 during a procedure.

Additional and alternative embodiments are also illustrated in FIGS. 28-33 of the present disclosure.

Construction of the Device

As illustrated in FIGS. 1A-2E, in certain embodiments, a device of the present disclosure may be constructed as mostly a single-piece unit. Specifically, the device may be constructed as a single housing containing the various functional elements discussed herein. The housing may be separable from a base such that, for example, the base can be positioned first on the patient, and then the housing can be positioned onto the base. However, in other embodiments, the housing and base may also be a single, monolithic unit such that the entire device is positioned onto the patient at once.

Additionally, regardless of the configuration of the housing and base of the device, the inserter assembly may be separable from the housing and base such that, for example, once the base and housing are positioned (whether as a single unit or as individual engageable units), the inserter assembly can then be inserted into the device for subsequent utilization on the patient. Further, providing a needle that can be engaged by the device after the device is already in place may allow for increased flexibility in function as the operator can select the appropriately sized and shaped needle for a selected blood vessel.

In one embodiment, the housing is a reusable element. This is useful as the housing will include various electronics and other higher cost components. The base can also be reusable, or alternatively, the base can be formed of low cost polymer, fabric, paper-based materials, or the like, so as to be disposable. As such, in one example, a new base would be used with each patient, with the reusable, housing being connected to each new base. The reusable housing may also be serializable, and/or capable of withstanding known methods of high level disinfection such as hydrogen peroxide chambers, vacuum cleaning systems, and/or be submersible (e.g., IP67 or greater) for immersion or processing through other washing systems, such as Steris, or the like. The housing may be solid state, with zero or close to zero internal air voids, and/or include hermitical seals to prevent ingress of fluids and/or gases. For instance, base 200 shown in FIGS. 1A-1B may be disposable whereas housing 100 may be reusable and allow for housing 100 to be docked in a new base 200 for every insertion procedure. Alternatively, base 200 can be sterilized and used for a predetermined number of applications and replaced thereafter. A reusable base may also be mounted on a visor 700, which may be new with each use, whereby the base may be protected from contamination, particularly during initial positioning and locating of the desired puncture site. A sterility barrier other than, or in lieu of, the visor may also be added around the base and removed just prior to final positioning. Such a removable sterility barrier can be particularly helpful where the device will navigate a relatively large area of skin before selection of a puncture site, such that sterilization of a large skin area is not required. For example, the sterility barrier may be a flexible plastic film which can be slid, peeled, etc. off of the base upon selection of the puncture site.

In another embodiment, the needle and base may be packaged together as a kit. Optionally, visor 700 can be positioned on the base to keep the needle together with the base. For example, as in FIGS. 1A-1B, the visor can cover at least a portion of the aperture 204 and can include a recess, or other engagement feature, to maintain the needle or inserter assembly 300 in position, relative to the aperture, for simplified collection of the needle by the housing. Then, once the housing is attached to the base, the needle may then attach to the housing or otherwise be held in place relative to the base and housing. Optionally, the visor may automatically fall away upon engagement of the base to the housing—for example, as the housing engages the base and inserter assembly, the inserter assembly may press downwardly into the aperture to push the visor away from and off of the base.

The housing may include any elements desired, and as discussed above, the housing may be reusable, and thus, would house the various electrical and mechanical components. For example, the housing may include a graphical user interface ("GUI") to display 3D scanned dynamic and static images of puncture site vein insertion points, servomotors for insertion and retractions of the needle, and the like. A GUI would be included in semi-autonomous devices, while autonomous device may or may not include a GUI. Alternatively, either autonomous or semi-autonomous devices may include an external GUI rather than a GUI as part of the housing. As shown throughout, the various device embodiments envisioned herein are small enough to be portable and may be carried by operators. Although certain devices, such as those shown in FIGS. 1A-4F and 6A-6B, are generally rectangular, the device may be fabricated in other shapes as well, as discussed herein, such as those shown in FIGS. 4G-4I and 5A-5D. Furthermore, the various devices disclosed herein may be fabricated in different sizes and have contoured shapes for specific applications, examples of which are discussed herein.

The base portion of the device may be made of rigid or flexible materials. For example, if the desire is for the base to be usable at a variety of anatomical locations, the base may include flexible components that can engage the anatomy to configure to the specific geometry. Additionally, alternative engagement features may be included in a kit including the base, such as snap-fitting features, straps, adhesives or other similar attachments to provide flexibility in attachment of the device to the patient.

The device may also be made available as a kit. In one embodiment, the kit includes at least one base, at least one strap, at least one insertion assembly with various needle and component combinations for different applications, at least one protective visor, and at least one, or a range of coupling gel pads, etc. A tourniquet can also be included and used in conjunction with this kit, for example for facilitating vein and puncture site location identification and for stabilizing the skin surface during insertion. Such a kit may be combined with a reusable housing, or the kit may include at least one new housing for single or multiple use.

In another embodiment, a kit includes at least one base and at least one inserter assembly. The kit may also include a housing, or a reusable housing can be used with the kit. In a further embodiment, a kit includes at least one housing and at least one base. At least one inserter assembly can also be included, or can be supplied separately with at least one, or a range of coupling gel pads.

In any of the above exemplary embodiments of a kit, each component can be packaged individually or come together in a single package. For example, a single package may include one housing and then a multitude of separately packaged/sterilized bases and/or needles. Further, if more than one base and/or inserter assembly are in the kit, a single base can be packaged with an individual inserter assembly, as a sterile combination. Any of the above kits can also include at least one protective visor, at least one tourniquet, and/or the like.

The device may be fully or partially assembled depending on specific applications. For example, a fully assembled device may be used in emergency situations by emergency medical technicians to readily use and establish intravenous access to a patient. A fully assembled device will reduce the number of steps required to perform a needle insertion procedure during an emergency situation. Such a fully assembled, ready to use device may be useful in emergency rooms, battlefields and field hospitals, on ambulances, and the like. Alternatively, a partially assembled device may offer more flexibility and may be used in a broader range of applications by allowing the operator to customize the device for the specific application. Such partially assembled devices may be useful in operating rooms, blood banks, labs, doctor offices, and the like.

In one embodiment, the device includes a sensor structure having a wafer-like shape, integrated with a protective housing which may include ergonomic aid(s) and operational controls, such as manual controls, a graphical user interface (GUI, also referred to as a display herein), or the like. Additionally, other external features may be included which can help the user in the cannulation process by, for example, providing sub-surface imaging capability, needle or cannula tracking, or the like.

In one exemplary embodiment of a method of use, as illustrated in FIGS. 65A-65B, the user grasps a device 4000 and positions it on or over a patient's skin 4002. Device 4000, as discussed below, includes a sensor or sensor array 4004 to study the patient's subdermal anatomy to locate a suitable blood vessel as shown in FIG. 65A. Locating a suitable blood vessel also determines a desired puncture site 4008 on the skin surface, whereby entering the skin at the puncture site will ultimately position a needle 4006 in the desired blood vessel. Device 4000 can then track needle 4006 as it approaches the puncture site 4008 as shown in FIG. 65B. The user then manipulates needle 4006 to the puncture site and through the skin at the puncture site as shown in FIGS. 65C and 65D. Once inside the patient, a tip 4010 of the needle is tracked using the sensor/sensor array 4004 of the device to observe the needle tip approaching the blood vessel and guiding the user to direct the needle tip into the blood vessel as shown in FIG. 65E. Once needle tip 4010 is positioned in the blood vessel, the blood vessel is said to be cannulated and the user may proceed to perform the desired procedure.

FIGS. 66A-66E illustrate various exemplary positions that device 4000 disclosed herein may be used on a patient, from the hand (FIGS. 66A and 66E), to the arm (FIG. 66A) to the neck (FIG. 66B), to the foot (FIG. 66D), etc. While these illustrated positions are generally known to be the primary locations for cannulation of the circulatory system, other positions on the body may also be a desirable location to use these devices, and are also envisioned.

The following representative physical embodiments and sub-variants for such a devices are hereby presented. While certain embodiments may illustrate certain features, components and/or functions, it is understood that any of these features, components, or functions may be incorporated in any of the other representative embodiment in any combination or configuration desired or useful.

Referring to FIGS. 67A-67C, there is shown a substantially flat rectangular device 5000 according to one embodiment of the present disclosure. A bottom surface 5014 is at least partially or completely covered by imaging sensors 5004. As shown in FIG. 67B, device 5000 is of a size to be manipulated by a hand of the user. An opposite side is at least partially or completely formed with a viewing screen 5012. The viewing screen may also be or incorporate a GUI, or have other control capability, for allowing a user to interface with the device.

FIG. 67C illustrates a cut-away to expose the components of device 5000 of the present invention. As illustrated, the device includes a display 5012 on a top surface, an imaging sensor such as CMUT 5004 or any other sensor may be used or combined with CMUT, a battery 5016, and a main pcb (printed circuit board) 5007 and a camera pcb 5005. As described above, a PMUT sensor array can be used instead of a CMUT array.

A housing 5009 is shaped to accommodate positioning by a user's hand, and may also include a cut out 5011 to provide an improved shape for positioning a needle or cannula 5006 therewith. In particular, cut out 5011 may serve to allow the needle or cannula to better approach the anatomy being viewed on the display—in other words, the needle can arrive closer to the portion of the blood vessel being shown on the display.

Further, as shown FIG. 67B, device 5000 may also include a capability of marking 5013 a suggested puncture site 5008 for initial insertion of the needle or cannula into the skin. For instance, a laser, a camera, a focused light (e.g., LED), or a mechanical aiming device may be included to assist the user in locating the best puncture site on the patient's skin.

Optionally, the device may include a pad or other intermediate layer which can be positioned between the bottom surface of the device and the skin. For example, the pad could be formed of a conductive gel to accentuate visualization. The pad could also impart sterilization, marking/aiming, or other features to the device. Further, while the device may be reusable, the gel pad may be disposable.

Referring now to FIGS. 68A-D, there is shown a device 6000 according to another embodiment of the present disclosure. Device 6000 is generally similar to device 5000, and therefore like elements are referred to with similar numerals within the 6000-series of numbers. Device 6000 of this embodiment includes an extended brick with a low-profile and a fixed ergonomic aid at one end. The ergonomic aid may be a clip 6014, which also doubles as a pocket clip for convenient carrying by a user. As illustrated, the device is of a size suitable for carrying in a pocket. Optionally, device 6000 may also include a charging coil 6017 for wireless charging, or it may include an adapter for wired charging.

FIG. 68C illustrates a cross-sectional view of device 600, includes CMUT 6004 as the sensor, a display 6012, and a pcb 6007. Optionally, this device may also include a charging coil for wireless charging, or it may include an adapter for wired charging. Optionally, this device may also include a laser, camera, or the like for assisting in locating the puncture site 6008 on the skin surface of the patient.

Referring now to FIGS. 69A-C, there is shown a device 7000 according to another embodiment of the present disclosure. Device 7000 is generally similar to device 5000, and therefore like elements are referred to with similar numerals within the 7000-series of numbers. Device 7000 has an ergonomic handle 7026 which deploys rotatably to aid user in manipulating the device. Handle 7026 folds flat for storage or may be slightly raised when undeployed to double as a pocket clip for convenient carry as shown in FIG. 69A.

Referring now to FIGS. 70A-C, there is shown a device 8000 according to another embodiment of the present disclosure. Device 8000 is generally similar to device 5000, and therefore like elements are referred to with similar numerals within the 8000-series of numbers. Device 8000 includes an ergonomic knob 8026 that deploys telescopically to aid the user in manipulating the device. Knob 8026 allows for two fingers to control the pressure/angle/traction of device 8000. Optionally, knob 8026 could be biased in an undeployed position such that it "clamps" onto the user's fingers for increased stability during use.

FIGS. 71A-D show a device 9000 according to another embodiment of the present disclosure. Device 9000 is generally similar to device 5000, and therefore like elements are referred to with similar numerals within the 9000-series of numbers. Device 9000 includes raised "ramped" areas 9028 at either end of the device which may aid the user when pressing and sliding the device on the skin. Ramped ends 9028 may also include an additional layer of friction-inducing material, such as co-molded polymer, for example a thermoplastic elastomer (TPE).

FIGS. 72A and 72B show a device 10000 according to another embodiment of the present disclosure. Device 10000 is generally similar to device 5000, and therefore like elements are referred to with similar numerals within the 10000-series of numbers. Device 9000 includes a two-piece structure joined near one end with a hinge 10030, which may be rigid (spring, door hinge, or the like) or semi-flexible (living hinge, elastic material, or the like).

Each of the pieces may be slimmer than the single-piece embodiments above, and the various components of the device may be positioned within one of the pieces, one such configuration is shown in FIG. 72A.

The two-piece structure allows a user to slide device 10000 onto a pocket edge for convenient carrying as shown in FIG. 72B. A tooth 10032 may enable the device to engage the shirt pocket edge (or other structure on which the device is to be clipped) by sliding the curved surface of the tooth against the edge to move the edge between the pieces to become engaged therein.

FIGS. 73A and 73B show a device 10100 according to another embodiment of the present disclosure. Device 10100 is generally similar to device 10000, and therefore like elements are referred to with similar numerals within the 10100-series of numbers. Device 10100 includes a two-piece structure joined near one end with a hinge 10130, which may be rigid (spring, door hinge, or the like) or semi-flexible (living hinge, elastic material, or the like). The hinge may be biased so as to bring the two layers together. Hinge 10130 is more inboard than the hinge of device 10000, and thus user can more easily squeeze the hinged end to separate the two pieces for easy clipping on to a pocket or other structure as shown in FIG. 73B.

FIGS. 74A-74C show a device 10200 according to another embodiment of the present disclosure. Device 10200 is generally similar to device 10100, and therefore like elements are referred to with similar numerals within the 10200-series of numbers. Device 10200 includes a two-layered structure where the two layers are joined in an arrangement via an extendable post 10232. Post 10232 can be telescopic or otherwise longitudinally expandable as shown in FIG. 74C or can have a pivoting or hinged relationship with the two layers as shown in FIGS. 74A and B. Post 10232 may be internally biased towards bringing the two layers together, and thus a user may engage the opposing curved edges of the two layers, and force her fingers between the layers, causing them to separate as shown in FIG. 74B. The biasing action provides for device 10200 to actively grip the user's fingers for stability during use. Alternatively, post 10200 could include a ratcheting mechanism to maintain a gap that is controlled by user. For example, the two layers could be expanded away from one another, and upon the user placing her fingers between the layers, the layers can be moved back towards one another along a ratchet and positioned (and held) at a location that comfortably seats the layers against the fingers. In the above variations where the layers are biased towards one another, the post may incorporate a dampener capable of slowing the movement of the layers towards one another.

As with any of the embodiments disclosed herein that include either biasing or ratcheting portions, or knobs or other handles, such structures may allow for a stable connection of the user to the device during use, and further, since such structures secure the device to the user, may allow the user to lift the device away from the patient's skin without having to better grip the device. Similarly, in such instances where the device is firmly attached to the user's fingers, it can be easier to apply reverse-traction on the patient's skin, which may help to stabilize a vein, with the thumb simultaneously (since the thumb is not needed to hold the device), and further may help prevent the user from dropping the device accidentally.

FIGS. 75A-75C show a device 10300 according to another embodiment of the present disclosure. Device 10300 is generally similar to device 5000, and therefore like elements are referred to with similar numerals within the 10300-series of numbers. Device 10300 includes a cut out 10336 at a location where needle 10306 can enter the skin, similar to other exemplary embodiments discussed above. As illustrated in FIG. 75B, cut out 10336 may be of any size desired to expose a puncture site 10308. Sensors positioned on two legs 10337 of the device, on either side of cut out 10336, can sense the area of the patient within the notch for better imaging of needle 10306 as it first enters the skin at puncture site 10308.

Further, the inner faces of cut out 10336 can be mounted with cameras, metal sensors or other above-surface sensors, for better imaging of the needle before and/or as it first enters the skin at the puncture site.

Figure 76B:
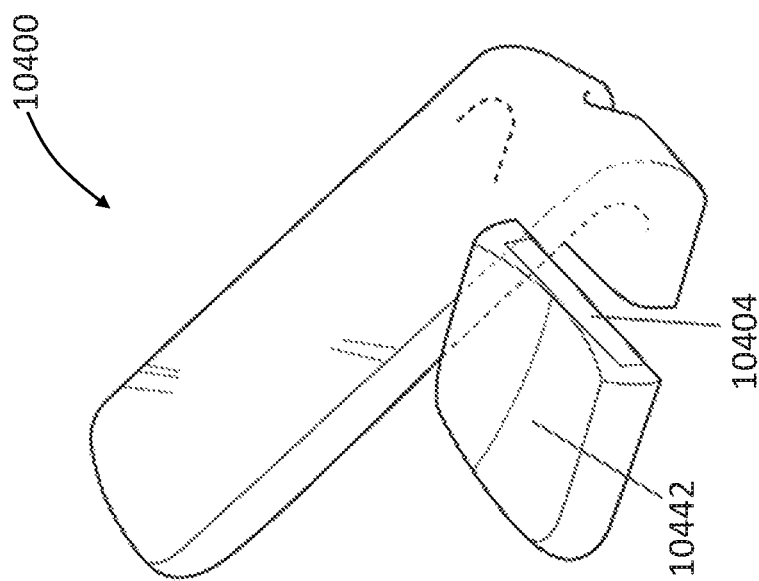
FIGS. 76A and 76B illustrate another embodiment of a device of the present disclosure.
Figure 76A:
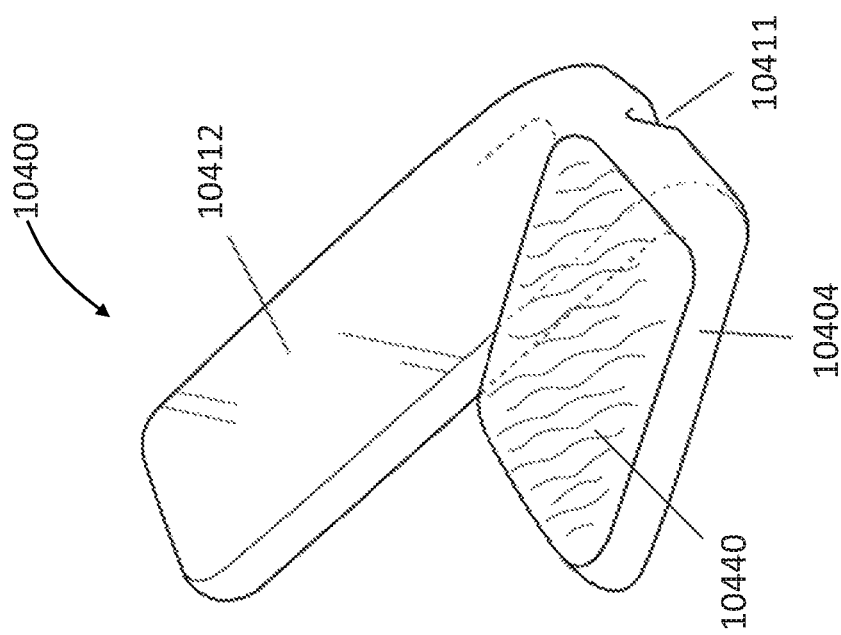

Referring now to FIGS. 76A and B, there is shown a device 10400 according to another embodiment of the present disclosure. Device 10400 is generally similar to device 5000, and therefore like elements are referred to with similar numerals within the 10400-series of numbers. Device 10400 includes a sensing layer 10404, to be positioned adjacent to or onto the skin of a patient, and a display 10412, where the sensing layer is positioned at an angle relative to the display. Such positioning of the display may provide for a viewing screen that is at a more perpendicular angle to the user's eyes, thereby allowing for improved and more accessible viewing, particularly in instances where the user is sitting in a chair next to the patient, or is otherwise positioned lateral to the puncture site and device. The angle may be any angle desired, for example, between and including about 1 degree and about 90 degrees.

The user can place their fingers on top of sensing layer 10404, resting on an ergonomically textured 10440 (FIG. 76A) and/or concave or recessed surface 10442 (FIG. 76B). Textured grip surface 10440 may be formed by a high-traction material (e.g., high-friction rubber pad). Note that FIG. 76B is cut away to show CMUT sensor 10404 (or other sensor). Device 10400 may further include a notch 10411 which, similar to other notches and cut outs discussed above, may provide a space for the needle to access a puncture site which may be positioned close to CMUT sensor array 10404.

FIGS. 77A-77C show a device 10500 according to another embodiment of the present disclosure. Device 10500 is generally similar to device 10400, and therefore like elements are referred to with similar numerals within the 10500-series of numbers. Device 10500 includes a sensing layer 10504 and a display 10512, angled relative to one another. The device of this embodiment also includes a knob 10548 on the device (as illustrated, positioned atop the sensing layer) for engagement by a user. The user can thus place their fingers in between the layers where the ergonomic knob aids the user in manipulating the device.

As shown in FIGS. 77B and C, knob 10548 may be collapsible for simplified storage or to broaden the possible ways to use the device. As discussed above, the knob may be expandable telescopically or otherwise, and may be biased towards a certain position, such as a collapsed position.

FIGS. 78A-78C show a device 10600 according to another embodiment of the present disclosure. Device 10600 is generally similar to device 10500, and therefore like elements are referred to with similar numerals within the 10600-series of numbers. Device 10600 includes a sensing layer portion 10604 and a display portion 10612, however, the portions are connected via a hinge 10652, which may be rigid (spring, door hinge, or the like) or semi-flexible (living hinge, elastic material, or the like). Hinge 10652 may be biased so as to bring the two layers together. Alternatively, the hinge may include a ratchet such that is will maintain the two portions at a constant set angle relative to one another.

In using device 10600, the portions may be separated either by the user inserting one or two fingers of their non-needle hand into the space between the portions, or by retracting one portion from the other and then placing one or two fingers in between the separated portions.

In the alternative where the hinge is biased, the two portions may close snugly around the fingers. Optionally, the hinge may be dampered such that the closing motion is slow and controlled. Conversely, in the variation of a ratcheted hinge, the use may close the portions around their finger(s) to snugly position the device onto the user's hand. Further, the inner surface of each portion may include a grip 10654 or other ergonomic material/shape to provide additional stability to the device during use. For example, a soft, high-traction material can aid in securing the device to the finger. The hinge may be capable of attaining any angle desired between and including 0 and 180 degrees, for example, between and including about 1 degree and about 90 degrees.

Figure 79A:
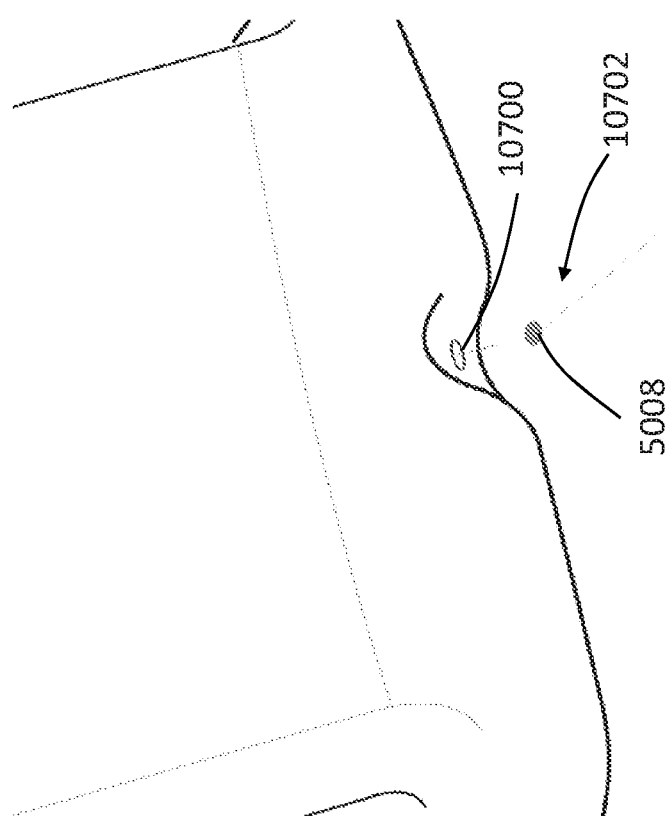

FIGS. 79A-H illustrate various embodiments of a notch 5011, or other targeting feature used to provide access to a puncture site 5008 and/or to provide guidance for the needle 5006 to the puncture site. For example, FIG. 79A illustrates an exemplary targeting device, namely a laser 10700, spotlight, or the like, which highlights 10702 desired puncture site 5008. This light position 10702 on the patient's skin may be constant and fixed relative to the device, or alternatively, may be movable based on the software of the device and its recognition of the underlying anatomy of the patient.

In another embodiment shown in FIG. 79B, a mechanical indicator 10800, represented as at least one, and as illustrated three, physical markers pointing towards a middle location 10802 in the notch of the device. The device use can utilize these marker(s) to direct the needle towards the skin within the notch—and to a puncture site 5008 located therein.

Figure 79C:
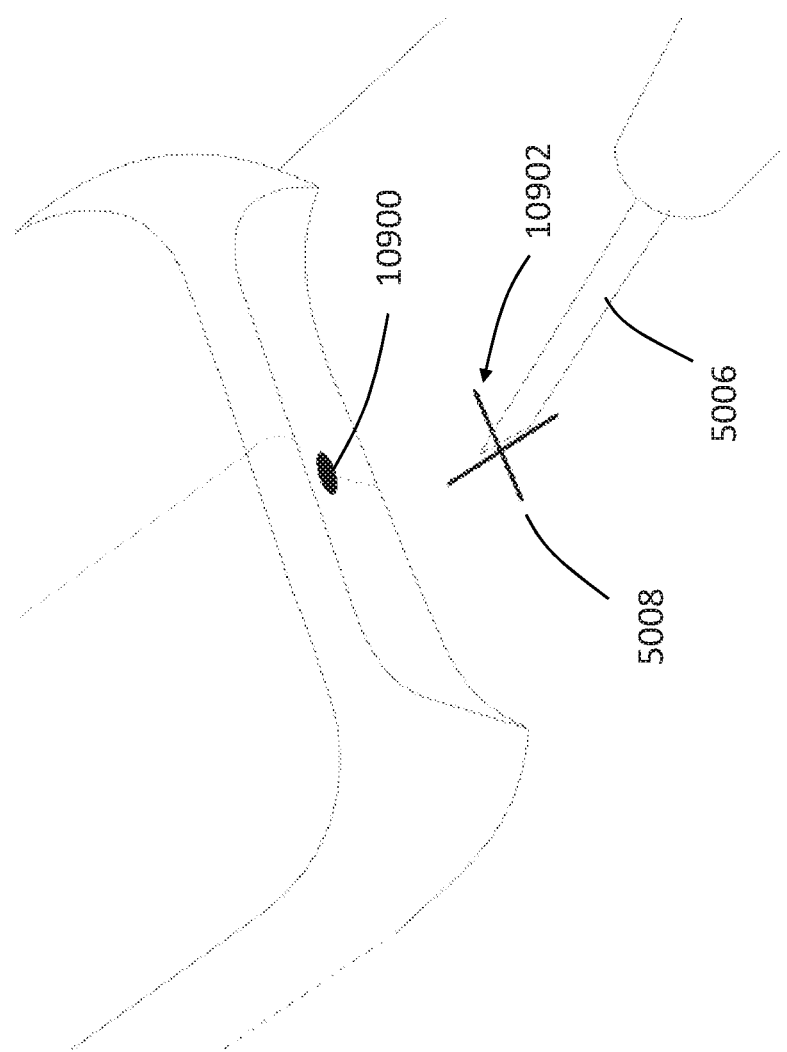
Figure 79D:
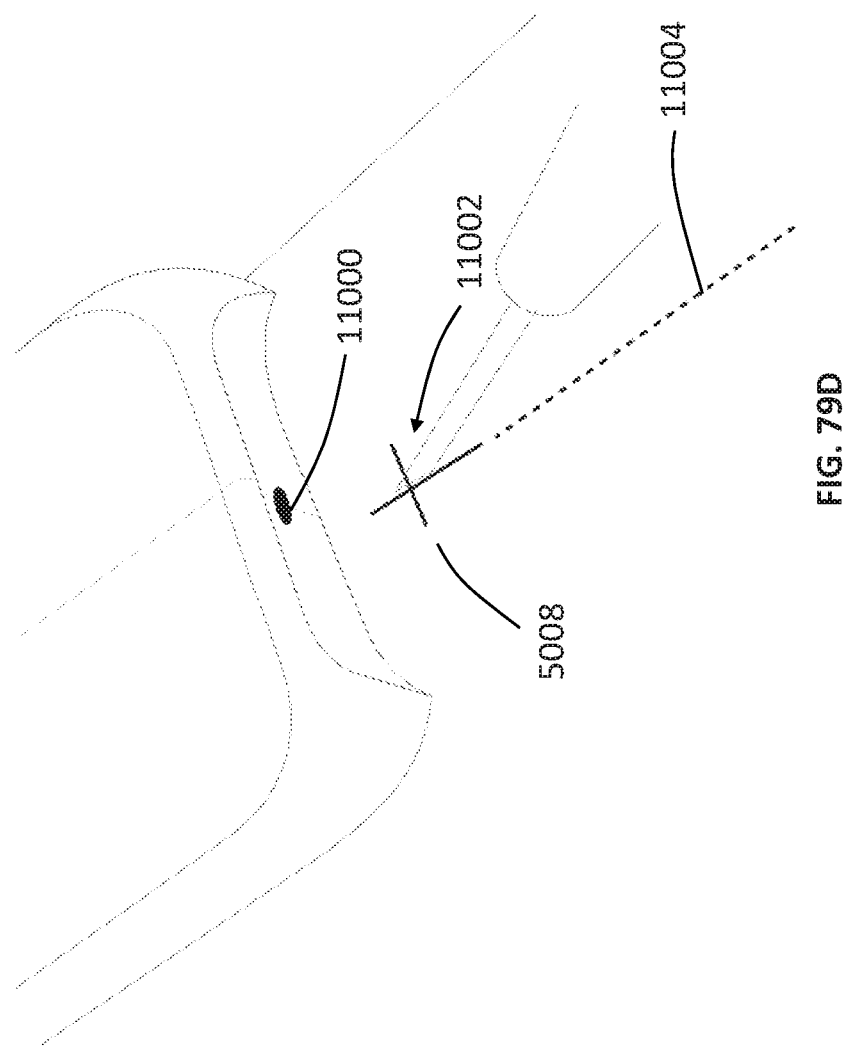

In another embodiment shown in FIG. 79C, a device can include a light-based targeting device 10900, whereby a puncture site 5008 is indicated on the skin by means of a projected illumination 10902 (e.g., laser dot, projected light crosshairs, laser line, or the like). The positioning on the patient's skin may be constant and fixed relative to the device, or alternatively, may be movable based on the software of the device and its recognition of the underlying anatomy of the patient.

In a further embodiment, a device can include a light-based targeting device 11000, similar to that described as to FIG. 79C, but as illustrated, the projected illumination 11002 also includes a line 11004 projected by the device onto the patient's skin. The line can further assist the user to align and aim the needle along the correct X-Y path before it touches the skin at puncture site 5008.

In another embodiment as shown if FIGS. 79E-G, device 5000 may include connectivity capability 12002, such as for example Bluetooth, for connecting wirelessly to a needle element 12004. The needle element may attach to a needle 5008, or be integrated into a needle, and wirelessly connect to the device (e.g., be Bluetooth-enabled). Needle element 12004 may be an accelerometer or gyro, or other sensor device. In the example of an accelerometer or gyro, the accelerometer may ascertain the position of needle 5008 relative to the device. Via the Bluetooth connection, the device may ascertain the needle's directional axis of aim, that axis's intersection at the surface of skin (and specifically the puncture site), and the like, and such information can be used to generate an image on the display of the device (as discussed above) and/or data on the position of the needle. Needle element 12004 may be simply clipped onto needle 5008 as illustrated in FIGS. 79E and F, or may have another attachment mechanism to secure to the body of the needle.

Figure 79H:
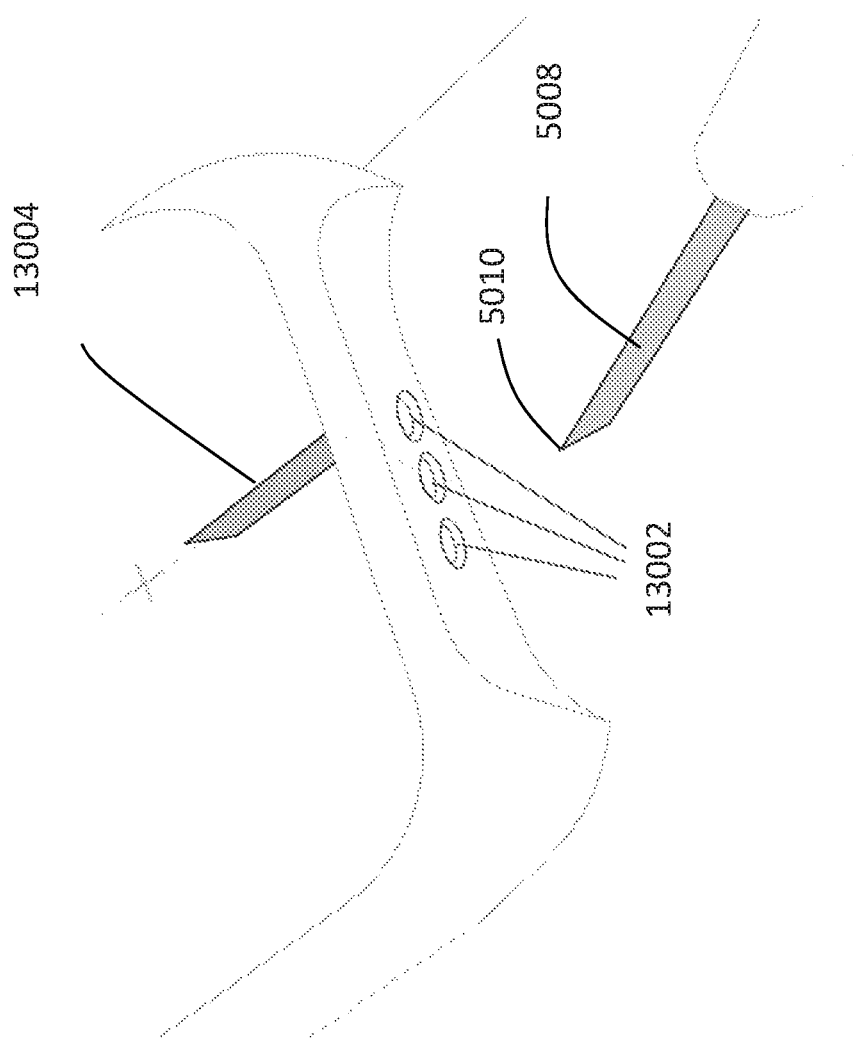

In another embodiment shown in FIG. 79H, the device includes at least one sensor 13002 above the skin (e.g., underneath the screen or, as illustrated, on the inner surface of the legs around a cut out) can determine the location of a needle tip 5010 and shaft angle before the needle tip touches skin. These sensors could be vision/camera based, or sense the metal of the needle (e.g., via magnetism), or the like. A virtual representation 13004 of the needle may appear on the screen before it is inserted in the skin, so it can be visually X-Y aligned with the sub-surface vein that appears on screen (even if the actual tip of the needle is obscured from the user's direct line of sight). Once underneath the skin, and through the puncture site, the needle may still be viewed on the screen via other sensors, such as CMUT sensors, or the like, on the device.

Any of the devices described above may also include a pad or other intermediate layer which can be positioned between the bottom surface of the device and the skin. One example of such a pad 14000 is illustrated in FIGS. 80A-C. For example, the pad could be formed of a conductive gel 14004 to accentuate visualization. A peel-away cover 14002 may protect gel 14004 prior to use. The pad could also impart sterilization, marking/aiming, or other features to the device. Further, while the device may be reusable, the gel pad may be disposable. The layers can be peelable to allow an operator to remove used layers to reuse the pad, or remove unwanted layers to customize the pad for patient-specific needs.

Navigation/Imaging

As discussed above, the device of the present invention includes various functionality suitable for semi-autonomous or autonomous use to, for example, locate a puncture site on a patient and insert a needle into the patent. With regard to the function of locating a puncture site, the device may include navigation capability to assist in internal visualization to locate a puncture site. The navigation capability can examine a patient's anatomy in search of a desirable blood vessel. For example, the navigation may include sensors utilizing ultrasound, X-ray, infrared ("IR"), near-infrared ("NIR"), diffuse IR, acoustic, optoacoustic, photoacoustic, light-emitting diode ("LED"), CMUT, polarized LED, video camera, transillumination or other technologies. Sensors using different technologies may also be combined in a single device. For example, a transillumination sensor may act as a first visualization tool to quickly provide preliminary visual data on general vein location, which will in turn allow an operator to place the device over the general vein location and use a secondary sensor to zone in and pin point the puncture site. The secondary sensor may be an ultrasonic sensor, which will provide precise and detailed imaging information. The dual-sensor approach will optimize navigation performance by balancing speed and precision. Regardless of the type of sensors, the navigational sensors may be fully translatable in the autonomous device having six degrees of freedom being able to automatically scan the patient's skin area once the device is placed thereupon. The semi-autonomous device may have fixed or partially translatable navigational sensors. For instance, a semi-autonomous device with ultrasound navigational sensors may include a first and a second transverse array of ultrasound transducers to map the veins in 3D.

The navigational output may be visually, audibly or tactilely communicated to the operator. A visual display may be provided through a GUI on the device or transmitted to a remote display screen which may show the three-dimensional mapping of the blood vessels and general subdermal condition at the puncture site. This mapping may include dynamic (real time) and/or static imaging as desired. For example, real time imaging may be obtained at the puncture site to monitor insertion by placing navigational sensors directly in sight of this area, whereas static imaging may be uses to generate a map of the larger area to improve visual feedback to the operator. The visual display may also be directly projected on the skin surface, indicating puncture site(s) with reference to the mapped veins, and augmented with laser or other light projections as puncture site guides. Image magnifiers, contrast resolution adjusters, and other image optimizing features may also be included to enhance visual feedback. Further, audible and haptic output feedback may also be integrated with the visual display to improve user interface. For instance, audible signals may also be incorporated to the device and used in conjunction with the visual display to further assist in precise location of the puncture site. For example, as explained above in the dual-sensor approach, the first sensor output may be communicated by only audible signals, and therefore allow an operator to quickly narrow down the puncture site for the second sensor scanning without any visual display feedback.

The navigation capability will include the ability not just to identify vein location and depth underneath the skin, but may include the ability to identify other key aspects of the blood vessels and blood flow. For example, a Doppler ultrasound may be used to detect and display blood flow direction and blood flow condition. This will enable the operator to distinguish between arteries and veins based on the direction of flow and evaluate blood flow conditions such as velocity, pressure and temperature to precisely identify puncture sites autonomously. Alternatively, the device may be able to process this information to identify and direct an operator to the puncture site in a semi-autonomous manner. Neural monitors may be included in the device to detect the proximity and location of nerves and ensure that puncture site and trajectory are spaced away from them. Venous valves and bifurcations may be identified and evaluated in determining ideal puncture sites.

The device may also have secondary sensors to provide feedback during needle insertion, needle securement, and needle retraction. For example, force sensors on the device may relay data about successful needle penetration and may complement the visual feedback obtained from the other sensors. Force and tactile sensors may be especially useful in procedures to access wrist veins and other similar vein locations providing tactile feedback to avoid excess insertion force causing the needle to penetrate through the vein.

Further, velocity or pressure sensors may be coupled with the device to allow an operator to ensure that the needle remains firmly in place after insertion. For example, if the needle is accidentally dislodged from the blood vessel after insertion, these sensors can detect changes in blood velocity or pressure and alert the operator.

While the navigational capability disclosed herein is generally discussed with reference to the circulatory system, they may also be used in subcutaneous and intraosseous needle injection procedures. Similar navigational systems may be employed for such procedures.

In certain locations on a patient's body, the target vessels may be at a relatively extreme location, such as being particularly deep and/or very shallow. For example, the anatomy of the hand includes blood vessels in these positions, particularly vessels that are superficial and extremely close to the skin surface. In order to create additional depth of view to these shallow veins, the housing and imaging system may be further spaced apart from the skin surface, by use of a thicker coupling material, or an expanding or inflating coupling material. The coupling material may include hydrogel, or another water based substrate, suitable to transmit ultrasound with minimum loss or distortion. The coupling material may be manually changeable, for example by selecting a thicker or thinner coupling pad depending on the vein depth. The thickness or properties of the coupling material may also be compressible, or dynamically adjustable, driven by a motor, a pump, heat transfer, or the like causing the coupling material to enlarge or change shape. The coupling membrane may alternatively include shape memory properties, for example stretchable supramolecular hydrogels or the like.

While the use of certain of the devices herein, such as devices 10, 20, allow the housing 100, 400 to be moved about the skin surface by the operator, certain embodiments do not have that capability for various reasons. For instance, in addition to the various sensors discussed above, in some instances, the navigational system may also have the ability to mechanically move the housing along the skin surface. For instance, device 30 of FIGS. 3A-3B, discussed above, include a base 800 which is secured to the patient such that it does not move. Thus, housing 700 includes an ability to move relative to the base 800 to scan along the skin of the patient to locate a puncture site. This ability to move housing 700 can be automated or can be controlled by the operator, using a GUI or the like. The navigational sensors used in this embodiment may be any desired, as discussed above.

Figures 9A, 9B:
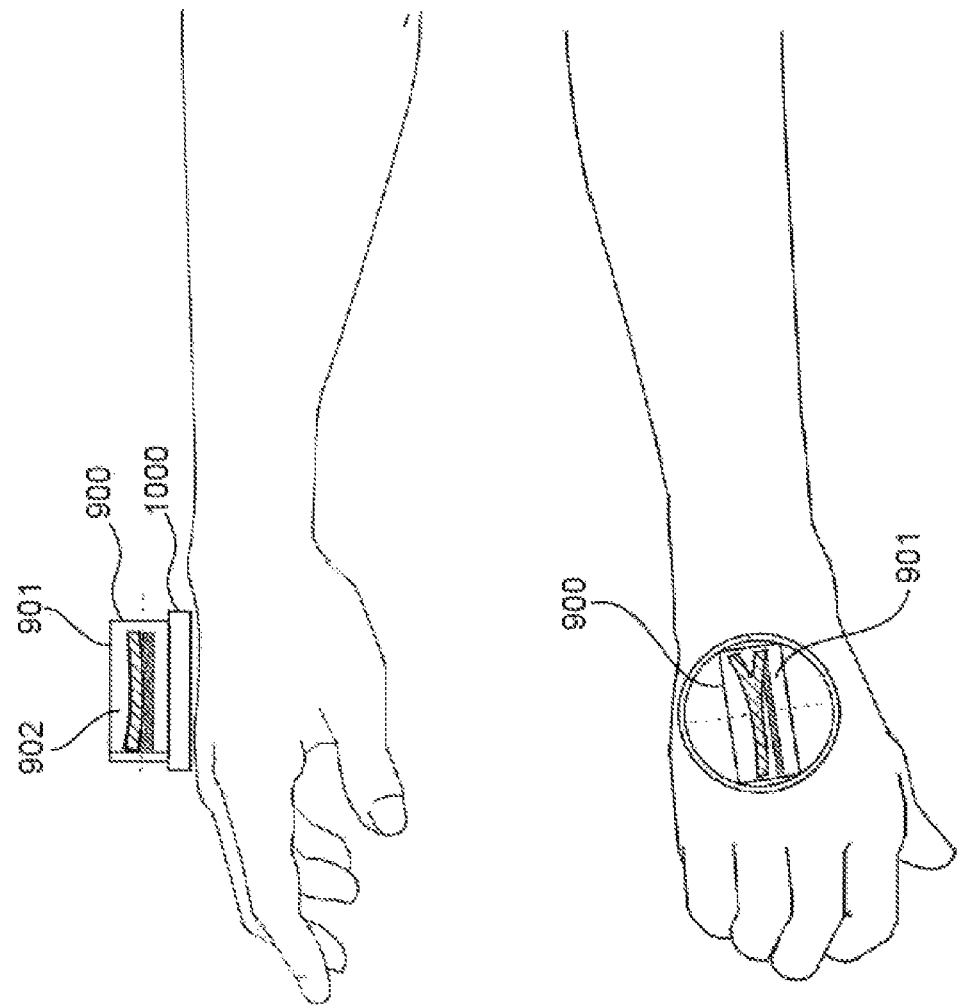
FIGS. 9A-9D illustrate another embodiment of a device of the present disclosure.
Figure 9D:
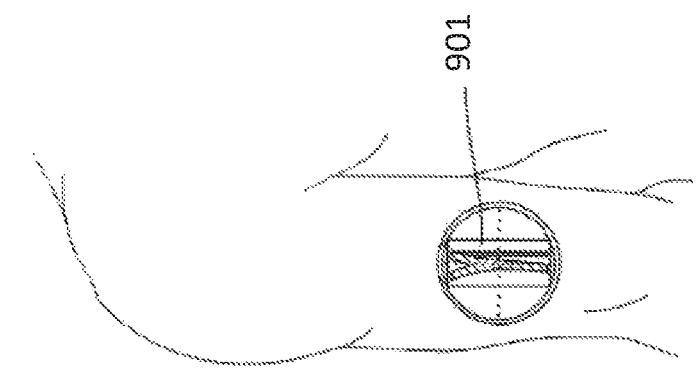
Figure 9C:
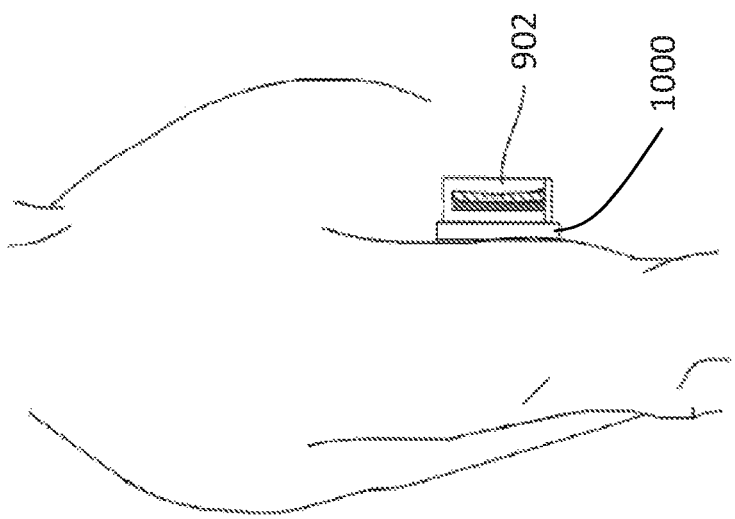
Figure 9E:
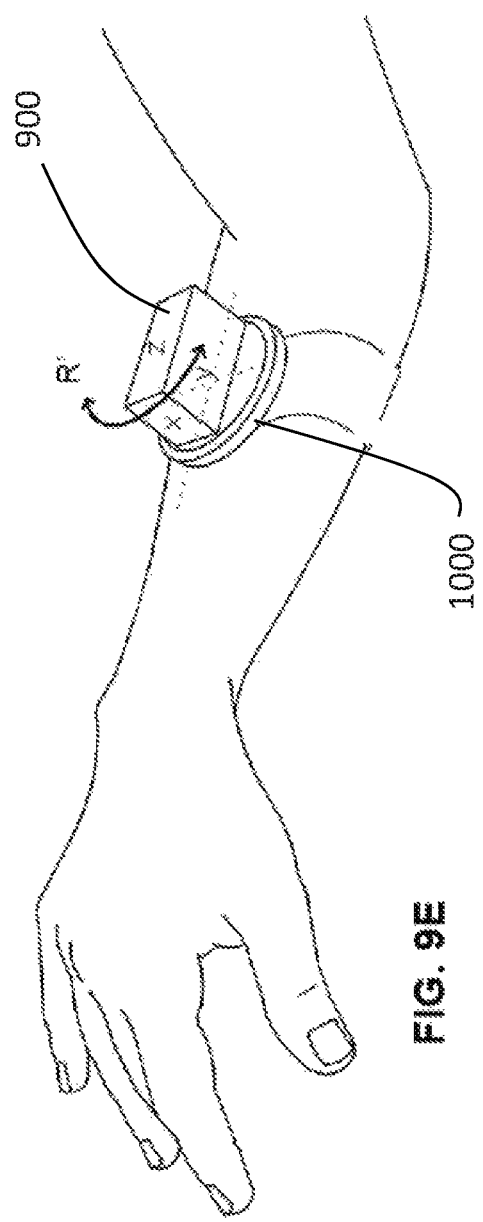

In other embodiment, such as for example FIGS. 4A-6B, such devices include a housing capable of moving relative to a base to perform at the least navigational functionality to scan a patient's anatomy and determine at least one puncture site. Another example of such a device is illustrated in FIGS. 9A-9B, housing 900 has at least one degree of motion, as illustrated housing 900 can rotate relative to base 1000 in direction R', as illustrated in FIG. 9E. Base 1000 can be similar to base 200, 500 of FIGS. 1A-2E but instead of an attachment where the base and housing cannot move relative to one another, the base 1000 includes a swivelable connection to housing 900. Once base 1000 is secured to the patient at a generally desired location, and by any attachment mechanism desired (e.g., adhesive, strap, and the like), the swivelable connection can allow housing 900 to scan along a patient's skin surface for at least one puncture site in the general area. As discussed above, the navigational function of housing 900 may be autonomous or semi-autonomous through an operator interface.

Additionally, FIGS. 9A-9D and 9G-9I illustrate another capability of this device, which can be used on the other devices disclosed herein. Specifically, a top surface 901 and at least one side surface 902 or 903 of housing 900 may include a screen capable of being a GUI, and thereby displaying the underlying anatomy for the user. As illustrated, top surface 901 may display a view from the top (i.e., from a z-direction, as in FIG. 9G), while the at least one side surface 902 may display a view from the side (i.e., from a y-direction, as in FIG. 9I). The ability to show two views can provide for improved viewing by the user, which may result in more accurate positioning of the needle. Alternatively, one or both of the displays may also show a cross-sectional view (i.e., from an x-direction, as in FIG. 9H), for additional viewing assistance. Alternatively, any of the displays on housing 900 would be capable of toggling between any of these views.

FIGS. 10A-10E, 11A-11C, 12A-12C, 13A-13B illustrate further embodiments of a GUI with which, if present on the device, the user can interact with the device of the present disclosure. While the below embodiments are examples of what types of information can be displayed on the GUI, other variations, or even combinations of the various embodiments, are envisioned. Still further, it is envisioned that the GUI could be tailored, either during manufacture or by the operator prior to use, to display the information desired by the particular operator. The GUI according to the present disclosure can include various renderings to the display to facilitate imaging and/or the surgical procedure. For example, different colors can be used to represent different body parts such as a vein, nerve, artery, etc. to enhance display of these body parts. The color scheme to represent body parts can be customized or provided in accordance with standard medical practice.

Figure 10E:
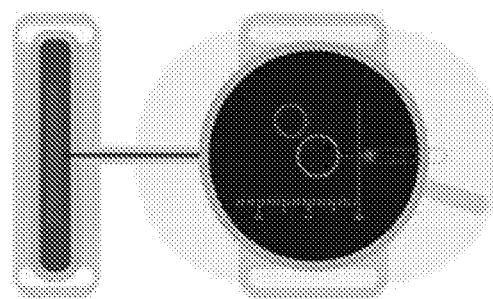
FIGS. 10A-13B illustrate various embodiments of a display (GUI) of the present disclosure.
Figure 10D:
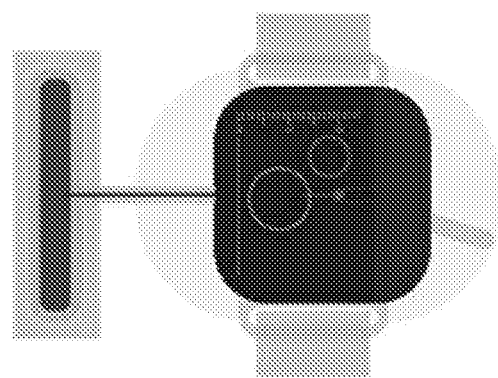
Figure 10C:
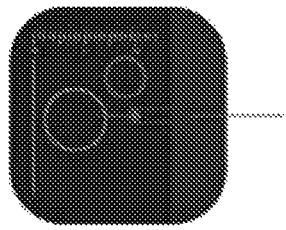
Figure 10B:
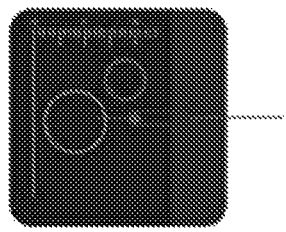
Figure 10A:
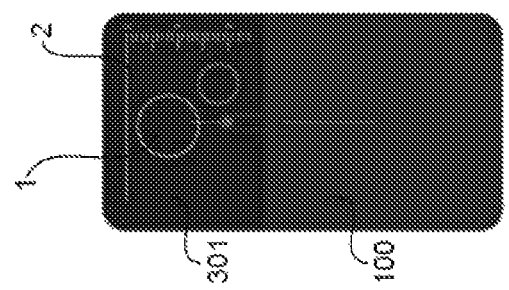

In one example of such navigational systems, FIGS. 10A-10E illustrate an exemplary GUI on housing 100. The GUI provides a representative image of vessels 1, 2 in the circulatory system, as well as a representation of needle 301. As represented in this example, a vein 1 and an artery 2 are both located by the navigational capability of housing 100, and shown in cross-sectional view, and the needle 301 is subsequently directed towards vein 1 (as discussed below). As illustrated, the GUI may also include various navigational aids such as the ruler on the right-hand side. As illustrated in FIGS. 10D-10E, a GUI may also be positioned on the tourniquet to provide information to the user at the tourniquet in addition to, or alternative to, that displayed on the housing GUI itself.

Figure 11C:
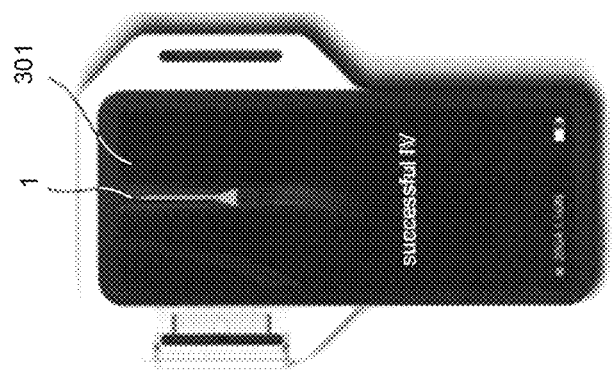
Figure 11B:
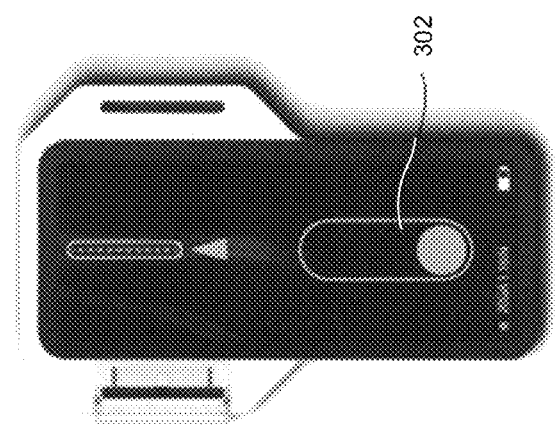
Figure 11A:
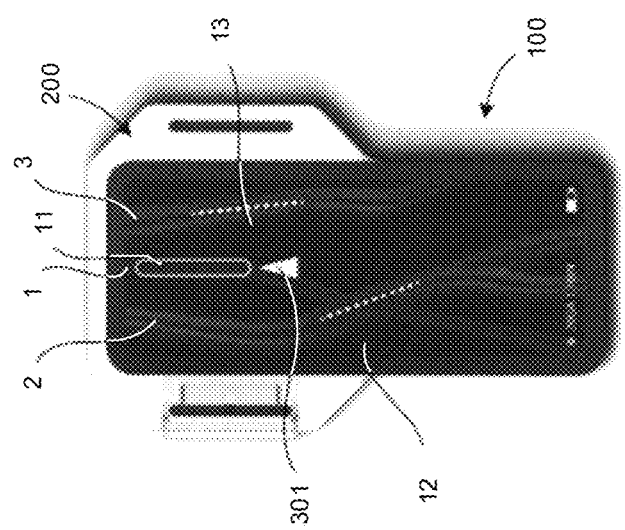

FIGS. 11A-11C illustrate another embodiment of the present disclosure, whereby vessels 1, 2, 3 are illustrated in bird's eye or top view and the needle 301 is represented as an arrow. In this example, three potential puncture sites are designated by dotted lines 11, 12, 13 along particular lengths in the respective vessels. The GUI of this example includes a box, illustrated at dotted line 11 on vessel 1, which designates which location has been selected for insertion of the needle (as in FIG. 11C). In this example, housing 100 includes the ability to determine the depth of location 11 on vessel 1 and extrapolate to a puncture site on the patient's skin surface (not shown) which may be positioned adjacent to base 200. As illustrated in FIG. 11B, once location 11 has been designated by the selection box, in the case of a semi-autonomous system, the operator may interact with the housing 100 to initiate needle insertion. As illustrated, this interaction may be with a button 302 on the GUI, in this example designated as a swipe button 302, though other forms of interaction are envisioned. FIG. 11C then illustrates the final inserted position of needle 301, which is now shown as an elongated arrow to illustrate the length of the needle 301 within vessel 1. As discussed above, any desired information can also be displayed on the GUI or elsewhere on the housing 100 (or separate interface), such as battery life, needle gauge, vessel diameter(s), and the like.

Figure 12A:
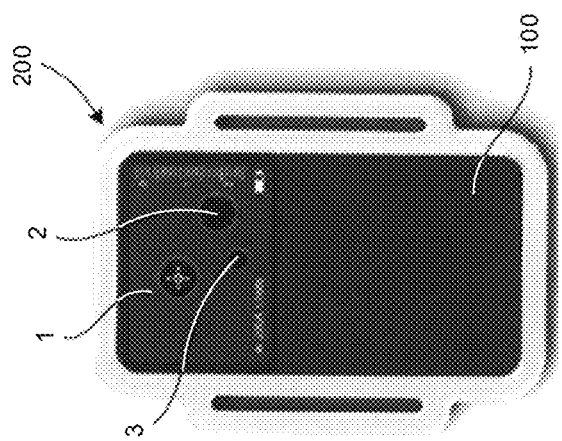
Figure 12B:
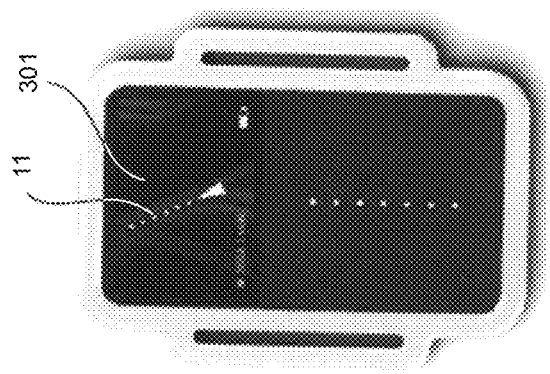
Figure 12C:
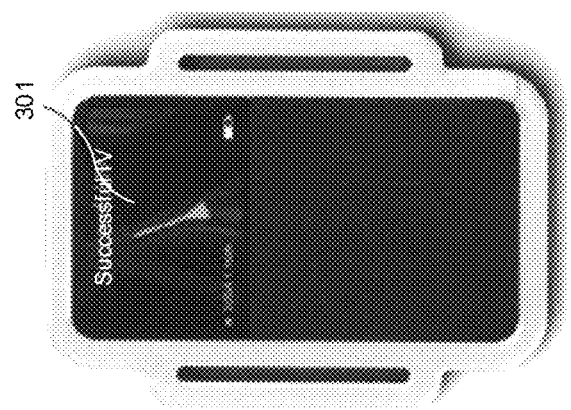

FIGS. 12A-12C illustrate another embodiment of the present disclosure which illustrates how housing 100 can have the capability to switch between multiple views including, for example, a cross-sectional view (FIG. 12A) and a bird's eye or top view (FIG. 12B). FIG. 12C illustrates, similar to FIG. 11C, the completed insertion of needle 301. As discussed above with reference to FIGS. 11A-11C, this embodiment can similarly include, for example, various information displayed on the GUI, a dotted line 11 designating a suggested insertion location for the needle 301, and a representation of the needle 301 by an arrow (FIG. 12B) and an elongated needle (FIG. 12C). Depending on the size of the display on the housing 100, the display may provide for split-screen viewing such that, for example, both the cross-sectional and top view images can be shown simultaneously. Such a capability could be particularly useful in operator-guided or assisted needle insertion procedures (i.e., semi-autonomously), since the multi-screen provides a more intuitive and realistic visual depiction of the blood vessels and consequently enable an operator to precisely locate the needle in a patient's vessel.

Figure 13B:
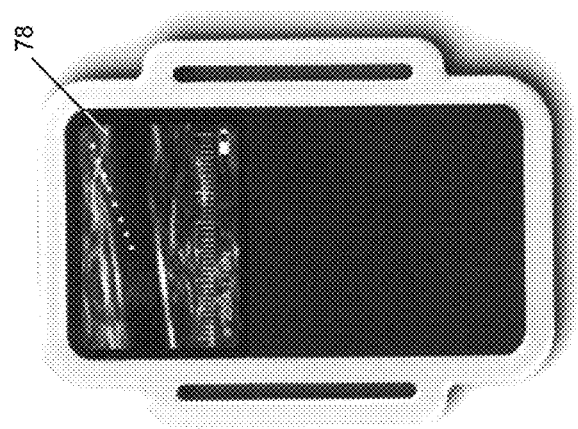
Figure 13A:
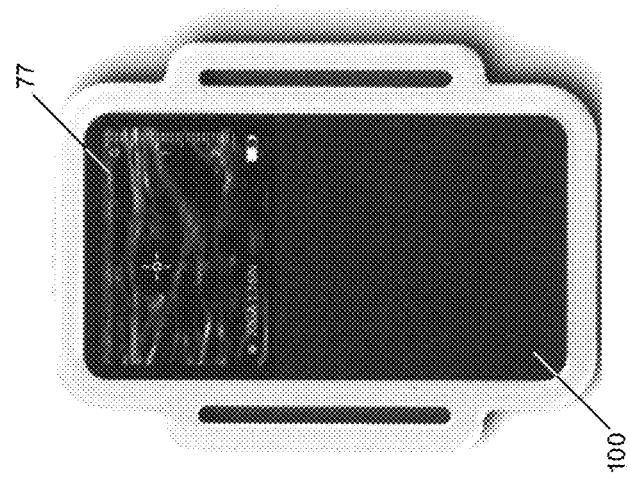

FIGS. 13A-13B illustrate a further embodiment of the present disclosure, wherein in this example housing 100 includes a GUI with the ability to display an ultrasound image and information overlaying the ultrasound image. As with the graphic representations of FIGS. 11A-12C, the ultrasound images may include cross-section 77 (FIG. 13A) and top view or side view 78 (FIG. 13B) displays, along with various overlaid information such as dimensions, rulers, position coordinates, battery life, etc.

FIG. 14 illustrates an embodiment of how a visual display (GUI) 430 of the present disclosure would utilize ultrasonic sensors as part of its navigation system. The capability to display ultrasound images of the device can include generation and depiction of a two-dimensional or three-dimensional view of a patient's anatomy. A two-dimensional image can generate views in the x- and y-directions 431, 432, 433 typically by including two separate ultrasonic scanners within the housing that an operator can toggle between to generate the cross-section and longitudinal (side or top) views, or the views are separately displayed on a multi-faced display. A three-dimensional ultrasonic image can be generated by incorporating another probe in a z-orientation, or alternatively, by providing another degree of freedom to the housing relative to the patient. The visual display (GUI) may be general ultrasound imaging depicting various regions based on the echo strength with white layers for a strong echo, and black layers for a weak echo, whereby the navigation system processes the ultrasound information to produce a diagrammatic color representation of the insertion area allowing for improved visual feedback.

Figure 15:
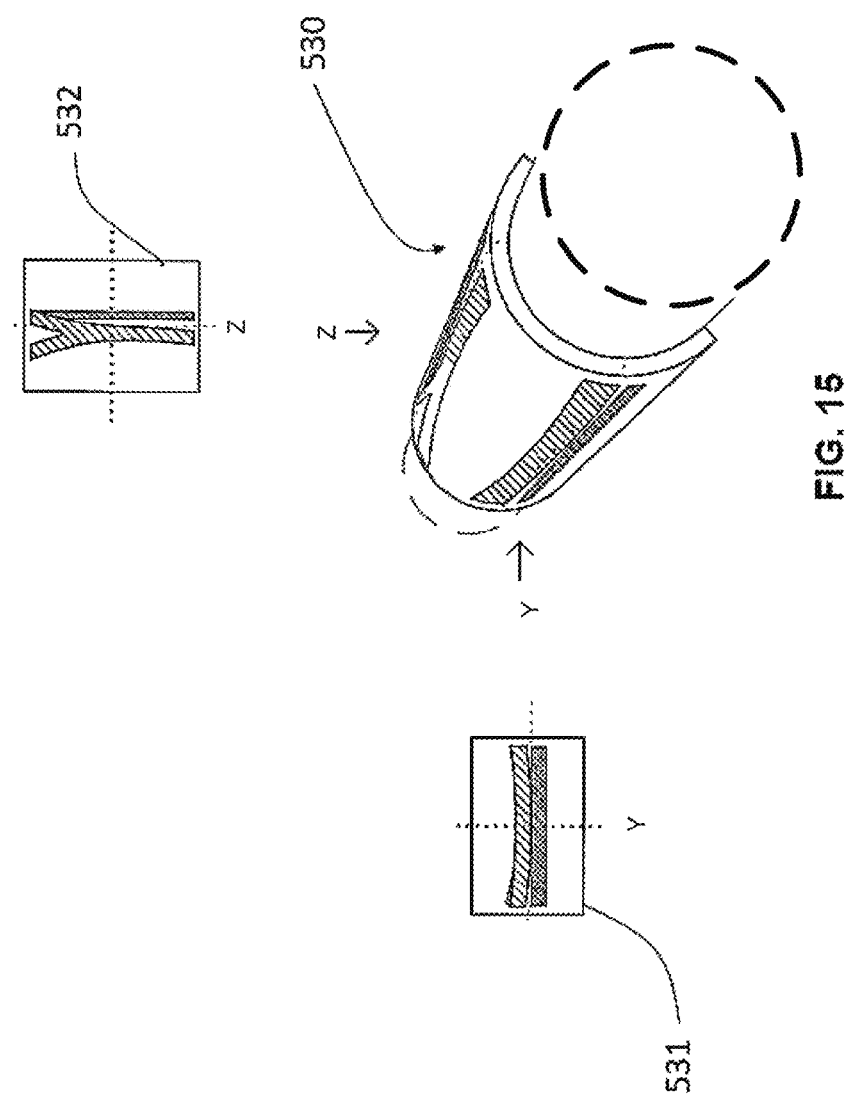

FIG. 15 provides still another embodiment of a GUI 530 which, similar to FIG. 14, can provide multiple views on different surfaces. In this embodiment, the surface of the device is curved, such that the different views (as illustrated, a z-direction view and a y-direction view, though other configurations are possible) are displayed along different portions of the curved surface. The surface of the device may be a single, continuous GUI or the GUI may be divided into multiple screens positions along particular portions of the curved surface.

In a further embodiment, the GUI may have anti-glare and/or privacy filters to hide or shield the display from the patient to limit or prevent patient anxiety. This application may be particularly useful when the device is being used on children. For example, the device may include two different displays depending on the direction of viewing. For example, from the operator's viewing angle, the above anatomical visualizations would be seen, while from the patient's viewing angle a pleasing picture would be seen to calm the patient. Alternatively, in embodiments where the device operates autonomously, and as such a GUI may not be required, a GUI may nonetheless be included on the housing such that the patient could view animations, videos, or video games to serve as a distractor during the needle insertion process. In certain instances, the video game or animation could coincide with the needle insertion process.

Referring now to FIG. 32, there is shown a visualization device 100' according to one embodiment of the present disclosure. Visualization device 100' includes a probe surface 102', a plan view display 104' and a first depth view display 106' and a second depth view display 108'. As more fully described below, probe surface 102' includes multiple transducers to generate two dimensional images of a volume 10' representing a target body zone in a patient. Volume 10' is located below a skin surface 12' and has a length 14', a width 16' and a depth 18' along a Z, X and Y axis respectively as denoted by an orientation reference 11'. As shown in FIG. 32, plan view display 104' and probe surface 102' is substantially the same size as width 16' and length 14', respectively, of volume 10'. Thus probe surface 102' defines an area that is sufficient to generate two dimensional images to cover volume 10'. Similarly first depth view display 106' and second depth view display 108' correspond to volume 10'. Other embodiments may have different display screen sizes. For example, displays 104', 106', 108' can be configured to be larger than corresponding dimensions of volume 10' to provide magnified views of volume 10' for improved visibility of the target body zone. Transducers on probe surface 102' can be configured to generate ultrasonic communication to vary depth 18' depending on the target body zone and visualization needs of the same.

While a generally rectangular shaped visualization device 100' is shown in FIG. 32, other embodiments can have various other shapes as more fully described below. Similarly, volume 10' can also have different shapes depending on probe surface 102' and the transducers positioned thereon. Visualization device 100' can be configured to be a stand-alone device including all other components such as a power source (batter), required circuitry to operate the transducers, image processing to combine the two dimensional images generated by the transducers to a three dimensional view of volume 10', etc. In other embodiments, visualization devices can be configured to connect to an external power source or a remotely located image processor. The image processor includes an advanced graphic processing unit ("GPU") configured to generate real time three dimensional visualization. Visualization devices configured to interface with external components will reduce the overall size and dimensions of the visualization device.

Figure 33:
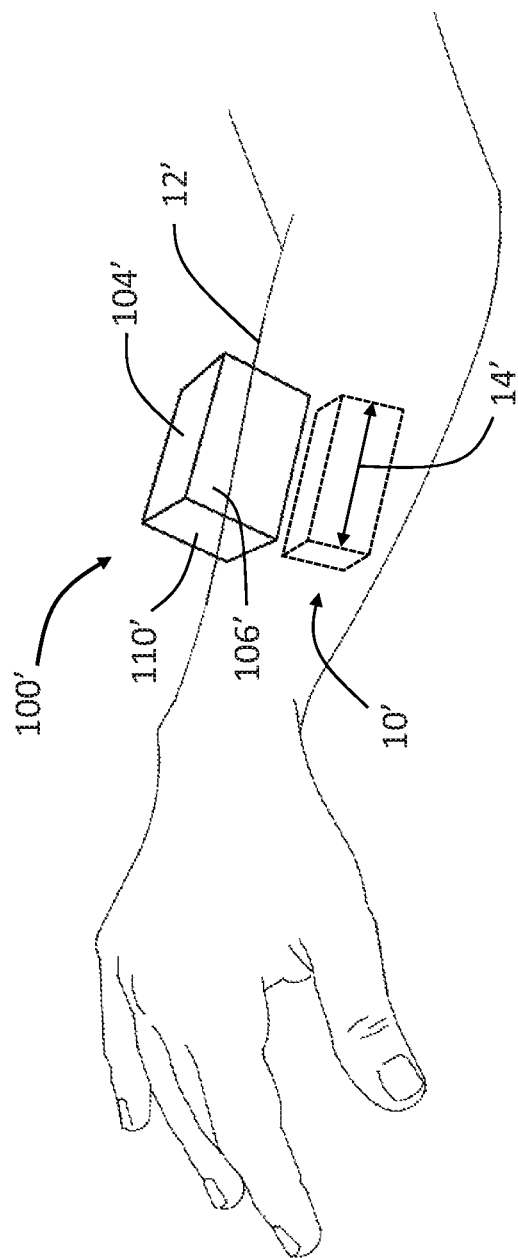
FIG. 33 is a schematic perspective view of the visualization device of FIG. 32 placed on a target body zone.

FIG. 33 shows visualization device 100' placed on a forearm of a patient to aid in a cannula insertion procedure. Volume 10' covers the relevant insertion zone including veins and nerves under skin 12'. As best shown in FIG. 34A, plan view display 104' shows a plan view of volume 10' including a vein 20', a vein branch 24' and a nerve 22' located under skin surface 12' in real time when visualization device is placed on the forearm as shown in FIG. 33. FIG. 34B shows first depth view display 106' showing a depth view of vein 20', vein branch 24' and nerve 22' along the Z-axis and Y-axis. FIG. 34C displays second depth view display 108' showing vein 20' and nerve 22' along the Y-axis and a X-axis. Thus, visualization device 100' provides an operator with real time three dimensional views representing veins and nerves to allow for precise cannula insertion. Other details of the target body zone, such as blood flow direction, valves, tissue condition, etc. can also be displayed on displays 104', 106' and 108'.

Referring now to FIGS. 35A and 35B, there is shown visualization device 100' placed on two different locations on a patient's body. As shown here, visualization device 100' is placed on two exemplary positions—a patient's biceps and a patient's wrist. Placing visualization device 100' on these various body locations may allow an operator to instantly view in real time three dimensional visualization volume 10' located under visualization device 100'.

Figure 36A:
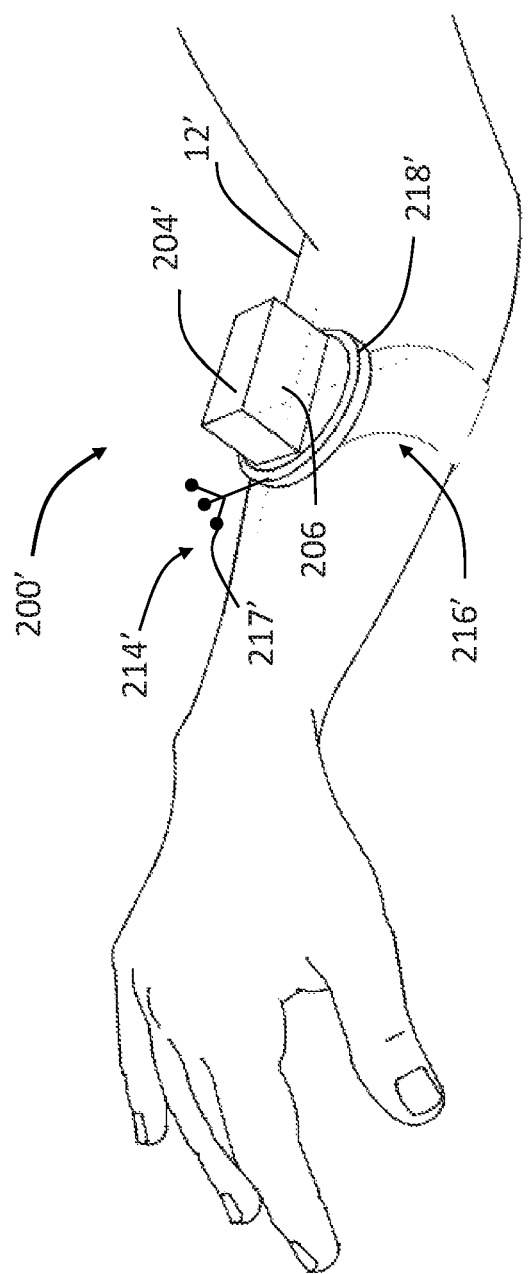
FIG. 36A is a schematic perspective view of a visualization device according to another embodiment of the present disclosure.
Figure 36B:
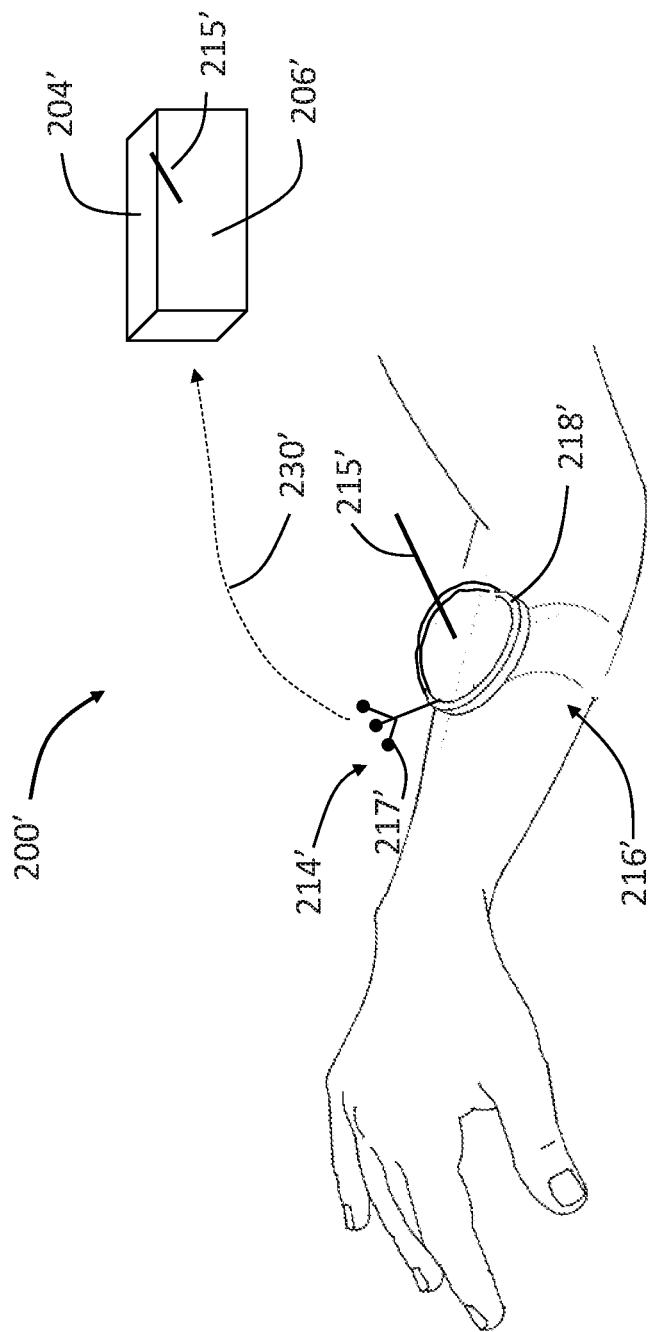
FIG. 36B is a schematic perspective view of a display detached from a frame of the visualization device of FIG. 36A.

FIGS. 36A and 36B show a visualization device 200' according to another embodiment of the present disclosure. Visualization device 200' is similar to visualization device 100', and therefore like elements are referred to with similar numerals within the 200'-series of numbers. For instance, visualization device 200' includes a plan view display 204' and a first depth view display 206'. However, visualization device 200' includes an attachment device 216' such as strap or tourniquet with a frame 218' as shown in FIG. 36A. Attachment device 216' is configured wrap around the patient's arm or other region. Frame 218' is configured to detachably seat displays 204', 206', 208' and probe surface 202'. Visualization device 200' includes a tracker 214' connected to frame 218'. Tracker 214' can include multiple tracking elements 217' configured to situate attachment device 216' with reference to volume 10'. As such, once volume 10' is visualized in three dimensions, tracker 214' can provide three dimensional coordinates of any point in volume 10'. As shown in FIG. 36B, displays 204', 206', 208' and probe surface 202' can be detached from attachment device 216'. Tracker 214' communicates three dimensional coordinates of volume 10' in real time through a direct or remote connection 230'. Remote connection mechanisms can include Bluetooth, Bluetooth Low Energy, cellular, Wi-Fi or other long range platforms. For example, a cannula image 215" of a cannula 215' is shown in real time on first depth view display 206' as cannula 215' approaches and enters volume 10'. Imaging or tracking means such as a video camera can be used to track the position of cannula 215 in volume 10. Thus visualization device 200' allows an operator to precisely locate cannula 215' within a patient's vein.

Figure 37:
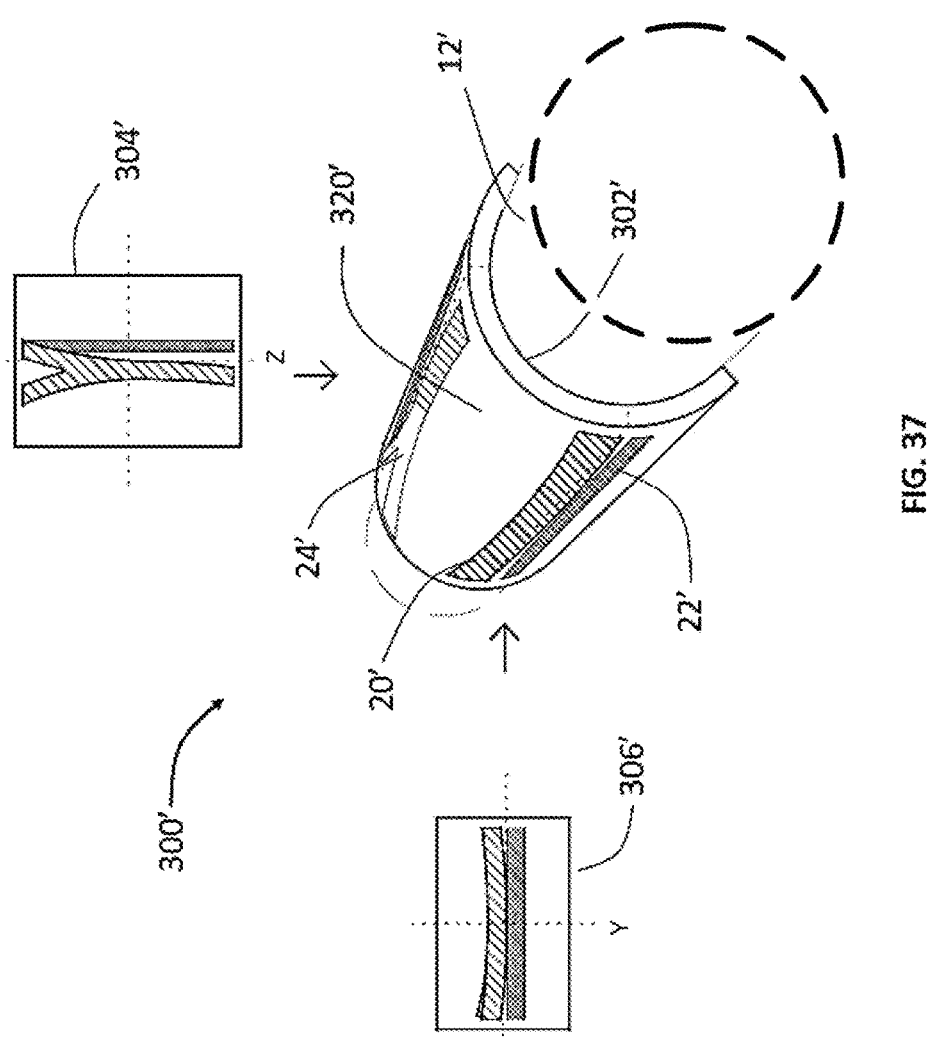
FIG. 37 is a schematic perspective view of a visualization device according to yet another embodiment of the present disclosure.

Referring now to FIG. 37, there is shown a visualization device 300' according to another embodiment of the present disclosure. Visualization device 300' is similar to visualization device 100', and therefore like elements are referred to with similar numerals within the 300'-series of numbers. For instance, visualization device 300' includes a plan view display 304' and a first depth view display 306'. However, visualization device 300' includes a curved screen 320' as best shown in FIG. 37. Curved screen 306' can be rigid and specifically adapted to fit body regions or may include a flexible probe surface area 302' (not shown) to allow visualization device 300' to be suitably placed over the target body region. An operator can view plan views and multiple depth views across curved display 320'.

FIGS. 38A and 38B show a visualization device 400' according to another embodiment of the present disclosure. Visualization device 400' is similar to visualization device 300, and therefore like elements are referred to with similar numerals within the 400-series of numbers. For instance, visualization device 400' includes a curved display screen 420'. However, visualization device 400' includes parallax viewing capability whereby a viewer's location can be tracked by a camera 425' or other device, such as a sensor, and a corresponding three dimensional view of volume can be displayed on curved screen 420' in relation to the viewer's location. For example, when the viewer is at a location 422', camera 425' tracks the viewer's location and displays a plan view 404' to align with the viewer's field of vision 424' shown in FIG. 38A. Similarly, when the viewer moves to a location 426', camera 425' locates this position and displays a first depth view display 406' on curved screen 420' to align with the viewer's field of vision 428' as best shown in FIG. 38B. In one particular example, the camera 425' or other sensor may track eye movements of the viewer and will adjust the display to account for such movements. The camera or other sensor can also track the distance between the viewer and the display to adjust the zoom of the image. Thus, visualization device 400' provides a parallax three dimensional view across curved screen display depending on a viewer's position (which may be fields of vision 422', 426', or any position in between). While a curved screen 420' is shown in this embodiment, other embodiments may have planar display screens with parallax three dimensional views as described above.

Figure 55:
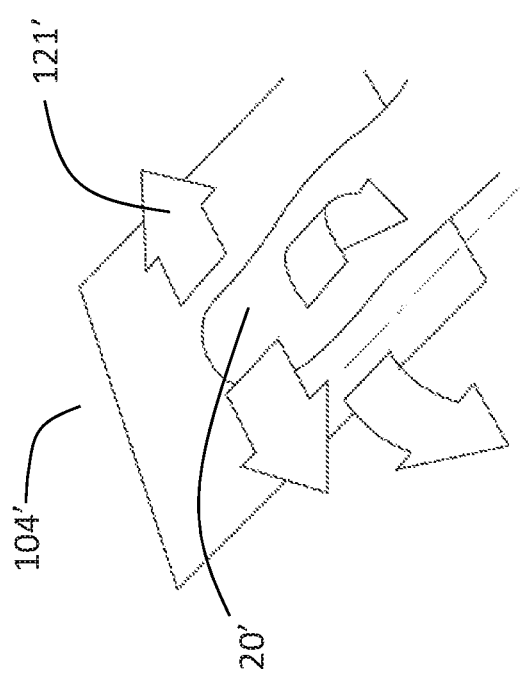
FIG. 55 is a schematic perspective view of the visualization device of FIG. 7C.

FIGS. 38C and 38D show another embodiment of a parallax view on visualization device 100'. It should be noted that the parallax view concepts described herein can be used in conjunction with any visualization device. A viewer positioned at locations 1, 2 or 3 observes a unique three dimensional perspective view of the volume 10' specific to each location. For example, when the viewer is positioned at location 1, the viewer observes a three dimensional plan view display 104' as shown in FIG. 38E. Similarly, when the viewer moves and is positioned at locations 1 or 2, the viewer observes a three dimensional third depth view 110' or a three dimensional first depth view 106' as best shown in FIG. 38F and FIG. 38G respectively. Thus, as above, according to movement of the viewer, such as eye movement of the user, the display will update accordingly to provide the particular visualization for the particular locations and movement of the viewer. The display screens displaying parallax views can include touch sensitive screen surfaces whereby the user can swipe the display as shown by direction arrows 121' in FIG. 55 to rotate views for parallax-enabled depth perception. In another embodiment, the visualization device can display only the cross-sectional view on each display. For example, display surfaces 108', 106' and 104' will each display only the cross-sectional view corresponding to each display—i.e., this embodiment may not include any three dimensional perspective views.

Figure 39:
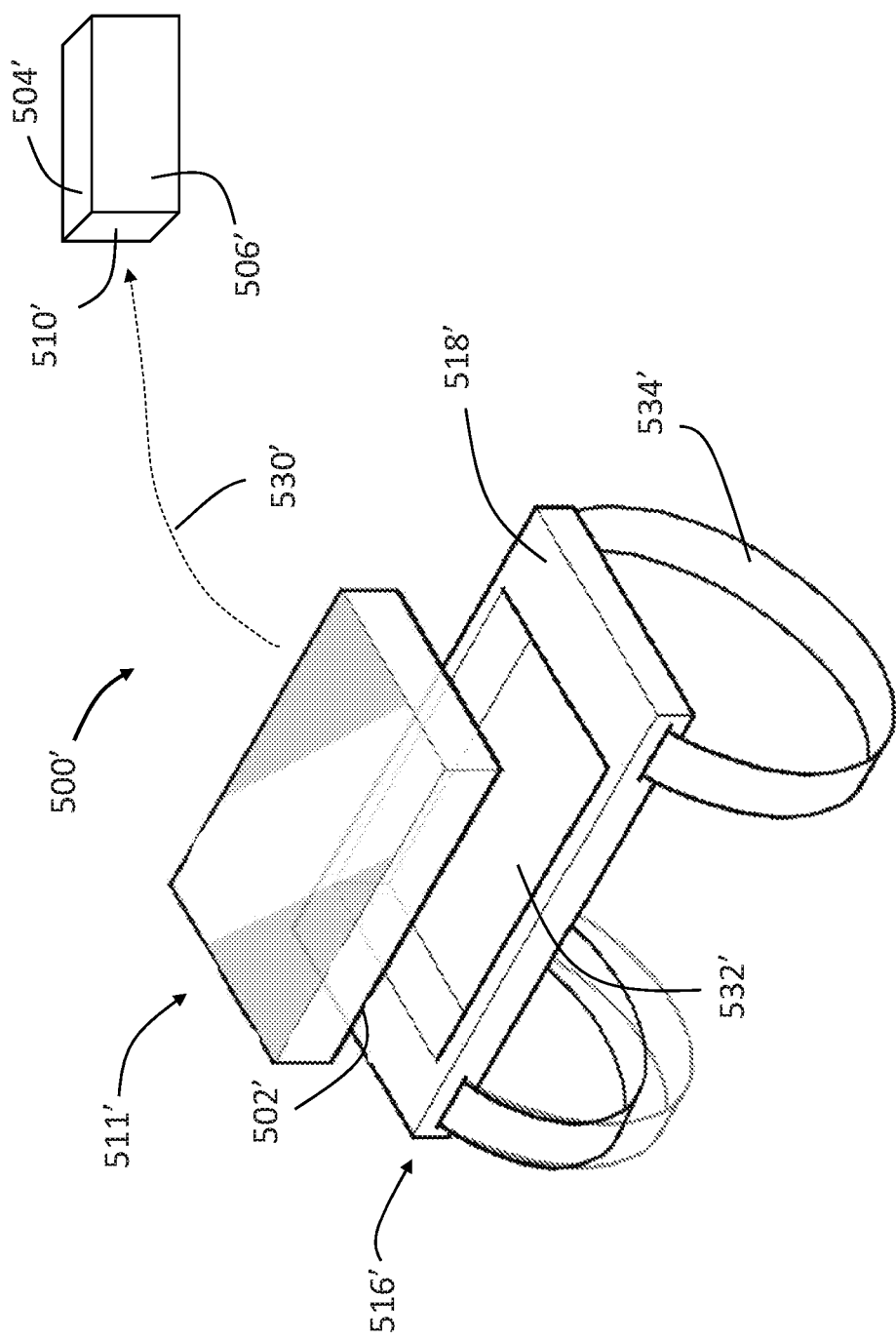
FIG. 39 is a schematic perspective view of a visualization device according to yet another embodiment of the present disclosure.

Referring now to FIG. 39, there is shown a visualization device 500' according to another embodiment of the present disclosure. Visualization device 500' is similar to visualization device 100', and therefore like elements are referred to with similar numerals within the 500'-series of numbers. For instance, visualization device 500' includes a plan view display 504', a first depth view display 506' and a third depth view display 510.' However, visualization device 500' includes a probe body 511' having a probe surface 502' that is separate from displays 504', 506' and 510'. Probe body 511' is configured to be placed in an opening 532' of an attachment device 516'. Attachment device 516' can include a base, such as a frame 518' and straps 534' as illustrated, which can be secured to a patient's body. As probe body 511' of visualization device 500' does not contain display screens, the probe body size and dimensions can be less than a visualization device including displays. Once probe body 511' is placed in opening 532', probe surface 502' can generate a three dimensional visualization of volume 10' and transmit same through a link 530' to displays 504', 506' and 510' to show real time three dimensional visualization of volume 10'.

Figure 40:
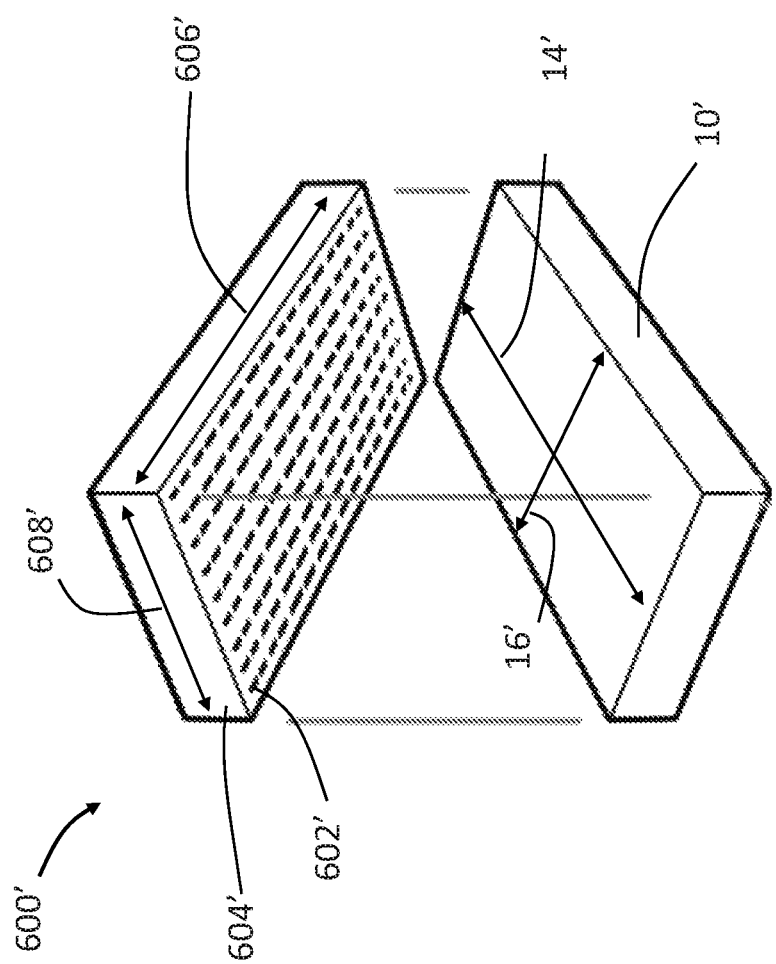
FIG. 40 is a schematic perspective view of a transducer array according to one embodiment of the present disclosure.

FIG. 40 shows a transducer array 600' on a probe surface 602' according to an embodiment of the present disclosure. Transducer array 600' can be utilized with any of the visualization devices described above. Transducer array 600' includes transducers 602' arranged in a grid defining a rectangular pattern having a length 606' and a width 604'. Transducers 600' are attached to a substrate 604'. Ultrasonic transducers or ultrasonic sensors such as capacitive micro-machined ultrasonic transducers ("CMUT"), ultrasonic transducers, piezoelectric transducers, or the like can be used to create the array. Other embodiments can have a combination of CMUT and piezoelectric transducers, or other such combinations, depending on the specific body regions being visualized. Substrate 604' can be a silicon substrate when CMUT are utilized. CMUTs can be placed within cavities in a silicon substrate 604'. Transducers 602' are configured to switch between transmission and reception modes to generate and capture ultrasonic reception. An algorithm can be used to activate individual CMUTs and switch them between transmission and reception modes as desired. As best shown in FIG. 40, the projected area of transducer array 600' is substantially the same as a surface area of volume 10' defined by length 14' and width 16'. Therefore, a three dimensional visualization of volume 10' can be generated by placing transducer array 600' at the body zone.

Figure 41C:
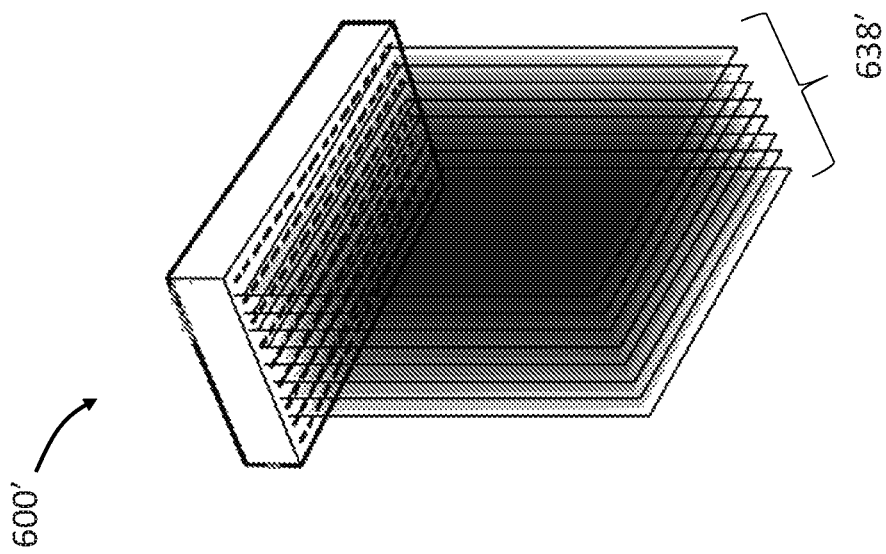
FIGS. 41A-41C are schematic perspective views showing three dimensional visualization from two dimensional images generated by the transducer array of FIG. 40.
Figure 41B:
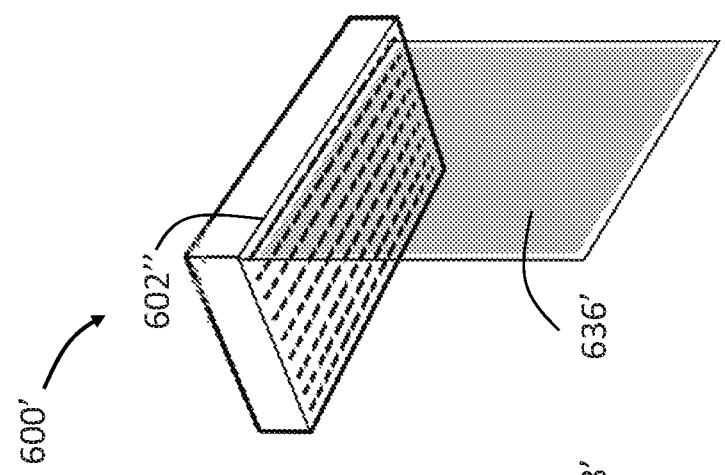
Figure 41A:
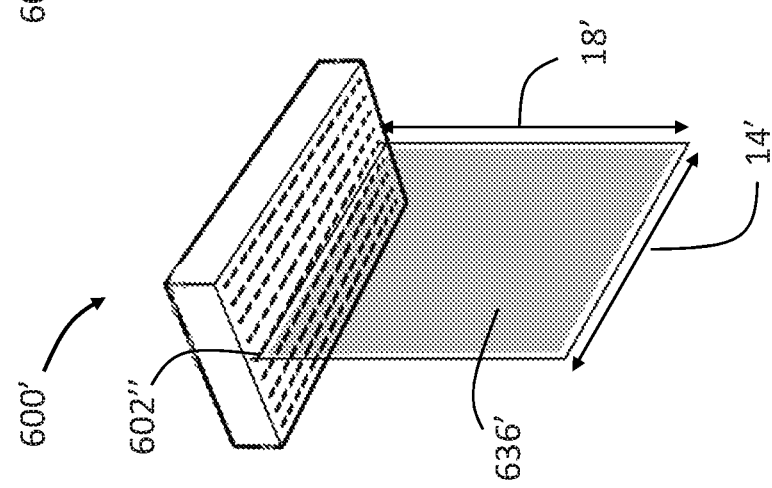

Referring now to FIGS. 41A-41C, there is shown the creation of three dimensional visualization of volume 10' utilizing transducer array 600'. An active transducer 602", i.e., a transducer in transmission or reception modes, can include a single transducer, a row of transducers or the entire transducer array 600'. FIG. 41A shows an active transducer row 602" generating a two dimensional image 636' capturing a two dimensional slice of volume 10'. Depth 18' of two dimensional image 636' depends on the type of transducer 602' and the power supplied through it. Both these parameters can be suitably varied depending on the application of the visualization device. For example, low power transmission through a coarse transducer array can be utilized to generate two dimensional images with low depth penetration, and high power transmission through a fine transducer array can be used to generate two dimensional images with greater depth penetration. The density of transducers 602' across transducer array 600' can be varied to adjust the quality of the two dimensional images. For example, a high density transducer array can be used to generate two dimensional images with high resolution, whereas a low density transducer array can be used to generate two dimensional images with low resolution. FIG. 41B shows a second row of transducers 602″ activated to generate two dimensional image 636′ at a second location. As described above, rows can be individually or simultaneously activated as shown in FIG. 41C. After generation of two dimensional images 636′ across volume 10, a two dimensional image collection 638′ is then processed by an image processor housed within a visualization device or externally to create a three dimensional visualization of volume 10′.

Figure 42:
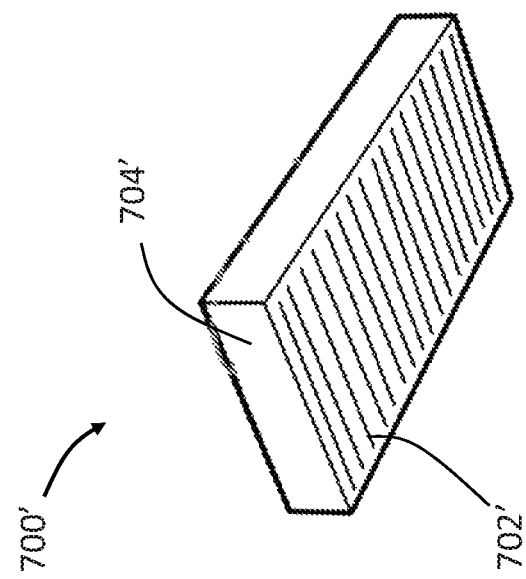
FIG. 42 is a schematic perspective view of a transducer array according to another embodiment of the present disclosure.

FIG. 42 is a transducer array 700′ according to another embodiment of the present disclosure. Transducer array 700′ is similar to transducer array 600′, and therefore like elements are referred to with similar numerals within the 700′-series of numbers. For instance, transducer array 700′ includes transducers 702′ disposed in a substrate 704′. However, transducer array 700′ has transducers 702′ along width 16′ of volume 10′ to generate two dimensional images along the width in some applications, rather than along the length as discussed above.

Figure 43:
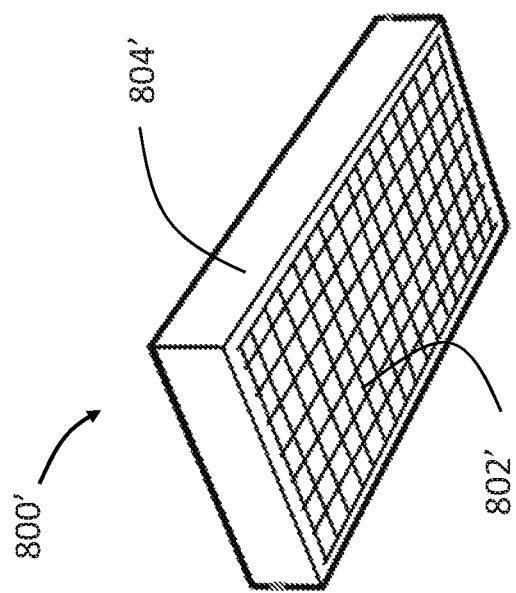
FIG. 43 is a schematic perspective view of a transducer array according to a further embodiment of the present disclosure.

FIG. 43 is a transducer array 800′ according to another embodiment of the present disclosure. Transducer array 800′ is similar to transducer array 600′, and therefore like elements are referred to with similar numerals within the 800′-series of numbers. For instance, transducer array 800′ includes transducers 802′ disposed in a substrate 804′. However, transducer array 800′ has transducers 802′ along both length 14′ and width 16′ of volume 10′. This allows transducer array 800′ to generate two dimensional images in multiple directions for high resolution three dimensional visualization of volume 10′.

Figure 44:
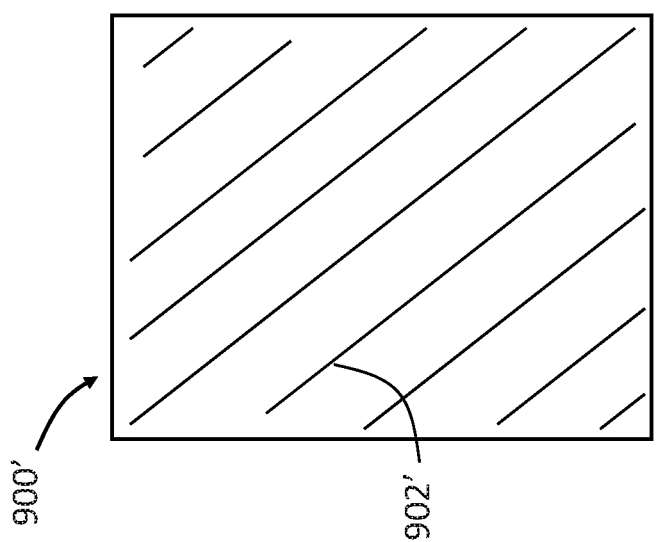
FIG. 44 is a front view of a transducer array according to yet another embodiment of the present disclosure.

FIG. 44 is a transducer array 900′ according to another embodiment of the present disclosure. Transducer array 900′ is similar to transducer array 600′, and therefore like elements are referred to with similar numerals within the 900′-series of numbers. For instance, transducer array 900′ includes transducers 902′ disposed in a substrate 904′. However, transducer array 900′ has transducers 902′ along a diagonal dimension to generate two dimensional images.

Figure 45:
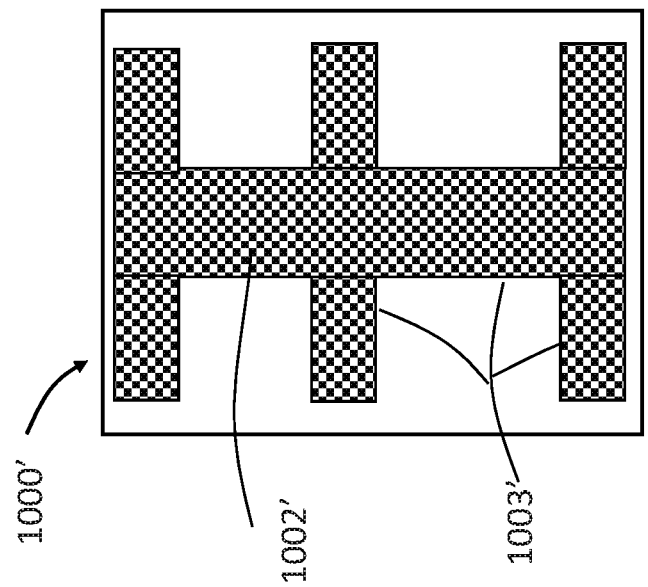
FIG. 45 is a front view of a transducer array according to still another embodiment of the present disclosure.

FIG. 45 is a transducer array 1000′ according to another embodiment of the present disclosure. Transducer array 1000′ is similar to transducer array 600′, and therefore like elements are referred to with similar numerals within the 1000′-series of numbers. For instance, transducer array 1000′ includes transducers 1002′ disposed in a substrate 1004′. However, transducer array 1000′ does not cover the entire probe surface area as described in the previous embodiments. Transducers 1002′ are strategically placed to allow projection of ultrasonic signals across the probe surface area to cover volume 10′ without the need to have transducers positioned directly over each location on volume 10′. This can be accomplished as best shown in FIG. 45 wherein the gaps between traducer rows 1003′ are configured to be covered by transducers 1002′ selected to transmit and receive ultrasonic signals in a plurality of directions.

Figure 46:
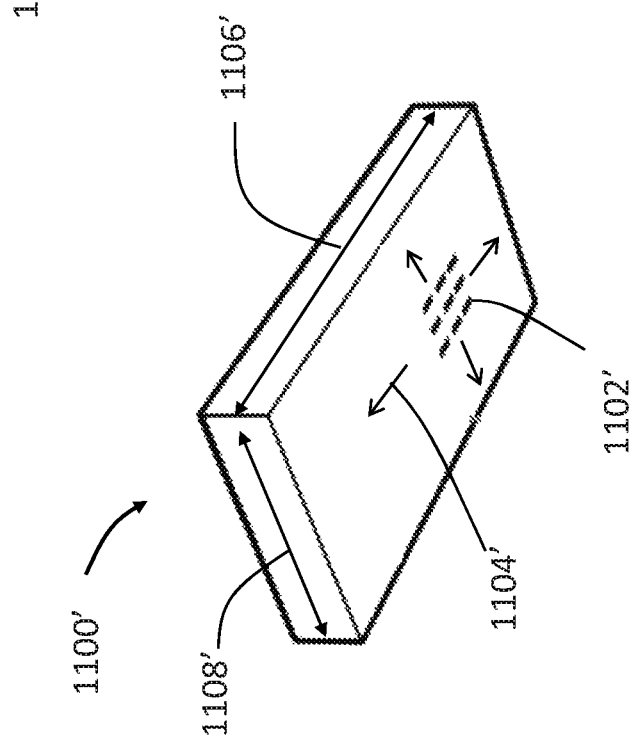
FIG. 46 is a schematic perspective view of a transducer array according to another embodiment of the present disclosure.

FIG. 46 is a transducer array 1100′ according to another embodiment of the present disclosure. Transducer array 1100′ is similar to transducer array 600′, and therefore like elements are referred to with similar numerals within the 1100′-series of numbers. For instance, transducer array 1100′ includes transducers 1102′ disposed in a substrate 1104′. However, transducer array 1102′ is configured to move around probe surface area as indicated by direction arrows 1104′. Thus, transducer array size 1102′ can be significantly smaller than the previous fixed transducer arrays described above. The resolution and coverage of volume 10′ can be controlled by controlling the speed of transducer array 1102′ across the probe surface area.

Figure 47:
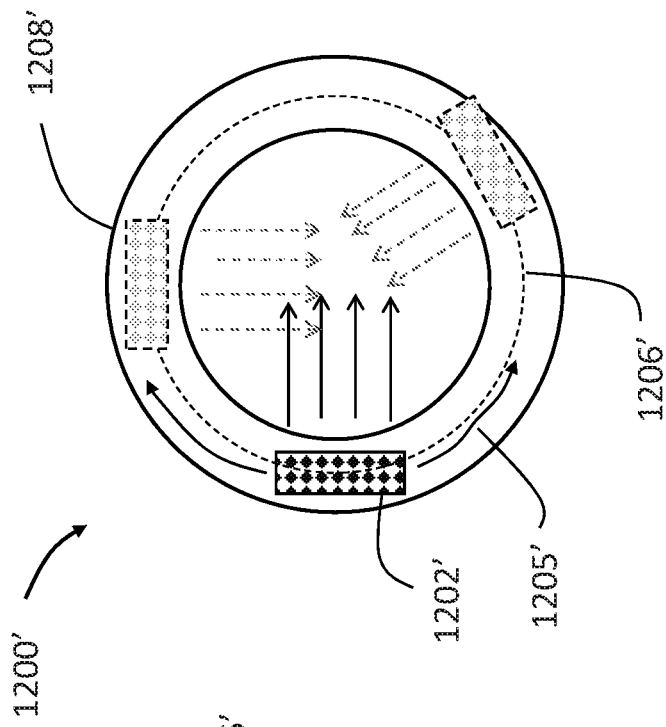
FIG. 47 is a front view of a transducer array according to a further embodiment of the present disclosure.

FIG. 47 is a transducer array 1200′ according to another embodiment of the present disclosure. Transducer array 1200′ is similar to transducer array 1200′, and therefore like elements are referred to with similar numerals within the 1200′-series of numbers. For instance, transducer array 1200′ includes transducers 1202′ disposed in a substrate 1204′. However, substrate 1204′ in this embodiment is circular and configured to be placed around a patient's body region. Transducers 1202′ is configured to move around probe surface area as indicated by direction arrows 1205′ along a circular path 1206′. Therefore, volume 10′ defined as the region within probe surface area is covered by mobile transducer array 1202′. Similar to transducer array 1100′, transducer array 1200′ requires only a small transducer array to generate three dimensional visualization of volume 10′.

Figure 48:
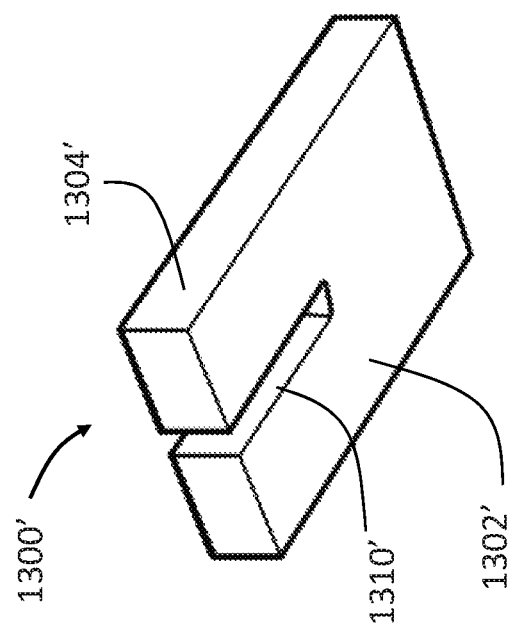
FIG. 48 is a schematic perspective view of a transducer array according to yet another embodiment of the present disclosure.

FIG. 48 is a transducer array 1300′ according to another embodiment of the present disclosure. Transducer array 1300′ is similar to transducer array 600′, and therefore like elements are referred to with similar numerals within the 1300′-series of numbers. For instance, transducer array 1300′ includes transducers 1302′ disposed in a substrate 1304′. Transducer array 1300′ includes a slot 1310′ to allow for surgical procedures to be performed within the area of the outer perimeter of substrate 1304′ while the transducer array is placed on the target body zone. Transducers 1302′ adjacent to slot 1310′ are configured to cover the portion of volume 10′ directly under slot 1302′. For example, transducers 1302′ adjacent to slot 1310′ may be angled towards the volume 10′ directly under the slot, such transducers may have the capability to cover a larger portion of volume 10′ than the others, or the like.

Figure 49:
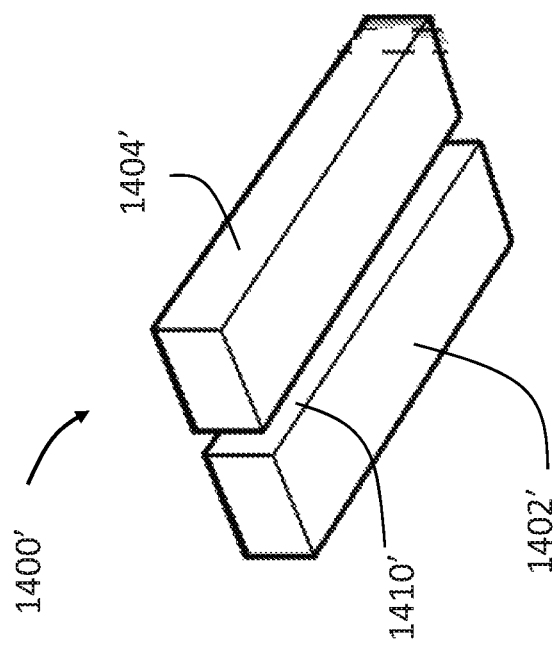
FIG. 49 is a schematic perspective view of a transducer array according to still a further embodiment of the present disclosure.

FIG. 49 is a transducer array 1400′ according to another embodiment of the present disclosure. Transducer array 1400′ is similar to transducer array 1300′, and therefore like elements are referred to with similar numerals within the 1400′-series of numbers. For instance, transducer array 1400′ includes transducers 1402′ disposed in a substrate 1104′. Transducer array 1400′ includes a slot 1410′ that extends across the array to allow for surgical procedures while the transducer array is placed on the target body zone. As discussed above relative to FIG. 48, transducers 1402′ adjacent to slot 1410′ are configured to cover the portion of volume 10′ directly under slot 1402′.

FIG. 50 is a transducer array 1500′ according to another embodiment of the present disclosure. Transducer array 1500′ is similar to transducer array 1300′, and therefore like elements are referred to with similar numerals within the 1500′-series of numbers. For instance, transducer array 1500′ includes transducers 1502′ disposed in a substrate 1504′. Transducer array 1500′ includes a slot 1510′ that extends across the array to allow for surgical procedures while the transducer array is placed on the target body zone. As discussed above relative to FIG. 48, transducers 1502′ adjacent to slot 1510′ are aligned and positioned to cover the portion of volume 10′ directly under slot 1502′.

Figure 51:
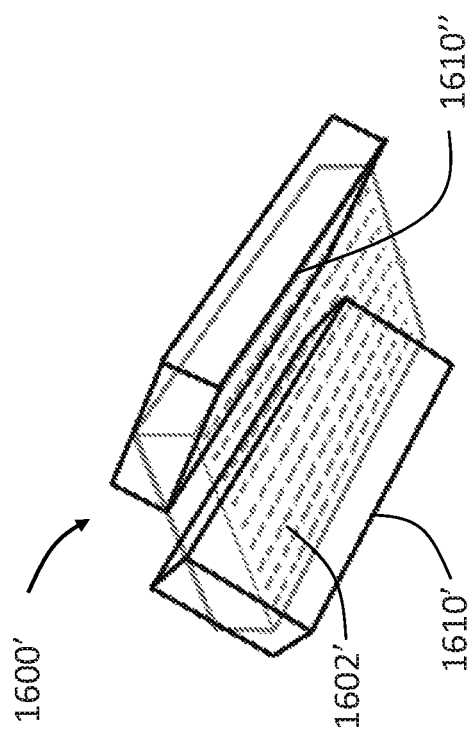
FIG. 51 is a schematic perspective view of a transducer array according to yet another embodiment of the present disclosure.

FIG. 51 is a transducer array 1600′ according to another embodiment of the present disclosure. Transducer array 1600′ is similar to transducer array 600′, and therefore like elements are referred to with similar numerals within the 1600′-series of numbers. For instance, transducer array 1600′ includes transducers 1602′ disposed in a substrate 1604′. Transducer array 1600′ includes a first block 1610′ and second block 1610″ which can be flexed apart as shown in FIG. 51. The separated first and second block allow for surgical procedures while the transducer array is placed on the target body zone.

Figure 52:
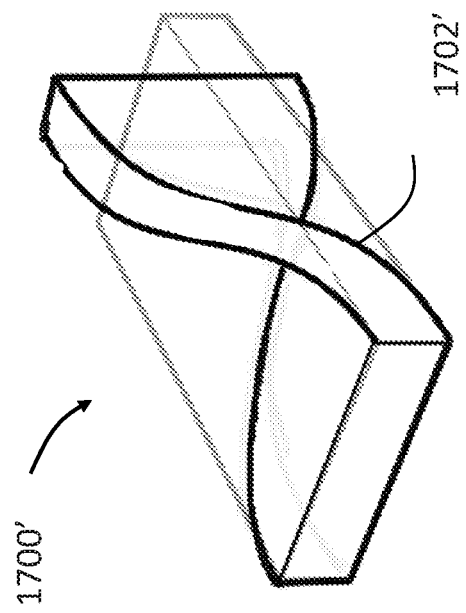
FIG. 52 is a schematic perspective view of a transducer array according to still a further embodiment of the present disclosure.

FIG. 52 is a transducer array 1700' according to another embodiment of the present disclosure. Transducer array 1700' is similar to transducer array 600', and therefore like elements are referred to with similar numerals within the 1700'-series of numbers. For instance, transducer array 1700' includes transducers 170'2 disposed in a substrate 1704'. Transducer array 1700' is flexible and can be contoured to any desired shape to be placed on specific body regions.

While a variety of transducer arrays have been illustrated and described above, other configurations are also envisioned. For example, the substrate may have a lower profile in any of all of the length, width or height directions, depending on the application or intended use or anatomy on which it will be used. Further, any portion of the substrate and/or array may be planar, curved, tapered, or the like as desired, such that any substrate and/or array shape may be achieved.

Figure 53:
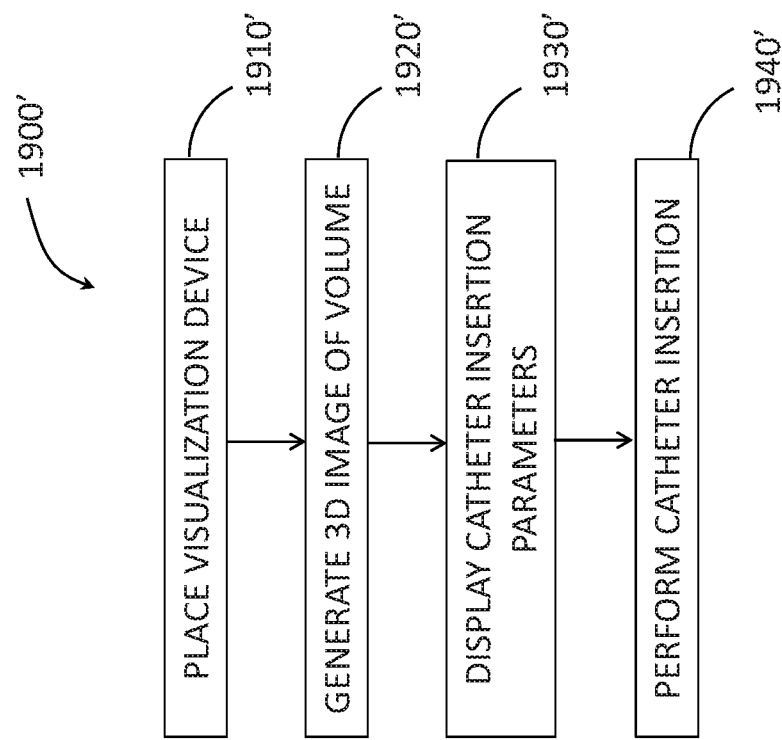
FIG. 53 is a flowchart showing the steps for performing a surgical procedure using a visualization device according to one embodiment of the present disclosure.

Referring now to FIG. 53, there is shown a flowchart depicting a method 1900' for performing a cannula insertion using visualization device 100' according to another embodiment of the present disclosure. While visualization device 100' is described here, any of the other visualization devices described or their various embodiments can be used to perform method 900'. Probe surface 102' is placed above the desired cannula insertion zone. Transducers disposed on probe surface area are activated by an algorithm to generate a series of two dimensional images across volume 10' in a step 1920'. The two dimensional images are combined to a three dimensional visualization by an image processor and shown on displays 104', 106' and 108'. Additional details such as projected cannula insertion location, projected cannula insertion depth, and projected cannula insertion path can be displayed by the visualization device 100' in a step 1930'. Cannula insertion parameters such as cannula insertion point location, vein puncture location, insertion depth, vein blood flow rate, blood pressure, and temperature can also be displayed by the visualization device 100'. An operator can evaluate the three dimensional visualization and cannula insertion parameters and initiate cannula insertion in step 1940". Cannula insertion can be performed manually or with aid of a cannula insertion assembly. Visualization device 100' can track position of cannula during positon of cannula in volume 10' to ensure precise cannula placement.

Figure 54:
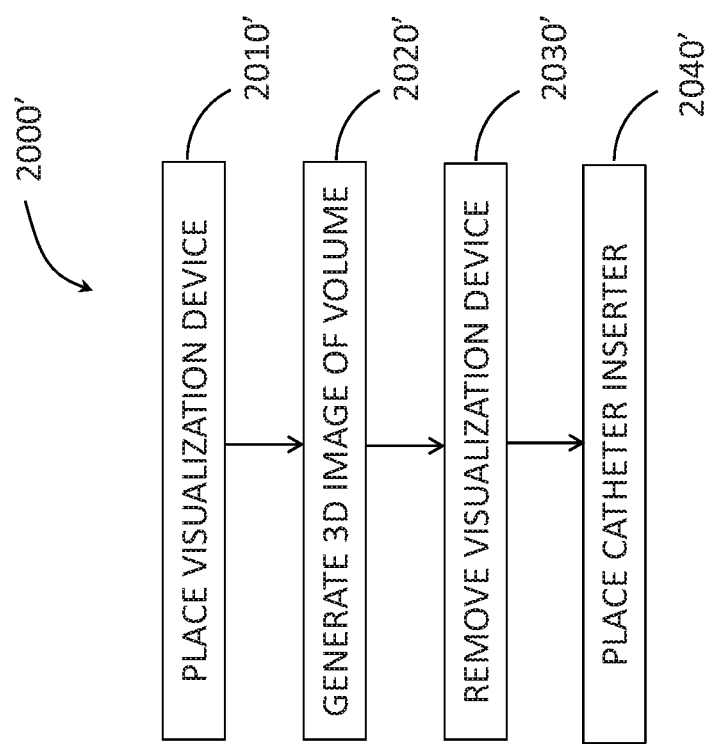
FIG. 54 is a flowchart showing the steps for performing a surgical procedure using a visualization device according to another embodiment of the present disclosure.

FIG. 54 shows a flowchart depicting a method 2000' for performing a cannula insertion using visualization device 200' according to another embodiment of the present disclosure. Method 2000' is similar to method 1900' and includes the step of placing visualization device 200' on the cannula insertion zone and generating a three dimensional image of volume 10'. However, once the three dimensional image is generated in step 2020', the displays and probe surface of visualization device 200' is detached from attachment device 216'. Tracker 214' communicates real time three dimensional data of volume 10' to displays of visualization device 200'. Cannula insertion can be performed manually or with aid of a cannula insertion assembly. Visualization device 200' can track position of cannula during positon of cannula in volume 10 to ensure precise cannula placement.

Figure 56:
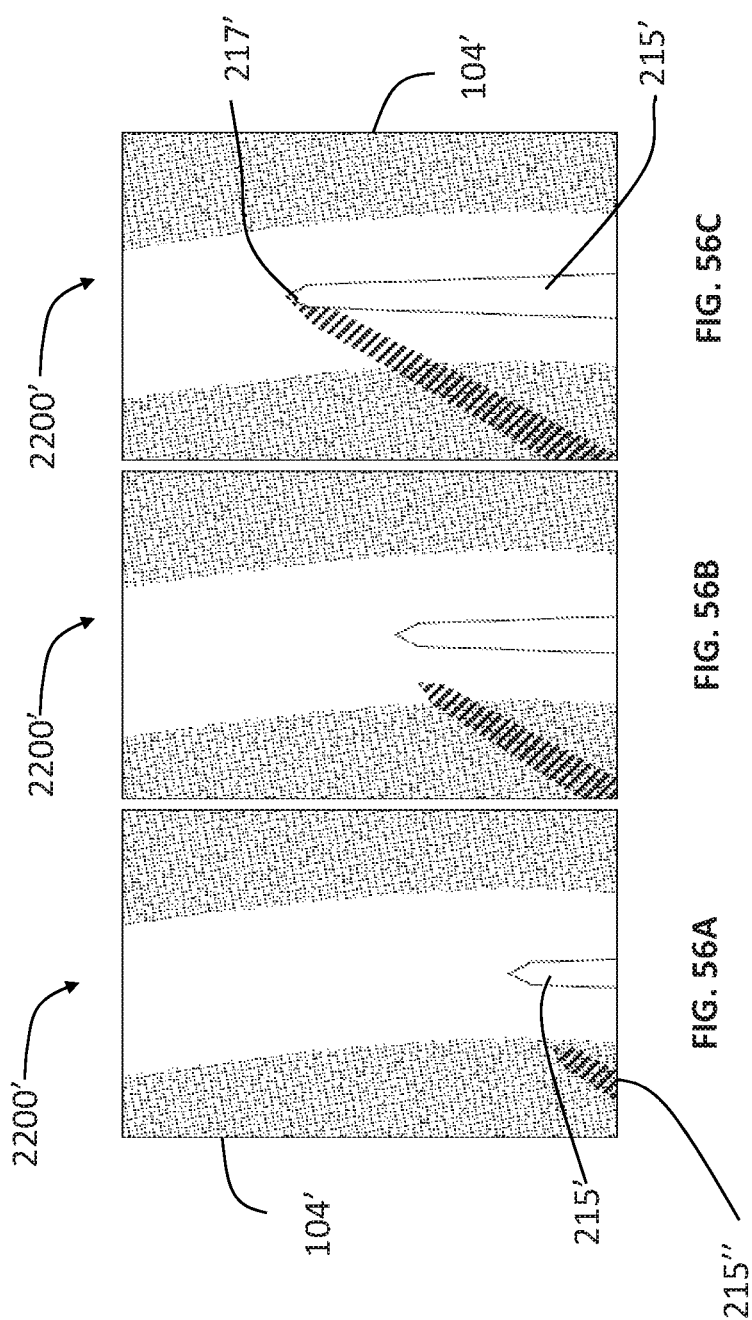
FIGS. 56A-56C are schematic top views of the visualization device of FIG. 32 showing a graphical user interface display according to one embodiment of the present disclosure.

FIGS. 56A-56C shows a GUI display 2200' according to another embodiment of the present disclosure. GUI display 2200' includes a virtual drop shadow 215" of cannula 215' to aid in the three dimensional perception of spatial relationship between a skin insertion target, a vein insertion target and cannula 215'. As shown in FIGS. 56A-56C, when cannula 215' approaches the insertion target, virtual drop show 215" converges towards cannula tip 217'. At insertion, cannula tip 217' and virtual drop shadow 215" are in virtual contact as best shown in FIG. 56C. Color variations can be applied to veins 20', nerve 22', etc. to guide cannula tip 215' to the desired insertion point. For example, the insertion zone can be shaded in green, whereas the nerves can be shaded in red to allow an operator to reach the target zone without inadvertently hitting objects to be avoided. GUI display 2200' can include tactile or auditory feedback to the operator to aid insertion of cannula 217' to the insertion zone. GUI display 2200' can also include hatched zones in some embodiments to indicate zones or regions that have not been imaged by the probe surface.

Figure 57:
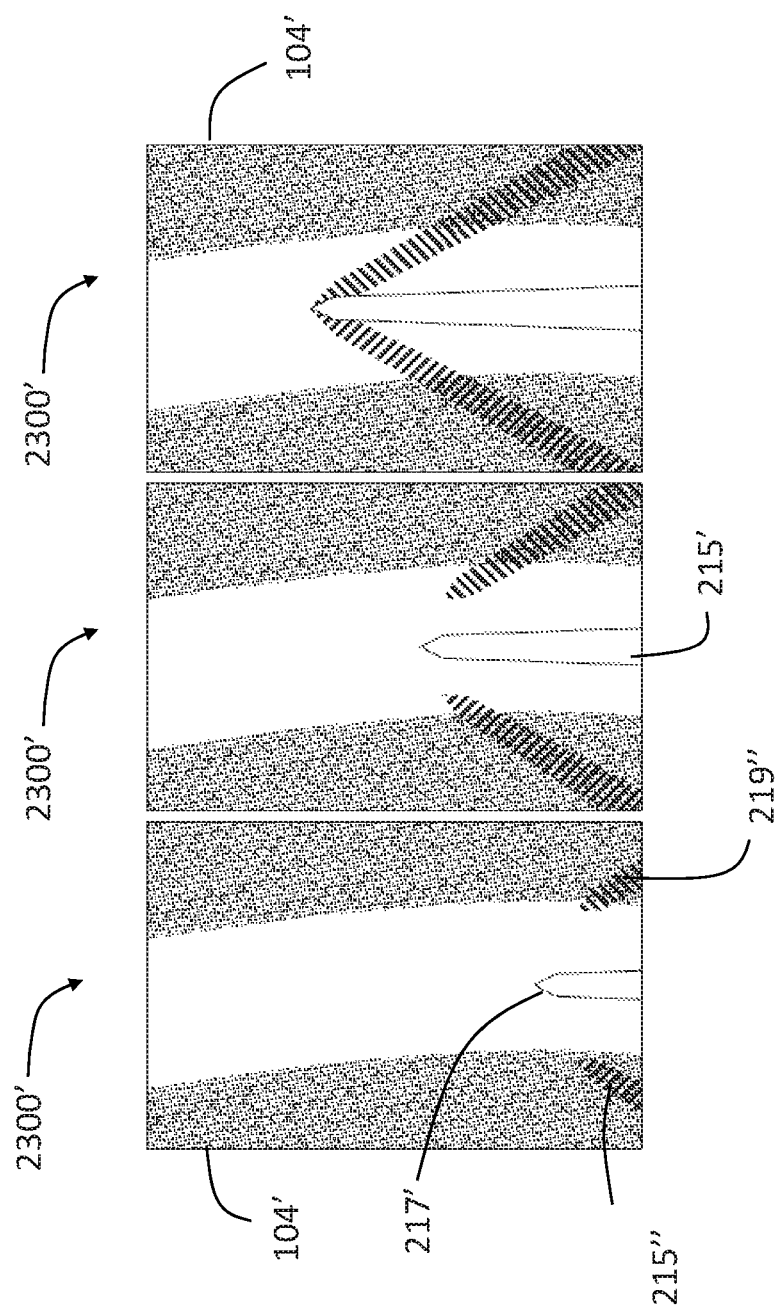
FIGS. 57A-57C are schematic top views of the visualization device of FIG. 32 showing a graphical user interface display according to another embodiment of the present disclosure.

FIGS. 57A-57C show a GUI display 2300' according to another embodiment of the present disclosure. GUI display 2300' is similar to GUI display 2200' but includes a second virtual drop shadow 219". Virtual drop shadows 215" and 219" converge toward cannula tip 217' as the cannula tip approaches the insertion zone. Second virtual drop shadow 219" provides additional visual guidance to an operator for successful cannula insertion.

Figure 58:
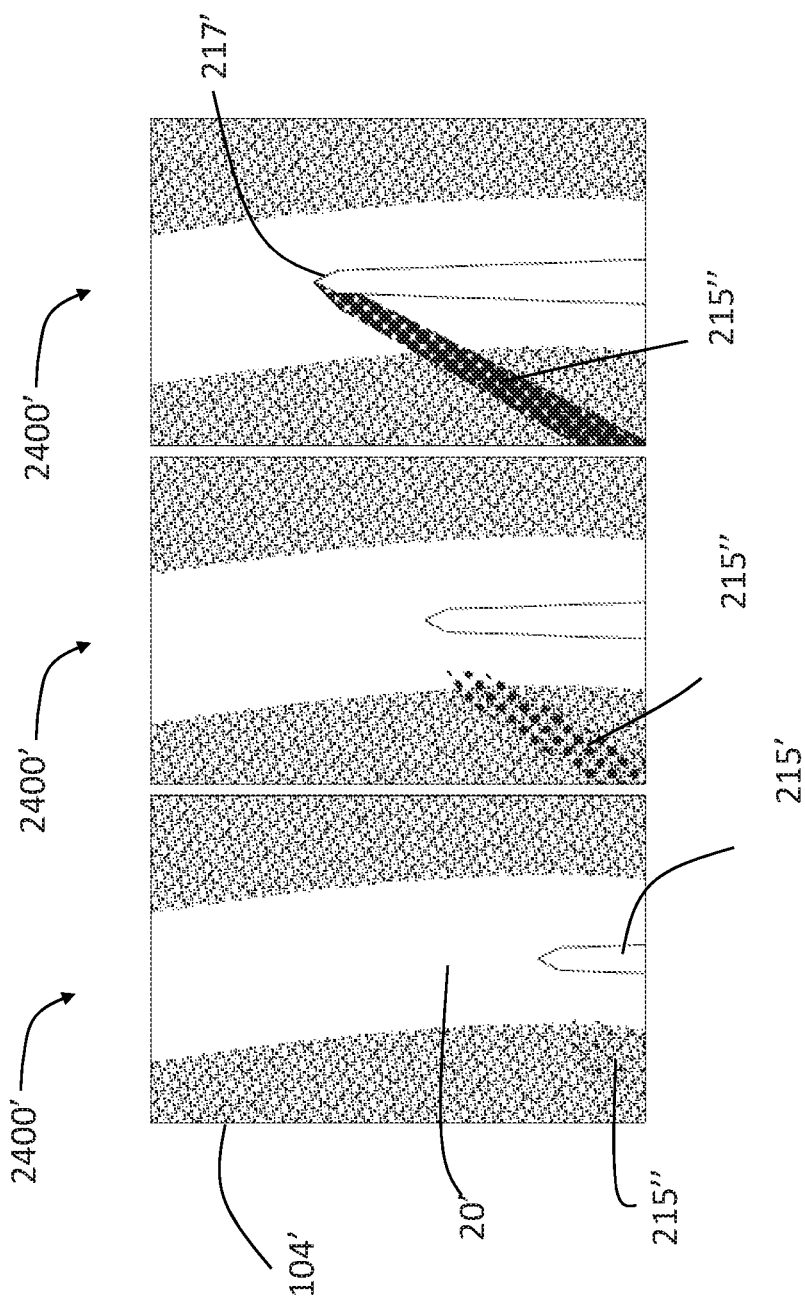
FIGS. 58A-58C are schematic top views of the visualization device of FIG. 32 showing a graphical user interface display according to another embodiment of the present disclosure.

FIGS. 58A-58C show a GUI display 2400' according to another embodiment of the present disclosure. GUI display 2400' is similar to GUI display 2200' and includes a virtual drop shadow 215" of cannula 215'. However, virtual drop shadows 215" gradually gets sharper and darker as cannula tip approaches the insertion zone.

Figure 59:
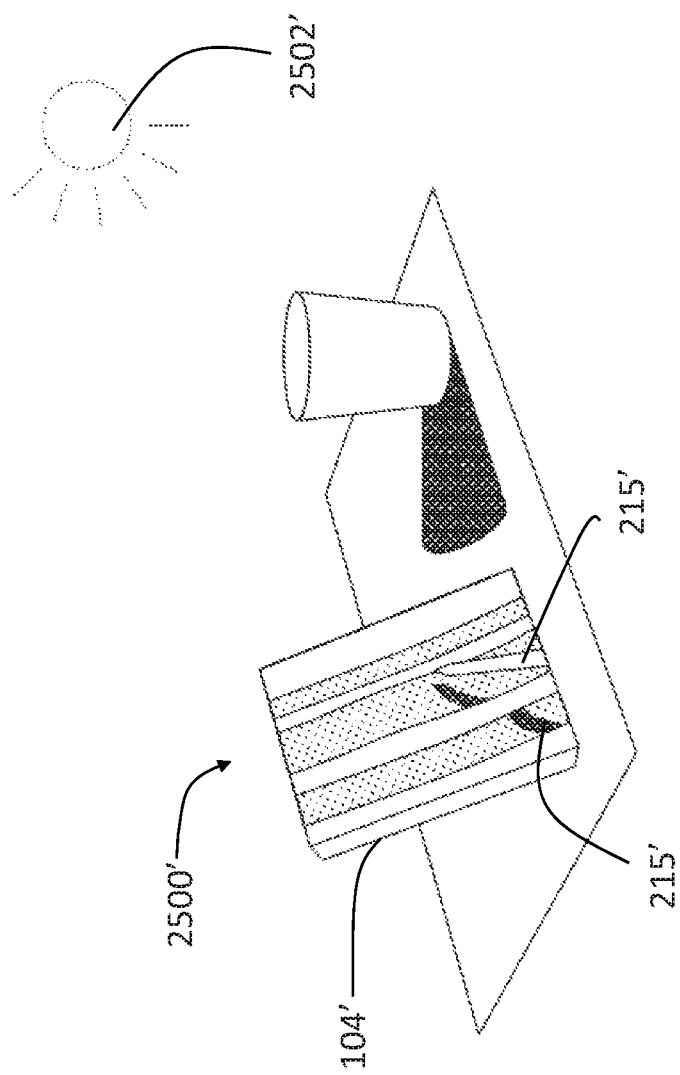
FIG. 59 is a schematic perspective view of the visualization device of FIG. 32 showing a graphical user interface display according to another embodiment of the present disclosure.

Referring now to FIG. 59, there is shown a GUI display 2500' according to another embodiment of the present disclosure. GUI display 2500 detects an ambient lighting source 2502' in the vicinity of the visualization device and orients virtual drop shadow 215" to match ambient lighting source 2502' for a seamless depth-perception effect. GUI display 2500' aids in preventing disorientation due to discrepancy in lighting angle in room with reference to the virtual lighting on screen.

Figure 60:
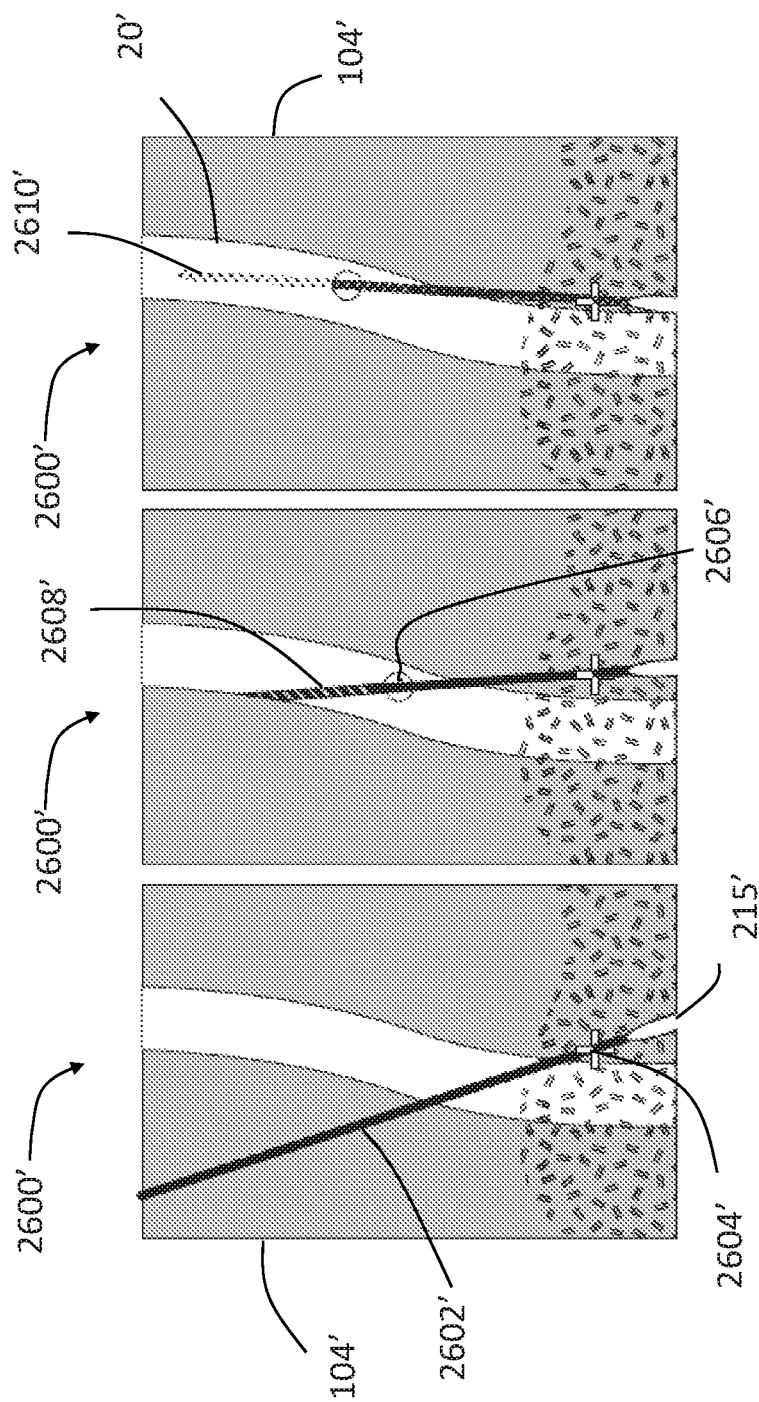
FIGS. 60A-60C are schematic top views of the visualization device of FIG. 32 showing a graphical user interface display according to another embodiment of the present disclosure.

FIGS. 60A-60C show a GUI display 2600' according to another embodiment of the present disclosure. GUI display 2600' includes a cannula path indicator 2602'. Cannula path indicator 2602' depicts the projected path of cannula 215' through the skin and volume 10' depending on an orientation of the cannula. For example, when cannula 215' is positioned as shown in FIG. 60A, a skin insertion point 2604' and cannula path indicator 2602' is shown on GUI display 2600'. When the cannula is properly aligned to insertion vein 20', a vein insertion point 2606' can be seen on GUI display 2600' as shown in FIGS. 60B and 60C. GUI display 2600' indicates the suitability of vein insertion point 2606' based on the projected path of the cannula within vein 20' as depicted by path indicator 2608' (unsuitable) or 2610' (suitable).

Figure 61:
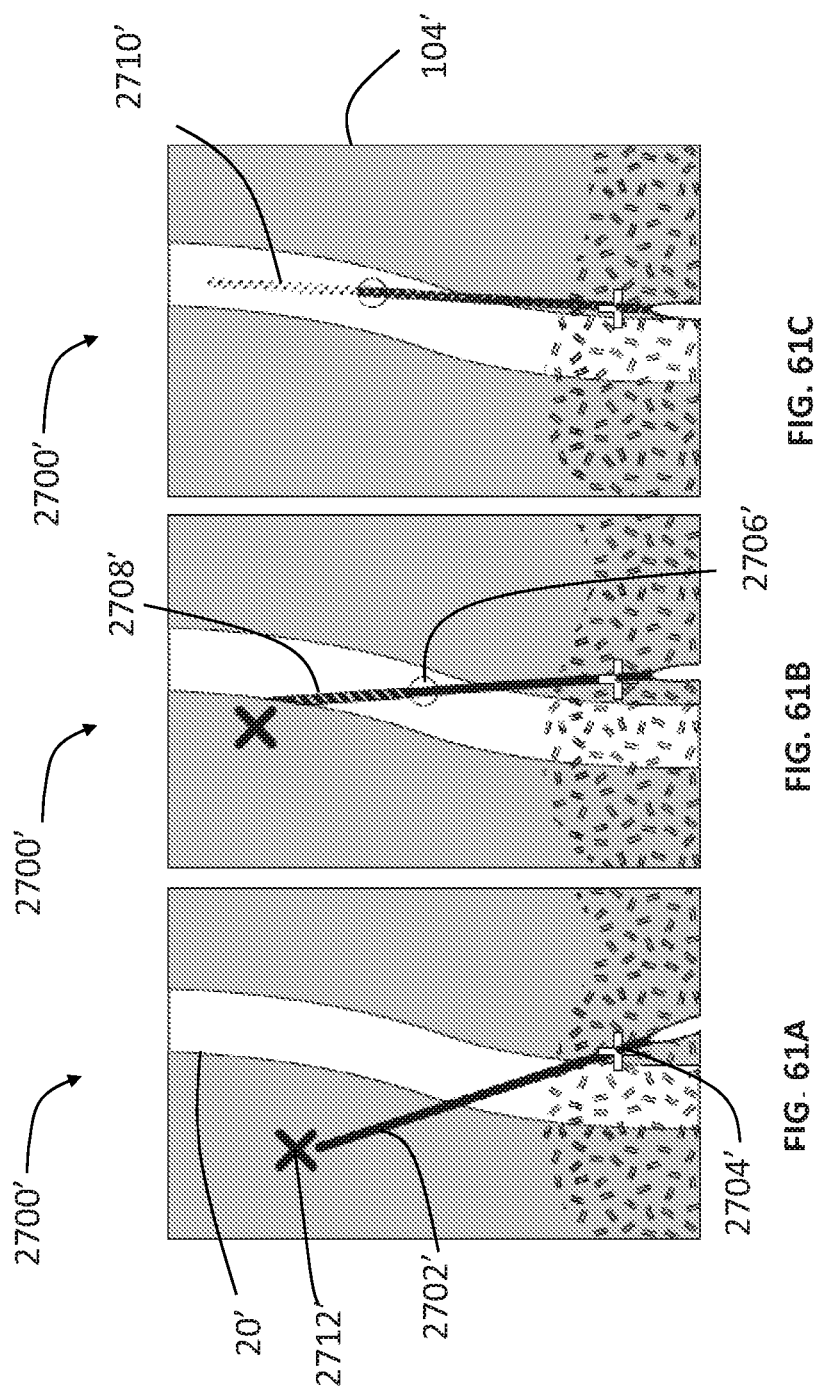
FIGS. 61A-61C are schematic top views of the visualization device of FIG. 32 showing a graphical user interface display according to another embodiment of the present disclosure.

FIGS. 61A-61C show a GUI display 2700' according to another embodiment of the present disclosure. GUI display 2700' is similar to GUI display 2600', and therefore like elements are referred to with similar numerals within the 2700'-series of numbers. For instance, GUI display 2700' includes a cannula path indicator 2702', a skin insertion point 2704' and a vein insertion point 2706'. However, GUI display 2700' includes a projected distal tip of cannula 2712' based on the cannula position and cannula alignment with volume 10'.

Figure 62:
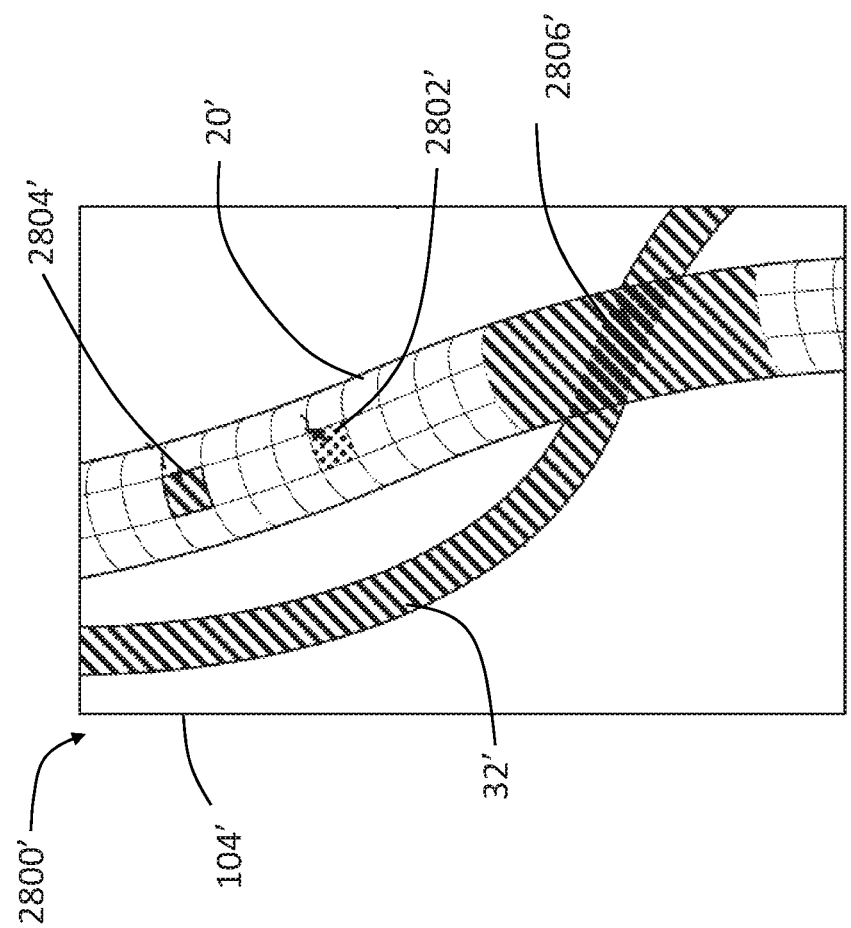
FIG. 62 is a schematic perspective view of the visualization device of FIG. 32 showing a graphical user interface display according to another embodiment of the present disclosure.
Figure 63B:
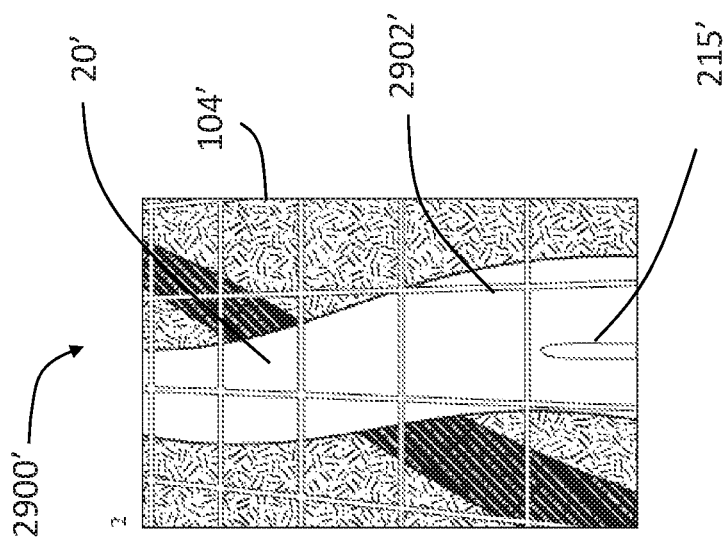
FIGS. 63A-63D are schematic top views of the visualization device of FIG. 32 showing a graphical user interface display according to one embodiment of the present disclosure.
Figure 63A:
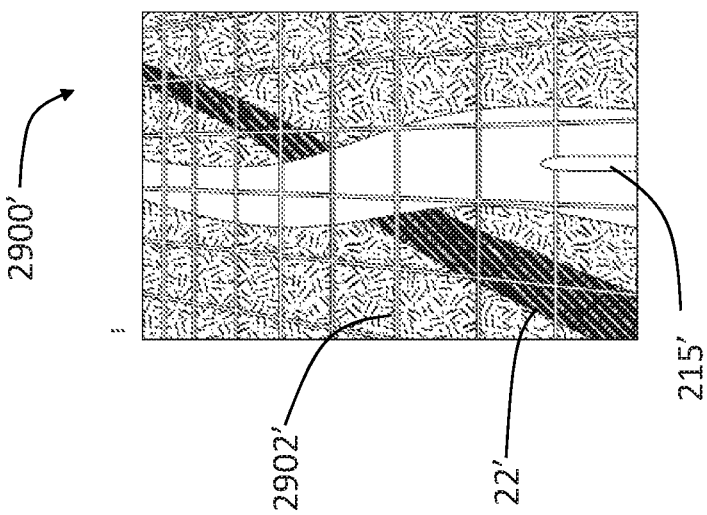
Figure 63D:
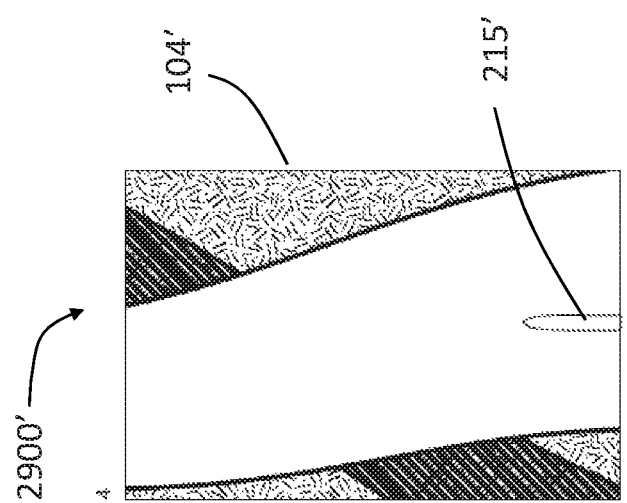
Figure 63C:
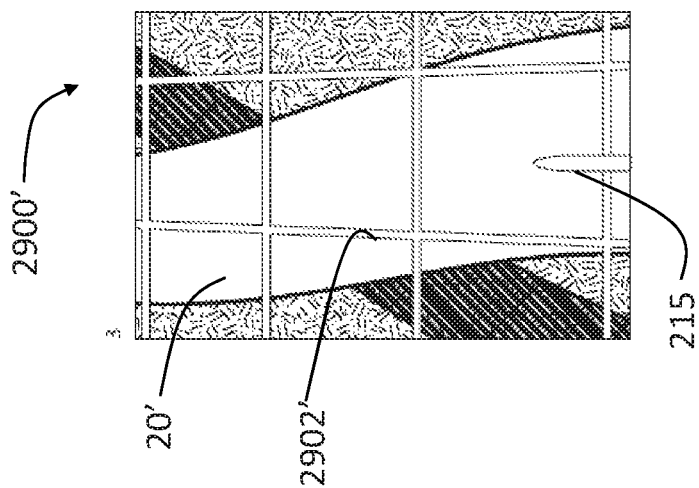

Referring now to FIG. 62, there is shown a GUI display 2800' according to another embodiment of the present disclosure. GUI display 2800' display an ideal cannula insertion point 2802' to aid in successful cannula insertion. Unsuitable insertion points such as vein regions suffering from sclerosis 2804' and vein areas 2806 directly below or above an artery 32' can be displayed on GUI display 2800'.

FIGS. 63A-63D show a GUI display 2900' according to another embodiment of the present disclosure. GUI display 2900' is capable of magnifying the display image of volume 10'. The magnification can be manually performed by the operator to enlarge and focus the image to the desired location such as the insertion point, or automatically performed by the visualization device based on the location of the cannula. Manual magnification can be performed via a touchscreen on GUI display 2900'. GUI display 2900' includes a grid 2902' to depict magnification level on the display screen.

FIGS. 64A and 64B show a GUI display 3000' according to another embodiment of the present disclosure. GUI display 3000' depicts depth perception by altering the brightness/darkness of object based on depth. For example, a second vein 23' appears darker than nerve 22', which is darker than vein 20' to indicate relative depth of each of these elements in FIG. 64A. Similarly, various color schemes and patterns can be used to indicate relative depth of each element as shown in FIG. 64B. It should be noted that any of the GUI display concepts disclosed herein can be individually or collectively utilized in the visualization devices. For example, GUI display 3000' can be utilized in conjunction with GUI display 2200', GUI display 2900' can be utilized in conjunction with GUI display 2800, etc.

Figures 102A, 102B:
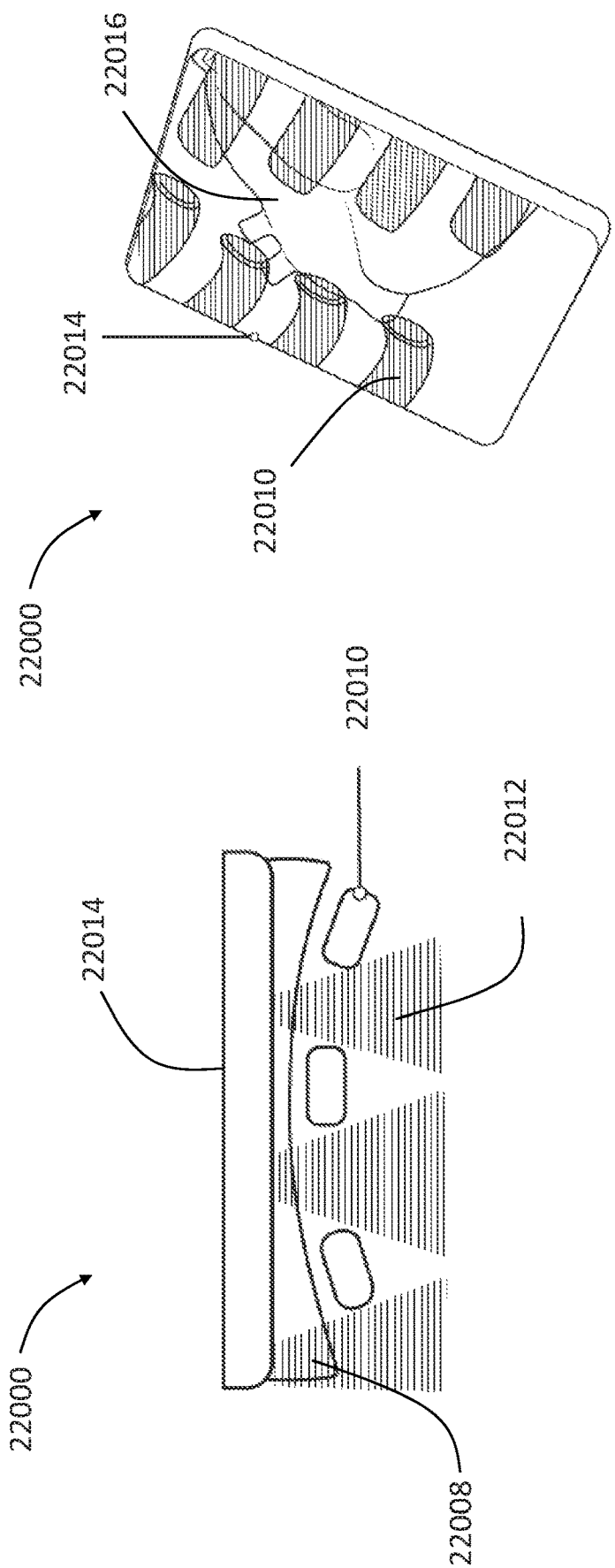

FIGS. 101A-102B show a visualization device 22000 according to another embodiment of the present disclosure. Visualization device 22000 has a relatively large surface area with transducers 22008 on a first side and a display 22014 on an opposite side as best shown in FIGS. 102A and 102B. The large surface area of visualization device 22000 provides sufficient coverage to visualize large anatomical features with a single placement of the device. Further, the large display ensures that the visualized anatomical features are displayed in detail to allow for proper imaging and/or procedures to be performed at the surgical site.

A strap 22002 with a pad 22004 is secured on the surgical site as shown in FIG. 101A. Pad 22004 includes a gel 22206 and securement features 22008 to allow for readily attaching and detaching visualization device 22000. As best shown in FIG. 102A, the transducer array 22008 spans over ribs 22010 when the visualization device is placed over the surgical site. Each transducer of the transducer array 22008 emits and receives signals 22012 that propagate through the rib 22010 spacing and diverge past the rib opening to cover the area below the ribs. Thus, all anatomical features below the ribs can be captured by placing visualization device 22000 at a single location. Display 22014 shown in FIG. 102B depicts ribs 22010 and soft tissue such as a heart 22016 located beneath the ribs.

Figure 103A:
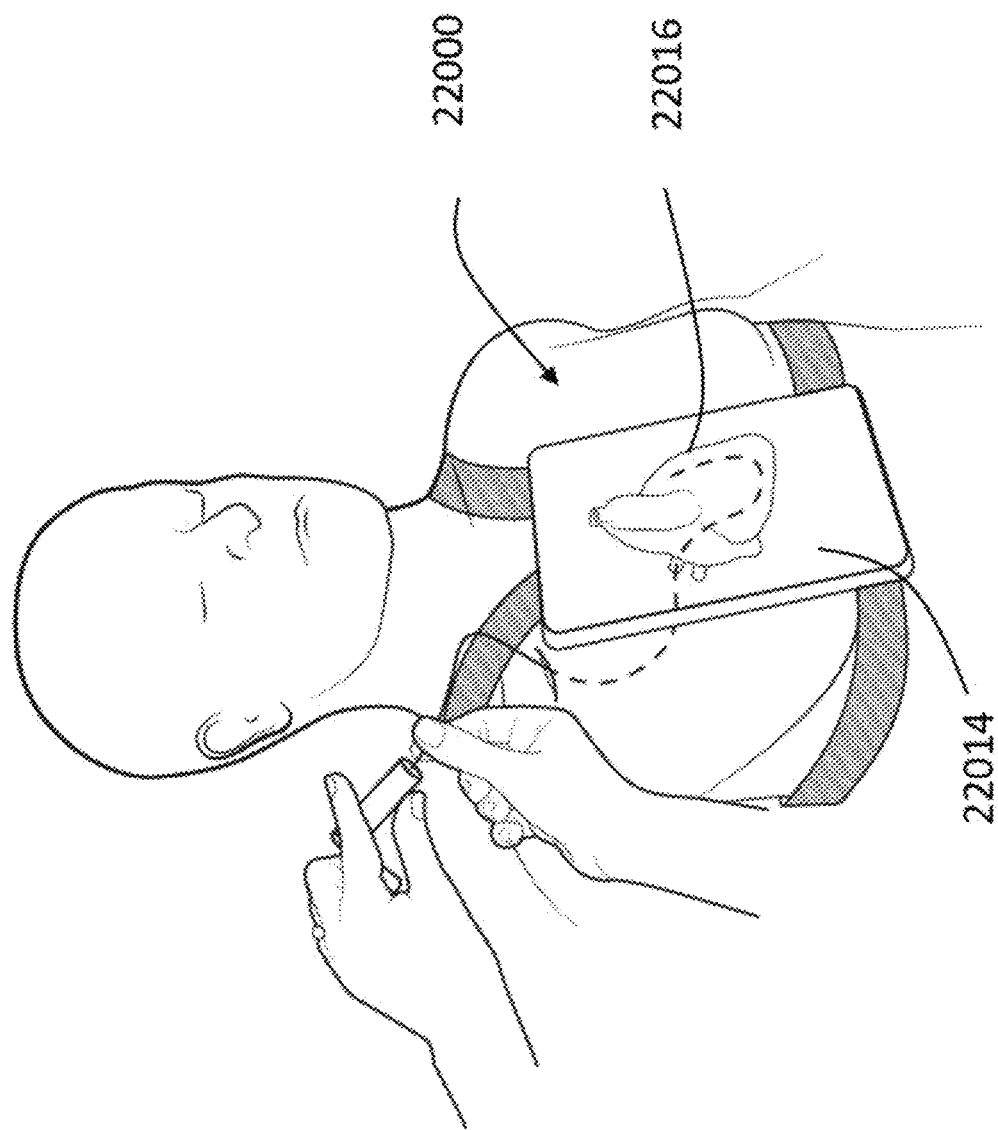
FIG. 103A illustrates a method of using the visualization device of FIG. 101A.

FIG. 103A shows visualization device 22000 providing 3D, real-time imaging of heart 22016 during a procedure. Straps 22002 and pad 22006 allow visualization device to be securely located at the surgical site and allowing a surgeon to operate and view real-time imaging of the procedure. While the visualization device 22000 images anatomical features located behind ribs in this embodiment, visualization device 22000 can be used in other applications to visualize anatomic features that are located behind or under other anatomical features that typically obscure and prevent visualization of the inner anatomical features. For example, hard tissue such as bones will prevent conventional ultrasound imaging from generating proper images of organs and soft tissue located below the hard tissue. Visualization device 22000 of the present disclosure can readily be used to generate 3D, real-time images of these organs and soft tissue by capturing image data through gaps or across the outer perimeter of the hard tissue.

Figures 103B, 103C:
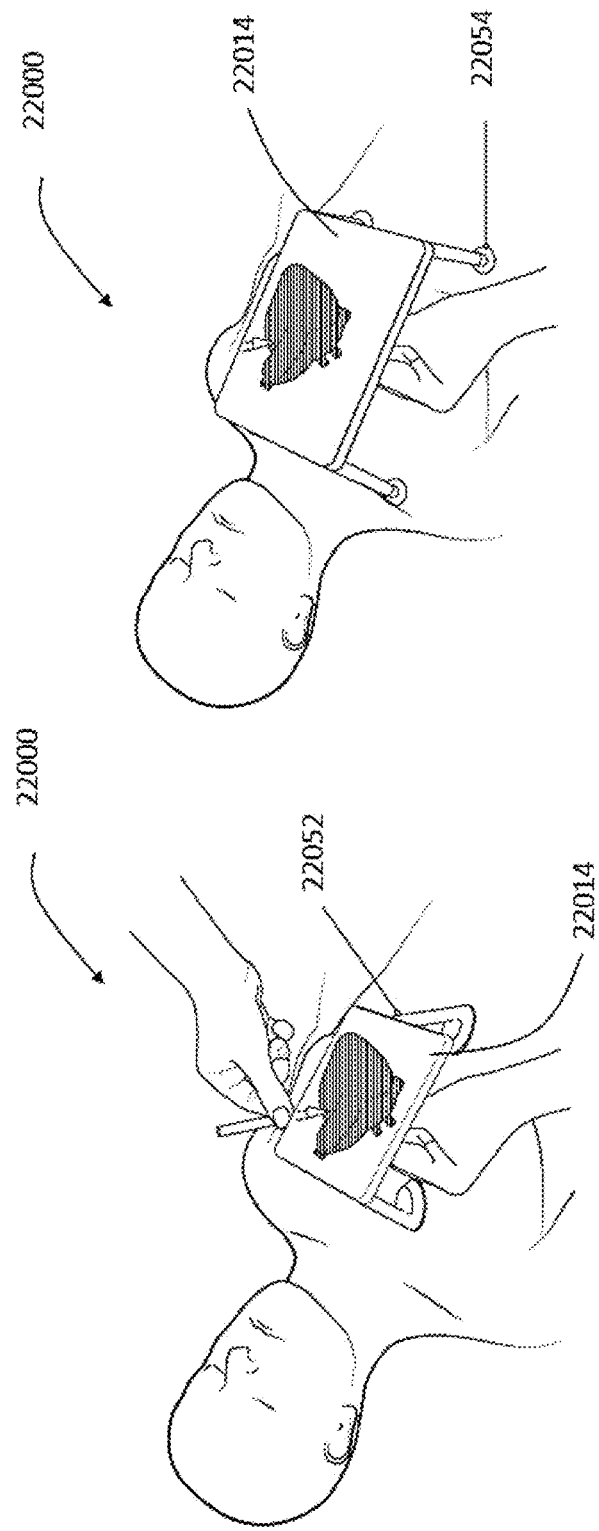
FIGS. 103B and 103C illustrate supporting accessories for the visualization device of FIG. 101A.

FIGS. 103B and 103C show a visualization device 22000 secured by a stand 22052, 22054 according to another embodiment of the current disclosure. The stand can be a tripod 22052 as shown in FIG. 103B or a frame 22054 with four legs as shown in FIG. 103C. The stands are configured to simultaneously ensure secure attachment of visualization device 22000 at the surgical site and to provide access to perform a medical procedure.

Figures 104A, 104B, 104C, 104D:
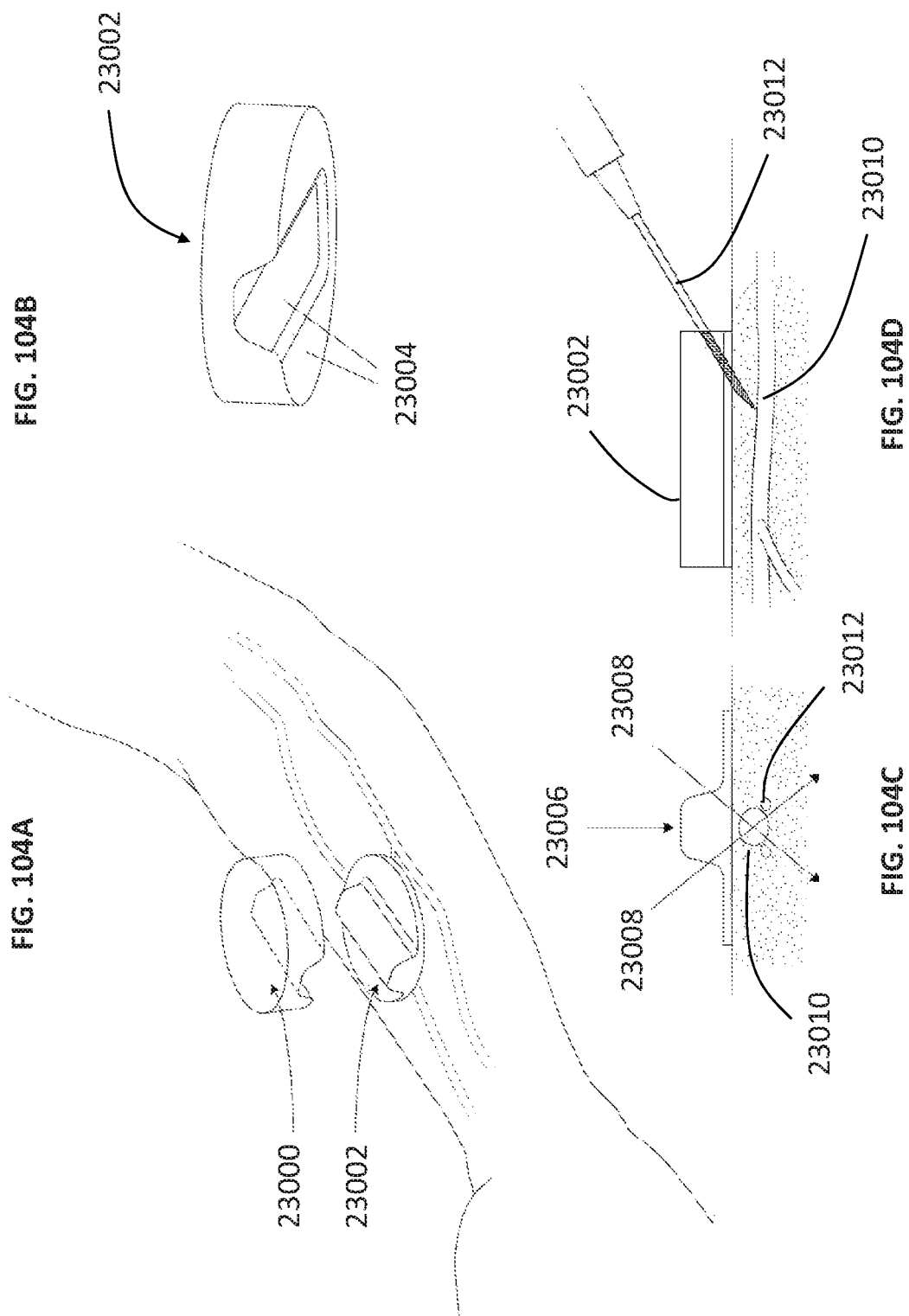
FIGS. 104A-104D illustrate a transducer and a pad according to another embodiment of the present disclosure.

A transducer 23000 according to another embodiment of the present disclosure is shown in FIGS. 104A-104D. Transducer 23000 includes a central groove to receive a raised portion of a pad 23002 as best shown in FIG. 104A. Transducer arrays are located on both surfaces 23004 of the central groove of transducer 23000 as shown in FIG. 104B. The transducer arrays located on these inclined faces with respect to the skin surface, allow for wave transmissions 23010 to converge and identify the anatomical feature. As shown in FIG. 104C, the anatomical feature in this example is a vein 23012. Once vein 23012, the transducer coupled to the pad can be positioned to allow the raised portion of pad 23002 to be directly over vein 23012 as shown in FIG. 104C. An operator or an inserter assembly can advance a needle 23012 along direction 23006 into the raised portion of pad 23002 and precisely into the vein. This ensures that the needle does not inadvertently penetrate or damage other anatomical features such as nerves 23012.

Referring now to FIG. 105, there is shown a visualization device 25000 according to another embodiment of the present disclosure. Visualization device 25000, as shown here, is coupled to brace 24000 in this example. Visualization device 25000 includes a mobile transducer array 25002 that moves across the distal surface of the visualization device to scan the distal surface. A button 25004 or other feature is provided on visualization device 25000 to allow for easy attachment to and detachment from brace 24000.

Figure 107E:
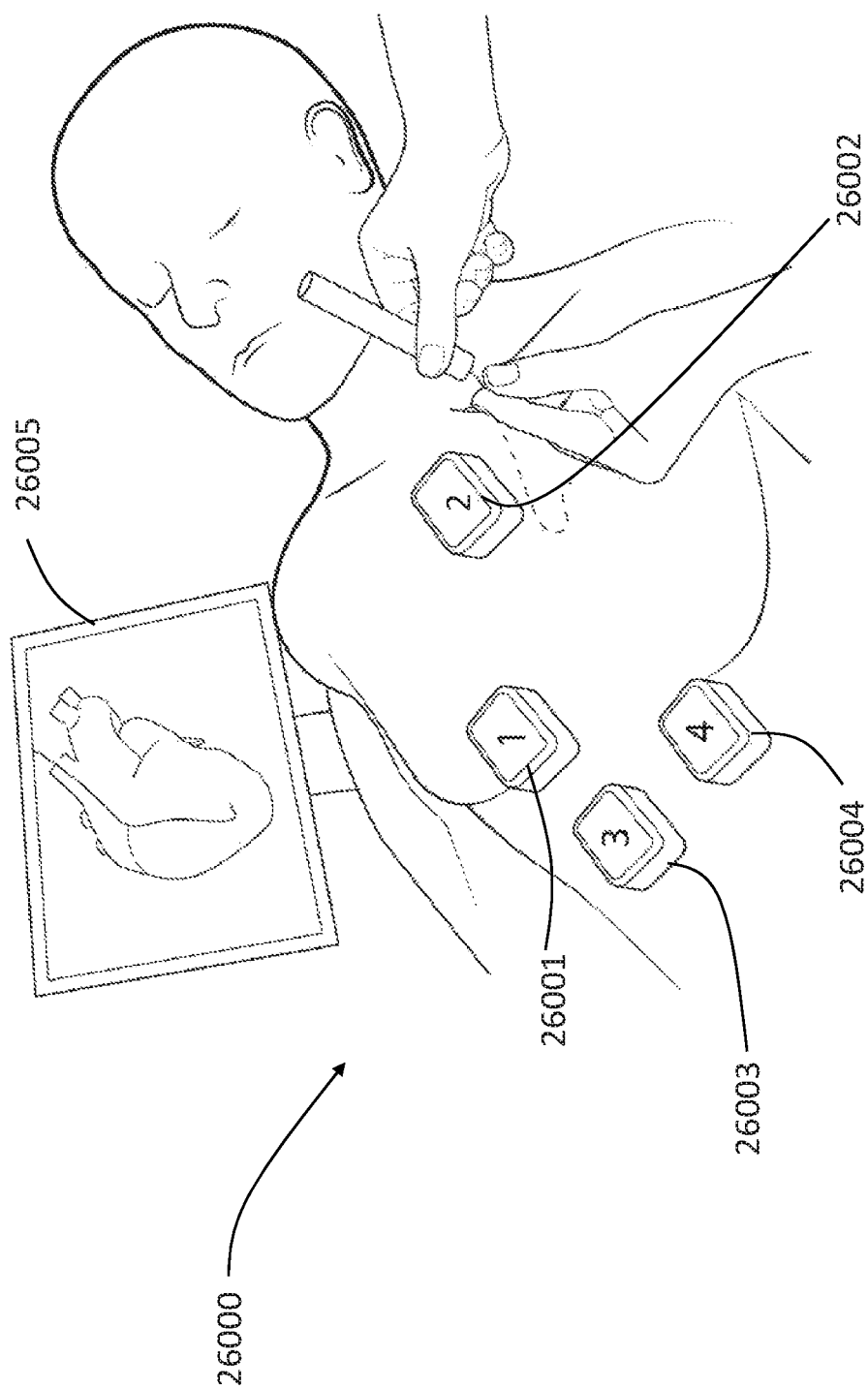

FIGS. 107A-E show a visualization system 26000 according to another embodiment of the present disclosure. Visualization system 26000 includes multiple transducers 26001, 26002, 26003, 26004 placed at different locations as shown in FIG. 107A. The multiple individual transducers are located at different locations about the target surgical site. As shown in FIG. 107A, transducer 26001 is located at a parasternal region, transducer 26002 is located at an apical region, transducer 26003 is located at a subcostal region and transducer 26004 is located at a suprasternal region. Each transducer generates an image data set of the heart based on the location of that transducer. The image data sets are then combined and processed to generate a complete image data set of all relevant anatomical features of the heart and displayed on a remote display 26005. An operator can manipulate the image data set to view specific features of the heart as shown in FIGS. 107B-107D.

Visualization system 26000 allows a surgeon to observe and analyze 3D, real-time images of the relevant anatomical site on a remote screen 26005. As best shown in FIG. 107E, this allows a surgeon to simultaneous conduct a procedure while viewing real-time 3D images of the anatomical structure generated by the multiple transducers. While a heart procedure is shown in this example, visualization system 26000 can conveniently be used for any medical procedure or used exclusively for imaging.

Figure 108A:
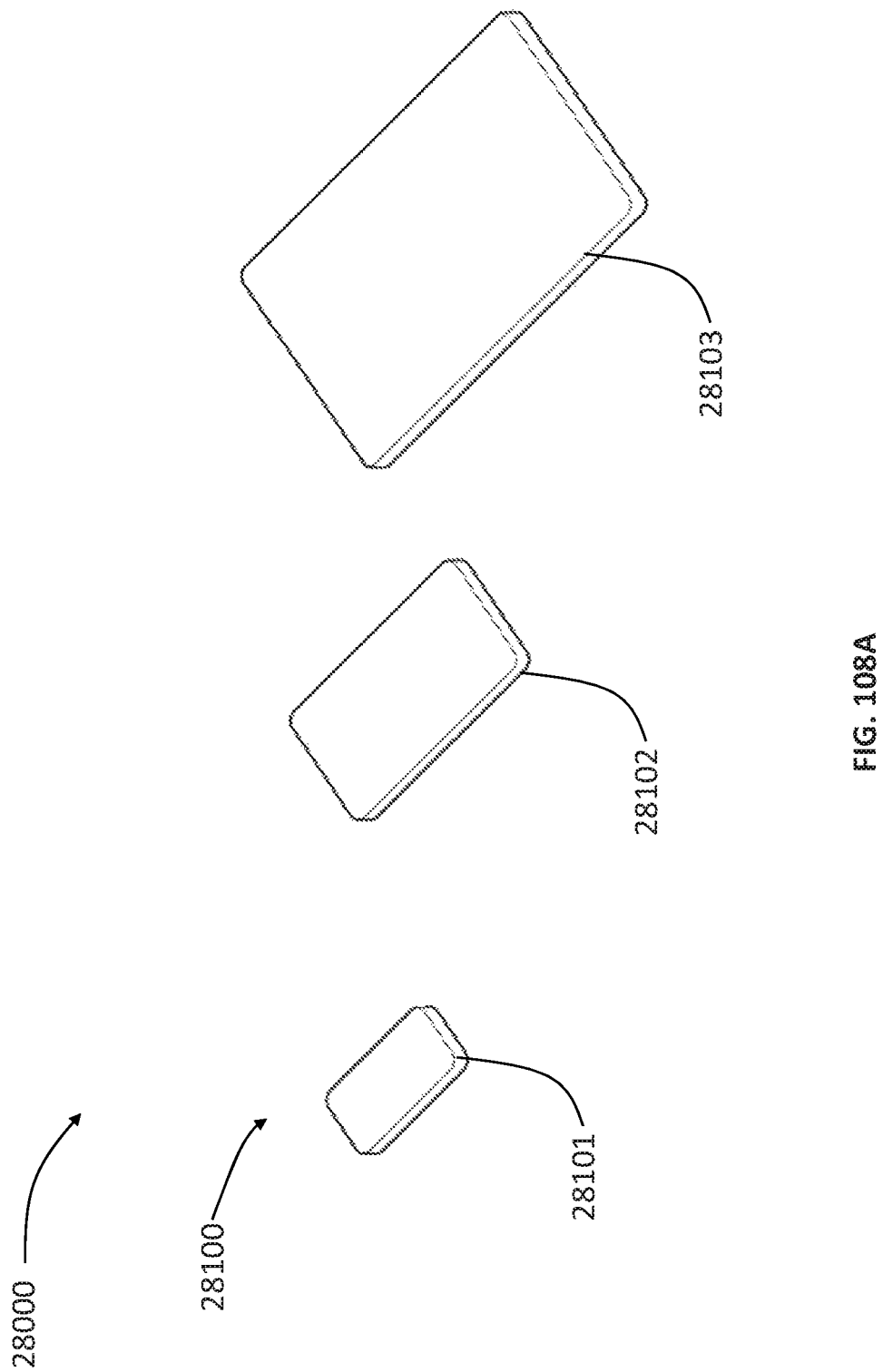
FIGS. 108A-108C illustrate a kit according to another embodiment of the present disclosure.
Figure 108B:
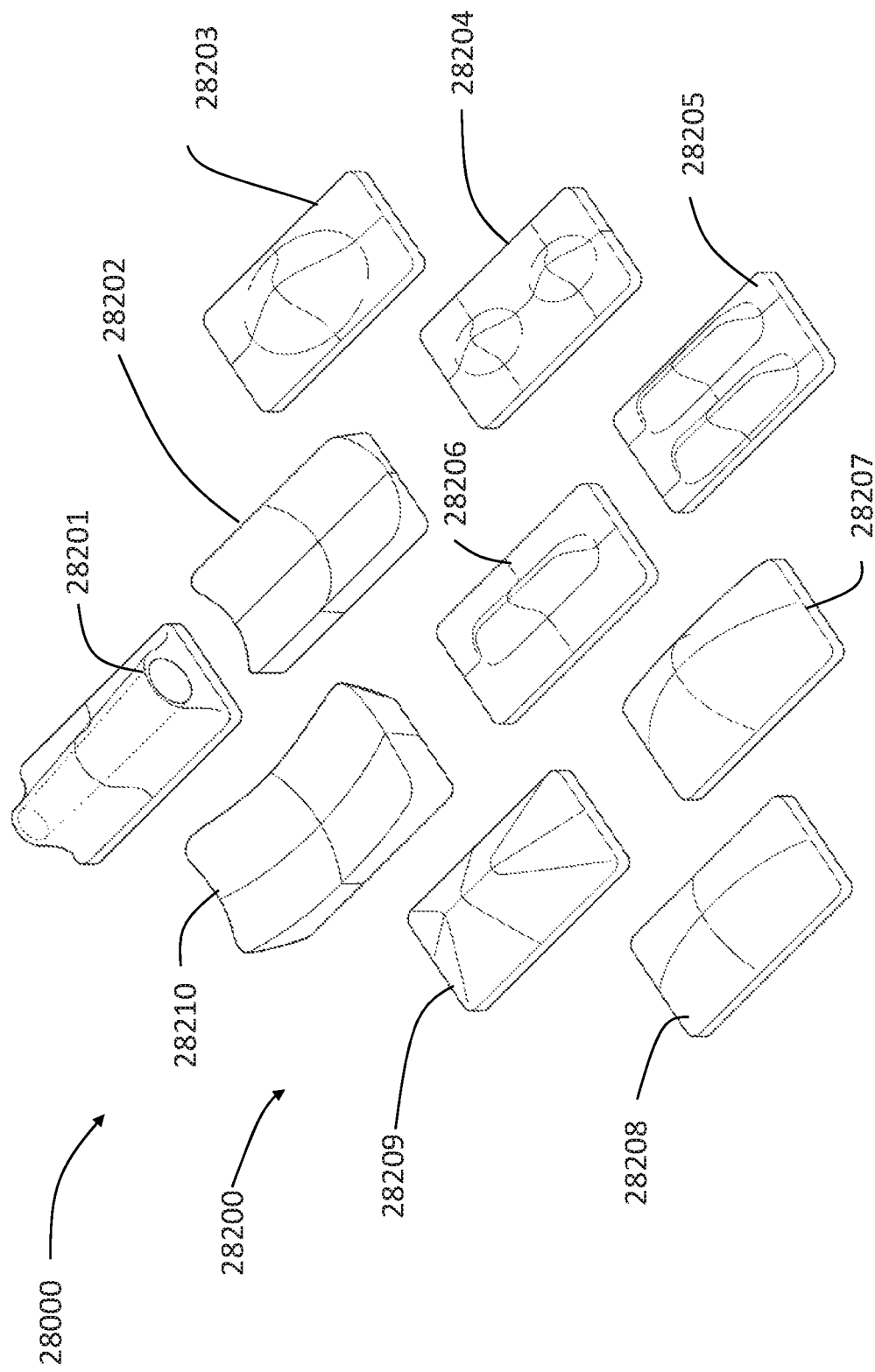
Figure 108C:
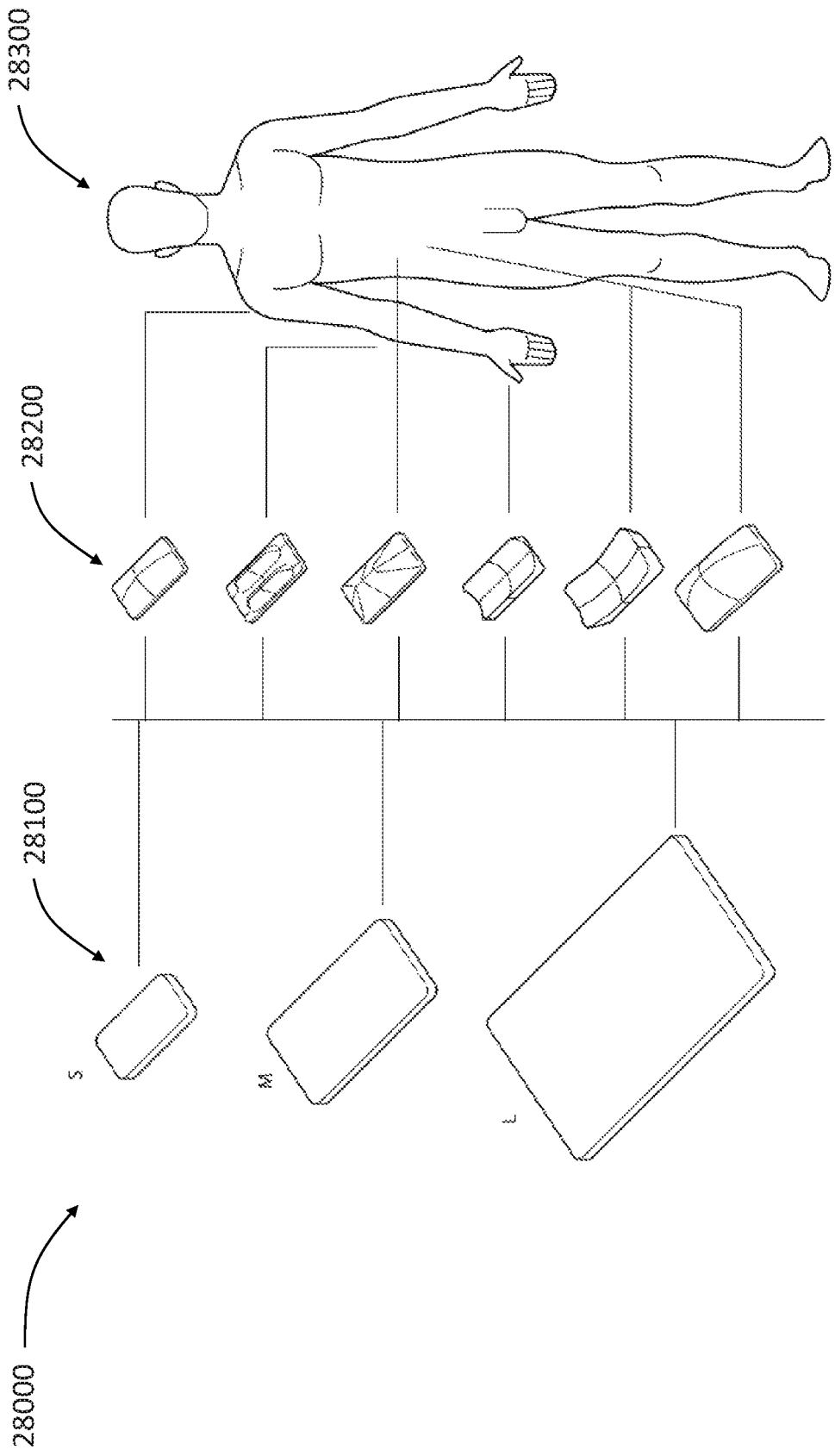

Referring to FIGS. 108A-C, there is shown a kit 28000 according to another embodiment of the present disclosure. Kit 28000 can include multiple visualization devices 28100

(FIG. 108A) which can be paired with multiple pads 28200 (FIG. 108B). Visualization devices 28100 can have different shapes, sizes, array configurations, displays, etc. In the present example, three visualization devices 28100 in a small 28101, medium 28102 and large 28103 are provided in kit 28000. Similarly, pads 28200 can various configurations to pair with all or some of the visualization devices in kit 28000. As shown in FIG. 108B, pads 28201, 28202, 28203, 28204, 28205, 28206, 28207, 28209, 28210 have various shapes and configurations. An operator can select a visualization device 28100 to be paired with a corresponding pad 28200 from kit 28000 for a specific visualization and/or procedure as shown in FIG. 108C. Kit 28000 allows an operator to customize the visualization device and pad based on patient-specific requirements.

Figure 108D:
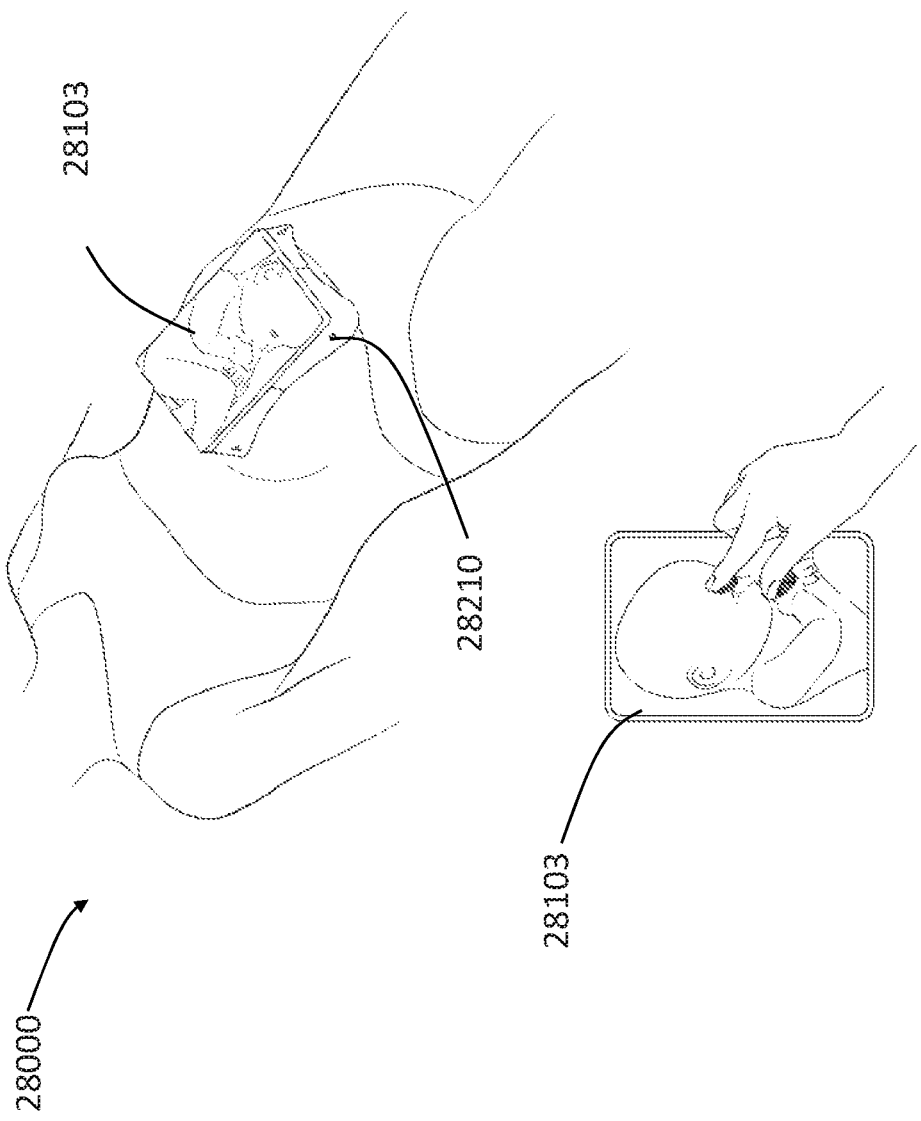
FIGS. 108D-108G illustrate various applications of the kit of FIG. 108A.

FIG. 108D shows a first example of a visualization device paired with a pad from kit 28000 to perform a specific image visualization. Visualization device 28103 is paired with pad 28210 having a concave surface to track the contours of a patient's abdomen in a gynecologic visualization. The visualized image, a baby in this example, can be viewed and manipulated by an operator on visualization device 28103.

Figure 108E:
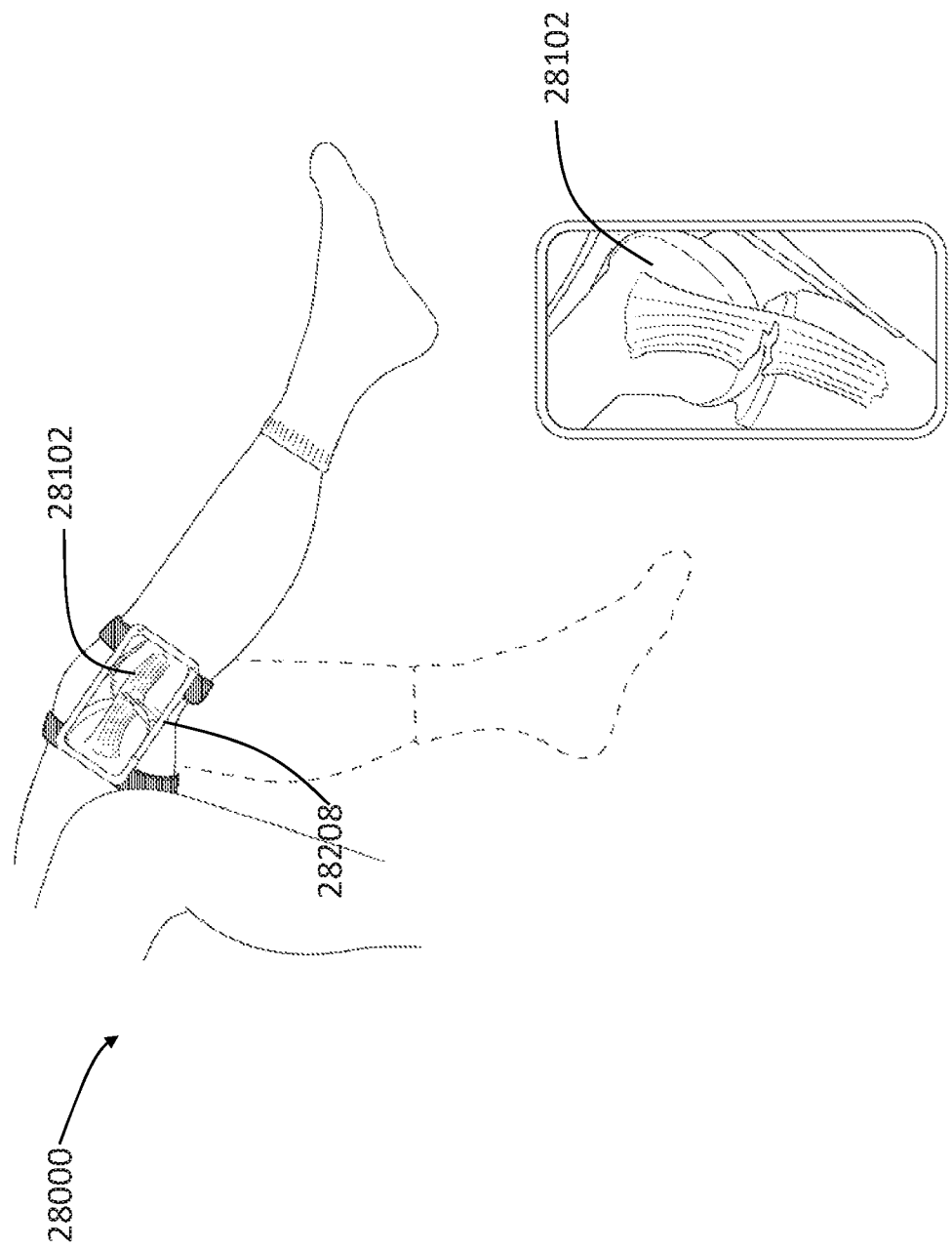

FIG. 108E illustrates another example of kit 28000. Visualization device 28102 is paired with pad 28208 in this example and mounted on the side of a patient's knee to visualize the knee joint. In this example the paired visualization device and pad can be secured to the patient's knee to allow imaging of the patient's knee during flexion and extension. A surgeon can visualize the knee joint in real time across a full range of motion of the knee to evaluate joint condition.

Figure 108F:
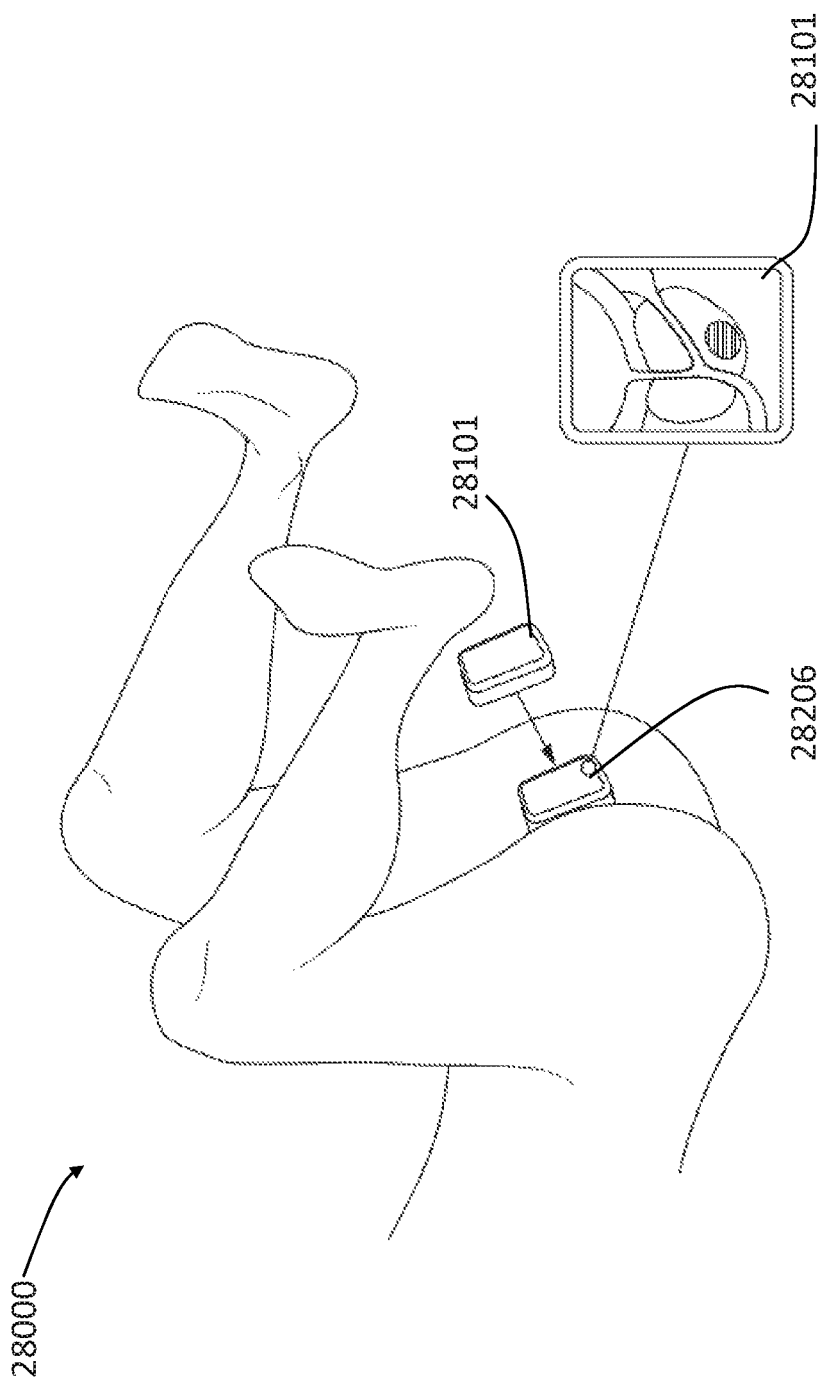
Figure 108G:
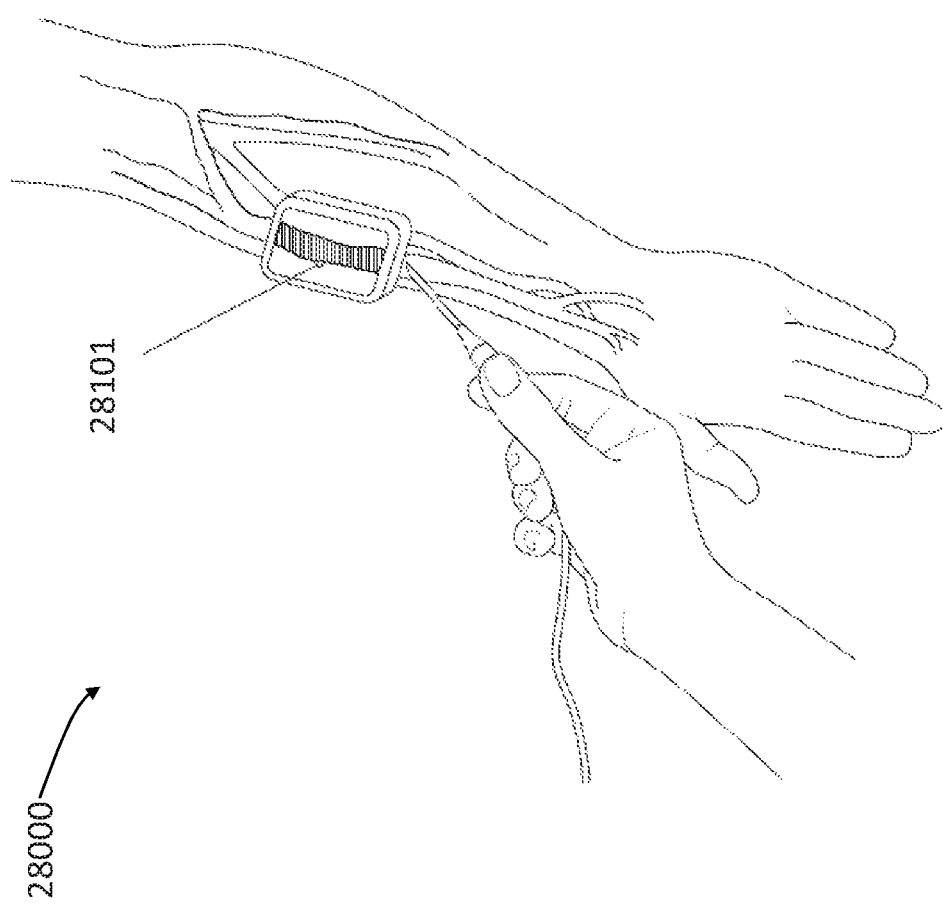

FIG. 108F illustrates a third example of kit 28000. Visualization device 28101 is paired with pad 28206 in this example to examine a patient's prostrate. The compact size of visualization device 28101 and the contoured shape of pad 28206 allows a surgeon to conveniently place this assembly and perfume a visualization without the need for invasive scanning. Another example of kit 28000 is shown in FIG. 108G. Visualization device 28101 can be paired with any of the pads in kit 28000 to view and a graft implanted into a fistula tract. The compact size of 28101 and the secure placement of the assembly allows a surgeon to simultaneous view the anatomical site in 3D, real time and perform the procedure.

FIG. 108H shows a table with technical specification of various visualization devices according to an embodiment of the present disclosure. Exemplary technical specifications for small, medium and large visualization devices are listed in this table. Technical specifications include certain attributes of these devices including size, battery requirement and performance metrics. Values shown in FIG. 108H are exemplary and not intended to limit the embodiments of the present disclosure.

Figure 109:
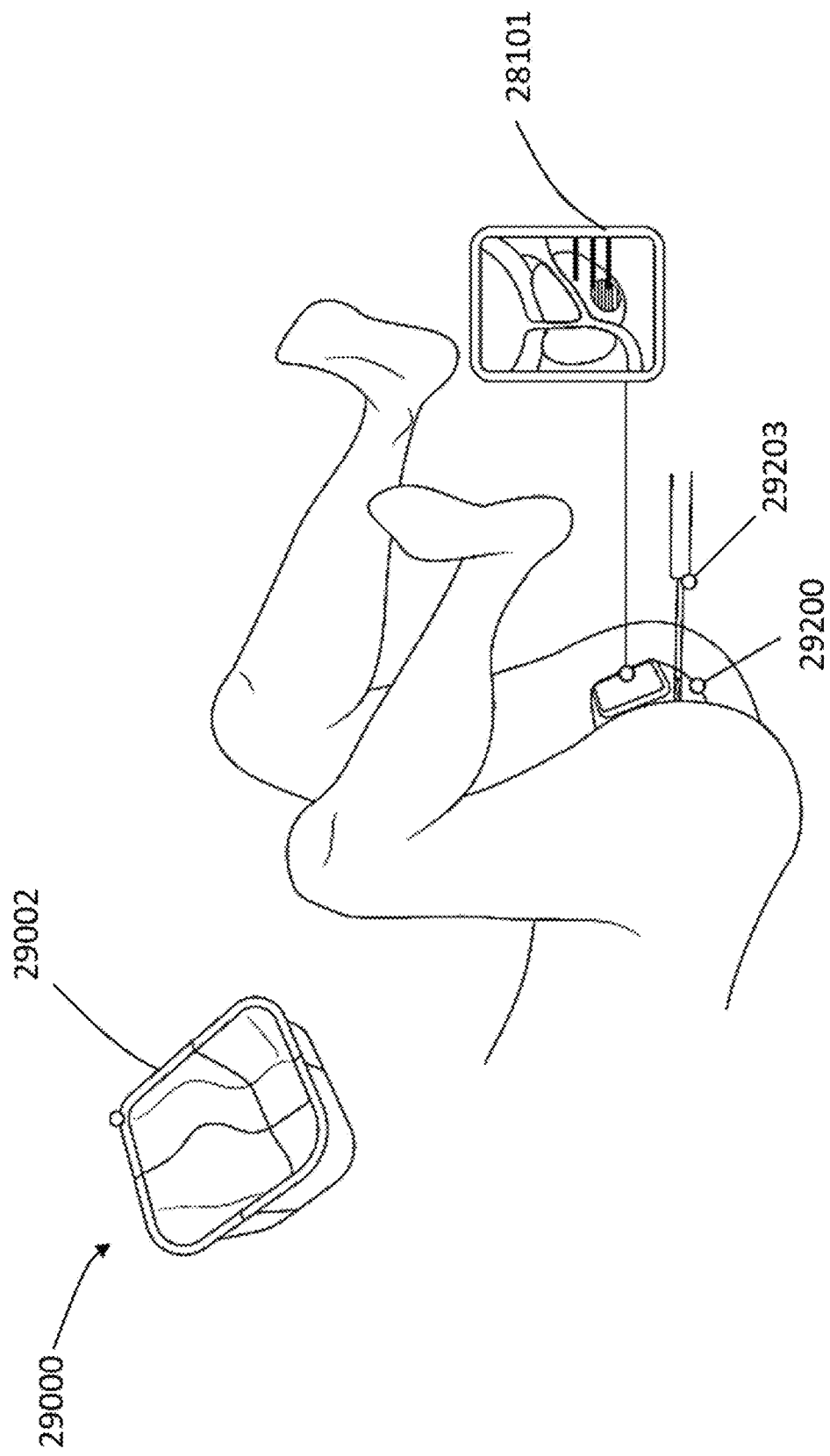
FIG. 109 illustrates another application of the kit of FIG. 108A with a customized pad according to another embodiment of the present disclosure.

Referring to FIG. 109, there is shown a customized kit 29000 according to another embodiment of the present disclosure. A customized pad 29200 is created and paired with visualization device 28101. Pad 29200 can be formed using a 3D-printed mold 29002. Mold 29002 can be customized to patient-specific needs and the unique requirements of the procedure. In this example, a surgeon performs a brachytherapy procedure utilizing tools 29203 as shown in FIG. 109.

FIGS. 110A-D show a visualization system 30000 according to another embodiment of the present disclosure. Visualization system 30000 includes a visualization device 30002 and a pad 30004. As a needle tip 30006 approaches an insertion point 30008, sensors located on visualization device track and display the approaching needle tip on visualization device 30002. As shown in FIG. 110B, both the needle tip and the insertion point are displayed on visualization device 30002. This allows an operator to position and align the needle for precise entry into the insertion point. While PMUT or CMUT transducers are provided on the underside of the visualization device 30002 to track the needle tip when the needle tip is below the visualization device—i.e., within the transducer range, other sensors such as cameras, infrared, or near-infrared sensors can be provided to track a needle position adjacent but outside a projected footprint of the visualization device. In other embodiments, the PMUT or CMUT transducers can be provided on inclined surfaces to transmit signals outside the footprint of the visualization device to track and identify the approaching needle. Various rendering and image enhancements can be provided by visualization device 30002 to facilitate precise insertion. For example, a projected trajectory 30012 of the needle based on its current position can be displayed as shown in FIG. 110C. This will allow the operator to adjust and align the needle to precisely enter at insertion point 30008. As needle tip enters a vein 30014 through the insertion point, the vein and the needle tip are displayed on visualization device 30002 as shown in FIG. 110D. Visualization system provides real-time, 3D images with enhanced rendering to ensure proper pre-alignment, insertion and final placement of the needle.

Figure 116:
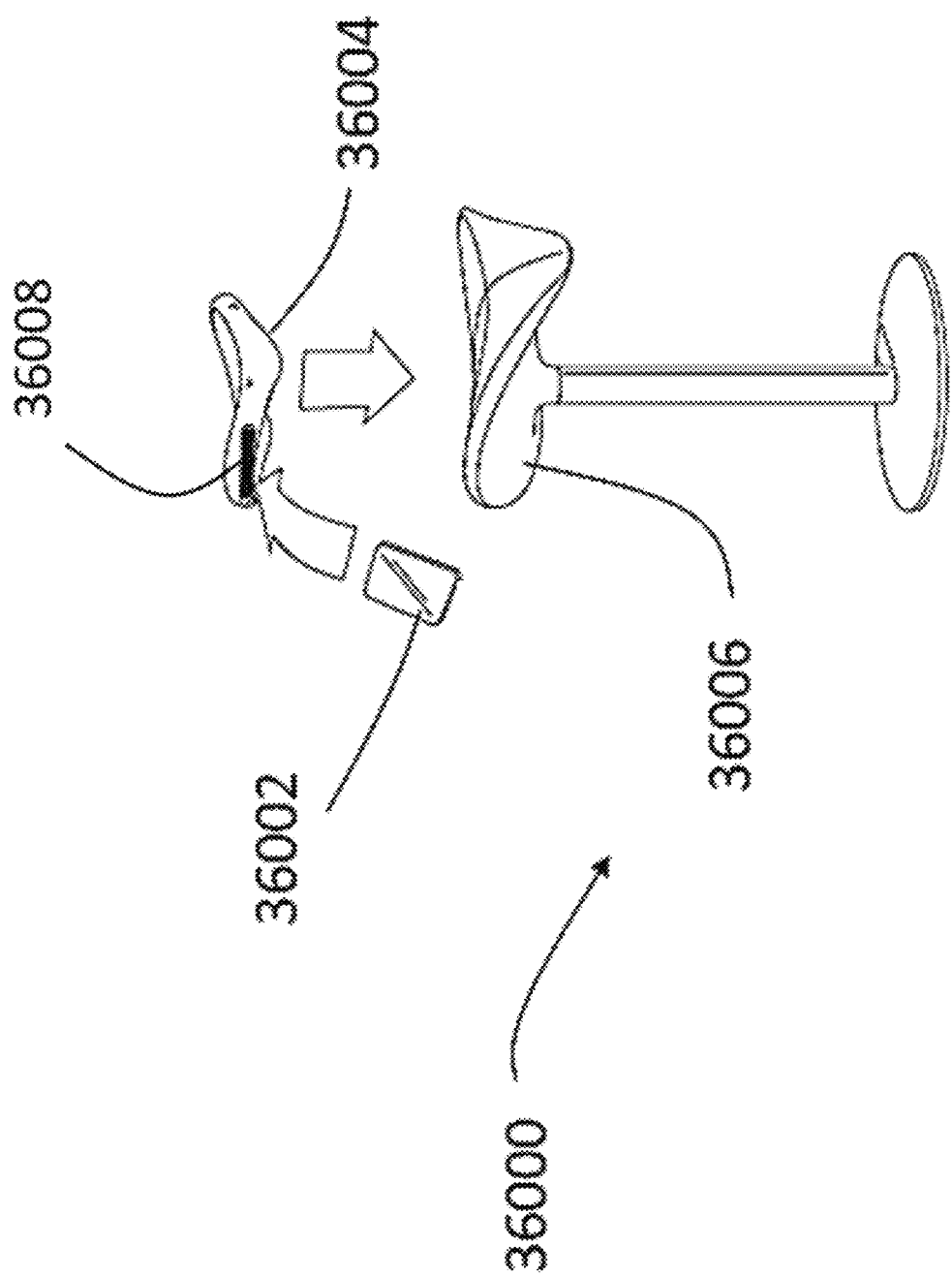
Figure 117:
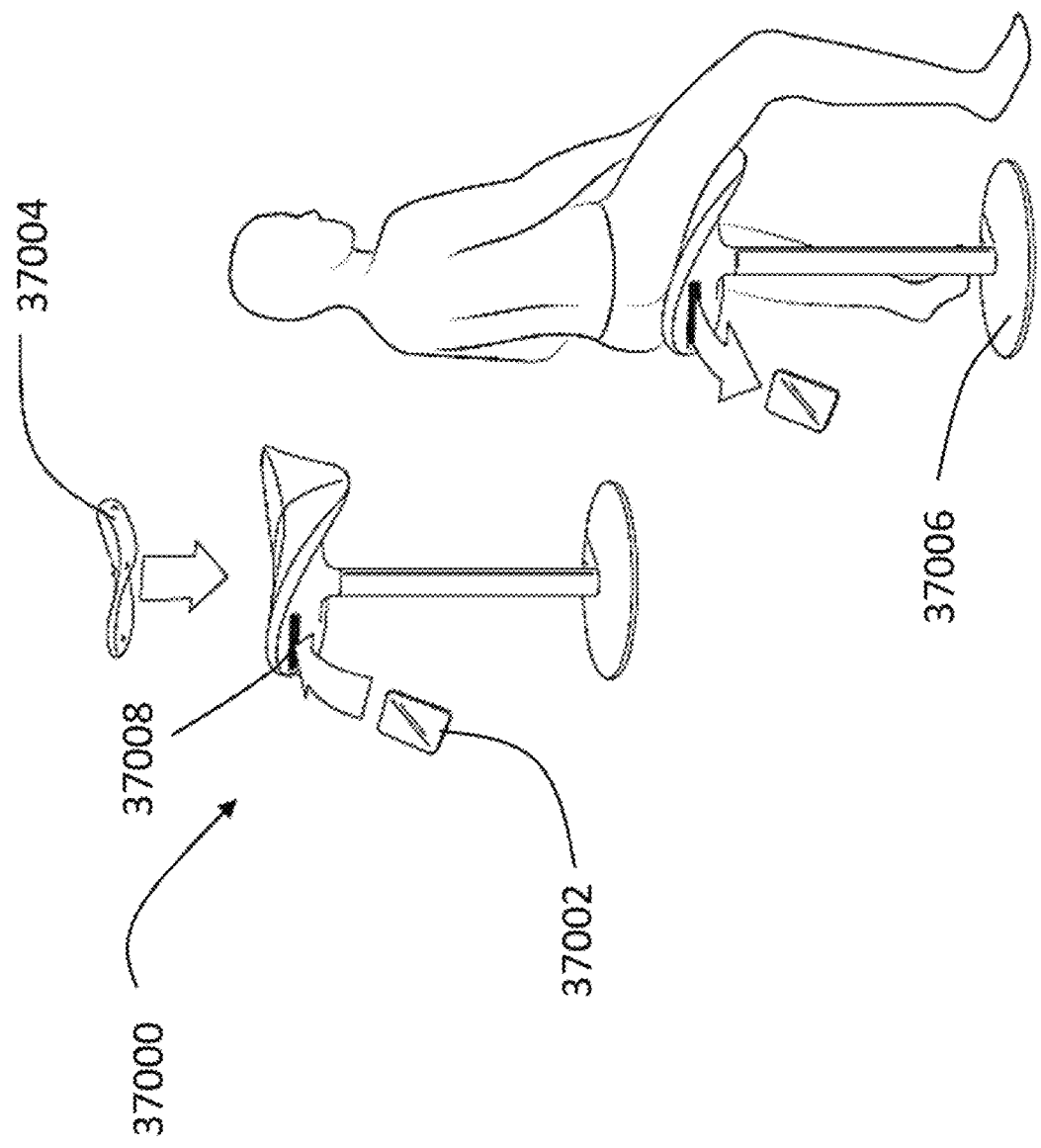

FIG. 116 shows a visualization system 36000 according to another embodiment of the present disclosure. Visualization system 36000 includes a visualization device 36002 that can be placed in a pad 36004 via a slot 36008 provided in the pad. Visualization assembly 36000 can be placed over a stool 36006 to allow imaging of a patient seated on the stool. FIG. 17 illustrates a visualization system 37000 according to another embodiment of the present disclosure. Visualization system 37000 is similar to visualization system 36000, but visualization device 37002 is directly inserted into a stool 37006 via a slot 37008 in the stool in this embodiment. In other embodiments, the visualization assembly can be configured to be placed in other medical furniture for convenient imaging and/or procedures.

Figure 119B:
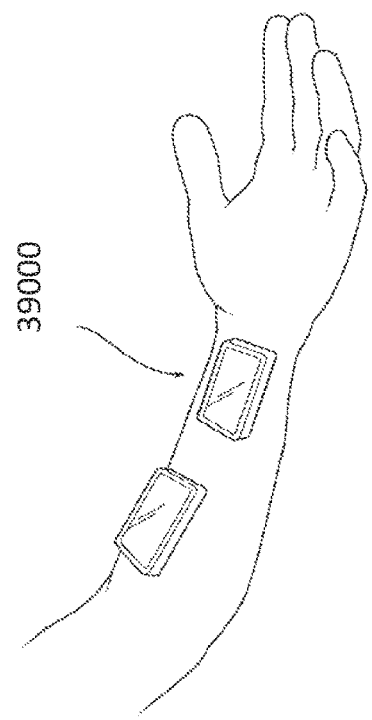
Figure 119A:
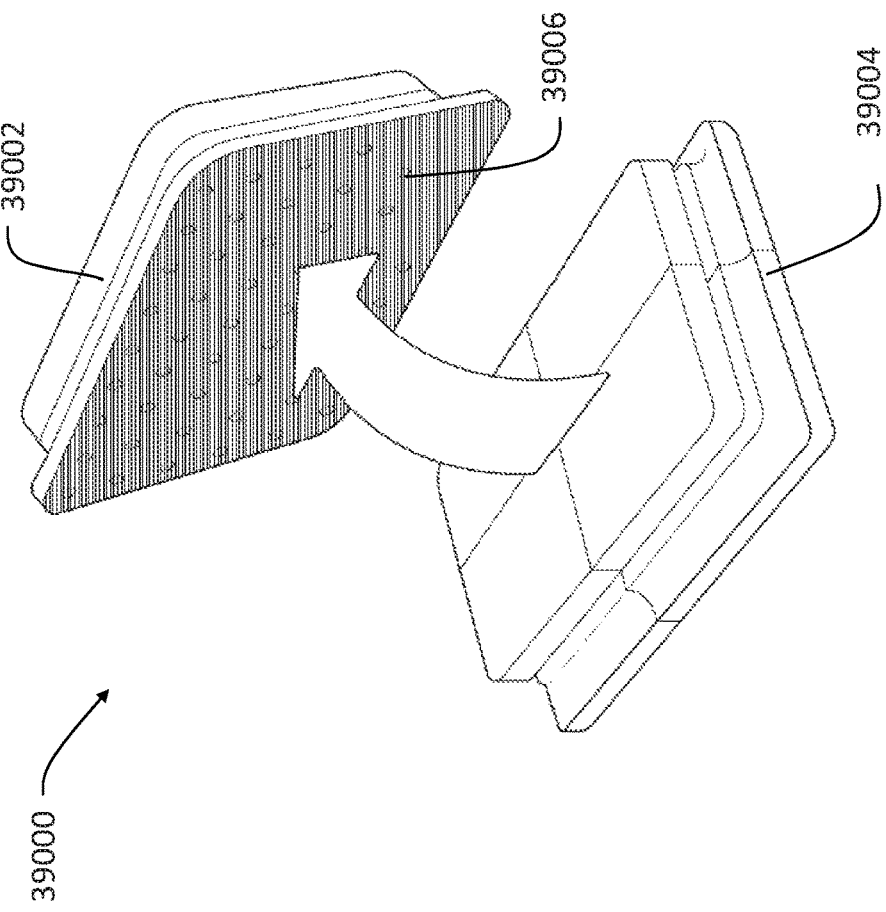

FIGS. 119A and B show a visualization system 39000 according to another embodiment of the present disclosure. Visualization assembly 39000 includes a visualization device 39002 with multiple air vents 39006 as shown in FIG. 119A. A fan or other pressure inducing element disposed within or connected to visualization device 39002 pulls air through the air vents creating a suction force. Further, the air movement will facilitated cooling of the electronic components of the device and ensure proper function of the visualization device. Visualization device 39002 is coupled with pad 39004.

FIGS. 122A-D show a visualization device 42000 according to another embodiment of the present disclosure. Visualization device 42000 includes a dual display window showing a plan view 42002 and a cross-sectional view 42004 as shown in FIG. 122A. The dual display can be deactivated to show a single display if desired. An operator can choose to view only the plan view as shown in FIG. 122D or the cross-sectional view as shown in FIG. 122C. The circular shape of visualization device 122D allows an operator to conveniently hold and slide the device across a patient's skin to locate a suitable insertion location. Once a location has been identified, the operator can rotate the 3D images to further evaluate the anatomical conditions at the potential insertion side as shown in FIG. 122C.

Figure 123:
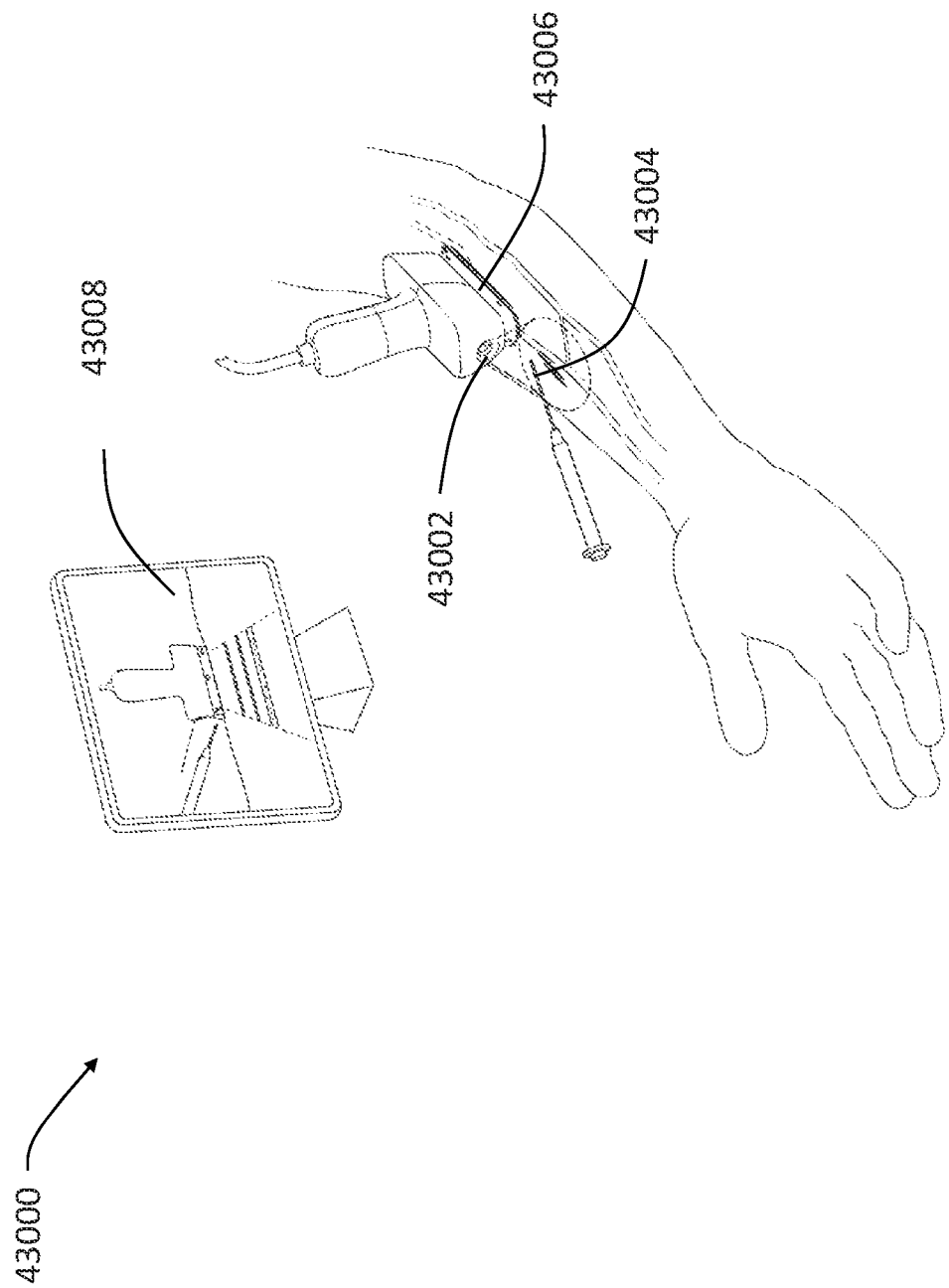

FIG. 123 shows a visualization device 43000 according to another embodiment of the present disclosure. Visualization device 43000 includes a camera or other sensor 43002 positioned on a lateral surface of the probe to identify and track a needle 43004. A display 43008 combines visuals of the anatomical features scanned by the PMUT or CMUT transducers with real-time images of the advancing needle captured by camera 43002. Visualization device 43000 allows needle tracking to determine ideal needle angle and location prior to the needle entering pad 43006 and the insertion zone subsequently.

Figure 127B:
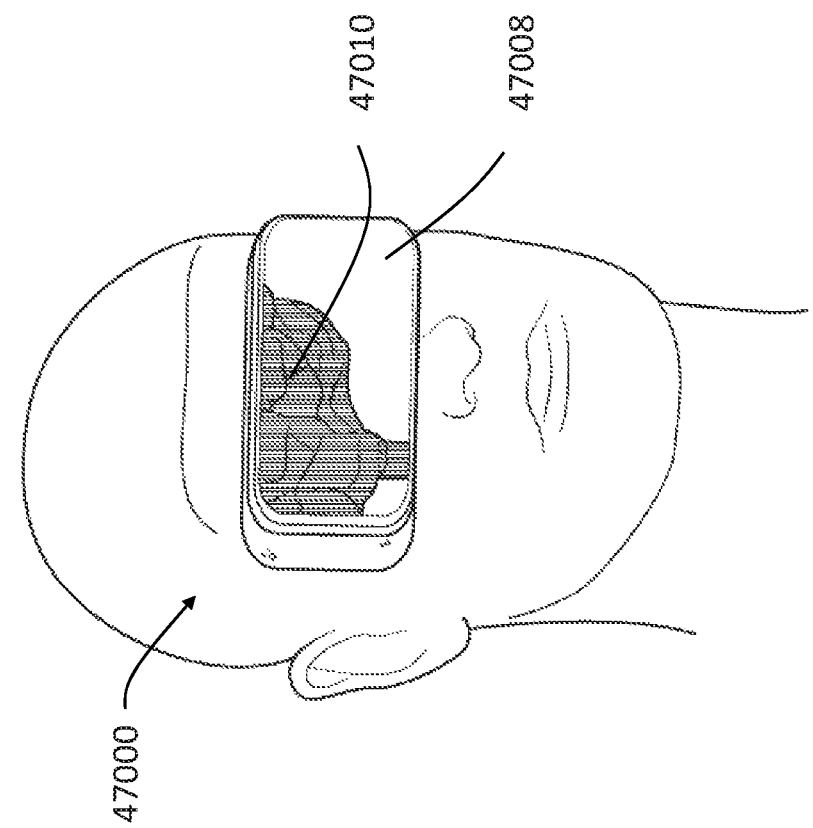
Figure 127A:
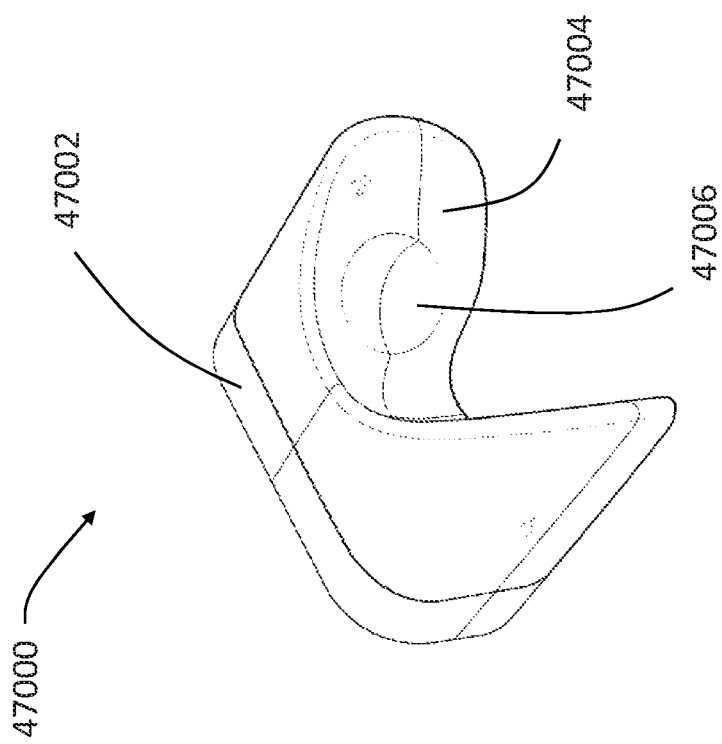
Figure 127D:
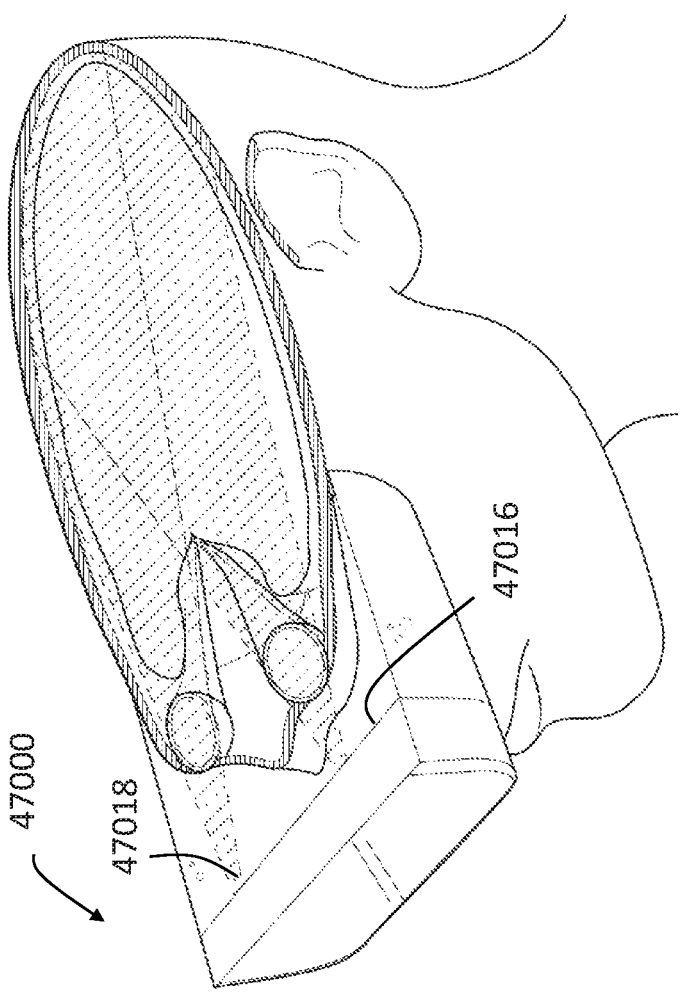
Figure 127C:
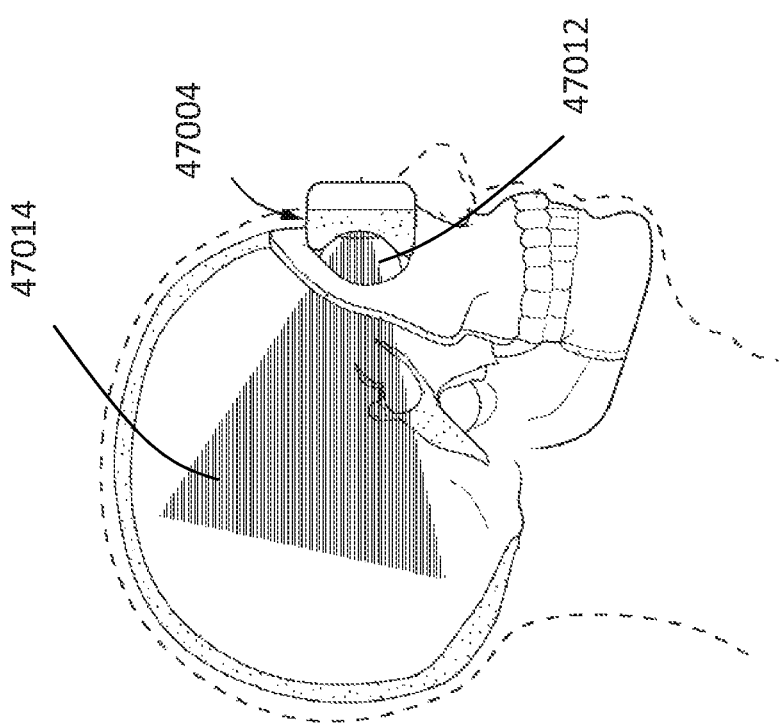

Referring now to FIGS. 127A-127D, there is shown a visualization assembly 47000 according to another embodiment of the present disclosure. Visualization assembly 47000 includes a visualization device 47002 that can be coupled to pad 47004. Visualization device 47002 and pad 47004 are designed to be placed on a patient's face, skull, limb or body as best shown in FIGS. 127B-D. The skin-contacting surface of pad 47004 can include various features to couple conveniently with the patient's face, skull, limb or body. As shown in FIG. 127A, recessions 47004 are provided in pad 47004 to accommodate the patient's eyes. Visualization device 47002 includes a display 47008 to show real-time, 3D images of brain 47010. While a distal face of visualization device 47002 includes an array of transducers distributed all across this face, only transducers that are not obstructed by bone—i.e., the skull in this example, will be activated to transmit and receive signals. As best shown in FIGS. 127C and 127D, active transducers 47018 propagate signals 47012 that diverge 47014 and cover brain tissue well beyond the eyes of the patient. The active transducers transmit and receive signals between gaps in the eye socket as shown in FIG. 127D. The sweeping, diverging signals 47014 generate real-time 3D images of the brain. Transducers 47016 blocked by bone are not activated during the imaging. The activation of specific transducers can be automatically performed by the visualization device or manually controlled by an operator. A strap or other securement device can be used to securely attach visualization assembly 47000 to a patient's face, skull, limb or body.

As shown here, 3D, real-time imaging can be performed using a transducer array with one or more independent arrays—i.e., a continuous transducer array is not necessary. A processor of visualization device 47002 determines the relative locations and orientations of the multiple transducers positioned on the patient's face, skull, limb or body to allow them to work in concert. Image data can be acquired by combining any of these transducers. For example, imaging data can be acquired by transmitting and receiving from a single transducer array, or by transmitting from one transducer array and receiving from one or more of the other arrays. Image formation and generation for each transducer array is similar to a single transducer array. Once this data is obtained, the processor can triangulate the array locations and combine the data to generate the volumetric image data set. Therefore, the strategic activation of particular transducers and the ability to process the resulting image data sets allows the visualization device to produce high-quality real-time image data of anatomical features located behind hard tissue such as bone, body fluid and other features that are impediments to imaging. Further, the visualization device of the present disclosure can be placed on a single location to generate these images without the need to move the device around the surgical site.

As the number of arrays increases, a more detailed image of the tissue of interest can be built up. The image formation for each array is similar to the single-array case, while triangulation between arrays can be used for combining the data sets from multiple arrays.

Visualization device 47002 can include standard ultrasound signal processing that can determine anatomical features of tissue in B-Mode and Tissue Harmonic Imaging. Visualization device 47002 can also utilize the Doppler effect to detect blood flow at the surgical site. Autocorrelation estimators in the visualization device can provide displays combining spatial and flow information in flow modes by using colors to display this information to a surgeon. Fourier analysis can be used to show the spectral distribution of the Doppler shift in pulsed Doppler and CW Doppler modes. Visualization device 47002 can also provide elastography data identifying tissue stiffness.

Visualization device 47002 can include Quantitative Ultrasound ("QUS") to quantify the returning echoes. The unique value of QUS processing allows the visualization device to identify and differentiate various tissue types. For example, nerve and muscle tissue can be distinguished, even though these appear very similar in a standard ultrasound display.

QUS algorithms to estimate quantities such as the concentration of acoustic scatterers in tissue, and the average separation of these scatterers can be performed by the visualization device. QUS algorithms can operate in the time domain or the frequency domain. A QUS algorithm operating in the time domain can be based on statistical measures applied to the radio-frequency signal coming from a beam-former of the visualization device. A QUS algorithm operating in the frequency domain can be based on Fourier transform of a portion of the radio-frequency signal received by the device. The estimated quantities by the QUS algorithms will reveal data which is encoded in the signal received by the visualization device but is invisible on the standard grayscale or color display. Different tissues have different values for the QUS parameters, which can be processed by a machine learning system to create and show the type of tissue that exists at each location in the imaged volume.

FIGS. 128A and 128B show a visualization assembly 48000 according to another embodiment of the present disclosure. Visualization assembly 48000 includes a visualization device 48002 that is configured to be coupled to pad 48004. In one embodiment, pad 48004 can include a moldable material that acquires the shape of visualization device 48002 when the visualization device 48002 is pressed onto the pad as shown in FIG. 128B. Visualization assembly 48000 is configured to be placed on a patient's eye to generate a single-eye as shown in FIG. 128A. A display 48004 shows the eye scan in real time. In other embodiments, the visualization assembly can be customized for scanning various other body parts for pelvic imaging, abdominal imaging, transabdominal imaging, transrectal imaging, obstetric imaging, carotid imaging, abdominal aorta imaging, etc.

Moving Needle

As discussed above, with reference to FIG. 1A for ease of reference, once the inserter assembly 300 is coupled to housing 100, housing 100 can manipulate inserter assembly to adjust the orientation of the inserter assembly relative to the patient and the selected puncture site. For example, the inserter assembly may undergo small movements, in light of data provided by the navigation system, to ensure the needle of the inserter assembly enters the patient at the puncture site, and enters the puncture site at the appropriate angle, depth and trajectory.

The housing function of moving the inserter assembly can be semi-autonomous or fully autonomous—for example, the housing may be capable of operating autonomously to move the needle into the optimal position and ready for insertion at the puncture site and into the intended position in the circulatory system (or bone or other location in the anatomy). The actual step of inserting the needle into the patient can then be performed either autonomously (e.g., once the optimal position is located, the needle is automatically inserted into the patient) or semi-autonomously (e.g., by having the operator interact with the device via a button or the like to initiate insertion).

In light of these functions, the housing may include various sensors, mechanical elements, and the like, all of which add to the ultimate positioning of the needle at the puncture site.

Figure 16A:
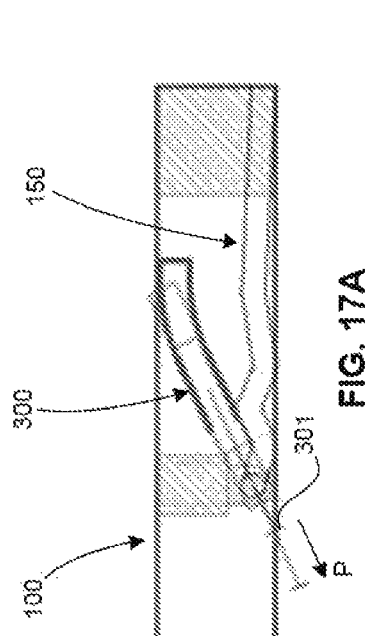
FIGS. 16A-17B illustrate various embodiments of a needle actuation system of the present disclosure.
Figure 16B:
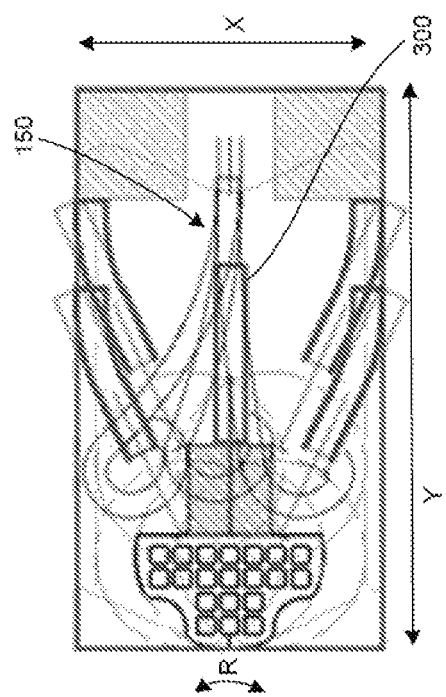

For instance, one embodiment of the present disclosure includes an insertion assembly 300 with needle 301 in housing 100, as shown in FIGS. 16A-16B. The housing 100 includes a needle actuation system 150 which may include the aforementioned elements such as sensors and mechanical elements, such as motors or servomechanisms for precision control, positioning, insertion and extraction of the needle. For example, servo motors may allow fine linear translation in all three directions, i.e, front to back, left to right and up down movement as shown in FIG. 16B. The needle actuation system may also have a rotational or pivot joint to allow the inserter assembly to be rotated in one or more planes. This will allow the needle to be aligned along a predetermined insertion trajectory.

As illustrated in the embodiment of FIGS. 16A-16B, the needle actuation system 150 is positioned within the housing 100 along with a sensor array 160 which can be part of the navigation system and/or can be sensors which feed information to the needle actuation system 150 to control the inserter assembly 300. The system 150 includes a primary control arm 151 which connects the inserter assembly 300 to the housing 100 and needle actuation system 150. The primary control arm 151 is controlled by one or more servos (not shown) that are also positioned within housing 100. The directions and extent of movement of the inserter assembly 300 are defined by the size of the inserter assembly and the size of the housing 100. FIG. 16B illustrates a top view of housing 100 to show the extent of movement of the inserter assembly 300 in the X- and Y-directions within housing 100. Further, control arm 151 may have the capability to rotate the inserter assembly in at least the R-direction to allow movement of the inserter assembly to include the Z-direction (i.e., into and away from the page and perpendicular to both the X- and Y-directions). Movement in the Z-direction may provide an adjustment of the angle of entry of the needle 301 at the puncture site, and ultimately, into the vessel or other anatomy of the patient.

Figure 17A:
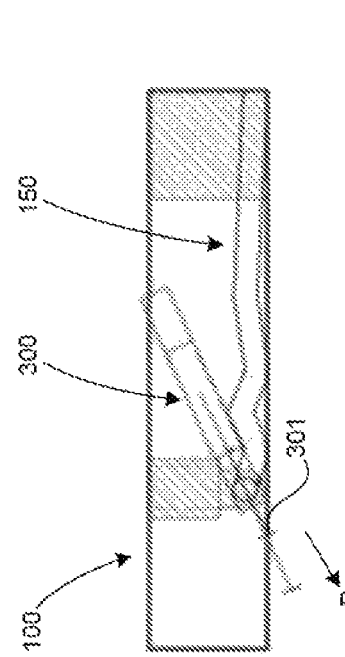
Figure 17B:
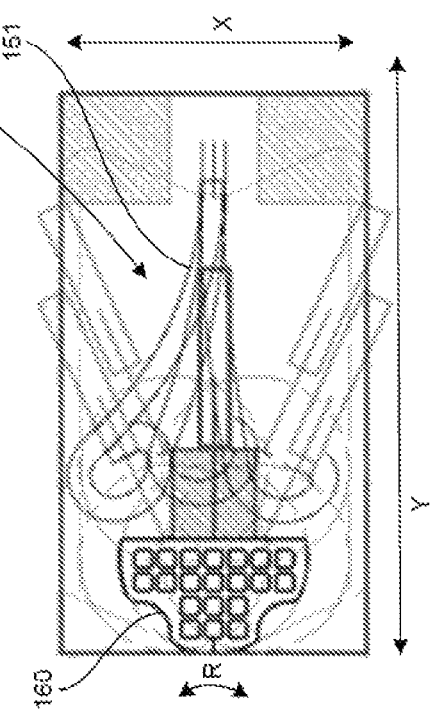

FIGS. 17A-17B illustrate another embodiment of the needle actuation system 150 similar to FIGS. 16A-16B, except in this embodiment inserter assembly 300 is flexible. As illustrated, the flexibility of assembly 300 may allow for increased movement of the assembly 300 within the housing. Alternatively, the flexible assembly 300 may allow for the use of a smaller housing 100 while still maintaining a similar range of movement as possible with the embodiment of FIGS. 16A-16B. The flexible portion of the inserter assembly 300 may simply be a flexible housing over the various element of the assembly 300, and/or could include flexible elements of the assembly 300 such as tubes, vials, needles, etc.

In a particular embodiment, the device may provide for a needle 301 that can be positioned in an infinite number of positions by the use of a "universal" joint. Such a joint requires multiple servos capable of moving the needle in any direction desired, including the X-, Y- and Z-directions, rotational direction, the T-direction (i.e., direction of needle tilt) and the D-direction (i.e., direction of needle drive) ("XYZRTD" movement). In such an example, this universal movement may require a relatively larger housing 100 to provide clearance for the inserter assembly 300 to move within the housing.

As more fully described above, the navigation system may provide information to the needle actuation system 150 to guide the needle 301 to the correct location on the patient. As such, the needle actuation system accumulated this data and, based on this data, actuates the servos to move the needle to the desired position as instructed by the navigation system. Additionally, the servos may receive feedback through other sensors measuring such information such as the position of the needle and inserter assembly 300, the force the needle is applying to the patient, the force of the patient's anatomy pushing back on the needle, and the like. As such, additional sensors such as force sensors or tactile sensors may be coupled to the needle actuation system to control and monitor proper needle insertion. The precision servos and motors ensure needle insertion motion is precisely executed based on, inter alia, translation velocity, penetration depth, penetration angle, and insertion force to puncture skin, etc. For example, the needle translation velocity may be adjusted to reduce patient discomfort or increased to achieve skin puncture. The needle actuation system may provide for variable needle translation velocity, wherein the needle punctures the skin rapidly (to reduce discomfort) and then slows down while puncturing the vessel to maximize precision. Similarly, needle retraction velocity may be variably controlled for optimized performance.

In one embodiment, the needle actuation system may be capable of being controlled by an operator as a semi-autonomous element. In such a configuration, a haptic force feedback system may be used. Specifically, a virtual haptic geometry of the needle insertion position, trajectory and depth may be created to generate virtual boundaries enabling an operator to perform the insertion with the aid of the navigation system and GUI. The needle actuation system may also include micromanipulators coupled with force sensors for precision control of the needle motion in the semi-autonomous system.

Inserter Assembly

The device may be configured to be used with different inserter assemblies containing various needle and needle accessories. In one embodiment, once the needle is attached, the navigational sensors detect and calibrate the device to perform the insertion with the dimensions of the attached needle. This will allow the device to be available for universal use with many different needle in varying procedures as expected in a typical hospital use. As discussed above, the desired needle can be included onto the base prior to setup or, in certain embodiments, the needle can be attached to the device once the base and housing are already positioned on the patient.

Alternatively, a kit with at least one needle and at least one inserter assembly may be provided. The kit may include needles of various sizes along with various accessories for use with the needle and positioned within the inserter assembly. For example, the inserter assembly may be a universal element, capable of being used with any sized needle and any needle accessories desired.

Solid needles, i.e., without cannulation may be used with the present device, though cannulated needles can also be used to allow flashback, whereby an operator can ensure that needle insertion into the blood vessel has been achieved. However, the present device may not need this visual confirmation to ensure that needle insertion has been successfully achieved due to the feedback received from the navigation and needle insertion systems. Consequently, this device can function with solid needles which may reduce patient discomfort during needle insertion. Other needles may also be used with this device, such as flexible needles, adjustable needles (e.g., needles having telescopic features that allow for needle size minimization), and the like may also be use with the device.

A kit containing a patch 750 with an inserter assembly 760 is shown in FIGS. 20A-B according to another embodiment of the present disclosure. Inserter assembly 760 includes a skirt 762 positioned on a needle. The skirt may operate as an additional sterility shield around the inserted needle (and eventually, optionally, a cannula) at the puncture site. The skirt includes an adhesive surface which secures itself to the patient's skin at the puncture site, or the skirt can be combined with integrated pre-applied patch 750 which is or can be positioned on the patient's skin. Patch 750 includes an upper layer 751 to couple with a device and the inserter assembly 760, and a bottom surface 754 to adhere to a patient's skin. Bottom surface 754 can be self-sealing member that seals after needle penetration to prevent infections of the puncture site, and also to keep any blood from the puncture site away from the operator. Bottom surface 754 can include adhesive properties that can be activated or deactivated by the operator or any other response. Additional layers such as a flexible layer 752 with venous preparation components to dilate veins for insertion is located between bottom surface 754 and upper layer 751. The venous preparation component can include heating, electrical and chemical agents. An analgesic layer 753 is also provided as shown in FIG. 20A to reduce pain and discomfort during needle insertion. Bottom surface 754 may be secured to the skin via adhesion, light or vibration activated adhesion, friction, interlocking mechanism or the like. This can be particularly useful for long-term IV use, which typically requires additional taping to secure the cannula to the patient. Instead of the additional taping steps, the operator can instead quickly slide the skirt into position which can help hold the needle/cannula in place relative to the patient.

With specific reference to FIGS. 28 to 31, disclosed therein are various exemplary embodiments of how motions, including micromotions, of the inserter assembly and/or housing are achieved within any of the devices envisioned herein.

Figure 28:
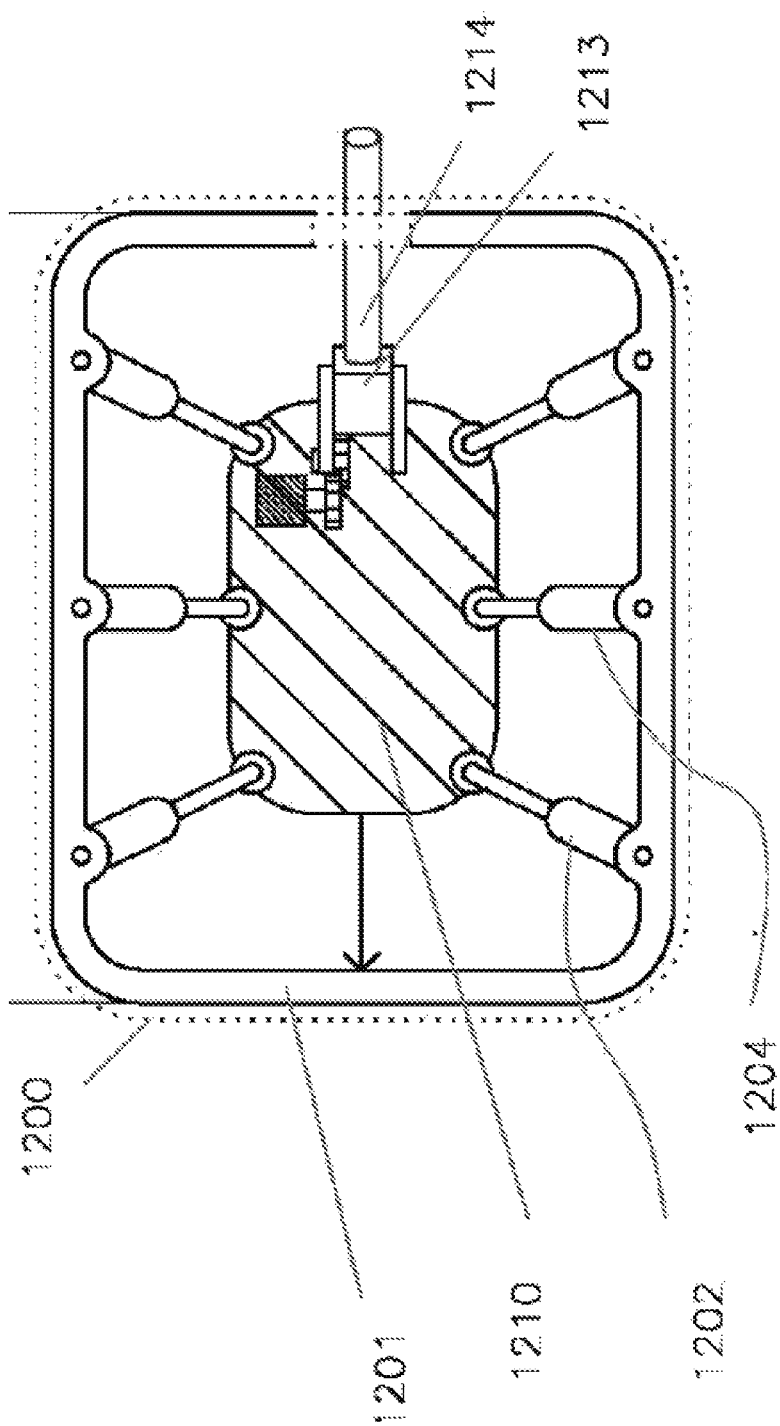
FIGS. 28-31C illustrate various embodiments of inserter assemblies of the present disclosure.
Figure 29:
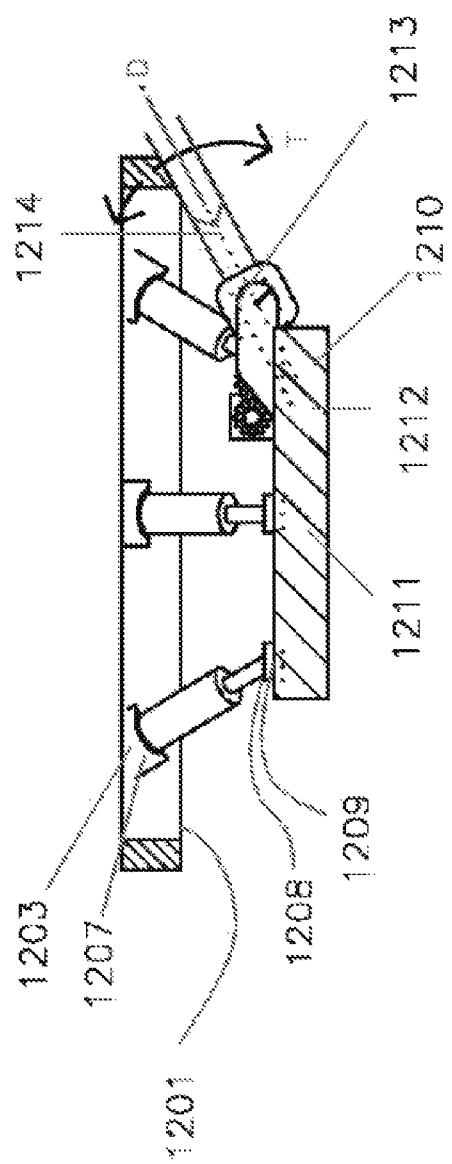
Figure 30:
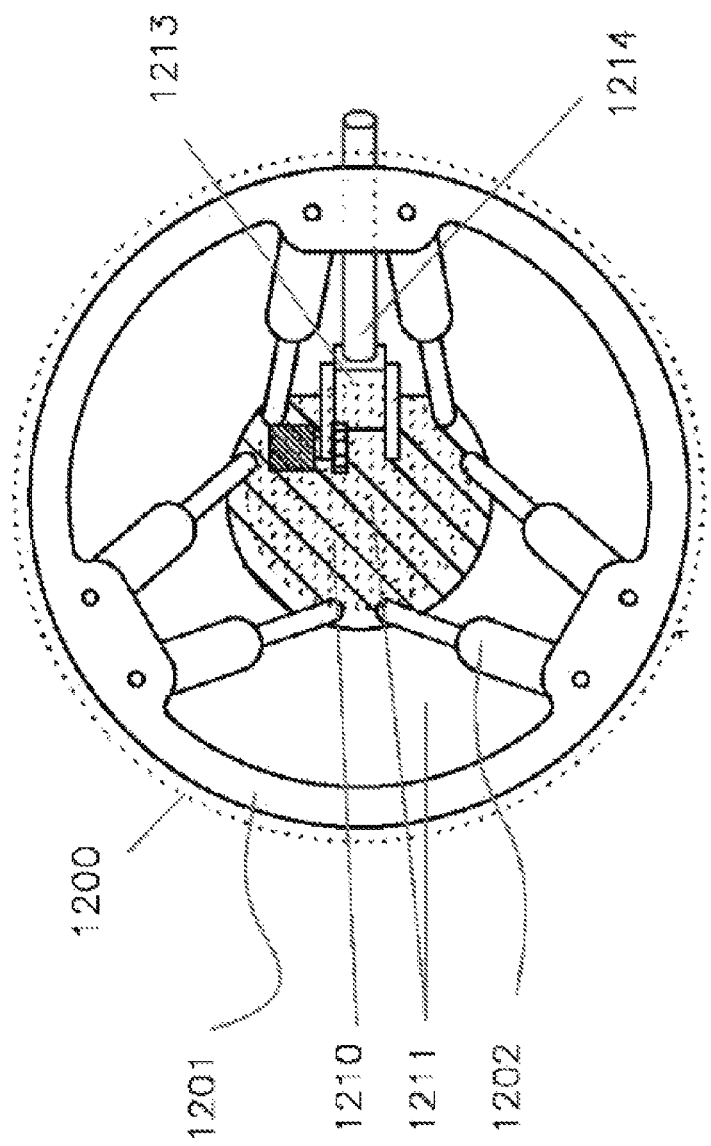
Figure 31A:
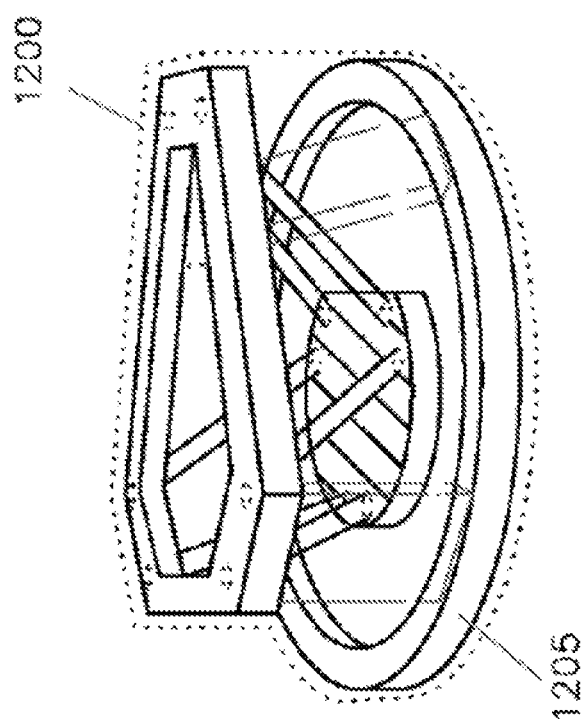
Figure 31B:
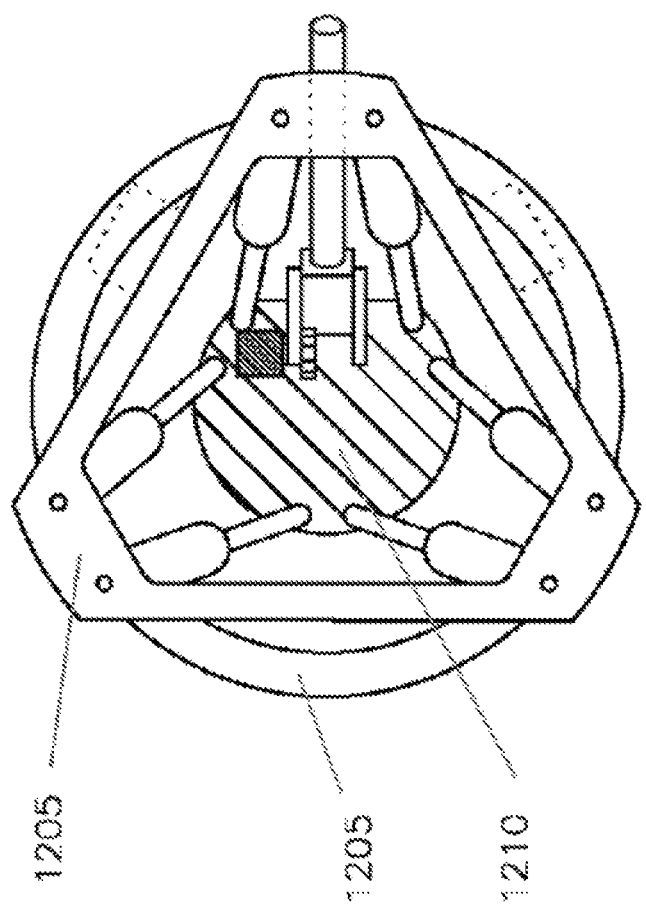
Figure 31C:
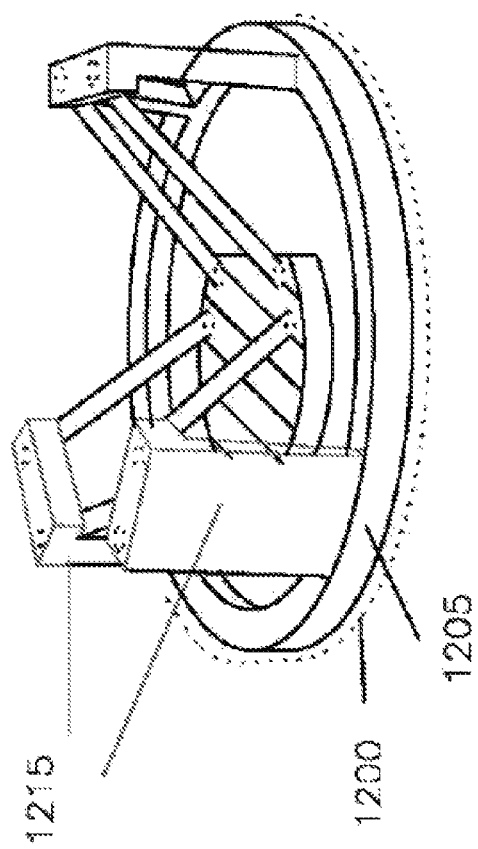

FIGS. 28 to 31C illustrate various embodiments of the present disclosure. As illustrated, device 1200 includes a strut mounting structure or strut mounts 1201, to which a plurality of articulating struts 1202 are mounted at a first end 1207 with articulating joints 1203, such as a hinged, universal or ball joint, or the like. The struts 1202 may provide a linear motion, driven by an integrated or adjacent linear motor 1204 such as a piezoelectric linear motor such as a squiggle motor, pull wires with a remote motorized drive, or a pneumatic drive. The struts may alternatively include a hinged portion. The advantage of these articulation and drive types is to achieve extreme miniaturization, and accuracy. The strut mounting structure 1201 may be a full or open sided aperture, with a generally rectangular form as shown in FIG. 28, or generally circular FIG. 30, or generally triangular FIGS. 31B and 31C. The strut mounting structure 1201, may consist of upright or angled posts 1215, as illustrated in FIG. 31C, mounted from below or laterally to the strut mounts, for example the strut mounts may be structurally joined to a region of the outer casing, structure, frame within or integral to the device 1200. FIGS. 31A and 31B show one embodiment where the strut mounting structure is integrated with a rigid aperture 1205 of the device 1200. The device may additionally include a floating platform 1210, to which a second end 1208 of each of the plurality of struts may be mounted, with an articulating joint 1209, such as a hinged, universal or ball joint, or the like. In operation the platform 1210 is positioned substantially adjacent to, and/or parallel to a patient's body, for example at or in the vicinity of a target intravenous needle injection site. The plurality of struts can mechanically articulate in order to move the platform in up to 6 degrees of motion. In the shown embodiments of FIGS. 28 to 31C, device may have 6 struts 1202, often referred to a Hexapod, which together are capable of moving the platform in all of the X (side) Y (longitudinal), Z (into and away from the body), yaw (rotate), roll (sideways tilt) and pitch (forward and back tilt). In alternative embodiments the device may include 3 struts, here referred to as a Tripod, or 4 struts, here referred to as a Quad-pod.

Continuing with FIGS. 28 to 31C, the floating platform 1210 may include an anatomical imaging module, capable of gathering 2d, 3d or 4d data from a target site, below the patients' skin. The platform is capable of being moved in various degrees of motion so to align with a preferred site. The platform may additionally be moves in a manner that causes its underside to press into, or massage an area of the patient, for example of assess the properties of certain vessels under compression. This may provide important additional information in determining a vein, versus a (typically less compressible) artery. The platform may additionally vibrate or implement a tapping motion to stimulate vessels so to be more optimal, more dilated, or raise closer to the dermal surface, for more cannulation conditions, i.e., so to increase the size of the lumen, and become an easier target. As illustrated in FIGS. 29 and 30, the platform and/or surrounding area may include a heating element 1211 in order to warm and encourage the dilation of the vessels below. Vibration of the platform vibration, caused for example by a high frequency micro movements generated by one of more of the struts 1201, may be activated at time of needle insertion so to act as a pain gate stimulus, to confuse the local, adjacent or surrounding peripheral nerve system, through stimulation. As illustrated in FIG. 29, the platform may include a cooling element 1212 targeted in the vicinity of, or adjacent to, the insertion site may be activated to cause a temporary numbing effect, as a means to numb the sensory effects caused at time of needle incision, e.g., pain management.

Furthermore, the platform may include a fixed or articulating conduit 1213 may also be referred to as a mount, and may hold a needle or cannula, or an injection module 1214 that houses a needle and/or cannula. The conduit may provide additional degrees of motion relative to the platform 1210, herein referred to a local motion, as a complement to the degrees of motion provided by the plurality of struts 1202, which may be referred to a global motion. At an upper extent, the conduit may provide 6 degrees of local motion, such as X, Y, Z, R yaw, roll, pitch. More preferably the conduit would provide local rotation (local-yaw), local tilt (local-pitch). Further motions provided by the platform mounted conduit 1213, or within an inject module or cannula itself, herein referred to as super-local movement, may include drive (to push or pull a needle or cannula along its own axis), and twist (to revolve a needle or cannula about its own longitudinal axis). The conduit 1213 and injection module 1214 in certain embodiments may be provided as one assembly.

Once the device 1200 has lined up a target vessel, guided by its imager module, should the target then move, for example due to a patient or operator shake or tremor, or the device otherwise moves off target, the device may auto correct the position and trajectory of the needle as held by the conduit, so as to keep the target in line—hence the term floating platform.

Additionally, the device 1200, with integrated strut mount structure, is preferably configured to be compact in outer dimension, yet while also providing maximal extents of motion to the floating platform within, so to provide the ability to scan a relatively large area of the anatomy so that optimal needle or cannula insertion conditions can be found. The overall device 1200 height may be between and including 8 and 22 mm. The circular embodiment of FIG. 29, may have a diameter of between and including 25 mm and 75 mm. The platform 1210 may be mechanically lockable, so that the user can move the device around the arm as an initial locating step, and thereafter, the device, with integrated floating imaging platform can perform the finer, or micro degrees of motion, and image and needle alignment.

Also, the device 1200 may include a control unit and display. The display may be substantially the same size as the devices top surface, and may include touch controls. The device may alternatively, or additionally include a controller stick, or joy-stick. These controls could be used by the operator to operate any or all of the mechanized degrees of motion, to align and place a needle or cannula, with robot assist.

Figure 86A:
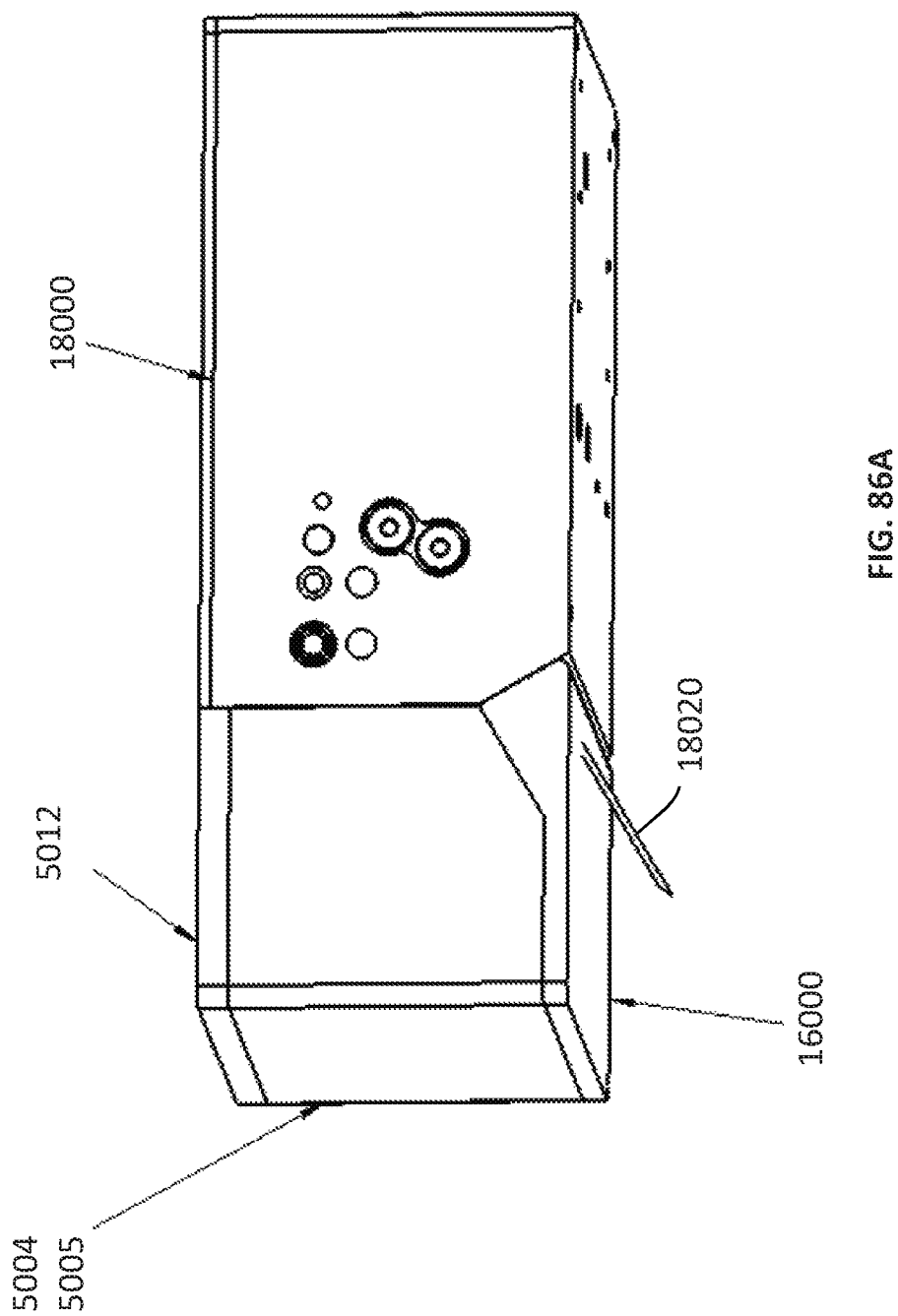
FIG. 86A illustrates a device with an inserter assembly according to an embodiment of the present disclosure.
Figure 86B:
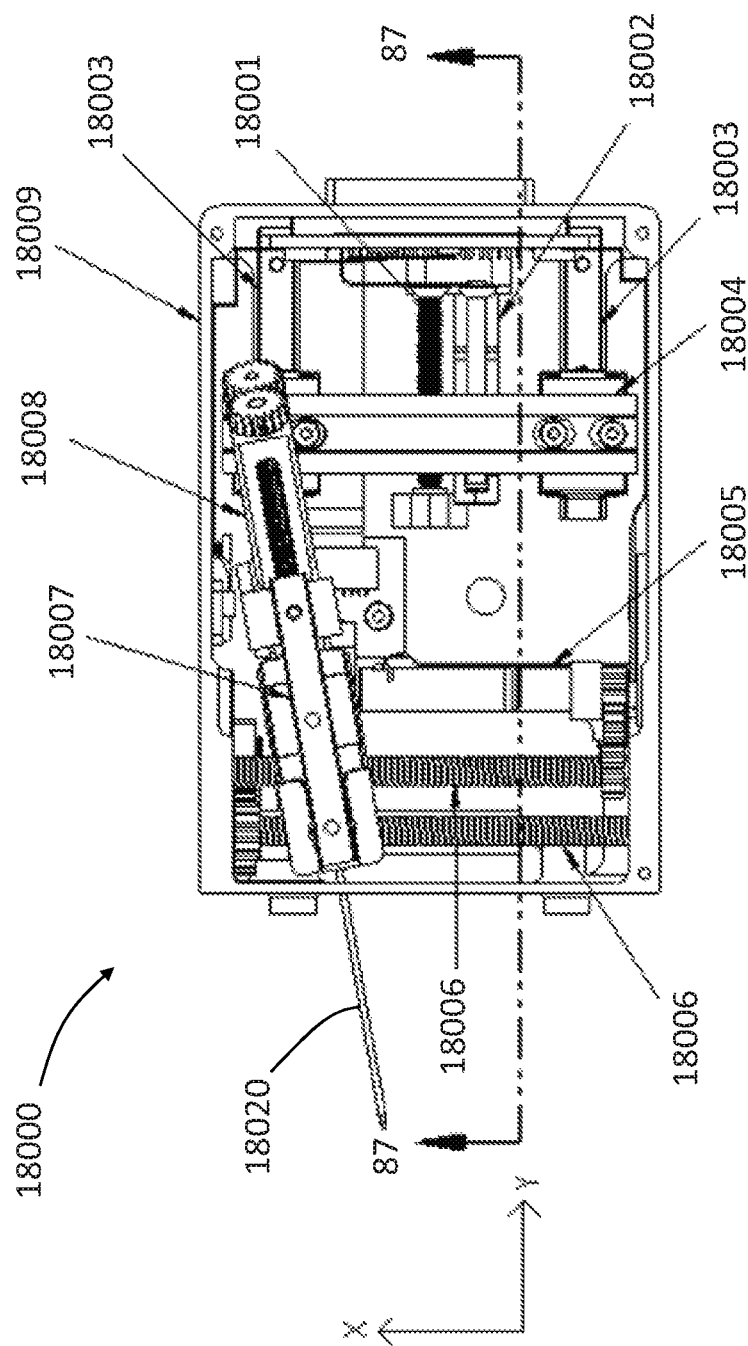
FIG. 86B illustrates a top view of the inserter assembly of the device of FIG. 86A.
Figure 87:
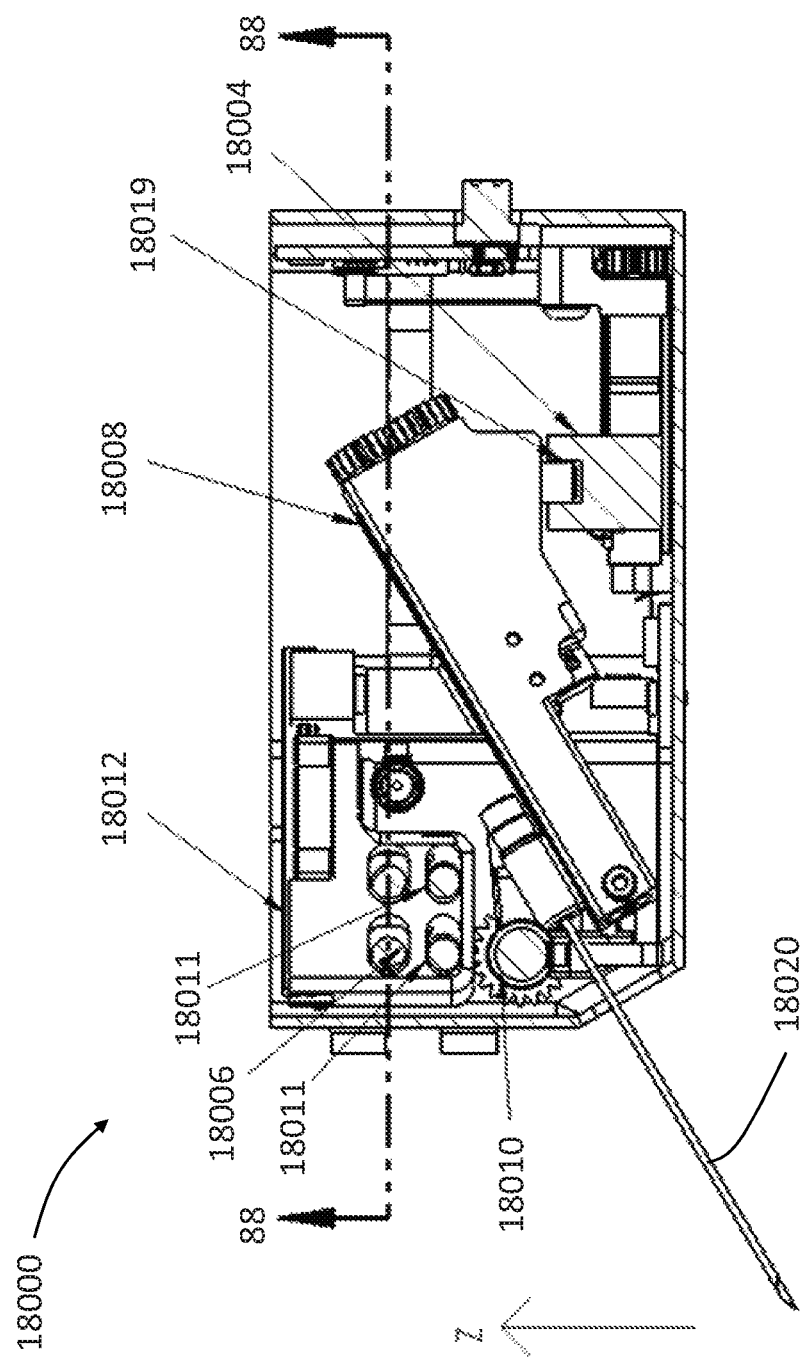
FIG. 87 illustrates a cross-sectional view of the inserter assembly of FIG. 86B.
Figure 88:
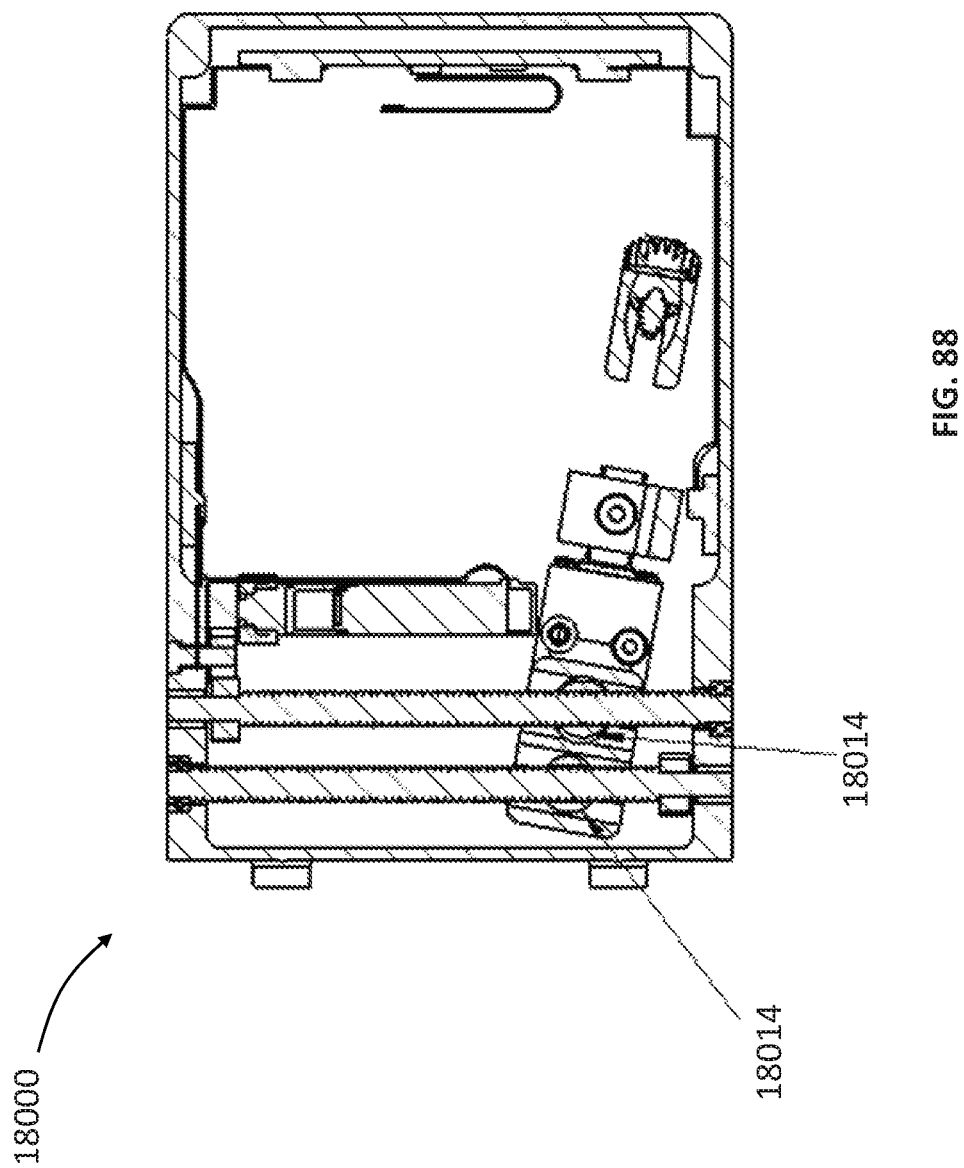
FIG. 88 illustrates another cross-sectional view of the inerter assembly of FIG. 86B.

FIGS. 86A-89C show an inserter assembly 18000 according to another embodiment of the present disclosure. Inserter assembly 18000 includes a three-degree-of-freedom parallel mechanism that positions a needle drive mechanism 18001. Needle drive mechanism 18001 carries and moves a needle 18020 to perform the insertion. A single-degree-of-freedom mechanism drives a needle driver 18008 into the patient's anatomy and retracts the needle when the procedure is complete. As best seen in FIG. 86A, inserter assembly 18000 can be attached to device 5000 and pad 16000.

Needle 18020 is mounted to a leadscrew 18017 and a threaded carriage 18016 as shown in FIG. 89C. Carriage 18016 is constrained by a housing 18015 in such a way that the housing supports off axis loads and requires no additional support. This design allows inserter assembly to have a compact size.

Needle 18020 can be contained in a single use, sterile container, through which motion is controlled while maintaining a sterile barrier between the mechanism and needle.

Two parallel linear mechanisms, such as leadscrews 18006 shown here jointly control the angle and position along the x axis of a main carriage 18012 to control the needle insertion location. The linear mechanisms are coupled to main carriage 18012 in such a way that when moved synchronously, main carriage 18012 will maintain a constant orientation and move along the x axis. Further the coupling between the linear mechanisms and main carriage 18012 allows the main carriage to rotate with zero translation when moved asynchronously. This motion can controlled by the independent movement of two threaded pins 18014 which are driven by leadscrews 18006. Main carriage 18012 being free to rotate with respect to one pin and free to rotate and translate with respect to the other. In alternative embodiments, the function of the pins and main carriage may be combined by a compliant structure containing flexural hinges and threaded features that interface with leadscrews.

Two support shafts 18011 are provided to prevent moments and loads put on the needle that do not align with the x axis. This improves the efficiency and extends the useful life of linear mechanism 18006.

A linear guide 18007 is the interface between the needle driver and main carriage 18012 allowing free movement along the y axis while constraining movement in other directions. A rail 18004 controls the Y position of needle driver 18008, while allowing unconstrained movement of the needle driver along the x direction. A connecting pin 18019 interfaces between rail 18007 and needle driver 18013.

Linear mechanism 18001, such as a leadscrew shown here, controls the movement of rail 18004 along the Y direction. Two linear guides 18003 prevent moments put on the rail and thereby improve the efficiency of linear mechanism 18001 and extend its useful life.

Four electromagnetic rotational motors 18002, 18005, 18010, 18018 are used to power the linear mechanisms due to their high power-density. In other embodiments these motors can be piezoelectric motors which may reduce noise emitted by the device. Hydraulic or pneumatic motors can also be used. In other embodiments, linear motors are used to power the linear mechanisms. In other embodiments, no support shafts 18011 may be provided, instead linear mechanisms 18009 can prevent off axis loads directly. This is advantageous because it makes the mechanism more compact.

Through the use of leadscrews for all four axes, the linear resolution of inserter assembly 18000 is increased considerably, so that for a full rotation of the motor, the needle may move a fraction of the diameter of a vein. In addition, the effects of backlash in the motors are dramatically reduced. Accidental over loads put on the device due to operator error or an accident will not be transmitted to the motors due to the non-back drivability of leadscrews and the gear coupling between motor and leadscrew. Positioning and insertion speeds of inserter assembly 18000 are on the same order of magnitude as a human operator. Further, inserter assembly 18000 is configured to apply similar force as a human operator to insert and manipulate the needle within human anatomy.

Figure 90:
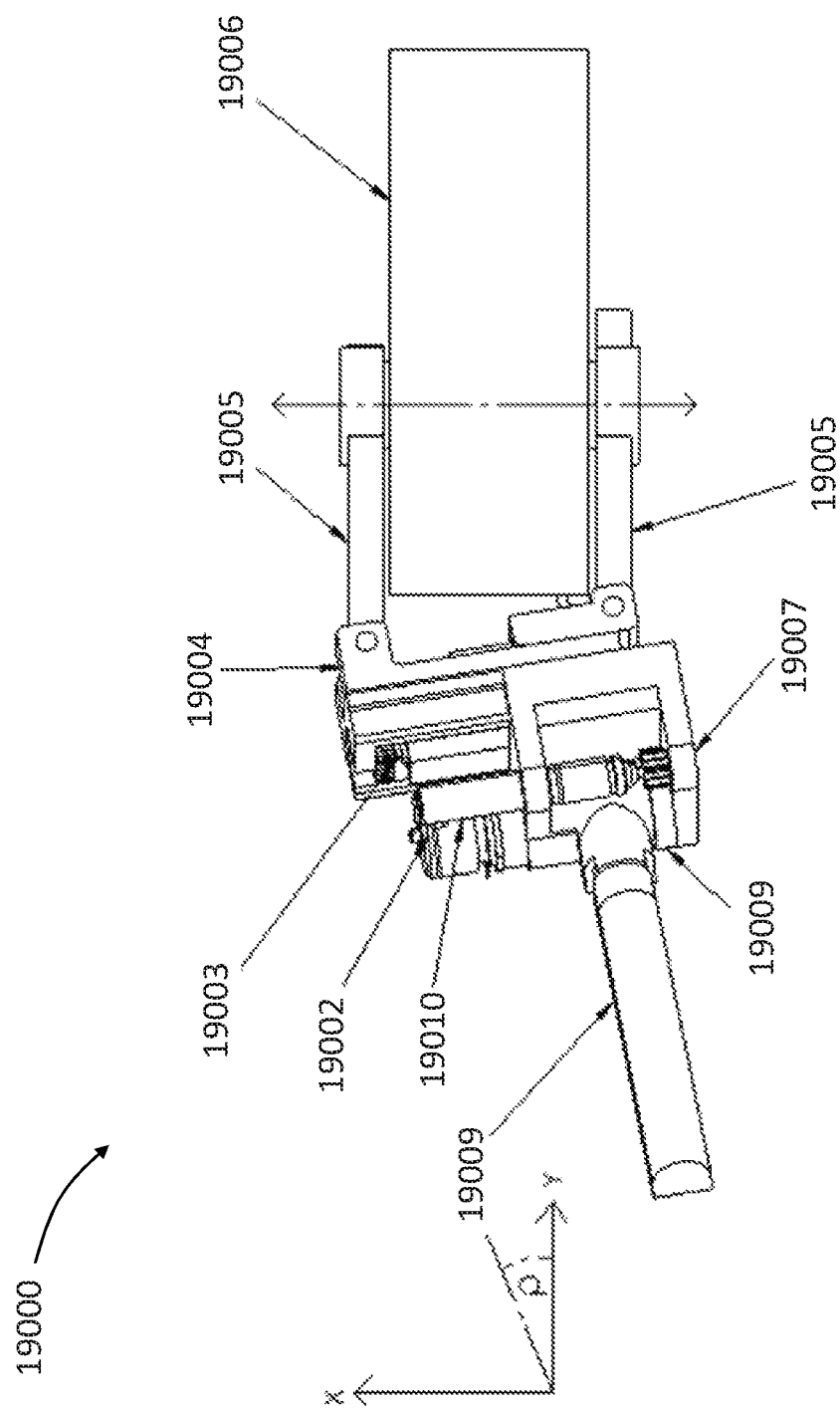
FIG. 90 illustrates a front view of an inserter assembly according to another embodiment of the present disclosure.

FIGS. 93A-F show an inserter assembly 19000 according to another embodiment of the present disclosure. Inserter assembly 19000 includes two members 19005 which can be moved in opposed directions to create a rotation of a linear mechanism 19004 and control an angle ρ of the needle drive mechanism as best shown in FIG. 90. One member 19005 is coupled to the linear mechanism through a pinned joint 90012 which can rotate with respect to the member and translate with respect to the linear mechanism.

Members 19005 can be controlled by a gearbox, which links the two members in such a way that their movement in the X direction is opposite to one another, and is driven by a single gear. The gearbox is capable of rotating the members about axis P to affect a rotation of the linear mechanism about axis P and a movement of the needle axis principally in the Y direction.

Figure 93:
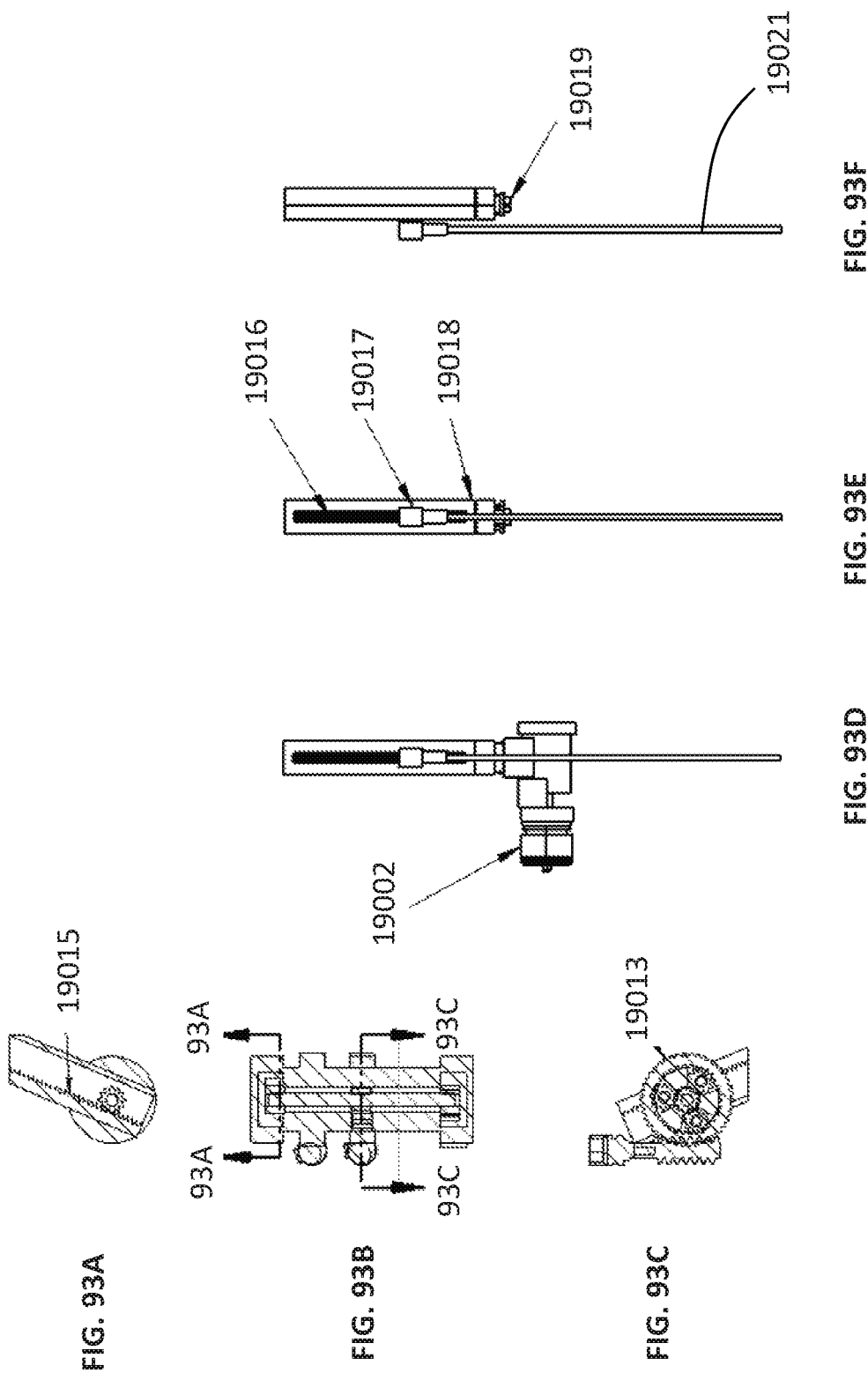
FIGS. 93A-93F illustrate views of components of the inserter assembly of FIG. 90.

The gearbox is driven by two worm gears 19011 that can independently control the rotation of the gearbox and the movement of the linkages. The movement of the linkages are controlled by a rack and pinion 19015 with power being transmitted through central shaft driven by a large sun gear 19013. A linear mechanism 19004 controls the position of a main carriage 19007 principally along the X direction. Main carriage 19007 is moved by the linear mechanism, which carries a needle driver mount 19009 as best shown in FIGS. 93D-93F.

Figure 91:
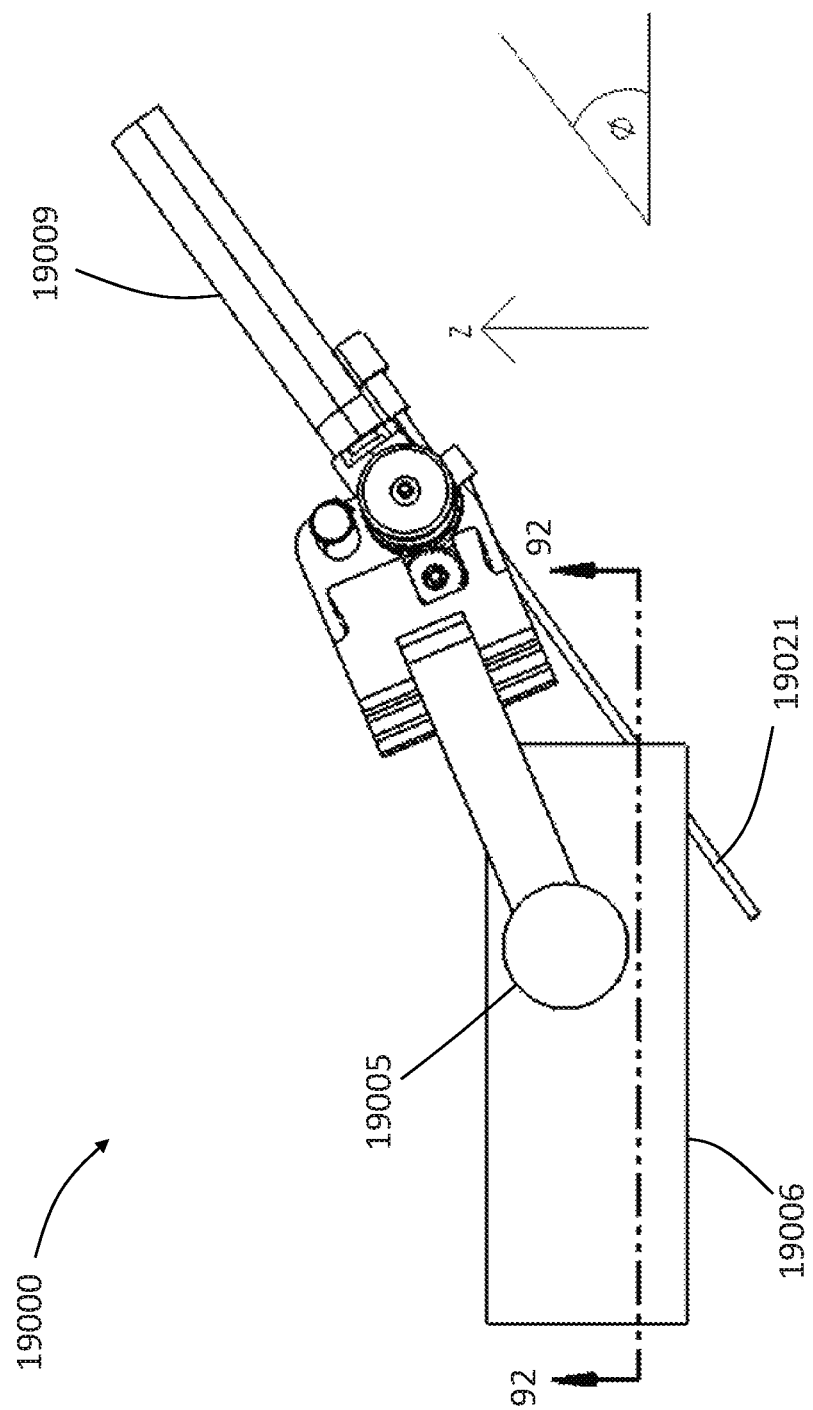
FIG. 91 illustrates a top view of the inserter assembly of FIG. 90.
Figure 92:
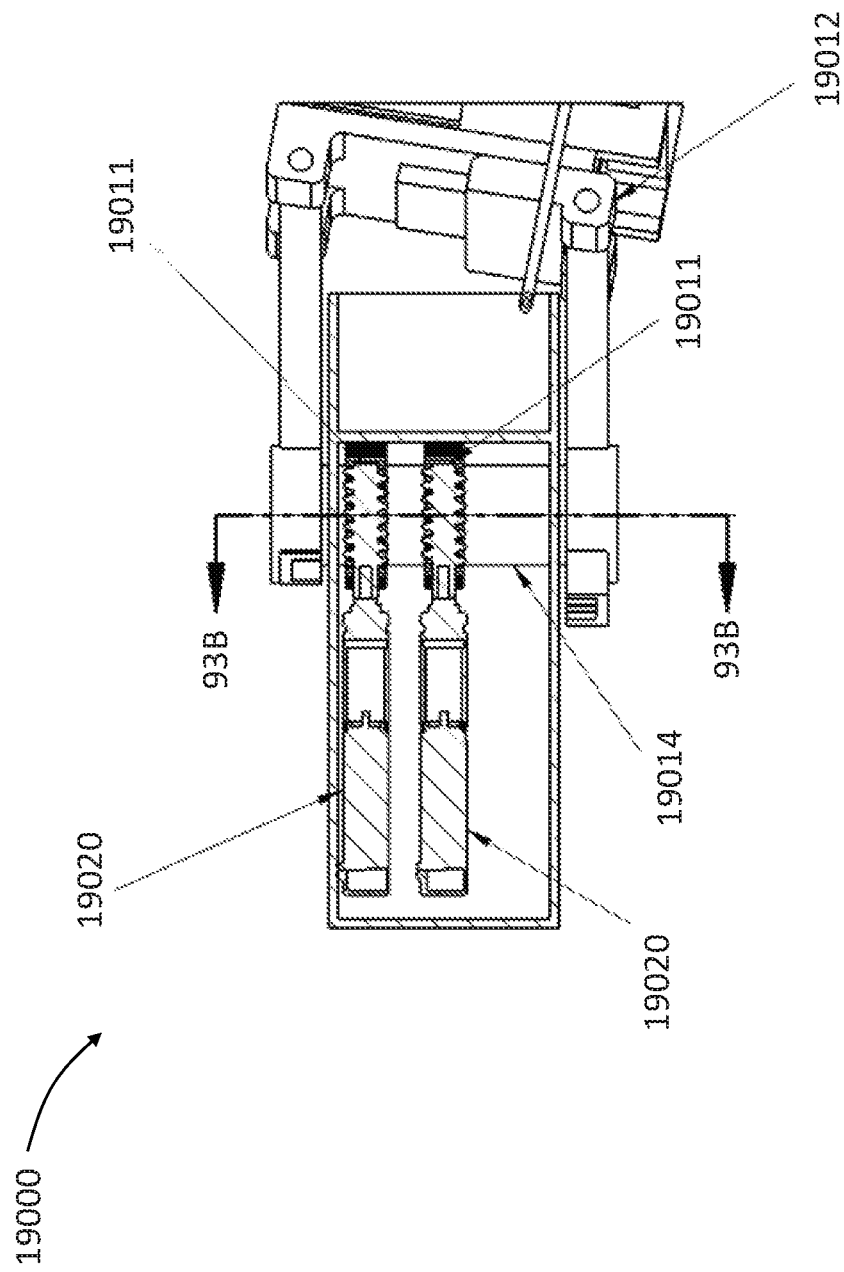
FIG. 92 illustrates a cross-sectional view of the inserter assembly of FIG. 90.

The linear mechanism can include a leadscrew 19017 which drives the carriage. Needle driver mount 19009 connected the needle driver is attached before a procedure begins. Needle driver mount 19009 is attached to the carriage in such a way that it has a single rotational degree of freedom which is precisely controlled. The rotational degree of freedom effecting rotation of the needle driver, controlling the angle $\Phi$ as shown in FIG. 91.

Five electromagnetic rotational motors 19002, 19003, 19010, 19019, 19020 can be used to power inserter assembly 19000 due to their high power-density. Power can be transmitted through a shaft to the linear mechanism that drives the needle. Torque can be transmitted to the leadscrew through mating pins 19019 and the housing temporarily secured to inserter assembly 19000 by the user through a push and twist motion. The cartridge can be a single use, sterile, non-powered, self-contained assembly.

The mechanical design of the arm 19005 linkage and the differential gearbox in inserter assembly 19000 is particularly advantageous in that it allows highly accurate and independent control of both the $\Phi$ orientation and $\rho$ orientation of main carriage 19007 from a remote location.

Figure 94:
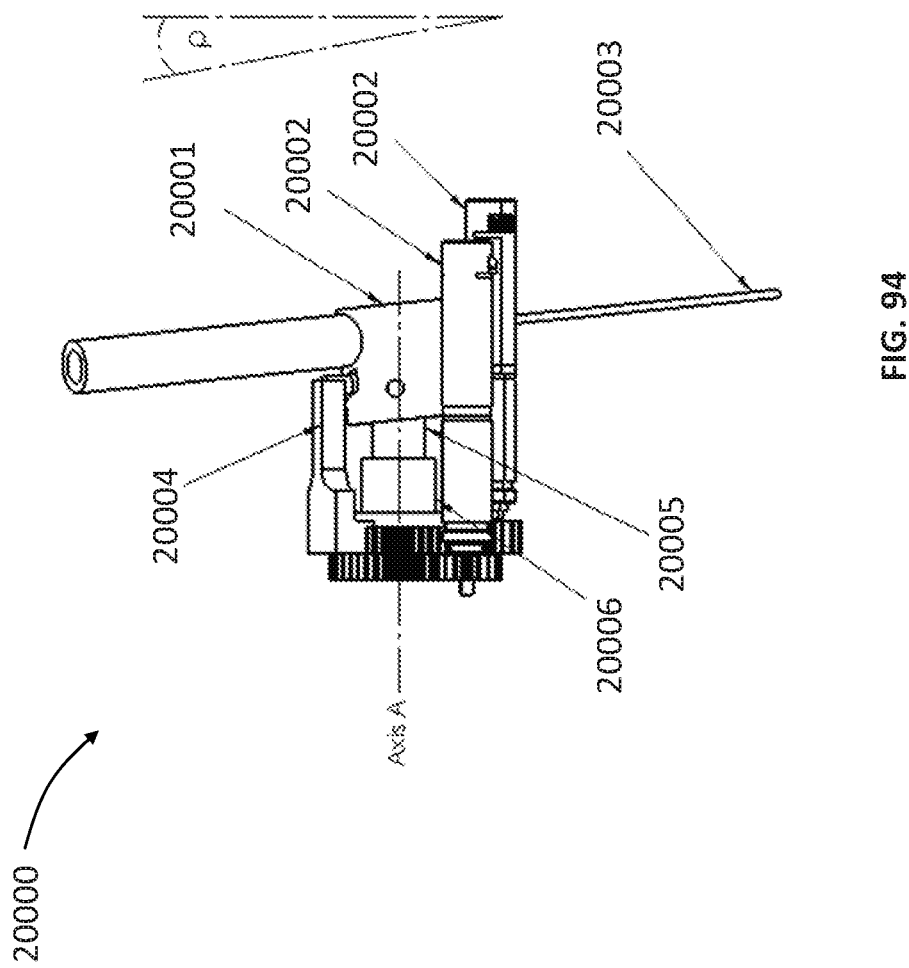
FIG. 94 illustrates a front view of an inserter assembly according to another embodiment of the present disclosure.
Figure 95:
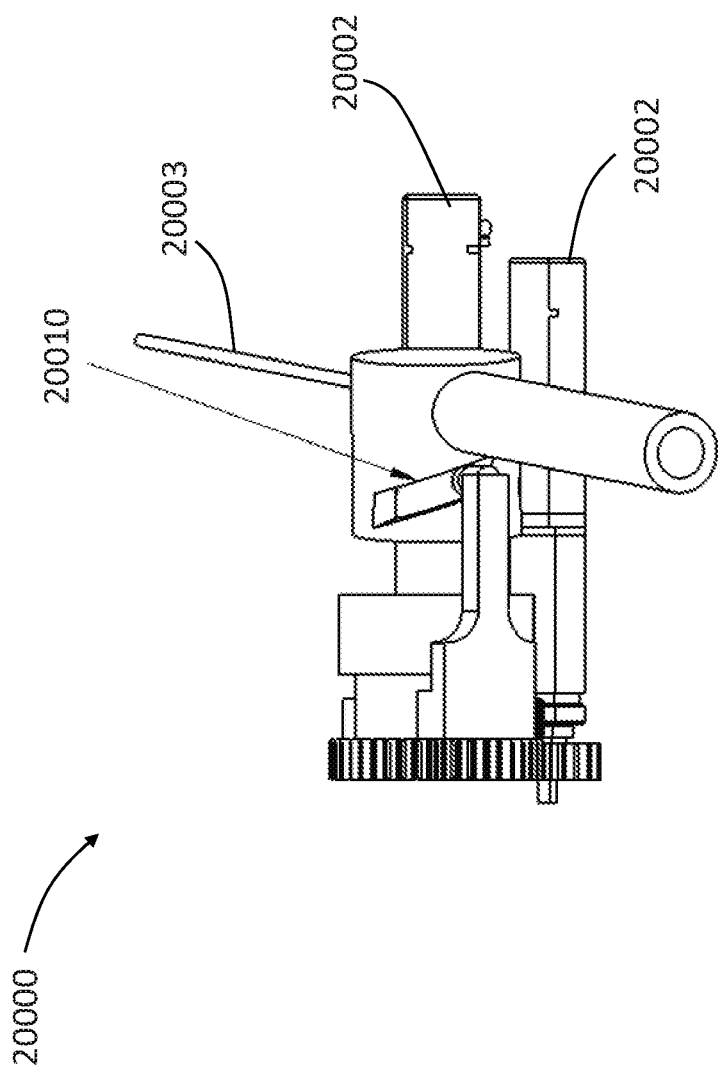
FIG. 95 illustrates a top view of a mechanism of the inserter assembly of FIG. 94.
Figure 96:
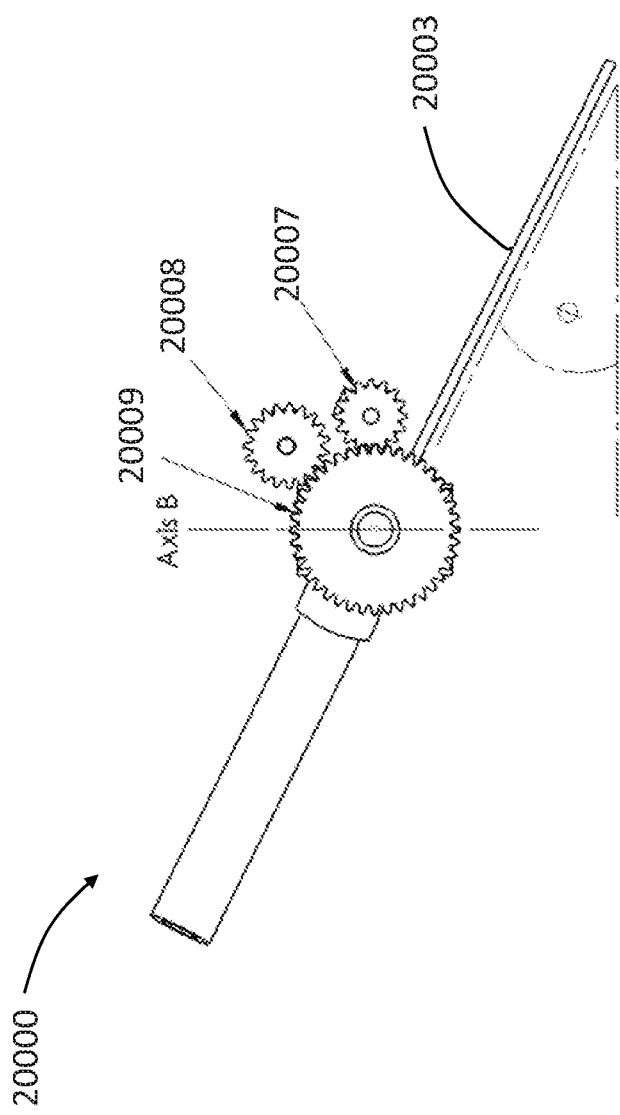
FIG. 96 illustrates a side view of the mechanism of the inserter assembly of FIG. 94.
Figure 97:
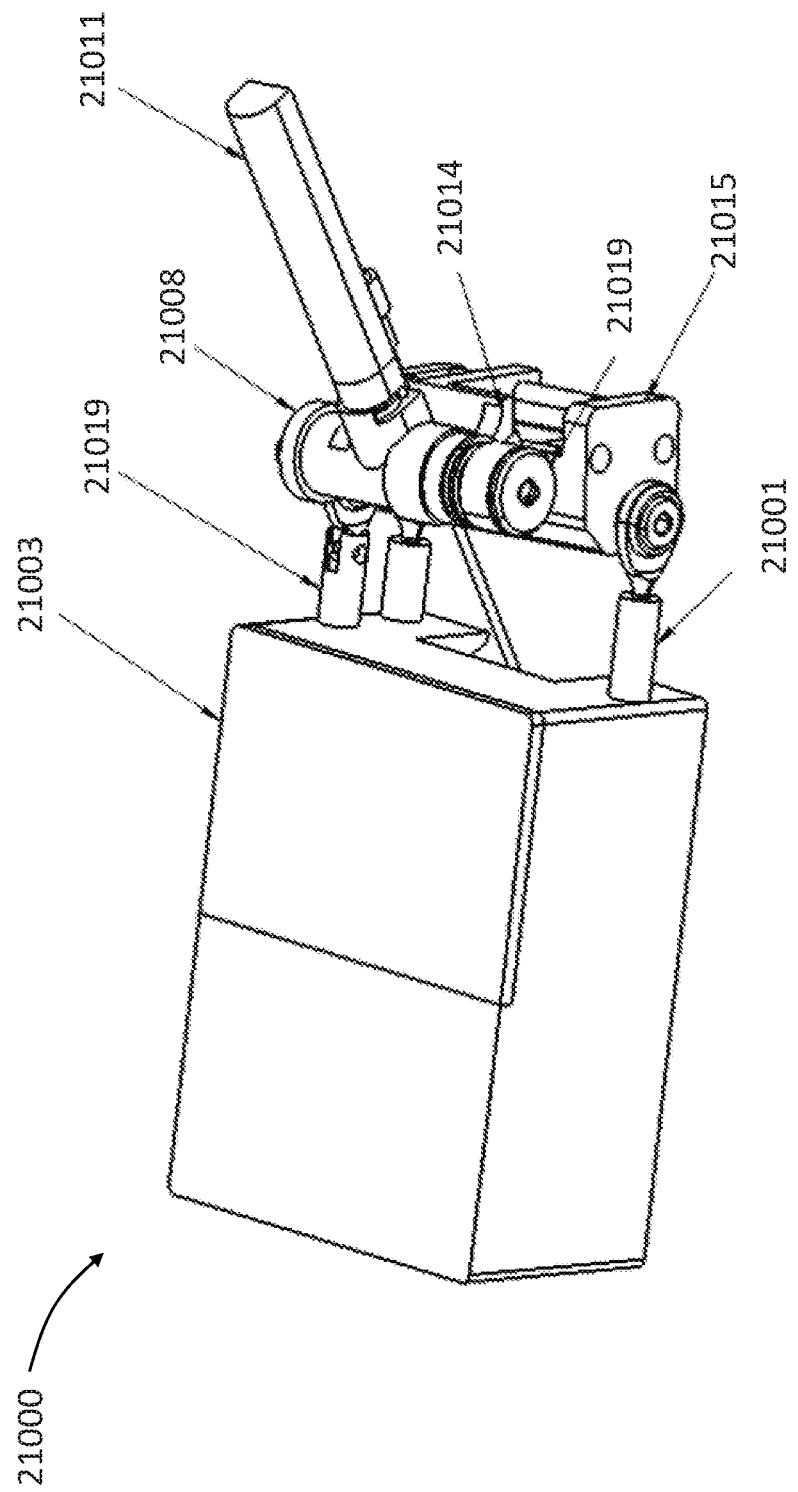
FIG. 97 illustrates an isometric view of an inserter assembly according to another embodiment of the present disclosure.
Figure 98:
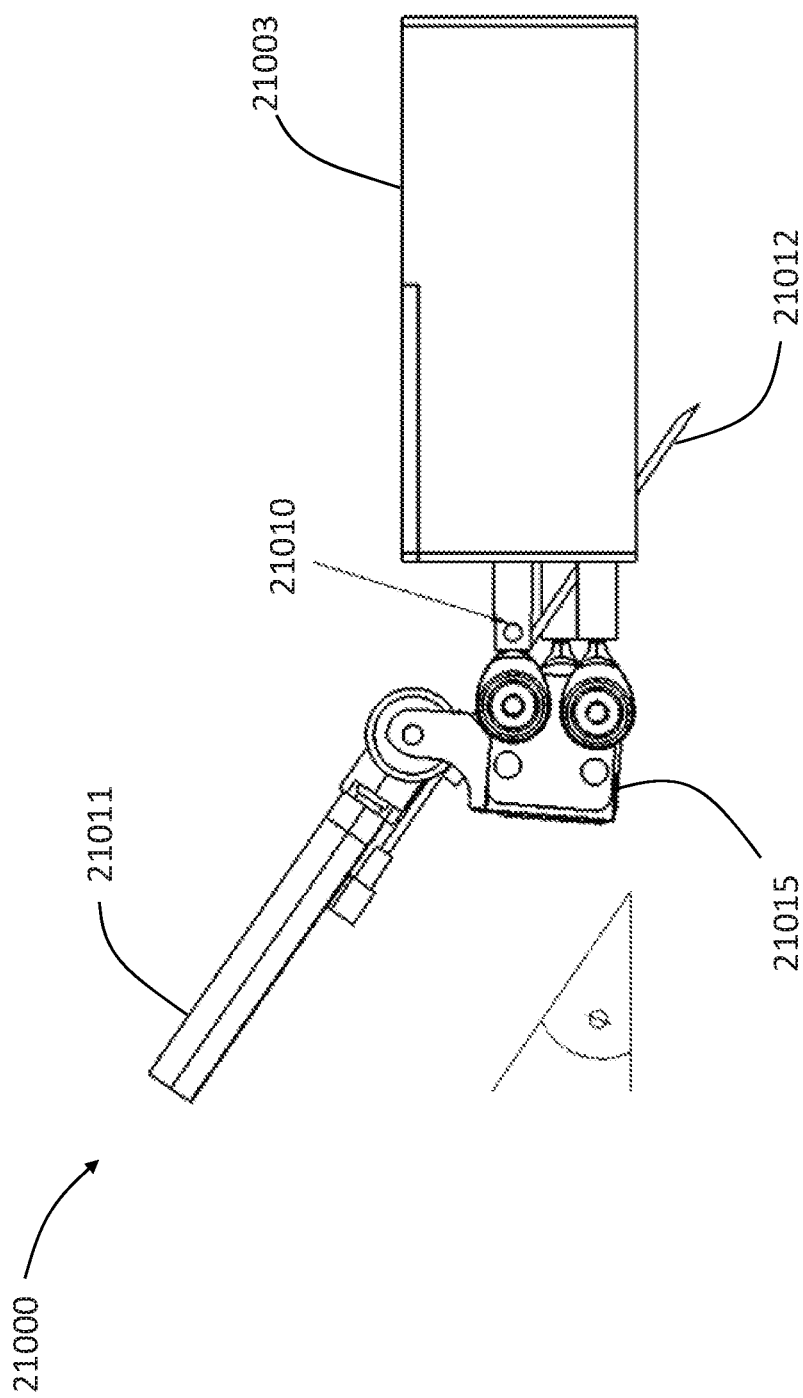
FIG. 98 illustrates a schematic side of a mechanism of the inserter assembly of FIG. 97.

FIGS. 94-96 show an inserter assembly 20000 according to another embodiment of the present disclosure. Inserter assembly 20000 includes a needle guide 20001 which functions as an interface between the inserter assembly and a needle 20003. Needle guide 20001 is configured to drive the needle into a patient's anatomy. Needle guide 20001 can also serve as a guide for manual insertion of needle 20003. Needle guide 20001 has a cylindrical slot 20010 that converts a rotary motion of a cam driver 20004 about axis A into rotary motion of the needle guide about axis B as best shown in FIGS. 94 and 96.

Two rotary actuators 20002 drive the mechanism to translate needle 20003. Actuators 20002 may be electromagnetic, piezoelectric, pneumatic or hydraulic motors. A cam driver 20004 coupled to one of the rotary actuators contains a feature that is contained by cylindrical slot 20010, but is free to rotate within the cylindrical slot. This feature can be sphere-shaped in one embodiment.

A pivot pin 20005 coupled to one of the rotary actuators controls rotation of needle guide feature 20001 about axis A. Pivot pin 20005 is coupled to the needle guide feature to ensure that the needle guide's rotation about axis B is generally unconstrained.

In one embodiment, for the purpose of design compactness and further mechanical advantage, rotary motion is transmitted from rotary actuators 20002 to cam driver 20004 and pivot pin 20005 through intermediate gears 20007, 20008, 20009 as best shown in FIG. 96. In other embodiments, the rotary actuators may be directly coupled to the cam driver and pivot pin or coupled through worm gears to allow inserter assembly 20000 to fit inside a different envelope, or for the purpose of increasing force and/or speed of the needle insertion.

Inserter assembly 20000 is particularly easy to miniaturize due to the similarity in scale of the motors and mechanical parts. The stationary motors of inserter assembly 20000 have reduced inertial mass. The mechanism of inserter assembly 20000 rotates the needle about two independent, perpendicular axes A and B, allowing the control of angles $\Phi$ and $\rho$ respectively as best shown in FIGS. 94 and 96. This allows a rotation about axis A to be driven directly by the rotary actuator and a rotation about axis B to be driven indirectly through the cam follower.

Figure 99:
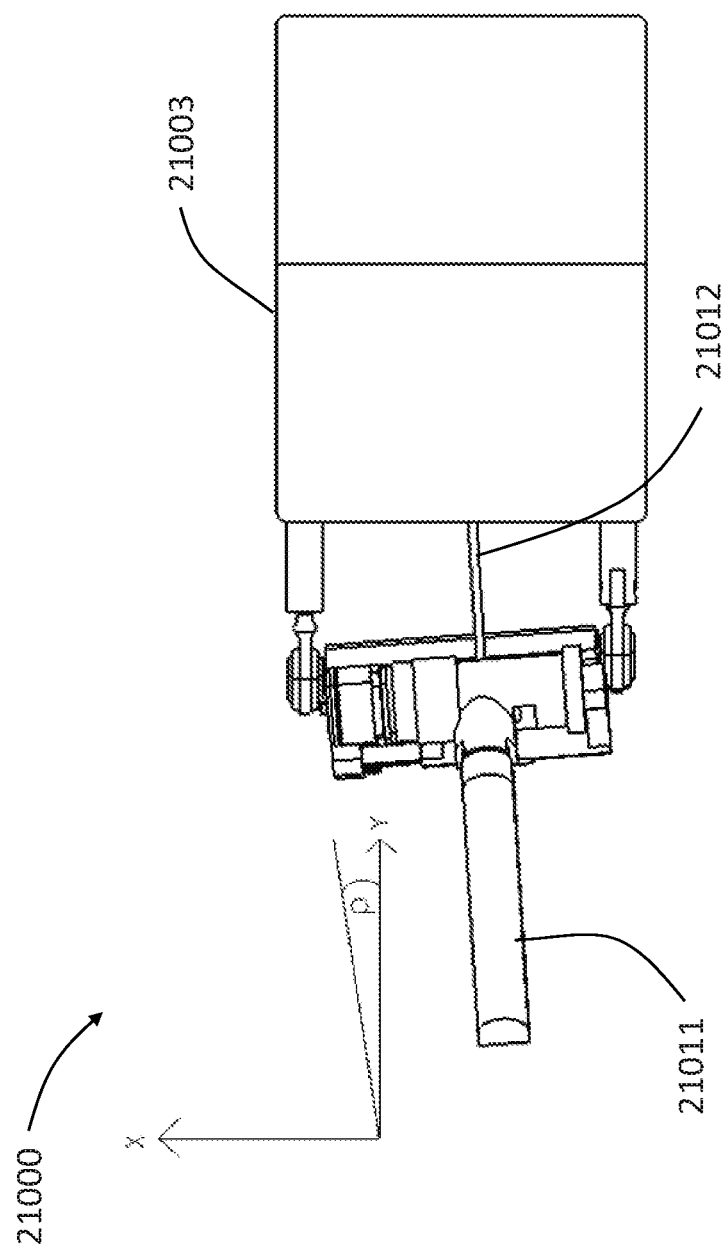
FIG. 99 illustrates a top view of the mechanism of the inserter assembly of FIG. 97.

Referring now to FIGS. 97-100, there is shown an inserter assembly 21000 according to another embodiment of the present disclosure. Inserter assembly 21000 includes three linkages 21001, 21002, 21003 which jointly control the position and orientation of a linear mechanism 21004. In one embodiment, linkages 21001, 21002, 21003 each having a single degree of freedom of movement in a y direction as shown in FIG. 99. Each of these linkages are driven by an independent linear actuator. Control of the angle $\Phi$ is substantially accomplished by opposing movement of linkages 21002 and 21003. Control of the angle $\rho$ is substantially accomplished by opposing movement of linkages 21001 and 21002 or 21003.

Each of the linkages interface with the linear mechanism through a joint that can pivot with 2 degrees of freedom, such as a ball joint. Linkage 21002 contains an additional single degree of freedom joint 21010 to prevent binding during a $\Phi$ rotation.

Linear mechanism 21004 contains an actuator to drive a carriage 21005 substantially in the x direction. An actuator 21009 mounted to carriage 21004 transmits torque to a needle driver 21006 through a needle mounting interface 21008 to power the insertion and retraction of a needle 21012 into the patient's anatomy.

Needle driver 21006 may drive the needle into and out of the patient's anatomy. In one embodiment, this motion may be controlled by a leadscrew. The needle driver may be a single use, sterile, assembly, protecting the healthcare provider and patient from pathogen contamination. A housing 21007 can contain actuators which power the linkages. The housing can secure inserter assembly 21007 so as to prevent unwanted movement during a procedure.

Figure 100:
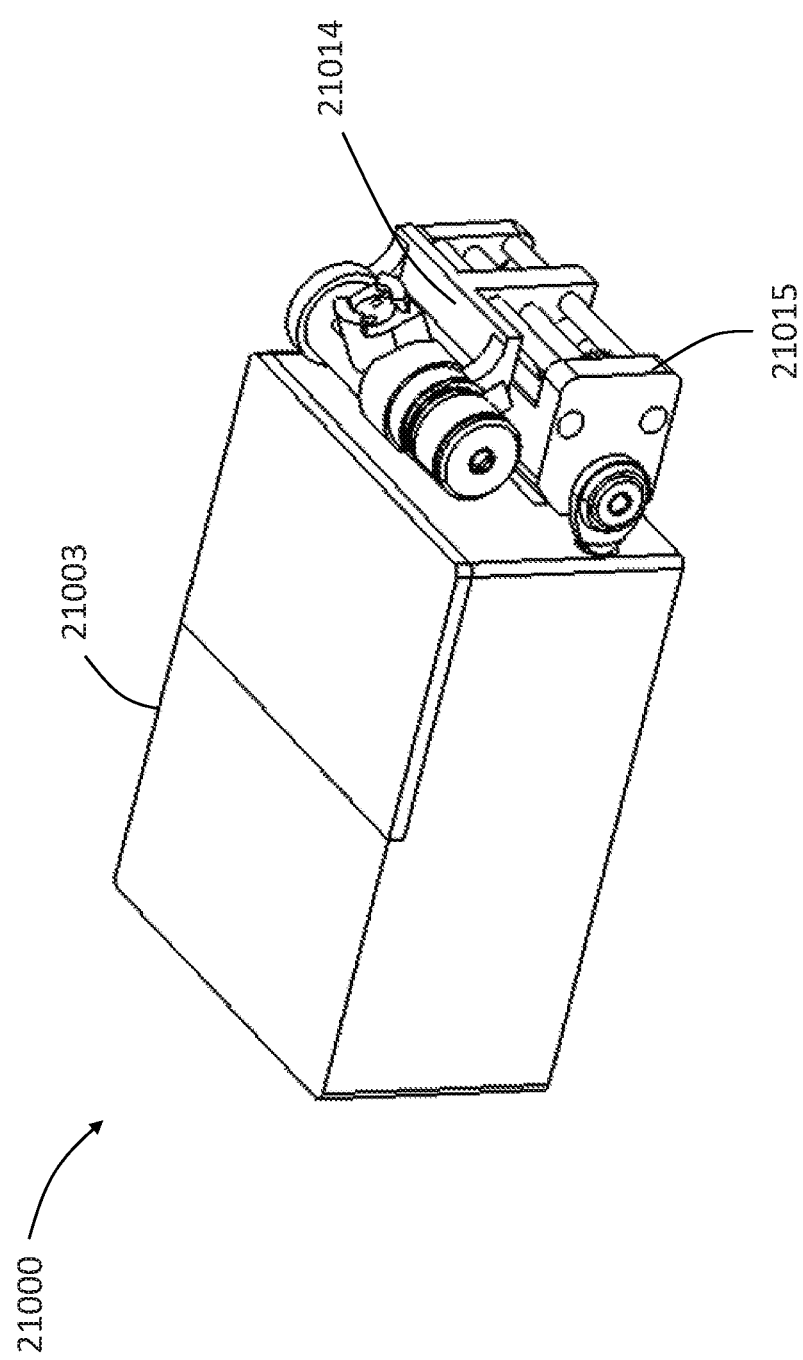
FIG. 100 illustrates an isometric view of the mechanism of the inserter assembly of FIG. 97.

Inserter assembly 21000 offers complete control over the position and orientation of the needle with 4 degrees of freedom allowing for complex entry trajectories. When single use/sterile needle canister is not installed, inserter assembly 21000 collapses to a small volume relative to the length, width and depth of the workspace it can access as best shown in FIG. 100. Inserter assembly 21000 can house needles with a variety of lengths, gauges and configurations and can provide resistance to breakage in all five axis of motions through the use of non-backdrivable leadscrews.

Figure 118B:
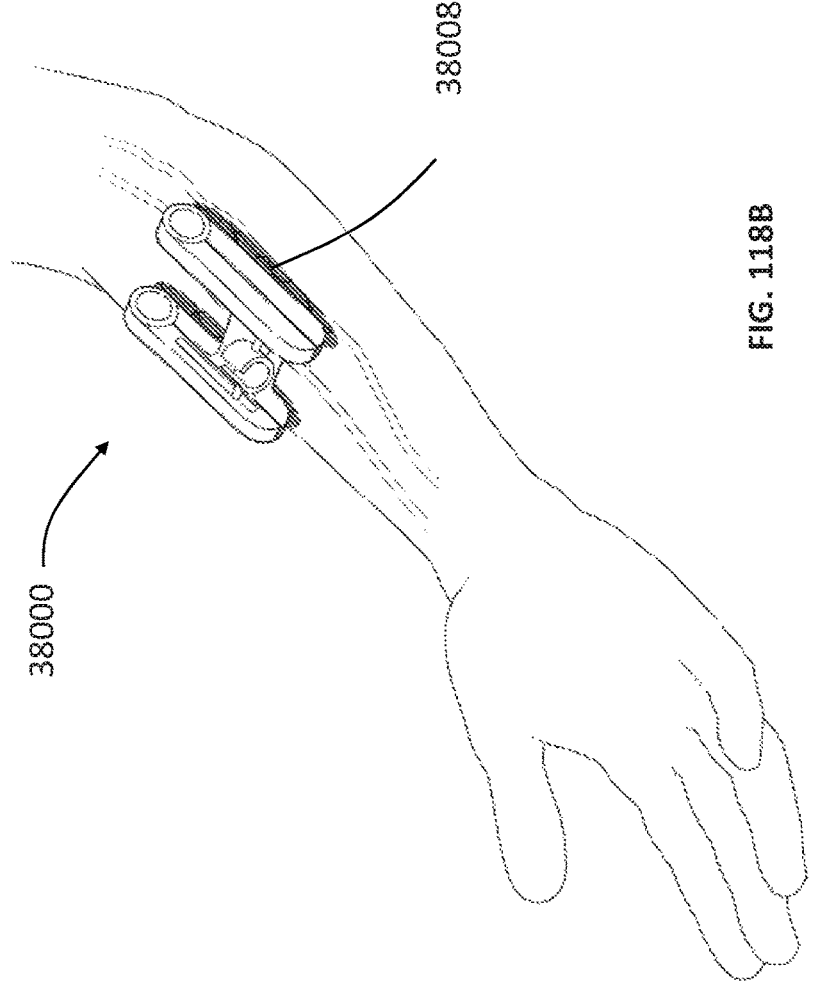
Figure 118A:
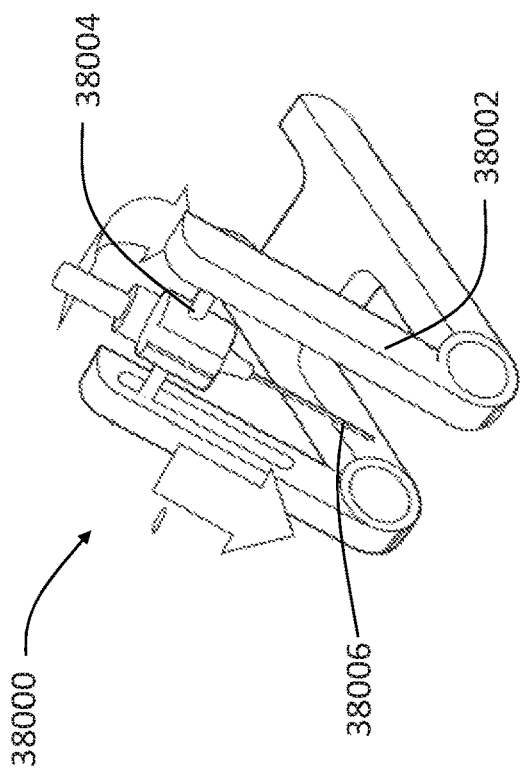

FIGS. 118A and B show an inserter assembly 38000 according to another embodiment of the present disclosure. Inserter assembly 38000 includes a foldable frame 38002 that can hold a needle 38006. The inclination of the foldable frame can be adjusted to adjust the angle of entry of needle 38006. A needle holder 38004 on a swivel allows for further adjustment of the needle entry angle. The needle can be manually advanced or retracted after the precise insertion location and needle angle trajectory is determined. Inserter assembly 38008 includes an adhesive surface 38008 to firmly secure the inerter assembly at the target surgical site as best shown in FIG. 118B.

Figure 121:
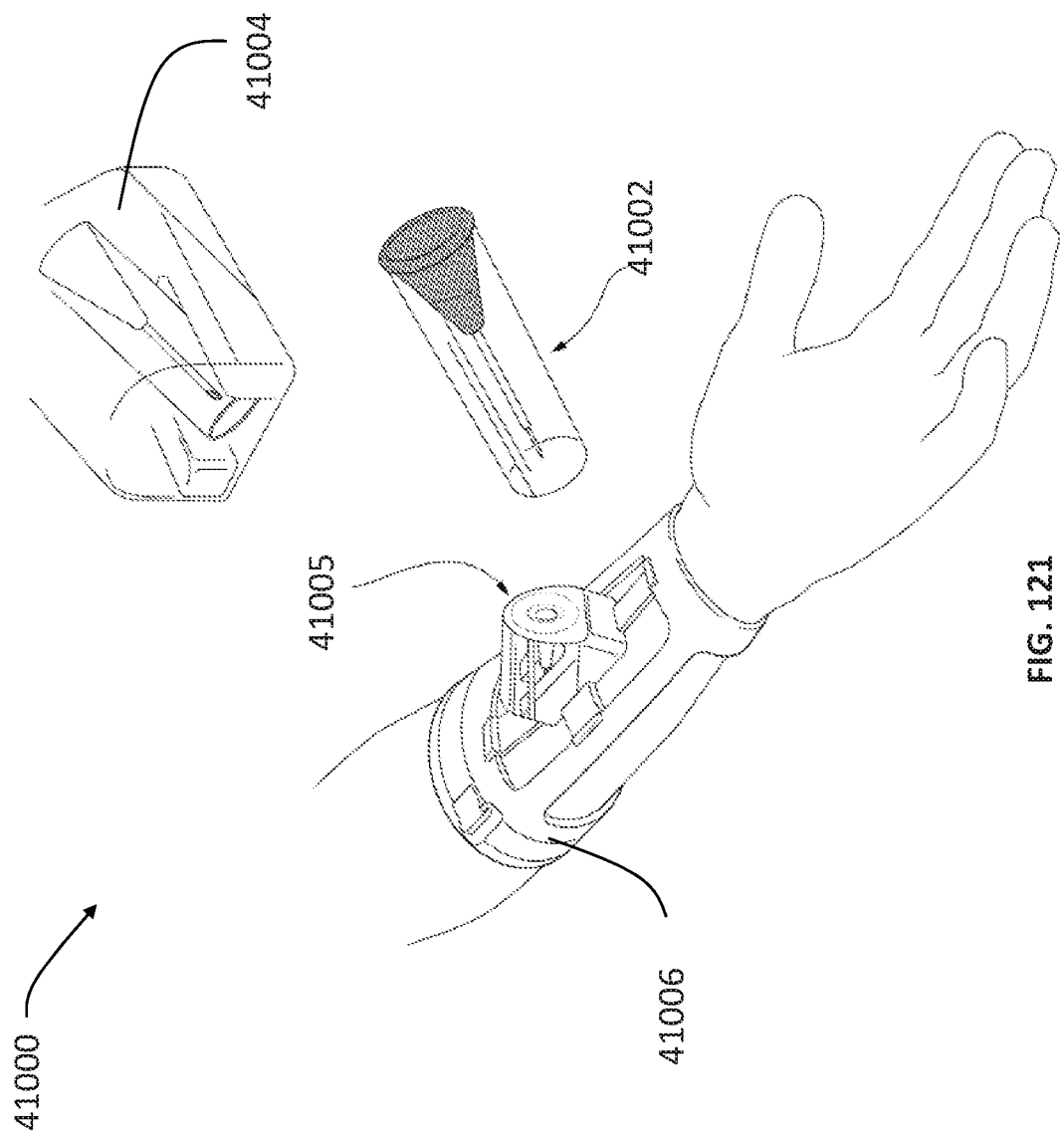

FIG. 121 shows an inserter assembly 41000 according to another embodiment of the present disclosure. Inserter assembly 41000 includes a cartridge 41002 containing a needle. Cartridge 41002 can be placed in a frame 41005 that is mounted on the surgical site via a brace 41006. Frame 41006 allows for motions in three axes to locate the needle at optimal insertion point. Frame 41006 can be made of transparent material 41004 to provide the operator with a clear view of the insertion. Cartridge 41002 can be a reusable cartridge which can be conveniently replaced for each insertion.

Referring now to FIG. 126, there is shown an inserter assembly 46000 according to another embodiment of the present disclosure. Inserter assembly 46000 can be secured to a strap 46004. A needle 46008 can be loaded into a loading chamber and activated by a button 46002 to perform needle insertions. A manual override button 46006 is also provided to allow an operator to stop an insertion procedure if necessary. The loading chamber includes a window to allow an operator to view and ensure that the needle entry is at insertion point 46010. The insertion point can be highlighted by laser crosshairs or other indicators to assist the operator.

Methods of Use, Generally

A method of performing a semi-autonomous needle insertion using device 10 will now be described. The puncture site skin area for insertion is prepared by either manually swabbing or sterilizing the area or by applying a protective visor. The visor may also include ultrasound compliant hydrogels to facilitate ultrasonic scanning precluding the need for manual application of ultrasonic gel. After preparing the skin area, the user can dock housing 100 to base 200 and place this assembly over the puncture site area. Straps or other securing elements may be used to secure the device to the patient. However, the secured straps in this embodiment will have sufficient laxity to allow the operator to move the base across the puncture site area to scan the patient's vessels. 3D scanning using any of the technologies described herein may be used to generate a 3D map of the patient's vessels. The 3D map may include real-time and/or static images such that, for example, the area directly in view of the 3D sensors can be shown in real-time and the other areas not in line of the 3D sensors can be scanned and saved to produce a 3D map of the patient's vessels. The GUI on device 10 may project the 3D map of the puncture site on a display screen located on housing 100 or transmit this data to another monitor located remotely from device 10. Device 10 may include puncture site reference markers which can assist the operator in precisely locating the device over the puncture site by aligning the puncture site reference markers in line with 3D mapped vessels. Once the device has been successfully positioned on the puncture site, the operator may initiate the insertion mechanism to insert the needle along a predetermined trajectory to the puncture site. After needle insertion is established, housing 100 can be detached from the base without disturbing the needle leaving behind the needle assembly secured to the patient by the base.

A method of performing an autonomous needle insertion using device 20 will now be described. The puncture site skin area for insertion is prepared by either manually swabbing or sterilizing the area or by attaching device 20 to the puncture site skin surface. Device 20 may include sterilizing features such as ultraviolet light or other disinfectants. Alternatively, a protective visor may be first placed on the puncture site surface, and device 20 may be mounted on the visor. As described above, the visor may include various features such as an ultrasound compliant hydrogel to facilitate ultrasonic scanning precluding the need for manual application of ultrasonic gel. After preparing the skin area, the user can dock housing 400 to base 500 and place this assembly over the puncture site area. By docking housing 400 to base 500, plate 550 can be removed from the device 20 as the inserter assembly 600 is now secured by the housing 400. Straps 508 may be used to secure the device to a patient's skin. The operator may then initiate 3D scanning through the GUI, whereupon the device scans and 3D maps the patient's vessels. The 3D map may include real-time and/or static images wherein, for example, the area directly in line of the 3D sensors can be shown in real-time and the other areas not under the line of the 3D sensors can be scanned and saved to produce a 3D map of the patient's vessels. The GUI on device 20 may project the 3D map of the puncture site on a display screen located on housing 400 or transmit this data to another monitor located remotely from device 20. Device 20 may include puncture site reference markers which can assist the operator in precisely locating the device over the puncture site by aligning the puncture site reference markers in line with 3D mapped vessels. Once the device has successfully identified a puncture site insertion site and determined a trajectory to achieve the insertion, the operator may initiate the insertion mechanism to insert the needle along a predetermined path to the puncture site. The operator may be located away from the device, and may remotely initiate the insertion mechanism. Alternatively, the device may be fully autonomous, whereby the device automatically initiates insertion after identifying the puncture site with little or no operator input. Upon needle insertion, housing 400 can be detached from the base without disturbing the needle, leaving the needle assembly secured to the patient by the base.

In other methods, once the appropriate puncture site, insertion trajectory, and target vein have been identified, the operator may then use this information to select and attach a needle to the device for subsequent insertion of the needle at the puncture site.

Level of Automation

As described above, the device may be semi-autonomous or fully autonomous. The individual components such as the navigational system, display and user interface and the inserter assembly may each have different levels of automation in the semi-autonomous device. For example, a device may have a manual navigational system requiring the operator to position and scan the puncture site skin area, but may include a fully autonomous insertion assembly which performs the needle insertion and retraction with no manual input. It is envisioned that the devices may have modular components that are compatible with each other. For instance, an operator may only attach the navigational and sterilization components to the housing to perform specific functions. This will allow the housing to be used over a broad range of applications by being customizable to each of these applications.

Additional Designs

Figure 18:
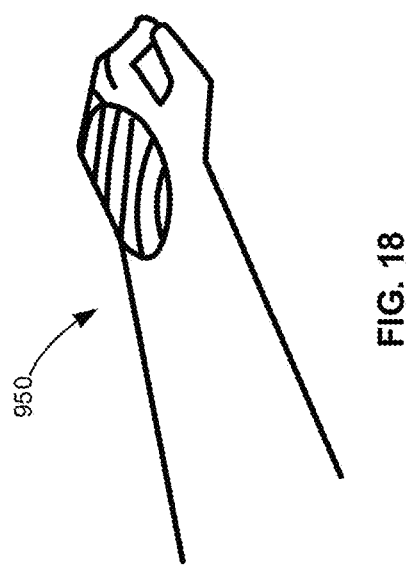
FIGS. 18 and 19 illustrate various embodiments of a patch of the present disclosure.
Figure 19:
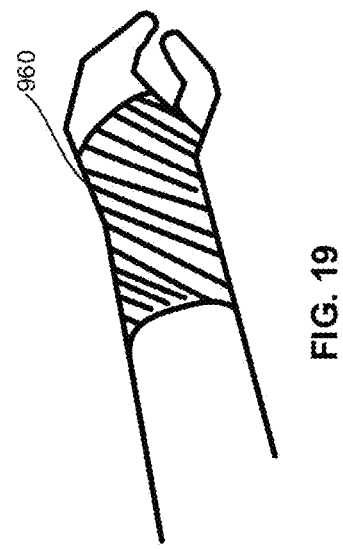

FIGS. 18 and 19 illustrate various embodiments of a patch that can operate as both the pre-injection patch and the base as discussed above. As illustrated in FIG. 18, a patch 950 can be applied to an area of the patient where the puncture site is desired. A patch 960 can wrap around a patient's appendage such as an arm as best shown in FIG. 19. A housing, as described above, can then interface with the patch. For example, such patches may be particularly useful where the housing includes an ultrasonic navigation function whereby the patch would include a hydrogel or other such ultrasound conductive layer. The patch of these embodiments is also useful in that the housing may move freely around the surface of the patch, which is sterile, without concern for moving the housing outside of the sterility field.

Described below are further exemplary embodiments of gel-based pads that may be used as part of a device of the present disclosure.

FIGS. 81A-C show an embodiment of a pad 15000. Pad 15000 is a flexible, 3D, device-integrated, dry-gel coupling agent which improves ease of use by facilitating the consistent transmission of ultrasound waves and simplifying the transition between the organic and variable human form and the rigid and exemplary device 5000 shown here.

Currently, a viscous liquid gel is required as a coupling agent to create a transition between ultrasound ("US") probe and patient body to successfully carry ultrasonic waves back and forth. This gel is messy, cumbersome, and unhygienic. With flexible formed 'dry gels,' sometimes referred to as hydrogels, these pain points can be eliminated. Further pad 15000 offers improved ergonomic transition from probe to body. Seamless and easy to achieve device transitions means better data capture and image quality.

One major challenge this solution addresses is the mismatch between the organic and variable nature of the human body and the rigid and limited shapes of US probes. The transition, or coupling between these two disparate surfaces is very difficult to overcome with wet gel or even the current dry gel products currently available. The procedure still requires a good deal of finesse from the operator to achieve a quality image.

The dimensions, thickness, density, consistency, flexibility, material, and surface treatment, enable pad 15000 to effortlessly couple to device 5000 to any part of any body large or small with ease as shown in FIGS. 81B and 81C. A cavity 15002 is shaped to readily receive CMUT array 5004.

Pad 15000 facilitates easy interface with a patient's body. CMUT array 5004 is designed and engineered with high quality data capture. Any layers, material, forms, or production processes that are added to the probe face to improve the interface with the human body can be deprioritized as pad 15000 addresses these requirements.

Further, pad 15000 can be customized or provided in standard sizes, rather than a one size fits all approach to US usage. For example, a suite of pads 150000 can be used to improve coupling in special cases from neonates to the elderly, infirmed to the obese.

Pad 15000 can be made of a highly flexible but solid clear material that fits snugly onto and integrates seamlessly with device 5000 and makes coupling anywhere on the body as easy as placing the device and making contact with the skin. Small movements and changes in pressure are easily absorbed by the dry-gel, while a clear and precise image is captured on display 5012. Curvature and inconsistencies on the surface of the patient's body are easily overcome by the flexibility of pad 15000.

FIGS. 82A-D show a pad 16000 according to another embodiment of the present disclosure. Pad 16000 is generally similar to pad 15000 but includes a distal surface that contours to any surface feature. As shown in FIGS. 82B-D, the distal surface of pad 16000 conforms to the corresponding surface to form a secure attachment.

Referring now to FIGS. 83A-I, there is shown various embodiments of pad 15000 according to the present disclosure. Pad 15000 shown in these figures includes variously designed and shaped 3D dry gel forms which enable 3-dimensional CMUT (US) configurations and surfaces, to improve data capture and ease of use.

Freed from the ergonomic restraints of interfacing directly with the patient's body, an exemplary device's 5000 CMUT array 5004 can be optimized entirely for data capture for venous access or other procedures. Pad 15000 can be provided in a variety of forms and configurations to capture all the essential details for venous access. For example, a flat rectangular shaped pad 15000 is shown in FIG. 83A.

Entirely flat arrays may not be the ideal configuration for venous access. Veins are superficial, small, and often mobile. Curvature, angles, steps, convexity, and concavity of the CMUT arrays could create triangulation and redundancy that will make image data sets more robust and our image quality more reliable. FIG. 83B shows a pad 15000 having a tapering distal end with a larger display 5012. FIG. 83C shows a pad 15000 with a distal end that flares from display 5012 leading to a pad with larger contact surface. Thus, a smaller screen 5012 can be used in the embodiment shown in FIG. 83C enabling a smaller and more compact device 5000.

FIG. 83D shows a pad 15000 that can be couple with a CMUT array 5004 that has one more openings. CMUT array 5004 has a single opening 15005 that allows a needle to pass through. Opening 15005 is filled by pad 15000 as shown in FIG. 83D. FIG. 83E shows a similar CMUT array 5004 where the two arrays are inclined on both sides of the opening. In still other embodiments, various different configurations of the CMUT array can be accommodated by pad 15000. For example, FIG. 83F shows with a stepped CMUT array 5004 and FIG. 83G shows a concave-shaped CMUT array 5004. In still other embodiments, pad 15000 can be concave or convex shaped as shown in FIG. 83H, and flexible as shown in FIG. 83I.

Figure 84:
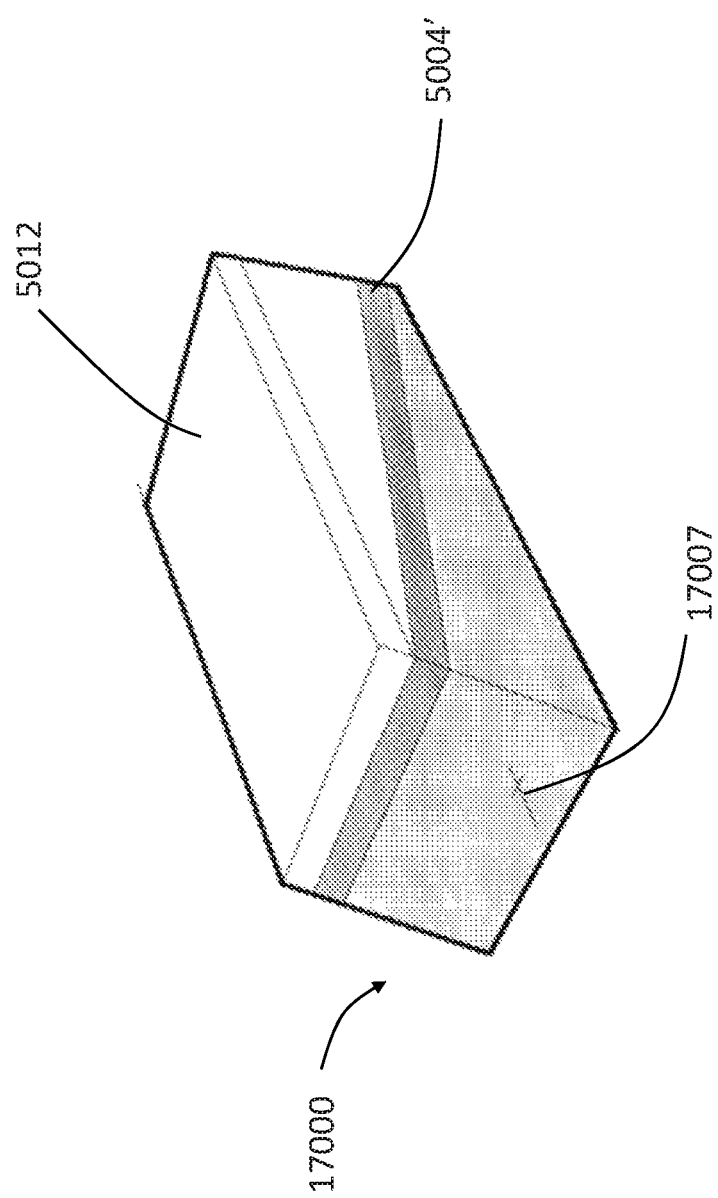
FIG. 84 illustrates a pad according to another embodiment of the present disclosure.

FIG. 84 shows pad 17000 coupled to a device 5000 according to another embodiment of the present disclosure. Pad 17000 is made from a clear gel to provide the operator with a clear view of an insertion site 17007 located beneath the pad. This allows an operator to image insertion site 17007 with device 5000 and view via display 5012, while simultaneously observing insertion site 17007 with a naked eye through the clear gel of pad 17000. As the device itself will typically obstruct the operator's view of the insertion site, an operator must slide the device to slide across the insertion area. Pad 17000 will enable an analog view of the site from above while also providing the subsurface view (US) of the insertion site on display 5012. Pad 17000 enables device 5000 to be recessed back from the insertion site by an angled CMUT array 5004' as shown in FIG. 84.

FIGS. 85A-C illustrate an insertion procedure utilizing different embodiments of the gel pad. Needle tip 5010 cannot be observed in display 5012 prior to insertion with a thin low profile pad 15000 shown in FIG. 85A. The thin low profile pad contacts the needle during insertion or just before insertion, and therefore the same cannot be observed with display 5012 prior to insertion.

A thicker pad 15000 shown in FIG. 85B allows needle tip 5010 to enter pad 15000' prior to insertion into the patient. Thus, needle tip 5010 can be tracked prior to insertion. As shown in FIG. 85B, the thickness of pad 15000' must account for the size of the needle, needle entry angle and the distance of the insertion zone from the edge of pad 15000'.

FIG. 85C illustrates needle insertion utilizing pad 17000 described above. As shown here, the angled shape of pad 17000 allows needle to enter the pad before reaching the insertion point. Thus, needle tip 5010 can be viewed on display 5012 prior to the needle actually puncturing the skin of the patient. Further, the clear nature of the gel used in pad 17000 allows the operator to view the insertion site and track the needle tip directly through the clear gel. As the needle is placed into the gel, the CMUT array gathers data regarding its position and incorporates it into the onscreen image. Any adjustments to the needle trajectory, the position of the pad (and imaging device), and the like which may be required can be made before puncturing the skin, but with the needle remaining in the pad and viewable by the naked eye or on the display. Therefore, pad 17000 conveniently allows for the imaging and procedure to take place simultaneously.

FIGS. 111A and 111B show a pad 31000 according to another embodiment of the present disclosure. Pad 31000 includes a recess 31002 configured to seat and align a needle 31004 to facilitate precise insertion. Pad 31000 can be coupled to a visualization device 31003 as shown in FIG. 111A.

Referring now to FIGS. 112A and 112B, there is shown a pad 32000 according to another embodiment of the present disclosure. Pad 32000 includes a flexible port 32004 to receive and align a needle 32004 to facilitate precise insertion. A visualization device 32003 can be coupled to pad 32000 as shown in FIG. 112A. In other embodiments, various type of recesses, ports and other receptacles can be included or integrated to the pad to receive, hold, and align a needle.

Figure 113:
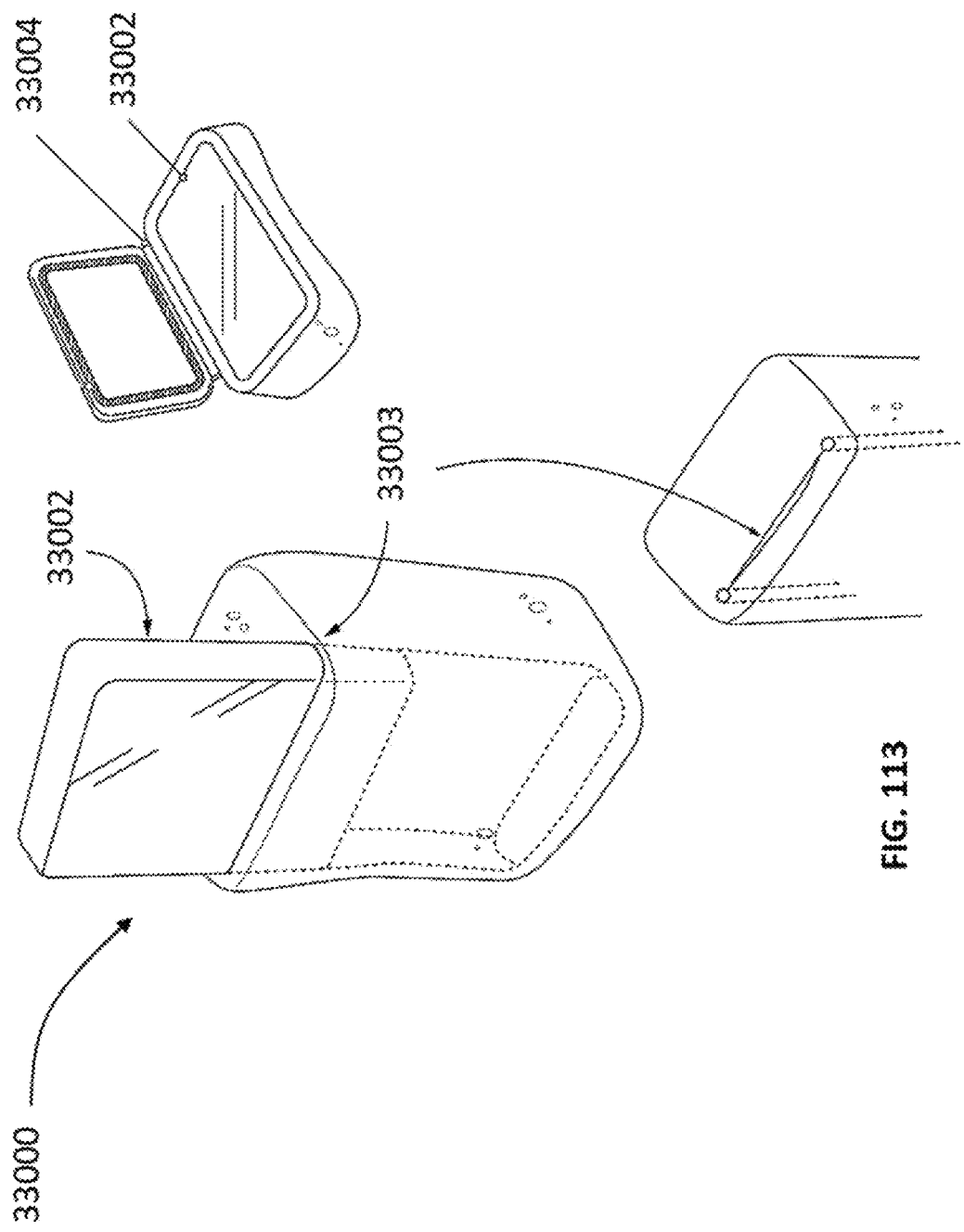
FIG. 113 illustrates a pad according to another embodiment of the present disclosure.

FIG. 113 illustrates a pad 33000 according to another embodiment of the present disclosure. Pad 33000 includes a self-sealing slit 33003 that can receive a visualization device 33002. Pad 33000 is configured to completely enclose and protect the visualization device as shown in FIG. 113. Pad 33000 can be made of a clear gel to enable an operator to view and utilize visualization device 33002 placed within the pad. In some embodiments, pad 33000 can include a split-body attached by a hinge 33004 to allow access to the embedded visualization device.

Referring now to FIG. 114A, there is shown a pad 34000 according to another embodiment of the present disclosure. Pad 34000 includes a gel layer 34004 and a skin-contacting adhesive layer 34002. Adhesive layer has an internal lattice structure that distributes downward pressure of needle 34006 as it advances through skin and vein 34008. This prevents the skin shifting from the advancing needle pressure (FIG. 114B) and the vein shifting from advancing needle pressure (FIG. 114C).

FIGS. 115A-C show a pad 35000 according to another embodiment of the present disclosure. Pad 35000 includes a pair of ridges 35002 that can be positioned on either side of a vein 35004 to stabilize the vein and prevent vein rolling under the approaching needle pressure.

Pads can be configured to perform a wide variety of functions. For example, pads can be customized to prevent infection, preserve skin health, secure component of the device, reduce pain, optimize veins or other anatomical features, etc.

In one embodiment, the pad can include a low-friction hydrogel device cover. The low-friction hydrogel device cover will enable the device to guide smoothly and stably across the skin surface with little effort from the operator.

In another embodiment, the pad can be configured as a large format stable pad that is highly conformable to readily transition from a flat sensor surface to unique contours of a patient's body. This pad can be independently secured directly over the desired surgical area such as a patient's chest or abdomen to ensure that the distal surface of the pad contacts the body. A device with a large format imager module can be coupled to the proximal surface of the pad. Transducers on the large format imager module are positioned to capture and display volumetric data of the surgical site. For example, the transducers of large format imager module being spread across the imager module to capture volumetric data of the chest cavity and heart through the opening between the ribs with a single reading—i.e., no sliding or moving across the target site is necessary to generate the image volumetric data. Alternatively, strategically placed transducers in specific locations across the imager module can generate volumetric data with a single reading to capture image volumetric data.

In another embodiment, pads can be customized to fit over specific body parts for specific examinations and/or procedures to ensure convenient imaging of areas with difficulty accessibility. The need for invasive scanning is also reduced by these customized pads. Further, the body-part-specific pads require less operator training and expertize to utilize these pads. Body-part-specific pads can be paired with devices and imager modules to create kits for specific examinations and/or procedures. Securement devices to secure the body-part-specific pads can be customized for these pads.

Pads can be designed to be patient specific pads according to another embodiment of the present disclosure. A custom pad for each patient can be generated prior to the examinations and/or procedures based on unique individual attributes of the patient.

In one embodiment, a pad can include various infection prevention properties. A pad according to this embodiment can include an anti-bacterial layer to prevent infection of the target site. The pad can be made of clear gel to provide a clear view of the target site and to allow a needle to pass directly through the pad.

In one embodiment, a kit may include at least one pad and at least one device. For example, such a kit may include a plurality of pads and one device, whereby the pads are sized and shaped to be used with the particular device. Further, each pad may have a shape that is different from at least one other pad, such that each pad may be specific to a particular procedure and/or anatomical location, while all pads may be used with the particular device. In another example, such a kit may include a plurality of pads and a plurality of devices, whereby each pad is sized and shaped to be used with at least one device. A user of this exemplary kit may select a desired pad and device combination for use in a particular procedure and/or anatomical location.

In another embodiment, a method of using a device may include selecting a particular pad and a particular device, and using the combined pad and device to view an anatomical location of the patient. Such a method may further include using the combined pad and device with one or more medical devices or instruments to view both the anatomical location of the patient and the medical device(s) and/or instrument(s) in the vicinity of the anatomical location. Such a method may also include using the combined pad and device, or a different combination of a pad and device, to view more than one anatomical location. In one example, visualization of a catheter being inserted transfermorally into a patient may be viewed using a first combination of a pad and device, and once the catheter enters into the abdominal or thoracic vasculature, a different pad and device combination may be used.

FIGS. 120A-D show a vein distender 40000 according to another embodiment of the present disclosure. Vein distender includes a needle 40008 that can be translated by a grip 40004. A skirt 40006 surrounds the needle and forms a seal with a patient's skin as shown in FIG. 120B. Once the needle has been inserted into a collapsed vein 40010 (FIG. 120C), a balloon member 40002 can be squeezed to push air through the needle and into collapsed vein 40010 to distend the vein as shown in FIG. 120D.

Figure 124:
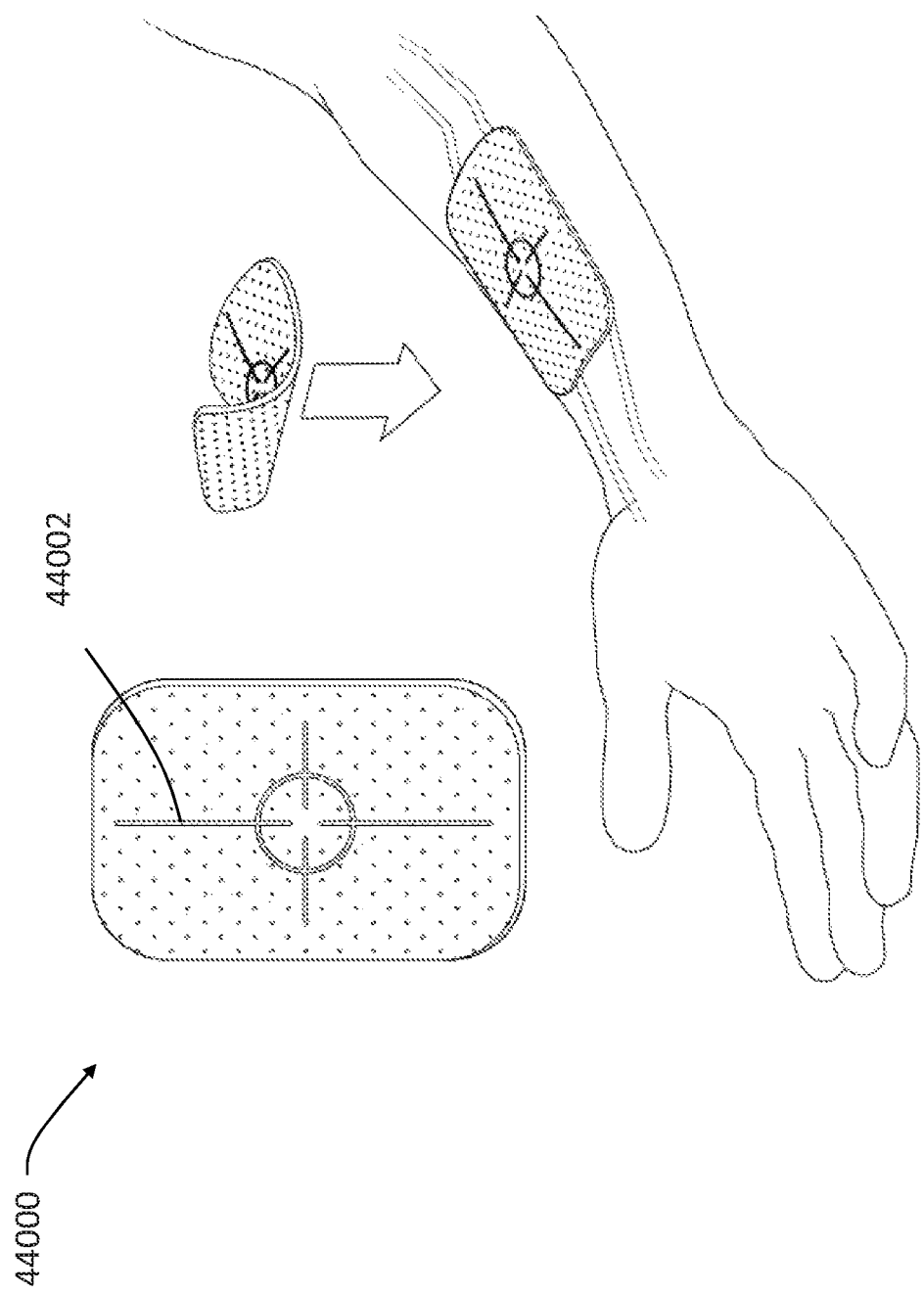

FIG. 124 shows a sterile adhesive 44000 according to another embodiment of the present disclosure. Sterile adhesive 44000 provides a sterile region through which a needle can be inserter. No additional sterilization is required when sterile adhesive is utilizes. Various features can be added to the sterile adhesives to aid needle insertion. For example, a targeting mark 44302 can serve as an alignment and location guide for needle insertion.

FIGS. 125A and B show a needle 45000 according to another embodiment of the current disclosure. Needle 45000 can be rotated to change a distal profile of the needle. As shown in FIG. 125B, the distal tip of needle 45000 can change from a piercing point 45002 to allow for smooth entry into a vein to a flat surface 45004 to ensure that the needle does not go past the vein.

Closed Loop

In another embodiment the automated or semi-automated mechanized intravenous needle positioning devices or systems may perform a number of output functions, in order to optimize anatomical targets, or other conditions associated with intravenous needle placement, such as reduce pain, assist with mechanized positioning of imager or inserted modules. The measurement of the various device outputs may be achieved with ultrasound imaging transducers such as CMUT, or camera sensors, NIR or other imaging systems, and monitoring changes in 2d or 3d data maps of the target anatomy, or temperature sensors. Other monitoring methods may include reading the patient's local or central temperate, level of hydration, heart rate, blood pressure, sweat levels, general or sudden movements, shakes and tremors, noise and distress level (some or all of these may also be monitored on the operator, for example a trainee). Environmental conditions such as room temperature, patient and/or device orientation, location, surrounding noise, lighting, time of day, certain weather conditions, or the like may also be monitored. Some or all of these readings may be fed back to the operator, or input to the electrical or electronic control system of the device or system, in order that adjustments to device outputs may be performed, and/or choreographed to occur when more optimal input readings or conditions are met. The feedback, or closed-loop system is designed to automatically achieve and maintain the desired output conditions by way of comparing it with actual conditions in real time.

Continuing with this embodiment, there are various examples as follows: mechanical or electrical stimuli performed to evoke a functional reaction in an organ, vessel, tissue or peripheral or central nervous system of a patient, or to guide mechanical imager or needle positioning devices within the system. Examples may include stimuli to optimize the characteristics of a target vessel or anatomy (such as vein dilation or stability) through the automatic tightening of an integrated tourniquet; applying heat to a target area injection site through an integrated heating element, for example to increase vein dilation; applying mechanical vibration or tapping for example to stimulate a target vessel; to cause a mechanical pressing force, or similar massaging effect at or around a target injection site in order to measure the vascular properties under compression or stimulus (veins typically are more compressible than arteries, or, weak or thin veins may roll or move more than heathy veins). These inputs are typically can be performed by a human operator in normal practice, but are time consuming, highly manual, require patience and skill to be performed effectively.

In another example, automated release of vein dilating agent, or analgesic agent into the body around the target insertion site, or to apply local cooling at the insertion site, or similar numbing techniques. This will typically be performed manually, and add unwanted additional manual preparations and time prior to a procedure. The effectiveness of these outputs may be monitored in real time by way of outputting, then monitoring physical stimulus to patient, i.e., to evoke and then measure a change in the nervous system response (i.e., is the pain relief or distraction working), or simply asking the patient (in this case the patients determination of pain sensation may be inputted to the device or system). The input feedback to the automated system may be to increase or decrease analgesic titration or cooling or similar outputs, or implement a distraction method at time of injection, such as an evoked reaction, as further discussed below. Or delay the procedure until more optimal conditions are met.

In a further example demonstrating fluidic control, pushing of fluids or therapies into the body, or drawing bloods from the body may typically be performed manually by the operator, or an external infusion pump or system. The envisioned device may mechanically assist such fluid control, either semi or fully automated. The effectiveness of these mechanical outputs may be monitored in real time, by way of sensory monitoring of vessel distension or collapse, fluid flow rates, obstructions, needle or fluid breach of vessel, for example with ultrasound transducers, and 2d or 3d or 4d anatomical data mapping. The input feedback send back to the automated system may cause the rate of fluidic flow to be increase or decrease, or stop altogether.

In another example, to evoke a reaction from the patient— in order to distract from the injection pain, or other physical inputs, the device or system, and/or its operator, may evoke a physical reaction from patient, such as to trigger rapid expulsion of air from the lungs (to cause or ask the patient to cough), or to shout on demand, or to make a rapid physical movement or sound, such as to clap hands, or strike an object, or for example to interact with an instant stimulation device or prop such as a jack-in-the-box. Or alternatively the system may be in communication and work in concert with external stimulus such as an audio system, or other device held by, attached to or in the vicinity of the patient, that when is activated captures the attention of the patient, perhaps with an element of surprise, or is mildly shocking, for example to momentarily elevate the heart rate of blood pressure. The evoked physical action may be monitored through integrated or external sensors, allowing input information to be looped back to the control system, for example so that the peak moment of pain (i.e., at needle injection) maybe choreographed with peak physiological distraction.

Furthermore, although the invention disclosed herein has been described with reference to particular features, it is to be understood that these features are merely illustrative of the principles and applications of the present invention. It is therefore to be understood that numerous modifications, including changes in the sizes of the various features described herein, may be made to the illustrative embodiments and that other arrangements may be devised without departing from the spirit and scope of the present invention. In this regard, the present invention encompasses numerous additional features in addition to those specific features set forth in the paragraphs below. Moreover, the foregoing disclosure should be taken by way of illustration rather than by way of limitation as the present invention is defined in the examples of the numbered paragraphs, which describe features in accordance with various embodiments of the invention, set forth in the claims below.

The invention claimed is:

1. A medical imaging system comprising:
   a first imager comprising:
      a first array of transducers on a first surface;
      a second array of transducers located on a distal surface of the first imager, the first surface being inclined to the distal surface, wherein waves generated by at least two of the first and second arrays of transducers are configured to contact each other to generate a first volumetric image data set of an anatomical site; and a second imager comprising:

a third array of transducers located on a distal face of the second imager, the third array being configured to generate a second volumetric image data set of the anatomical site; and a second surface transverse to the distal face of the second imager, wherein the first surface of the first imager is transverse to the second surface of the second imager such that when the first surface is oriented towards the second surface, the first surface and the second surface define a gap; and a display screen configured to display an anatomical volumetric image data set of the anatomical site, wherein the first and second arrays generate the first volumetric image data set and the third array generates the second volumetric image data set, the anatomical volumetric image data set being defined by the first and second volumetric image data sets, the anatomical volumetric imaging data set including anatomical features within the anatomical site.

2. The medical imaging system of claim 1, wherein the second imager includes a fourth array of transducers located on the second surface of the second imager, the fourth array being inclined to the third array, the third and fourth arrays configured to generate the second volumetric image data set.

3. The medical imaging system of claim 1, wherein the first and second volumetric image data sets are generated simultaneously.

4. The medical imaging system of claim 1, wherein the first volumetric image data set is generated prior to the generation of the second volumetric image data set.

5. The medical imaging system of claim 4, wherein the medical imaging system is configured to determine a placement of the second imager with respect to the anatomical site to generate the second volumetric image data set based on the first volumetric image data set.

6. The medical imaging system of claim 5, wherein the medical imaging system determines the placement of the second imager based on stored information pertaining to a medical procedure.

7. The medical imaging system of claim 1, wherein the first and second array of transducers are capacitive micromachined ultrasonic transducers (CMUT), piezoelectric micromachined ultrasonic transducers (PMUT), or any combination thereof, disposed on a substrate, the substrate disposed within the first and second imagers.

8. The medical imaging system of claim 1, wherein the anatomical features include hard and soft tissues.

9. The medical imaging system of claim 1, wherein the first volumetric image data set is generated by the first imager located at a first location with respect to the anatomical site and the second volumetric image data set is generated by the second imager at as a second location with respect to the anatomical site.

10. The medical imaging system of claim 1, wherein anatomical features obstructed by any of bones, body fluids and other image impediments in the first volumetric image data set are captured by the second volumetric image data set.

11. The medical imaging system of claim 1, wherein the anatomical volumetric image data displayed on the display screen includes three or more volumetric image data sets generated by the first and second imagers.

12. The medical imaging system of claim 1, wherein the display screen includes a plurality of screens, each screen being perpendicular to at least one other screen.

13. A medical imaging system comprising:

an imager configured to generate a volumetric image data set of an anatomical site;

a first array of transducers located on a first planar distal surface of the imager;

a second array of transducers located on a second planar distal surface of the imager, wherein the first planar distal surface being spaced from the second planar distal surface spaced to define a gap between the first and second distal planar surfaces; and a third array of transducers located on a third planar surface of the imager, wherein:

the third planar surface of the imager extends from at least one of the first planar distal surface or the second planar distal surface, the third planar surface being inclined to at least one of the first planar distal surface or the second planar distal surface, wherein the third planar surface defines a portion of a gap between the first planar distal surface and the second planar distal surface, and wherein at least two of a projected area of the first array, a projected area of the second array, or a projected area of the third array intersect such that a volume below the gap is included in the volumetric image data set generated by the imager.

14. The medical imaging system of claim 13, wherein the volumetric image data of the anatomical site includes all anatomical features within the volume.

15. The medical imaging system of claim 14, wherein the anatomical features include hard and soft tissues.

16. The medical imaging system of claim 15, further including a display screen to display the volumetric image data.

17. The medical imaging system of claim 16, wherein the volumetric image data displayed on the display screen is generated by combining a first volumetric image data set generated by the first array and a second volumetric image data set generated by the second array.

18. The medical imaging system of claim 17, wherein anatomical features obstructed by any of bones, body fluids and other image impediments in the first volumetric image data set are captured by the second volumetric image data set.

19. The medical imaging system of claim 18, wherein the display screen includes a plurality of screens, each screen being perpendicular to at least one other screen.

* * * * *